(12) United States Patent
Baker et al.

(10) Patent No.: US 8,394,829 B2
(45) Date of Patent: Mar. 12, 2013

(54) BI-FUNCTIONAL QUINOLINE ANALOGS

(75) Inventors: William R. Baker, Bellevue, WA (US); Shaopei Cai, Seattle, WA (US); Joshua Aaron Kaplan, Seattle, WA (US); Musong Kim, Bothell, WA (US); Jennifer Alissa Loyer-Drew, Seattle, WA (US); Stephane Perreault, Brier, WA (US); Gary Phillips, Issaquah, WA (US); Lafe J. Purvis, II, Seattle, WA (US); Marcin Stasiak, Seattle, WA (US); Kirk K. Stevens, Bothell, WA (US); Josh Van Veldhuizen, Seattle, WA (US)

(73) Assignee: Gilead Sciences, Inc., Foster City, CA (US)

(*) Notice: Subject to any disclaimer, the term of this patent is extended or adjusted under 35 U.S.C. 154(b) by 78 days.

(21) Appl. No.: 13/103,577

(22) Filed: May 9, 2011

(65) Prior Publication Data

US 2011/0275622 A1    Nov. 10, 2011

Related U.S. Application Data

(60) Provisional application No. 61/333,020, filed on May 10, 2010, provisional application No. 61/406,930, filed on Oct. 26, 2010, provisional application No. 61/477,263, filed on Apr. 20, 2011.

(51) Int. Cl.
C07D 215/38        (2006.01)
A61K 31/04         (2006.01)
(52) U.S. Cl. ........................ 514/312; 546/159
(58) Field of Classification Search .................. 546/159; 514/312
See application file for complete search history.

(56) References Cited

U.S. PATENT DOCUMENTS

| | | | |
|---|---|---|---|
| 3,885,047 A | 5/1975 | Seidehamel et al. | |
| 4,145,542 A | 3/1979 | Nakagawa et al. | |
| 4,761,421 A | 8/1988 | Muir | |
| 4,992,474 A | 2/1991 | Skidmore et al. | |
| 5,455,252 A | 10/1995 | Wilhelm et al. | |
| 5,712,298 A | 1/1998 | Amschler | |
| 5,728,712 A | 3/1998 | Montana et al. | |
| 5,776,983 A | 7/1998 | Washburn et al. | |
| 5,804,588 A | 9/1998 | Dyke et al. | |
| 5,834,485 A | 11/1998 | Dyke et al. | |
| 6,069,151 A | 5/2000 | Dyke et al. | |
| 7,482,456 B2 | 1/2009 | Dube et al. | |
| 7,566,786 B2 * | 7/2009 | Baldwin et al. | 546/159 |
| 7,572,915 B2 * | 8/2009 | Barker et al. | 546/159 |
| 2001/0056122 A1 | 12/2001 | Nieman et al. | |
| 2002/0103226 A1 | 8/2002 | Deschenes et al. | |
| 2002/0143032 A1 | 10/2002 | Macdonald et al. | |
| 2002/0183358 A1 | 12/2002 | Dyke et al. | |
| 2004/0039784 A1 | 2/2004 | Jacobs et al. | |
| 2004/0162314 A1 | 8/2004 | Dube et al. | |
| 2004/0192783 A1 | 9/2004 | Morley | |
| 2005/0234238 A1 | 10/2005 | Dube et al. | |
| 2005/0245513 A1 | 11/2005 | Gallant et al. | |
| 2006/0040981 A1 | 2/2006 | Dube et al. | |
| 2006/0178416 A1 | 8/2006 | Barker et al. | |
| 2006/0205806 A1 | 9/2006 | Killan et al. | |
| 2007/0049570 A1 | 3/2007 | Dean et al. | |
| 2007/0065366 A1 | 3/2007 | Soliani Raschini et al. | |

(Continued)

FOREIGN PATENT DOCUMENTS

| | | |
|---|---|---|
| WO | WO-97/18208 A1 | 5/1997 |
| WO | WO-98/57936 A1 | 12/1998 |
| WO | WO-01/094319 A1 | 12/2001 |
| WO | WO-2004/103998 A1 | 12/2004 |
| WO | WO-2006/023460 A2 | 3/2006 |
| WO | WO-2006/089689 A1 | 8/2006 |
| WO | WO-2007/107499 A1 | 9/2007 |
| WO | WO-2009/100169 A1 | 8/2009 |
| WO | WO-2009/142589 A1 | 11/2009 |
| WO | WO-2010/004517 A1 | 1/2010 |

OTHER PUBLICATIONS

Woodrow, Bioorg & MEd CHem Lett, vol. 19, pp. 5261-5265, 2009.*
Baker, J.G. (2005) *Brit. J. Pharmacol.*; 144:317-322.
Calverly et al., *Am. J. Respir. Crit. Care Med.* 2007; 176:156-61.
Calverly et al., *Lancet* 2009; 374:685-94.
Chong et al., *J. Pharmnacol, Toxicol. Methods* 1998;39:163-168.

(Continued)

*Primary Examiner* — D M Seaman
(74) *Attorney, Agent, or Firm* — Gilead Sciences, Inc.

(57) ABSTRACT

Provided are compounds of Formula I:

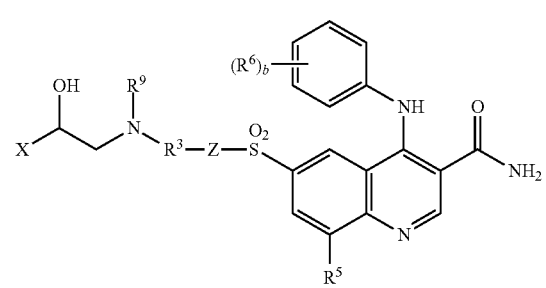

wherein X is:

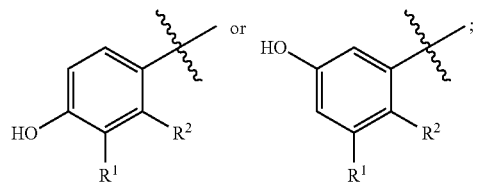

$R^1$ and $R^2$ together with the phenyl to which they are bound may form a bicyclic, fused heterocyclic ring, and all other variables are as defined herein, as well as their use in treating pulmonary inflammation or bronchoconstriction and compositions comprising and processes for preparing the same.

26 Claims, No Drawings

U.S. PATENT DOCUMENTS

| | | | |
|---|---|---|---|
| 2007/0142373 | A1 | 6/2007 | Baldwin et al. |
| 2007/0191426 | A1 | 8/2007 | Edlin et al. |
| 2008/0027112 | A1 | 1/2008 | Govek et al. |
| 2008/0096884 | A1 | 4/2008 | Edlin et al. |
| 2009/0093029 | A1 | 4/2009 | Usuda et al. |
| 2009/0312325 | A1 | 12/2009 | Baldwin et al. |
| 2010/0004215 | A1 | 1/2010 | Ray et al. |
| 2010/0261690 | A1 | 10/2010 | Burkamp et al. |
| 2011/0275623 | A1 | 11/2011 | Baker et al. |

OTHER PUBLICATIONS

Cockroft et al., (1976) Carbuterol : a double-blind clinical trial comparing carbuterol and salbutamol, *Current Therapeutic Research*, 19(2), 170-9.
Dastidar et al., (2007) Therapeutic benefit of PDE4 Inhibitors in inflammatory diseases, *Curr Opin Investig Drugs*, 8(5):364-372.
Fabbri et al., Lancet 2009; 374:695-703.
Hamid & Tulic, *Annu. Rev. Physiol.* 2009; 71:489-507.
Hekking et al., (1990) Long-term efficacy of formoterol compared to salbutamol, *Lung*, 168 Suppl 76-82.
Hughes, A. et al. (2001) *Bioorganic & Medicinal Chemistry Letters*, 21:1354-1358.
International Search Report—PCT/US2011/035738, dated Jun. 17, 2011.
International Search Report—PCT/US2011/035741, dated May 9, 2011.
Jacobsen, J. et al. (2010) *Prog Respir. Res. Basel, Karger,* 39:39-45.
Jones, L. et al. (2011) *Bioorganic & Medicinal Chemistry Letters,* 21:2769-2763.
Joseph et al., (2004) *Naun.-Sch. Arch. Pharm.*:369:525-532.
Knowles, R. et al. (2009) *Am J Respir Crit Car Med,* 179:A4581.
Kroegei & Foerster (2007) Phosphodiesterase-4 inhibitors as a novel approach for the treatment of respiratory disease: cilomilast, *Expert Opin. Investig. Drugs* 16(1):109-124.
Krymskaya, et al., (2007) Phosphodiesterases regulate airway smooth muscle function in health and disease, *Curr. Top. Dev. Biol.* 79:61-74.
Lofdahl et al., (1989) Formoterol fumarate, a new beta 2-adrenoceptor agonist, *Allergy,* 44(4), 264-71.
Lunniss et al., (2010) Addressing species specific metabolism and solubility issues in a quinoline series of oral PDE4 inhibitors, *Bioorganic & Medicinal Chemistry Letters,* 20(1), 137-140.
Lunniss, et al. (2009) Quinolines as a novel structural class of potent and selective PDE4 inhibitors: Optimisation for oral administration, *Bioorg & Med. Chem Letters* 19:1380-1385.
Molfino & Jeffery, Pulm. Pharmacol. Ther. 2007; 20:462-72.
Neale et al., (2010) Binding Mode Prediction of PDE4 Inhibitors: A Comparison of Modelling Methods, *Australian Journal of Chemistry,* 63(3), 396-404.
Nials, A. et al. (2011) *J Pharm. Exp. Ther., Fast Forward,* DOI:10.1124/jpet.110.173641.
Parkkonen, et al., (2008) Phosphodiesterase 4 inhibitors delay human eosinophil and neutrophil apoptosis in the absence and presence of salbutamol, *Pulmonary Pharmacology & Therapeutics,* 21(3), 499-506.
Pennock et al., *J Appl. Physiol.* 1979; 46:399-406.
Procopiou, P. et al. (2009) *J. Med. Chem.,* 52:2280-2288.
Rabe et al., *Lancet* 2005; 366:563-71.
Ray, N. et al. (2009) *Expert Opin. Ther. Patents,* 19(1):1-12.
Spina, *Brit. J. Pharmacol.* 2008; 155:308-15.
Traulau-Stewart, C. et al. (2011) *J Pharm. Exp. Ther., Fast Forward,* DOI:10:1124/jpet.110.173690.
Woodrow, et al., (2009) Quinolines as a novel structural class of potent and selective PDE4 inhibitors. Optimisation for inhaled administration, *Bioorg & Med. Chem Letters* 19:5261-5265.

\* cited by examiner

BI-FUNCTIONAL QUINOLINE ANALOGS

FIELD OF THE INVENTION

The present invention relates to novel anti-inflammatory, bronchodilator compounds, compositions containing the same, therapeutic methods and uses for the same and processes for preparing the same.

BACKGROUND OF THE INVENTION

The chronic inflammatory processes underlie respiratory diseases such as Chronic Obstructive Pulmonary Disease (COPD) and asthma. These diseases involve active inflammation in the bronchial airways, parenchyma and pulmonary vasculature of the lungs. The inflammatory process in such diseases are characterized by increased numbers of activated immune cells such as macrophages, neutrophils, eosinophils and lymphocytes and the release of a range of pro-inflammatory signaling molecules, namely cytokines and chemokines from immune and resident lung cells. The pathogenesis of these diseases is different but chronic inflammation is an underlying driving mechanism to both. COPD is strongly associated with exposure to noxious particles and gases from the external environment such as cigarette smoking and exposure to wood burning fires and is characterized by oxidative stress and an imbalance of harmful tissue proteinases with anti-proteases. These processes can lead to distinctive pathologies such as goblet metaplasia and mucus hypersecretion which cause bronchitis, alveolar wall destruction leading to emphysema and inappropriate tissue repair and smooth muscle thickening causing small airways remodeling (reviewed by Molfino & Jeffery, *Pulm. Pharmacol. Ther.* 2007; 20:462-72). In asthma, allergic immune mechanisms underlie the chronic inflammatory processes which contributes to airway hyperresponsiveness and structural changes in the bronchial airway, termed remodeling, such as airway smooth muscle thickening and goblet cell hyperplasia. (reviewed by Hamid & Tulic, *Annu. Rev. Physiol.* 2009; 71:489-507).

Bronchodilator medications that can improve lung function and improve expiratory flow are used as a standard of care for symptom relief in the treatment of respiratory diseases. Inhaled long-acting $\beta_2$ adrenoceptor agonists (LABA) such as salmeterol or formoterol, or inhaled long-acting muscarinic receptor antagonists (LAMA) such as tiotropium are commonly prescribed to provide symptom relief.

Inflammation is a central process underlying many respiratory diseases and treatments that are anti-inflammatory may be efficacious and have the potential to impact disease progression. The phosphodiesterase-4 (PDE4) enzyme is a ubiquitously expressed enzyme that is responsible for catalyzing the hydrolysis of cyclic adenosine monophosphate (cAMP). Inhibition of the enzymatic activity of PDE4 with use of selective inhibitors elevates cellular levels of cAMP and this has anti-inflammatory effects in multiple immune and resident pulmonary cell types (Spina, *Brit. J. Pharmacol.* 2008; 155:308-15). Use of the oral PDE4 inhibitor roflumilast has demonstrated anti-inflammatory activity clinically showing a reduction of exacerbations and modest increases in lung function in COPD patients (Rabe et al., *Lancet* 2005; 366:563-71; Calverly et al., *Am. J. Respir. Crit. Care Med.* 2007; 176:154-61). Additionally, roflumilast improves lung function in severe and symptomatic patients with COPD treated with salmeterol or tiotropium but remains dose-limited due to side-effects including nausea, head-ache, diarrhea, and weight loss (Fabbri et al., *Lancet* 2009; 374:695-703; Calverly et al., *Lancet* 2009; 374:685-94). Forest Research Institute's product Daxas (roflumilast) has been approved as a once daily oral PDE4 inhibitor for the treatment of COPD. While it was accepted that Daxas demonstrated consistent evidence of efficacy concerns over a number of adverse event signals led the committee to deny approval based on the overall poor risk-to-benefit ratio. Topical delivery of a PDE4 inhibitor could therefore provide efficacious anti-inflammatory activity in the lungs whilst reducing the potential for side-effects by limiting it's exposure to the systemic circulation. Additionally, direct topical delivery may allow for higher local concentrations of the PDE4 inhibitor than could be achieved through oral dosing, and thus potential for further improvement in anti-inflammatory efficacy. PCT Publication No. WO2004/103998 relates to quinoline derivatives of formula (I)

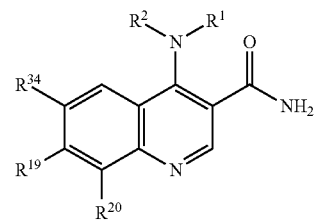

as phosphodiesterase inhibitors. The application also refers to the use of such compounds for the treatment of inflammatory diseases.

C. J. Lunnis, et al., Quinolines as a novel structural class of potent and selective PDE4 inhibitors: Optimisation for oral administration, *Bioorg & Med. Chem. Letters* (2009) 19:1380-1385, refers to the following compound:

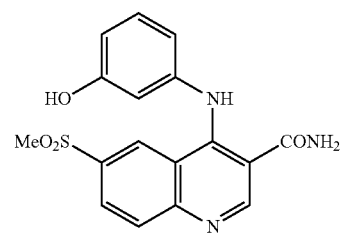

and analogs thereof wherein the 4-amino substituent is modified, the linker to the 4-substituent is modified, the primary carboxamide is modified and the quinoline 8-substituent is modified. Two of the analogs referenced therein are:

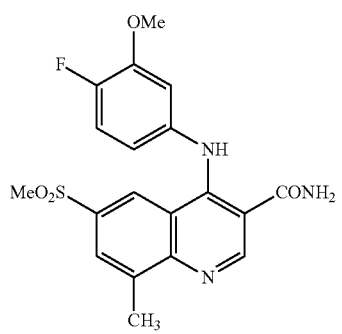

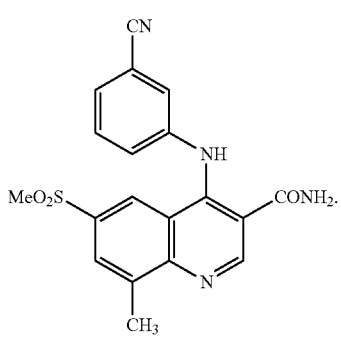

M. D. Woodrow, et al., Quinolines as a novel structural class of potent and selective PDE4 inhibitors. Optimisation for inhaled administration, *Bioorg & Med. Chem. Letters* (2009) 19:5261-5265, refers to the following compound:

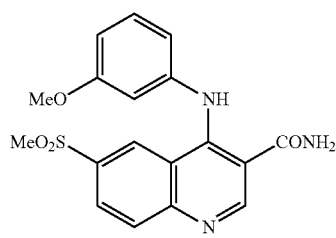

and analogs thereof including analogs defined by the following formulas were the variables are defined in the paper:

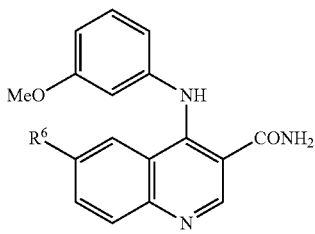

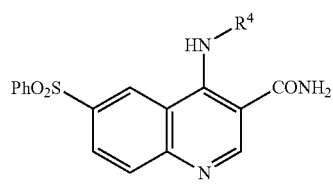

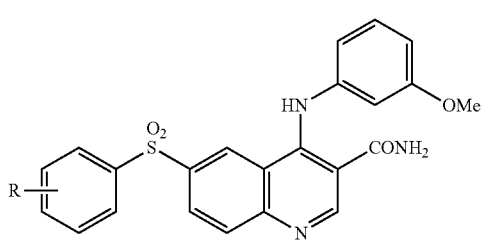

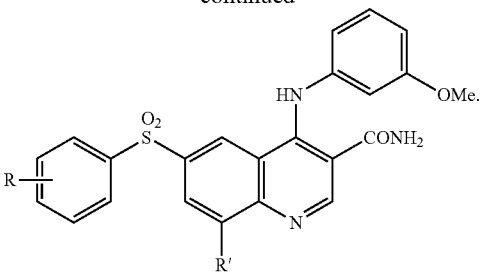

Conventional therapeutic agents for the treatment of inflammatory respiratory conditions suffer from limited efficacy and undesired side-effect profiles. Accordingly, there remains a need in the art for new drugs designed to treat respiratory conditions including inflammatory respiratory conditions such as asthma, COPD, chronic bronchitis, bronchiectasis, cystic fibrosis, etc.

SUMMARY OF THE INVENTION

As one aspect, the present invention provides compounds Formula I:

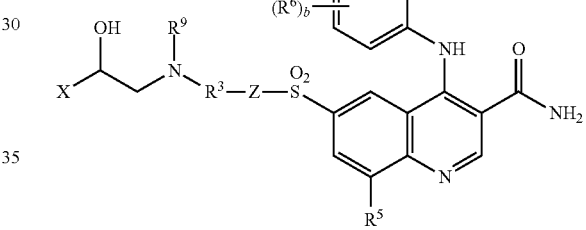

wherein
X is a substituted phenyl ring selected from:

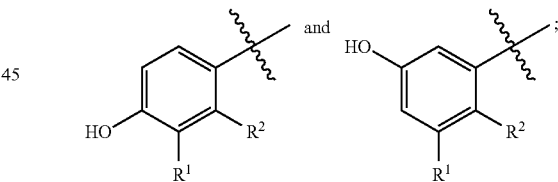

Z is a bond or a moiety selected from:

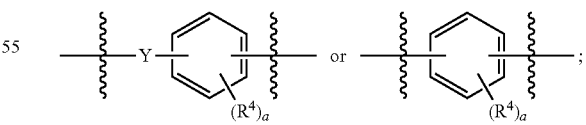

$R^1$ is $CH_2OH$, $CH_2CH_2OH$, $N(H)C(O)H$, or $N(H)S(O_2)C_1$-$c_3$ alkyl, and $R^2$ is H;

or $R^1$ and $R^2$ together with the phenyl to which they are bound form a bicyclic, fused heterocyclic ring having 9 or 10 ring atoms wherein 1 or 2 ring atoms are selected from N, O and S, wherein said bicyclic fused heterocyclic ring is optionally substituted with one, two or three additional substituents independently selected from alkyl, oxo and OH;

R³ is selected from C₄₋₁₂alkylene, C₄₋₁₂alkenylene, C₄₋₁₂alkynylene, R⁸—O—R⁸, R⁸—N(R⁷)—R⁸, C₃₋₆cycloalkylene, R⁸—C₃₋₆cycloalkylene, R⁸—C₃₋₆ cycloalkylene-Het, C₃₋₆cycloalkylene-R⁸, R⁸—C₃₋₆cycloalkylene-R⁸, C₆₋₁₀arylene, R⁸—C₆₋₁₀arylene, C₆₋₁₀arylene-R⁸, R⁸—C₆₋₁₀arylene-R⁸, R⁸—C₆₋₁₀arylene-O—R⁸, R⁸—C₆₋₁₀arylene-N(R)—R⁸, R⁸—C₆₋₁₀arylene-C₆₋₁₀arylene, Het, R⁸-Het, Het-R⁸, R⁸-Het-R⁸, R⁸—O-Het, R⁸—C₆₋₁₀arylene-O-Het, R⁸—C₆₋₁₀arylene-C(O)-Het, R⁸—C₆₋₁₀arylene-N(R⁷)-Het, R⁸-Het-C₆₋₁₀arylene, R⁸—C₆₋₁₀arylene-Het, and R⁸—O—R⁸—C₆₋₁₀arylene;

wherein said alkylene, alkenylene or alkynylene are each optionally substituted with 1, 2 or 3 substituents selected from halo, oxo, and OR⁷;

wherein said phenylene groups are each optionally substituted with 1, 2, 3, or 4 substituents selected from halo, alkyl, and OR⁷;

Het is 5-6 membered saturated or unsaturated monocyclic heterocyclene or an 8-10 membered saturated or unsaturated bicyclic heterocyclene wherein 1 or 2 ring atoms are selected from N, O and S, and wherein said monocyclic or bicyclic heterocyclene is optionally substituted with 1, 2 or 3 substituents selected from halo, alkyl, alkoxy, oxo and OH;

Y is C(O), OC(O), C(O)N(R⁷), C(O)N(R⁷)CH₂, OC(O)NR⁷CH₂, N(R⁷)C(O), or N(R⁷)C(O)N(R⁷);

a is 0, 1, 2, 3, or 4;

R⁴ is selected from halo, alkyl, and OR⁷;

R⁵ is H or alkyl;

b is 1, 2, 3, 4, or 5;

R⁶ is selected from halo, alkyl, haloalkyl, OR⁷, O-haloalkyl, R⁸—OR⁷, O—R⁸—OR⁷, C(O)alkyl, O—R⁸—C(O)alkyl, CON(R⁷)₂, R⁸—CON(R⁷)₂, R⁸—N(R⁷)₂, N(R⁷)C(O)alkyl, N(R⁷)C(O)N(R⁷)₂, N(R⁷)SO₂alkyl, R⁸—SO₂N(R⁷)₂, and CN;

or two R⁶ on adjacent carbons, together with the phenyl to which they are bound form a bicyclic heterocyclic ring having 9 or 10 ring atoms wherein 1 or 2 ring atoms are selected from N, O and S;

R⁷ is H or alkyl; and

R⁸ is C₁₋₁₀alkylene, C₂₋₁₀alkenylene, or C₂₋₁₀alkynylene wherein each R⁸ is optionally substituted with 1, 2 or 3 substituents selected from halo, oxo, and OR⁷; with the proviso that the total number of carbon atoms in the C₂₋₁₀alkenylene, or C₂₋₁₀alkynylene chains of two R⁸ groups in any definition of R³ is not greater than 12;

R⁹ is H or C₁-C₃ alkyl;

or a pharmaceutically acceptable salt thereof.

In one embodiment, the present invention provides compounds of Formula I':

and pharmaceutically acceptable salts thereof, wherein all variables are as defined above.

As another aspect, the present invention provides a composition comprising a compound of Formula I or I' or a pharmaceutically acceptable salt thereof and a pharmaceutically acceptable carrier, diluent or excipient. In one embodiment, the composition is suitable for inhalation.

As another aspect, the present invention provides a method comprising administering to a human, an effective amount of a compound of Formula I or I' or a pharmaceutically acceptable salt thereof.

As another aspect, the present invention provides a method for treating pulmonary inflammation or bronchoconstriction in a human in need thereof. The method comprises administering to the human an effective amount of a compound of Formula I or I' or a pharmaceutically acceptable salt thereof.

As another aspect, the present invention provides a method for treating a disease associated with reversible or irreversible airway obstruction, chronic obstructive pulmonary disease (COPD), asthma, bronchiectasis (including bronchiectasis due to conditions other than cystic fibrosis), acute bronchitis, chronic bronchitis, post-viral cough, cystic fibrosis, emphysema, pneumonia, panbronchiolitis, transplant-associate bronchiolitis, sinusitis, and ventilator-associated tracheobronchitis or preventing ventilator-associated pneumonia, or treating sinusitis in a human in need thereof. The method comprises administering to the human an effective amount of a compound of Formula I or I' or a pharmaceutically acceptable salt thereof. In one embodiment, the present invention provides a method for treating chronic obstructive pulmonary disease (COPD) or asthma in a human in need thereof using a compound of Formula I or I' or a pharmaceutically acceptable salt thereof.

As another aspect, the present invention provides a compound of Formula I or I' or a pharmaceutically acceptable salt thereof for use as a medicament.

As another aspect, the present invention provides a compound of Formula I or I' or a pharmaceutically acceptable salt thereof for use in a method of treating of pulmonary inflammation or bronchoconstriction in a human.

As another aspect, the present invention provides a compound of Formula I or I' or a pharmaceutically acceptable salt thereof for use in a method of treating a disease associated with reversible or irreversible airway obstruction, chronic obstructive pulmonary disease (COPD), asthma, bronchiectasis (including bronchiectasis due to conditions other than cystic fibrosis), acute bronchitis, chronic bronchitis, post-viral cough, cystic fibrosis, emphysema, pneumonia, panbronchiolitis, transplant-associate bronchiolitis, sinusitis, and ventilator-associated tracheobronchitis or preventing

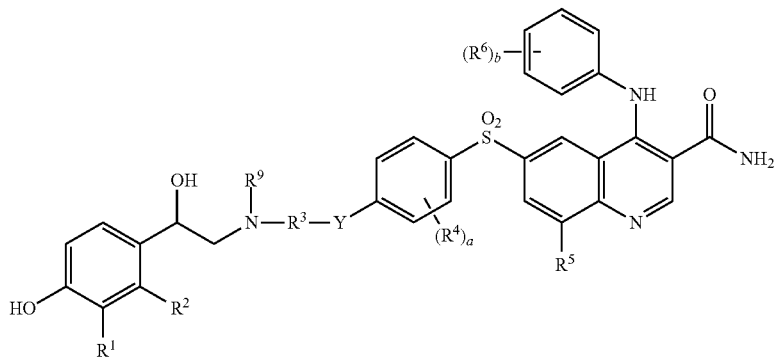

ventilator-associated pneumonia, or treating sinusitis in a human. In one embodiment, the present invention provides a compound of Formula I or I' or a pharmaceutically acceptable salt thereof for use in a method of treating a disease associated with chronic obstructive pulmonary disease (COPD) or asthma, in a human.

As another aspect, the present invention provides the use of a compound of Formula I or I' or a pharmaceutically acceptable salt thereof for the manufacture of a medicament for the treatment of pulmonary inflammation or bronchoconstriction in a human.

As another aspect, the present invention provides the use of a compound of Formula I or I' or a pharmaceutically acceptable salt thereof for the manufacture of a medicament for the treatment of a disease associated with reversible or irreversible airway obstruction, chronic obstructive pulmonary disease (COPD), asthma, bronchiectasis (including bronchiectasis due to conditions other than cystic fibrosis), acute bronchitis, chronic bronchitis, post-viral cough, cystic fibrosis, emphysema, pneumonia, panbronchiolitis, transplant-associate bronchiolitis, sinusitis, and ventilator-associated tracheobronchitis or preventing ventilator-associated pneumonia, or treating sinusitis in a human.

As another aspect, the present invention provides a composition comprising a compound of Formula I or I' or a pharmaceutically acceptable salt thereof for use in the preparation of a medicament for the treatment of pulmonary inflammation or bronchoconstriction in a human.

As another aspect, the present invention provides a composition comprising a compound of Formula I or I' or a pharmaceutically acceptable salt thereof for use in the preparation of a medicament for the treatment of a disease associated with reversible or irreversible airway obstruction, chronic obstructive pulmonary disease (COPD), asthma, bronchiectasis (including bronchiectasis due to conditions other than cystic fibrosis), acute bronchitis, chronic bronchitis, post-viral cough, cystic fibrosis, emphysema, pneumonia, panbronchiolitis, transplant-associate bronchiolitis, sinusitis, and ventilator-associated tracheobronchitis or preventing ventilator-associated pneumonia, or treating sinusitis in a human.

DETAILED DESCRIPTION OF THE INVENTION

A single molecule for inhaled use which has bifunctional activity as both a long-acting $\beta_2$ adrenoceptor agonist and a PDE4 inhibitor could provide both symptom control through bronchodilation and anti-inflammatory activity. Such compound would also have the potential to provide additive or synergistic anti-inflammatory activity through the complementary interaction of both molecular signaling pathways. Beta agonists when binding to a receptor through the action of G proteins will increase adenylate cyclase activity which causes elevation of cellular cyclic AMP. Inhibition of the PDE4 enzyme also serves to maintain cellular cAMP levels through inhibition of the enzyme responsible for its breakdown. An inhaled molecule that has both $\beta_2$ agonist and PDE4 inhibitory activity may provide additive effects and potentially synergistic anti-inflammatory activity, and thus could be dose-sparing. Deposition of a single bi-functional compound in the lung microenvironment should also maximize the opportunity for this molecular interaction to occur compared to a mixture of the single agents dosed together. High lung to systemic exposure levels through topical delivery allied with long lung retention times will dramatically reduce the opportunity for side-effects mediated through exposure via the systemic circulation to other tissues and organs.

As used herein, the following terms are defined as indicated.

"A compound of the invention" means a compound of Formula I or a salt, particularly a pharmaceutically acceptable salt thereof.

"A compound of Formula I" means a compound having the structural formula designated herein as Formula I or I' (as compounds of Formula I' are a subset of compounds of Formula I). Compounds of Formula I include solvates and hydrates (i.e., adducts of a compound of Formula I with a solvent). In those embodiments wherein a compound of Formula I includes one or more chiral centers, the phrase is intended to encompass racemic mixtures, each individual stereoisomer including optical isomers (enantiomers and diastereomers) and geometric isomers (cis-/trans-isomerism) and mixtures of stereoisomers. In addition, compounds of Formula I also include tautomers of the depicted formula (s).

"Alkyl" is a linear or branched hydrocarbon chain of 1 to 8 carbon atoms (i.e., $C_{1-8}$ alkyl), or typically, 1 to 6 carbon atoms (i.e., $C_{1-6}$ alkyl), unless the number of carbon atoms is otherwise specified. When the compound of Formula I includes more than one alkyl, the alkyls may be the same or different. Examples of suitable alkyl groups include, but are not limited to, methyl ("Me"), ethyl ("Et"), 1-propyl (n-propyl), isopropyl, n-butyl, isobutyl (2-methyl-1-propyl), sec-butyl (2-butyl), tert-butyl(—$C(CH_3)_3$), n-pentyl, 2-pentyl, 3-pentyl, hexyl, octyl, and the like.

"Alkenyl" is a linear or branched hydrocarbon chain with at least one site of unsaturation, i.e. a carbon-carbon double bond, and having from 2 to 8 carbon atoms (i.e., $C_{2-8}$ alkenyl), or typically, 2 to 6 carbon atoms (i.e., $O_{2-6}$ alkenyl) unless the number of carbon atoms is otherwise specified. When the compound of Formula I includes more than one alkenyl, the alkenyls may be the same or different. Examples of suitable alkenyl groups include, but are not limited to, ethylene or vinyl (—CH=$CH_2$), allyl (—$CH_2$CH=$CH_2$), 5-hexenyl (—$CH_2CH_2CH_2CH_2$CH=$CH_2$), and the like.

"Alkynyl" is a linear or branched hydrocarbon chain having at least one carbon-carbon triple bond, and optionally also one or more carbon-carbon double bonds, and having from 2 to 8 carbon atoms (i.e., $C_{2-8}$ alkynyl), or more typically 2 to 6 carbon atoms (i.e., $C_{2-6}$ alkynyl) unless the number of carbon atoms is otherwise specified. When the compound of Formula I includes more than one alkynyl, the alkynyls may be the same or different. Examples of suitable alkynyl groups include, but are not limited to, acetylenyl (—C≡CH), propargyl (—$CH_2$C≡CH), and the like.

"Alkylene" refers to a saturated, linear or branched divalent hydrocarbon radical having from 1 to 12 carbon atoms ("$C_{1-12}$ alkylene"), unless the number of carbon atoms is otherwise specified. When the compound of Formula I includes more than one alkylene, the alkylenes may be the same or different. Typical alkylene radicals include, but are not limited to, methylene (—$CH_2$—), ethylene (—$CH(CH_3)$— or —$CH_2CH_2$—), propylene (e.g., —$CH(CH_2CH_3)$—, —$CH_2CH(CH_3)$— or —$CH_2CH_2CH_2$—), butylene (e.g., —$CH_2CH_2CH_2CH_2$—), and the like. In one embodiment, alkylene is linear.

"Alkenylene" refers to an unsaturated, linear or branched divalent hydrocarbon radical having at least one carbon-carbon double bond, and having from 2 to 12 carbon atoms ("$C_{2-12}$ alkenylene"), unless the number of carbon atoms is otherwise specified. When the compound of Formula I includes more than one alkenylene the alkenylenes may be the same or different. Typical alkenylene radicals include, but are not limited to, 1,2-ethylene (—CH═CH—) and (—CH₂CH═CHCH₂CH₂—). In one embodiment, alkenylene is linear.

"Alkynylene" refers to an unsaturated, linear or branched divalent hydrocarbon radical having at least one carbon-carbon triple bond and optionally also one or more carbon-carbon double bonds, and having 2 to 12 carbon atoms ("C₂₋₁₂ alkenylene"), unless the number of carbon atoms is otherwise specified. When the compound of Formula I includes more than one alkenylene the alkenylenes may be the same or different. Typical alkynylene radicals include, but are not limited to, 1,2-ethynylene (—C≡C—) and (—CH₂C≡CCH₂CH₂—). In one embodiment, alkynylene is linear.

"Alkoxy" refers to O-alkyl, wherein "alkyl" is as defined above.

"Halo" or "halogen" are synonymous and refer to fluoro, chloro, bromo, and iodo. In one embodiment, halo is fluoro, chloro or bromo.

"Haloalkyl" is linear or branched hydrocarbon chain of 1 to 8 carbon atoms (i.e., C₁₋₈haloalkyl), or typically, 1 to 6 carbon atoms (i.e., C₁₋₆haloalkyl), unless the number of carbon atoms is otherwise specified, substituted by one or more halogens, fluoro, chloro, bromo and iodo. Haloalkyl include perhaloalkyls such as trifluoromethyl. When the compound of Formula I includes more than one haloalkyl, the haloalkyls may be the same or different. Examples of suitable haloalkyl groups include, but are not limited to, fluoromethyl, chloromethyl, trifluoromethyl, dichloromethyl, dichloroethyl, and the like.

"Oxo" as used herein refers to the group ═O attached directly to a carbon atom of a hydrocarbon ring or a C, N or S of a heterocyclic ring to result in oxides, —N-oxides, sulfones and sulfoxides.

"Cycloalkylene" refers to a divalent, monocyclic, saturated or partially unsaturated, non-aromatic ring having from 3 to 6 carbon atoms, (C₃₋₆cycloalkylene) unless a different number of carbon atoms is specified. When the compound of Formula I includes more than one cycloalkylene, the cycloalkylene groups may be the same or different. Examples of specific cycloalkylene groups include cyclopropylene, cyclobutylene, cyclopentylene, and cyclohexylene. Cycloalkylene also includes cycloalkyl groups optionally substituted with 1 or 2 substituents, which substituents are the same or different and are selected from halo, alkyl, hydroxyl, O-alkyl, oxo, amino (e.g., NH₂), alkylamino (e.g., N(H)alkyl), and dialkylamino (e.g., N(alkyl)₂), or any subset thereof. In one embodiment, the cycloalkylene is unsubstituted.

"Arylene" refers to a divalent, monocyclic or fused bicyclic, aromatic ring having from 6 to 10 carbon atoms, (C₆₋₁₀arylene) unless a different number of carbon atoms is specified. When the compound of Formula I includes more than one arylene, the arylene groups may be the same or different. Examples of specific arylene groups include phenylene and naphthylene. Arylene also includes arylene groups optionally substituted with 1 or 2 substituents, which substituents are the same or different and are selected from halo, alkyl, hydroxyl, O-alkyl, amino (e.g., NH₂), alkylamino (e.g., N(H)alkyl), and dialkylamino (e.g., N(alkyl)₂), or any subset thereof. In one embodiment, arylene is phenylene. In one embodiment, arylene is unsubstituted phenylene.

"Heterocyclic group" or "heterocycle" are synonymous and refer to monocyclic and fused bicyclic, saturated or partially unsaturated, or aromatic rings having 5, 6, 9 or 10 ring atoms wherein 1, 2, 3, or 4 ring atoms is/are a heteroatom independently selected from N, O and S and all remaining ring atoms are C. In one embodiment, the heterocyclic group has 5, 6, 9 or 10 rings atoms wherein 1, 2 or 3 ring atoms is/are a heteroatom independently selected from N, O and S. In all embodiments wherein the heterocyclic group includes 2 or more heteroatoms (N, O and S) the heteroatoms may be the same or different. In all embodiments wherein the compound of Formula I includes 2 or more heterocyclic groups, the heterocyclic groups may be the same or different. Examples of heterocyclic groups include but are not limited to furanyl, tetrahydrofuranyl, thiophenyl, tetrahydrothiophenyl, sulfur oxidized tetrahydrothiophenyl, pyrrolyl, pyrrolinyl, pyrrolidinyl, dioxolanyl, oxazolidinyl, oxazolyl, isoxazolyl, thiazolyl, isothiazolyl, imidazolyl, imidazolinyl, imidazolidinyl, pyrazolyl, pyrazolinyl, pyrazolidinyl, triazolyl, tetrazolyl, pyranyl, dihydropyranyl, tetrahydropyranyl, pyridyl, dihydropyridyl, piperidyl, dioxanyl, morpholinyl, dithianyl, thiomorpholinyl, pyridazinyl, pyrimidinyl, pyrazinyl, piperazinyl, triazinyl, indolizinyl, indolyl, isoindolyl, oxindolyl, indolinyl, benzofuranyl, dihydrobenzofuranyl, isobenzofuranyl, benzothienyl, indazolyl, benzimidazolyl, benzoxazolinyl, benzoxazolyl, benzisoxazolyl, benzthiazolyl, benzotriazolyl, benzopyranyl, purinyl, quinolizinyl, quinolinyl, isoquinolinyl, tetrahydroquinolinyl, tetrahydroisoquinolinyl, decahydroquinolinyl, octahydroisoquinolinyl, cinnolinyl, phthalazinyl, quinazolinyl, quinoxalinyl, naphthyridinyl, pteridinyl, thianaphthalenyl and the like. Heterocyclic groups may be bound through any available ring carbon or ring heteroatom, such as N.

"Heterocyclene" refers to a bivalent heterocyclic group as defined herein. For example, heterocyclenes include:

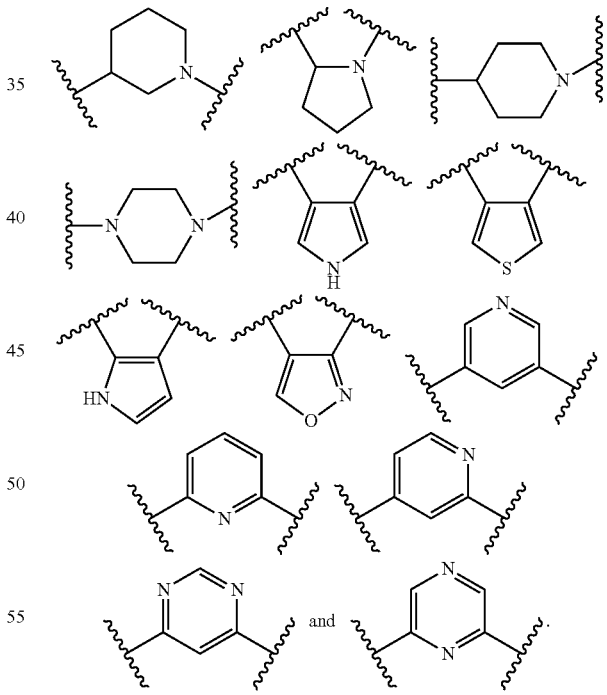

Preferably, the heterocyclene groups in the compounds of Formula I are monocyclic, saturated or partially unsaturated rings having 5 or 6 ring atoms wherein 1, 2, or 3 ring atoms is/are a heteroatom independently selected from N, O and S and all remaining ring atoms are C.

The term "optionally substituted" in reference to a particular moiety of the compound of Formula I (e.g., an optionally substituted alkylene) refers to that moiety having no substituents, and that moiety having the specified number of substituents; typically up to 4 substituents unless otherwise indicated. Unless otherwise indicated, when the term "substituted" is used in conjunction with groups which have multiple available sites for substitution or two or more moieties capable of substitution, the substituents can be attached to any available C or heteroatom.

Throughout the description and examples, compounds are named using standard IUPAC naming principles where possible.

In some chemical structure representations where carbon atoms do not have a sufficient number of attached variables or bonds depicted to produce a valence of four, the remaining carbon substituents needed to provide a valence of four are understood to be hydrogen. Similarly, in some chemical structures where a bond is drawn without specifying the terminal group, such bond is indicative of a methyl (Me, —$CH_3$) group, as is conventional in the art.

As one aspect, the present invention provides compounds Formula I:

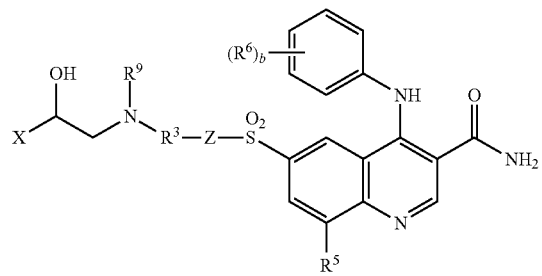

wherein:
X is a substituted phenyl ring selected from:

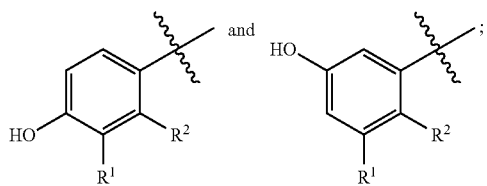

Z is a bond or a moiety selected from:

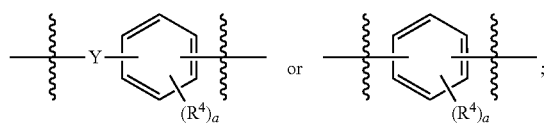

$R^1$ is $CH_2OH$, $CH_2CH_2OH$, $N(H)C(O)H$, or $N(H)S(O_2)C_1$-$c_3$ alkyl, and $R^2$ is H;

or $R^1$ and $R^2$ together with the phenyl to which they are bound form a bicyclic, fused heterocyclic ring having 9 or 10 ring atoms wherein 1 or 2 ring atoms are selected from N, O and S, wherein said bicyclic fused heterocyclic ring is optionally substituted with one, two or three additional substituents independently selected from alkyl, oxo and OH;

$R^3$ is selected from $C_{4-12}$alkylene, $C_{4-42}$alkenylene, $C_{4-12}$alkynylene, $R^8$—O—$R^8$, $R^8$—N($R^7$)—$R^8$, $C_{3-6}$cycloalkylene, $R^8$—$C_{3-6}$cycloalkylene, $R^8$—$C_{3-6}$ cycloalkylene-Het, $C_{3-6}$cycloalkylene-$R^8$, $R^8$—$C_{3-6}$cycloalkylene-$R^8$, phenylene, $R^8$-phenylene, phenylene-$R^8$, $R^8$-phenylene-$R^8$, $R^8$-phenylene-O—$R^8$, $R^8$-phenylene-N($R^7$)—$R^8$, $R^8$-phenylene-phenylene, Het, $R^8$-Het, Het-$R^8$, $R^8$-Het-$R^8$, $R^8$—O-Het, $R^8$-phenylene-O-Het, $R^8$-phenylene-C(O)-Het, $R^8$-phenylene-N($R^7$)-Het, $R^8$-Het-phenylene, $R^8$-phenylene-Het, and $R^8$—O—$R^8$-phenylene;

wherein said alkylene, alkenylene or alkynylene are each optionally substituted with 1, 2 or 3 substituents selected from halo, oxo, and $OR^7$;

wherein said phenylene groups are each optionally substituted with 1, 2, 3, or 4 substituents selected from halo, alkyl, and $OR^7$;

Het is 5-6 membered saturated or unsaturated monocyclic heterocyclene or an 8-10 membered saturated or unsaturated bicyclic heterocyclene wherein 1 or 2 ring atoms are selected from N, O and S, and wherein said monocyclic or bicyclic heterocyclene is optionally substituted with 1, 2 or 3 substituents selected from halo, alkyl, alkoxy, oxo and OH;

Y is C(O), OC(O), C(O)N($R^7$), C(O)N($R^7$)$CH_2$, OC(O)N$R^7CH_2$, N($R^7$)C(O), or N($R^7$)C(O)N($R^7$);

a is 0, 1, 2, 3, or 4;

$R^4$ is selected from halo, alkyl, and $OR^7$;

$R^5$ is H or alkyl;

b is 1, 2, 3, 4, or 5;

$R^6$ is selected from halo, alkyl, haloalkyl, $OR^7$, O-haloalkyl, $R^8$—$OR^7$, O—$R^8$—$OR^7$, C(O)alkyl, O—$R^8$—C(O)alkyl, CON($R^7$)$_2$, $R^8$—CON($R^7$)$_2$, $R^8$—N($R^7$)$_2$, N($R^7$)C(O)alkyl, N($R^7$)C(O)N($R^7$)$_2$, N($R^7$)SO$_2$alkyl, $R^8$—SO$_2$N($R^7$)$_2$, and CN;

or two $R^6$ on adjacent carbons, together with the phenyl to which they are bound form a bicyclic heterocyclic ring having 9 or 10 ring atoms wherein 1 or 2 ring atoms are selected from N, O and S;

$R^7$ is H or alkyl; and $R^8$ is $C_{1-10}$alkylene, $C_{2-10}$alkenylene, or $C_{2-10}$alkynylene wherein each $R^8$ is optionally substituted with 1, 2 or 3 substituents selected from halo, oxo, and $OR^7$; with the proviso that the total number of carbon atoms in the $C_{1-10}$alkylene, $C_{2-10}$alkenylene, or $C_{2-10}$alkynylene chains of two $R^8$ groups in any definition of $R^3$ is not greater than 12;

$R^9$ is H or $C_1$-$C_3$ alkyl;

or a pharmaceutically acceptable salt thereof.

In other embodiments the present invention provides compounds of Formula II(a) and Formula II(b):

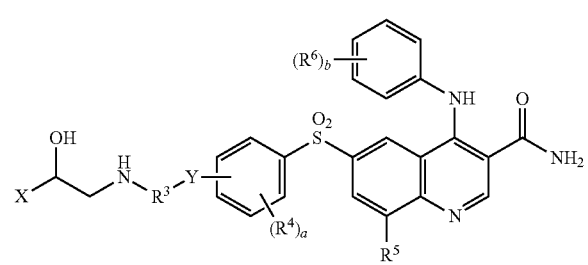

-continued

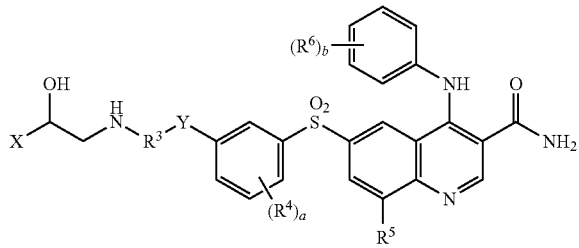

II(b)

or a pharmaceutically acceptable salt thereof;
wherein:
X is a substituted phenyl ring selected from:

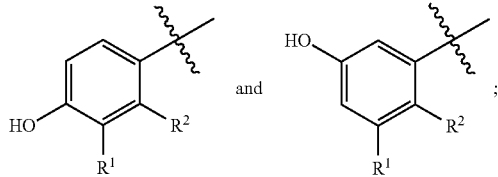

and $R^1$ is $CH_2OH$, $CH_2CH_2OH$, $N(H)C(O)H$, or $N(H)S(O_2)CH_3$, and $R^2$ is H;

or $R^1$ and $R^2$ together with the phenyl to which they are bound form a bicyclic, fused heterocyclic ring selected from;

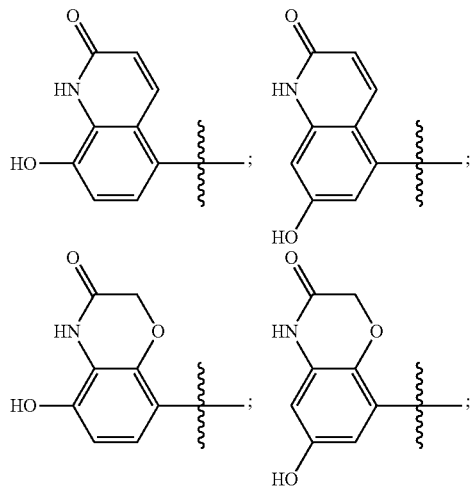

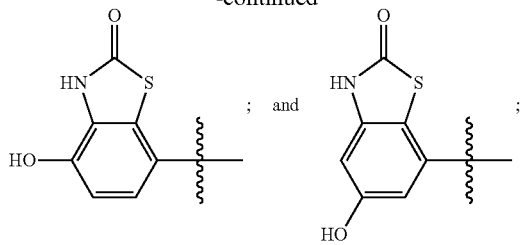

; and ;

$R^3$ is selected from $C_{4-12}$alkylene, $C_{4-12}$alkenylene, $C_{4-12}$alkynylene, $R^8$—O—$R^8$, $R^8$—$C_{3-6}$cycloalkylene-Het, $R^8$— phenylene, $R^8$-phenylene-O—$R^8$, $R^8$-phenylene-phenylene, Het, $R^8$-Het, $R^8$—O-Het, $R^8$-phenylene-C(O)-Het, $R^8$-Het-phenylene, $R^8$-phenylene-Het, and $R^8$—O—$R^8$-phenylene;
  wherein said alkylene, alkenylene or alkynylene are each optionally substituted with 1, 2 or 3 substituents selected from halo, oxo, and $OR^7$;
  wherein said phenylene groups are each optionally substituted with 1, 2, 3, or 4 substituents selected from halo, alkyl, and $OR^7$;
  Het is 5-6 membered saturated or unsaturated monocyclic heterocyclene or an 8-10 membered saturated or unsaturated bicyclic heterocyclene wherein 1 or 2 ring atoms are selected from N, O and S, and wherein said monocyclic or bicyclic heterocyclene is optionally substituted with 1, 2 or 3 substituents selected from halo, alkyl, alkoxy, oxo and OH;
Y is C(O), OC(O), C(O)N($R^7$), C(O)N($R^7$)$CH_2$, OC(O)N$R^7$$CH_2$, N($R^7$)C(O), or N($R^7$)C(O)N($R^7$);
a is 0, 1, 2, 3, or 4;
$R^4$ is selected from halo, alkyl, and $OR^7$;
$R^5$ is H or alkyl;
b is 1, 2, 3, 4, or 5;
$R^6$ is selected from halo, alkyl, haloalkyl, $OR^7$, O-haloalkyl, $R^8$—$OR^7$, O—$R^8$—$OR^7$, C(O)alkyl, O—$R^8$—C(O)alkyl, CON($R^7$)$_2$, $R^8$—CON($R^7$)$_2$, $R^8$—N($R^7$)$_2$, N($R^7$)C(O)alkyl, N($R^7$)C(O)N($R^7$)$_2$, N($R^7$)SO$_2$alkyl, $R^8$—SO$_2$N($R^7$)$_2$, and CN;
or two $R^6$ on adjacent carbons, together with the phenyl to which they are bound form a bicyclic heterocyclic ring having 9 or 10 ring atoms wherein 1 or 2 ring atoms are selected from N, O and S;
$R^7$ is H or alkyl; and
$R^8$ is $C_{1-10}$alkylene, $C_{2-10}$alkenylene, or $C_{2-10}$alkynylene wherein each $R^8$ is optionally substituted with 1, 2 or 3 substituents selected from halo, oxo, and $OR^7$; with the proviso that the total number of carbon atoms in the $C_{1-10}$alkylene, $C_{2-10}$alkenylene, or $C_{2-10}$alkynylene chains of two $R^8$ groups in any definition of $R^3$ is not greater than 12.

Additional embodiments independently comprise compounds of Formula III(a), III(b), III(c), III(d), and III(e) or a pharmaceutically acceptable salt thereof:

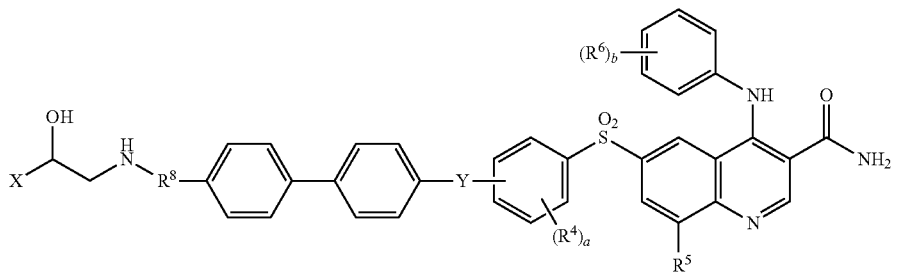

III(a)

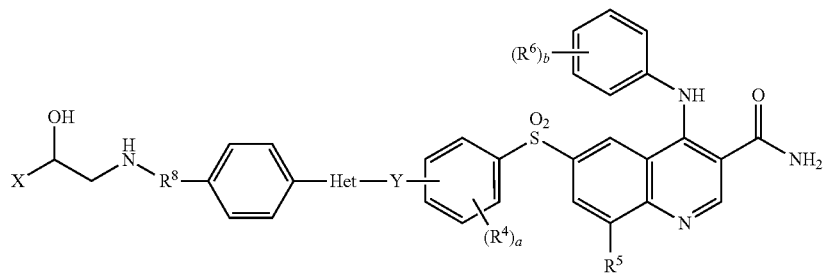

III(b)

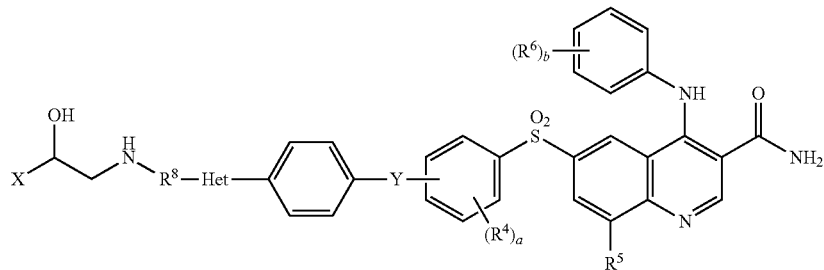

III(c)

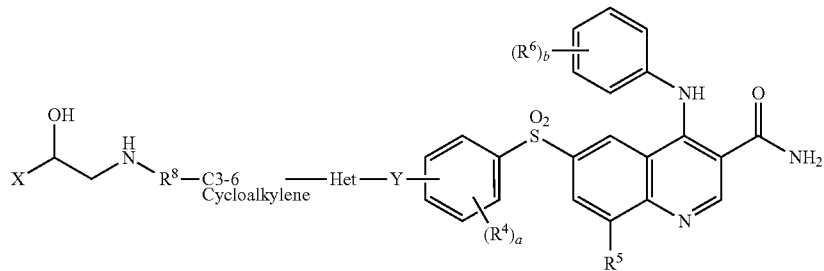

III(d)

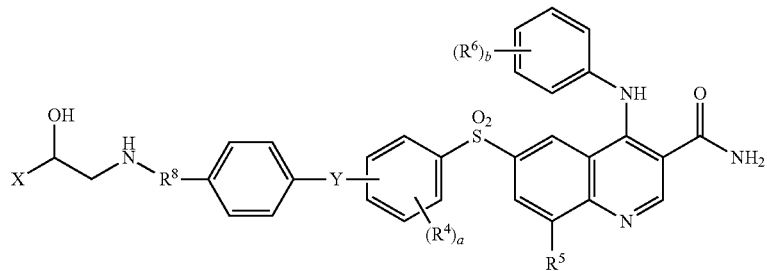

III(e)

wherein X, $R^1$, $R^2$, $R^4$, $R^5$, $R^6$, $R^8$, a, b, Het and all other variables are as defined for Formula II, above. Within the embodiments exemplified by Formula III(b), III(c), and III (d), there is another embodiment wherein Het is selected from piperidine and piperazine. Within each of these embodiments of Formula III(a), III(b), III(c), and III(d), is a further embodiment wherein $R^8$ is $C_{1-8}$alkylene.

Another embodiment comprises compounds of formula IV(a), or a pharmaceutically acceptable salt thereof:

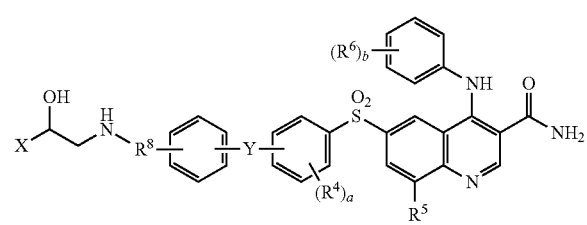

IV(a)

wherein X, $R^1$, $R^2$, $R^4$, $R^5$, $R^6$, $R^8$, Y, a, b, and all other variables are as defined for Formula II, above.

Another embodiment comprises compounds of formula IV(a), or a pharmaceutically acceptable salt thereof:

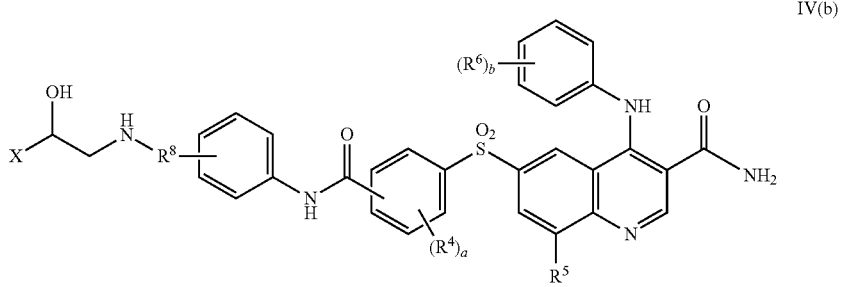

IV(b)

wherein X, $R^1$, $R^2$, $R^4$, $R^5$, $R^6$, $R^8$, a, b, and all other variables are as defined for Formula II, above.

A further embodiment comprises compounds of IV(b), or pharmaceutically acceptable salts thereof, wherein X, $R^1$, $R^2$, $R^4$, $R^5$, $R^6$, a, b, and all other variables are as defined for Formula II, above, and $R^8$ is $C_{2-8}$alkylene, $C_{2-8}$alkenylene, or $C_{2-8}$alkynylene, wherein each $R^8$ is optionally substituted with 1, 2 or 3 substituents selected from halo, oxo, and $OR^7$.

Another embodiment comprises compounds of formula IV(b), or a pharmaceutically acceptable salt thereof:

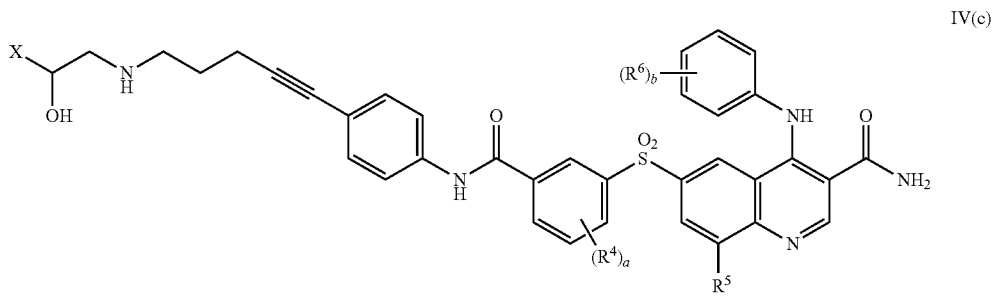

IV(c)

wherein X, $R^1$, $R^2$, $R^4$, $R^5$, $R^6$, a, b, and all other variables are as defined for Formula II, above.

Other independent embodiments comprise compounds of Formulas V(a), V(b), V(c), and V(d), or pharmaceutically acceptable salts thereof:

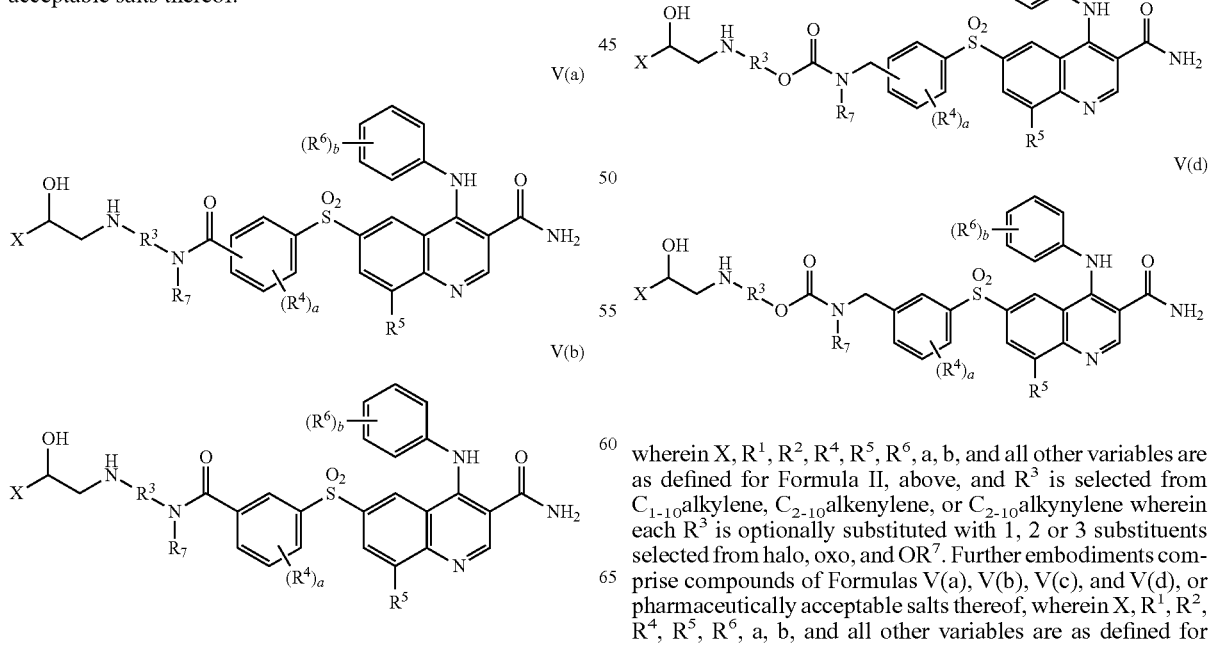

wherein X, $R^1$, $R^2$, $R^4$, $R^5$, $R^6$, a, b, and all other variables are as defined for Formula II, above, and $R^3$ is selected from $C_{1-10}$alkylene, $C_{2-10}$alkenylene, or $C_{2-10}$alkynylene wherein each $R^3$ is optionally substituted with 1, 2 or 3 substituents selected from halo, oxo, and $OR^7$. Further embodiments comprise compounds of Formulas V(a), V(b), V(c), and V(d), or pharmaceutically acceptable salts thereof, wherein X, $R^1$, $R^2$, $R^4$, $R^5$, $R^6$, a, b, and all other variables are as defined for Formula II, above, and R³ is selected from C₄₋₁₀alkylene, C₄₋₁₀alkenylene, or C₄₋₁₀alkynylene. Still further embodiments comprise compounds of Formulas V(a), V(b), V(c), and V(d), or pharmaceutically acceptable salts thereof, wherein X, R¹, R², R⁴, R⁵, R⁶, a, b, and all other variables are as defined for Formula II, above, and R³ is C₄₋₁₀alkylene.

Another embodiment comprise compounds of Formulas V(a), V(b), V(c), and V(d), or pharmaceutically acceptable salts thereof, wherein X, R¹, R², R⁴, R⁵, R⁶, a, b, and all other variables are as defined for Formula II, above, and R³ is R⁸—OR⁸, and R⁸ is in each instance independently C₁₋₁₀alkylene, C₂₋₁₀alkenylene, or C₂₋₁₀alkynylene wherein each R⁸ is optionally substituted with 1, 2 or 3 substituents selected from halo, oxo, and OR⁷; with the proviso that the total number of carbon atoms in the C₁₋₁₀alkylene, C₂₋₁₀alkenylene, or C₂₋₁₀alkynylene chains of two R⁸ groups in any definition of R³ is not greater than 12.

Another embodiment is provided by compounds of Formula VI, or a pharmaceutically acceptable salt thereof:

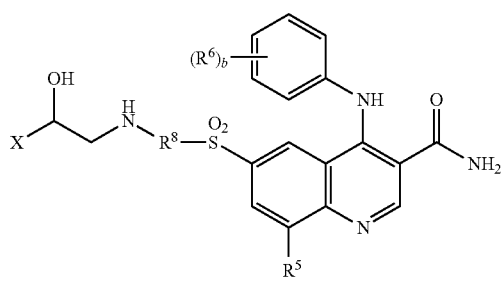

VI wherein X, R¹, R², R⁵, R⁶, R⁸, a, b, and all other variables are as defined for Formula II, above, Within each group of compounds, and the pharmaceutically acceptable salts thereof, described herein there are further embodiments. These include in each group, by themselves or in combination, one or more of the following:

a) compounds in which R³ is selected from C₄₋₁₂alkylene, C₄₋₁₂alkenylene, C₄₋₁₂alkynylene, R⁸—O—R⁸, R⁸—C₃₋₆cycloalkylene-Het, R⁸-phenylene, R⁸-phenylene-O—R⁸, R⁸-phenylene-phenylene, Het, R⁸-Het, R⁸—O-Het, R⁸-phenylene-C(O)-Het, R⁸-Het-phenylene, R⁸-phenylene-Het, and R⁸—O—R⁸-phenylene.

b) compounds wherein R⁸ in each instance is selected from C₁₋₆alkylene, C₃₋₆ alkenylene, and C₃₋₆ alkynylene;

c) compounds in which R³—Y is R⁸-phenylene-NHC(O);

d) compounds in which R³—Y is R⁸-phenylene-N(CH₃)C(O);

e) compounds in which R³—Y is R⁸—O—R⁸-phenylene-NHC(O);

f) compounds in which R³—Y is R⁸—O—R⁸-phenylene-N(CH₃)C(O);

g) compounds in which R³—Y is R⁸-phenylene-C(O)NHCH₂;

h) compounds in which R³—Y is R⁸-phenylene-C(O)N(CH₃)CH₂;

i) compounds in which R³—Y is R⁸—O—R⁸-phenylene-C(O)NHCH₂;

j) compounds in which R³—Y is R⁸—O—R⁸-phenylene-C(O)N(CH₃)CH₂;

k) compounds wherein X is selected from the group of:

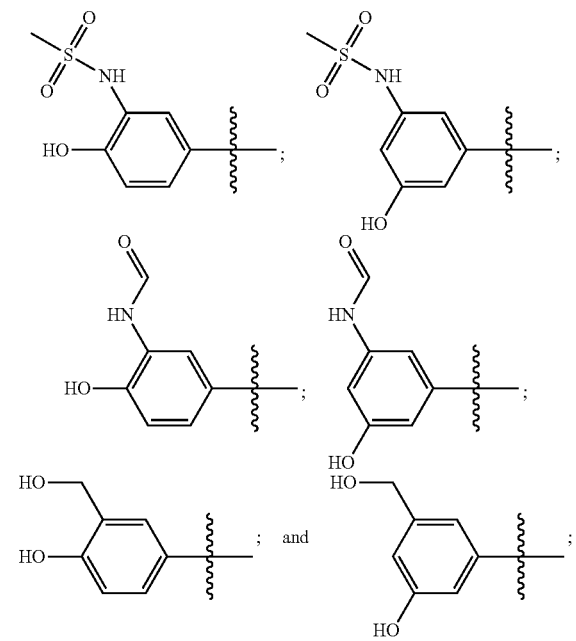

l) compounds wherein X is selected from the group of:

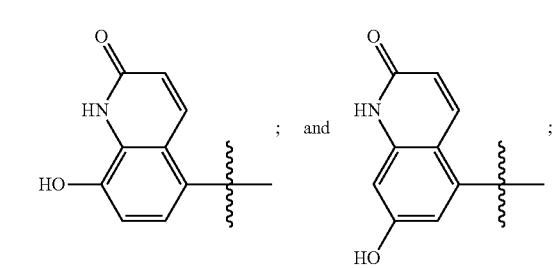 [SMILES: *c1ccc(O)c2[nH]c(=O)ccc12 ; *c1cc(O)cc2[nH]c(=O)ccc12]

m) compounds wherein X is selected from the group of:

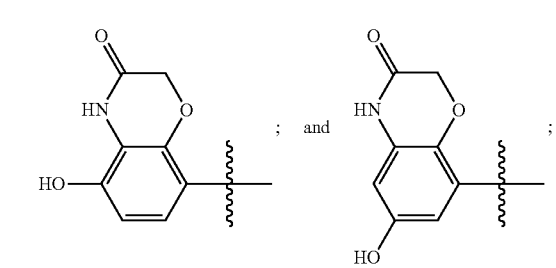 [SMILES: *c1ccc(O)c2c1OCC(=O)N2 ; *c1cc(O)cc2c1OCC(=O)N2]

n) compounds wherein X is selected from the group of:

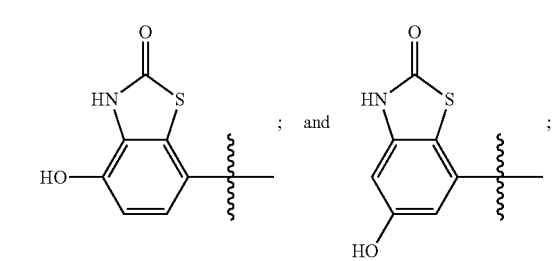 [SMILES: *c1ccc(O)c2[nH]c(=O)sc12 ; *c1cc(O)cc2[nH]c(=O)sc12]

o) compounds wherein $R^5$ is $C_1$-$C_3$ alkyl; $R^6$ is $OR^7$; $R^7$ is $C_1$-$C_3$ alkyl; and b is 1;

p) compounds wherein $R^9$ is methyl; and q) compounds wherein $R^9$ is hydrogen.

As noted above, there is a proviso that the total number of carbon atoms in the $C_{1-10}$alkylene, $C_{2-10}$alkenylene, or $C_{2-10}$alkynylene chains of two $R^8$ groups in any definition of $R^3$ is not greater than 12. For instance, when $R^3$ is —$R^8$—O—$R^8$—, if the first $R^8$ group is an ethylene (—$CH_2$—$CH_2$—) chain, the maximum number of carbon atoms in the second $R^8$ group in that $R^3$ member would be ten. It will be understood that the number of carbon atoms counted in the chain for these purposes does not count those carbon atoms in substituent groups on the chain. For instance, a 3,3-dimethylhexyl chain will be considered a chain of six carbon atoms.

In one embodiment, the compounds of the invention are defined wherein $R^1$ is $CH_2OH$, $N(H)C(O)H$, or $N(H)S(O_2)CH_3$, and $R^2$ is H. In one particular embodiment the compounds of the invention are defined wherein $R^1$ is $CH_2OH$ and $R^2$ is H.

In one embodiment, the compounds of the invention are defined wherein $R^1$ and $R^2$ together with the phenyl to which they are bound form a bicyclic, fused heterocyclic ring having 9 or 10 ring atoms wherein 1 or 2 ring atoms are selected from N, O and S, and the bicyclic fused heterocyclic ring is optionally substituted with one, two or three additional substituents independently selected from alkyl, oxo and OH. The phrase "one, two or three additional substituents" refers to one, two or three substituents in addition to the —OH indicated in Formula I as being bound to the same phenyl ring as $R^1$ and $R^2$. In one embodiment, wherein $R^1$ and $R^2$ together with the phenyl to which they are bound form a bicyclic, fused heterocyclic ring having 9 or 10 ring atoms wherein 1 or 2 ring atoms are selected from N, O and S, and the bicyclic fused heterocyclic ring is optionally substituted with one additional substituent selected from alkyl, oxo and OH. In one such embodiment, the compounds of the invention are defined wherein $R^1$ and $R^2$ together with the phenyl to which they are bound form

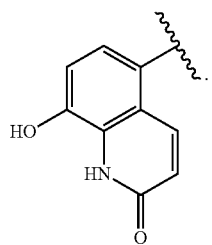 [SMILES: *c1ccc(O)c2[nH]c(=O)ccc12]

In one embodiment, the compounds of the invention are defined wherein $R^3$ is selected from $C_{4-12}$alkylene, $C_{4-12}$alkenylene, $C_{4-12}$alkynylene, $R^8$—O—$R^8$, and $R^8$—N($R^7$)—$R^8$, wherein said alkylene, alkenylene or alkynylene are each optionally substituted with 1, 2 or 3 substituents selected from halo, oxo, and $OR^7$. The alkylene, alkenylene or alkynylene groups of $R^3$ may be linear or branched. In one embodiment $R^3$ is selected from $C_{5-8}$alkylene, $C_{5-8}$alkenylene, $C_{5-8}$alkynylene, $R^8$—O—$R^8$, and $R^8$—N($R^7$)—$R^8$, wherein each $R^8$ is $C_{1-4}$alkylene, $C_{2-4}$alkenylene, or $C_{2-4}$alkynylene each alkylene, alkenylene and alkynylene optionally substituted with 1 or 2 substituents selected from halo, oxo, and $OR^7$. The alkylene, alkenylene or alkynylene groups of $R^8$ may also be linear or branched. In one embodiment $R^3$ is defined such that each alkylene, alkenylene and alkynylene and each group $R^8$ is unsubstituted. In one particular embodiment $R^3$ is unsubstituted $C_{5-8}$alkylene. In one preferred embodiment $R^3$ is unsubstituted, linear $C_5$alkylene. In one preferred embodiment $R^3$ is unsubstituted, linear $C_6$alkylene. In one preferred embodiment $R^3$ is unsubstituted, linear $C_8$alkylene. In one particular embodiment $R^3$ is unsubstituted, linear $C_5$alkynylene.

In one embodiment, the compounds of the invention are defined wherein $R^3$ is selected from $C_{3-6}$cycloalkylene, $R^8$—$C_{3-6}$cycloalkylene, $C_{3-6}$cycloalkylene-$R^8$, $R^8$—$C_{3-6}$cycloalkylene-$R^8$, $C_{6-10}$arylene, $R^8$—$C_{6-10}$arylene, $C_{6-10}$arylene-$R^8$, $R^8$—$C_{6-10}$arylene-$R^8$, $R^8$—$C_{6-10}$arylene-O—$R^8$, $R^8$—$C_{6-10}$arylene-N($R^7$)—$R^8$, $R^8$—$C_{6-10}$arylene-$C_{6-10}$arylene, Het, $R^8$-Het, Het-$R^8$, $R^8$-Het-$R^8$, $R^8$—O-Het, $R^8$—$C_{6-10}$arylene-O-Het, $R^8$—$C_{6-10}$arylene-C(O)-Het, and $R^8$—$C_{6-10}$arylene-N($R^7$)-Het. In one embodiment, $R^3$ is selected from $R^8$—$C_{6-10}$arylene, $R^8$—$C_{6-10}$arylene-$R^8$, Het, $R^8$-Het, $R^8$-Het-$R^8$, $R^8$—$C_{6-10}$arylene-O-Het, and $R^8$—$C_{6-10}$arylene-N($R^7$)-Het. In one embodiment, $R^3$ is selected from $R^8$-phenylene, $R^8$-phenylene-$R^8$, Het, $R^8$-Het, $R^8$-Het-$R^8$, $R^8$-phenylene-O-Het, and $R^8$-phenylene-N($R^7$)-Het. In one particular embodiment, $R^3$ is selected from $R^8$-phenylene, $R^8$-phenylene-$R^8$, Het, $R^8$-Het, $R^8$-Het-$R^8$, $R^8$-phenylene-O-Het, and $R^8$-phenylene-N($R^7$)-Het. In one particular embodiment, $R^3$ is selected from $R^8$-phenylene, Het, and $R^8$-Het. In one preferred embodiment, $R^3$ is selected from $R^8$-phenylene, Het, and $R^8$-Het, and $R^8$ is unsubstituted, linear or branched $C_{1-6}$alkylene, $C_{3-6}$alkenylene, or $C_{3-6}$alkynylene. In one preferred embodiment, $R^3$ is selected from $R^8$-phenylene, Het, and $R^8$-Het, and $R^8$ is unsubstituted, linear $C_{1-6}$alkylene, $C_{3-6}$alkenylene, or $C_{3-6}$alkynylene.

In one embodiment, Het is a 6-membered saturated heterocyclene wherein 1 ring atom is N, and one ring atom is selected from C, N, O and S, wherein the heterocyclene is optionally substituted once with halo, alkyl, alkoxy, oxo or OH. In one particular embodiment, Het is a 6-membered saturated heterocyclene wherein 1 ring atom is N, one ring atoms is selected from C, N, O and S, and all other ring atoms are C and wherein the heterocyclene is optionally substituted once with halo (particularly Cl), alkyl, alkoxy (particularly $OCH_3$), oxo or OH. In one particular embodiment, Het is unsubstituted heterocyclene. In one preferred embodiment, Het is unsubstituted, 6-membered saturated heterocyclene wherein 1 or 2 ring atom(s) is/are N, and all other ring atoms are C.

In those embodiments wherein $R^3$ includes a Het moiety, $R^3$ may be bound to Y through any suitable carbon or heteroatom. However, the selection of variables $R^3$ and Y should be made in view of each other in order to avoid embodiments which are clearly unstable or inoperative based upon the knowledge of those skilled in the art of organic chemistry. For example, when $R^3$ is Het and Het is a nitrogen-containing heterocyclene which is bound to Y through N, one skilled in the art will appreciate that Y is not $N(R^7)C(O)$ or $N(R^7)C(O)N(R^7)$ as such embodiments would result in a N—N bond.

In one embodiment, the compounds of the invention are defined wherein Y is C(O) or $N(R^7)C(O)$ or $C(O)N(R^7)CH_2$. In one particular embodiment Y is C(O) or $N(R^7)C(O)$. In one preferred embodiment Y is C(O). In one preferred embodiment Y is N(H)C(O). Y (and thus the group bound to phenyl through Y) may be bound at the ortho, meta or para positions of the phenyl. In one embodiment Y is bound in the meta or para position of the phenyl. In one preferred embodiment Y is bound in the para position of the phenyl, as depicted in Formula I':

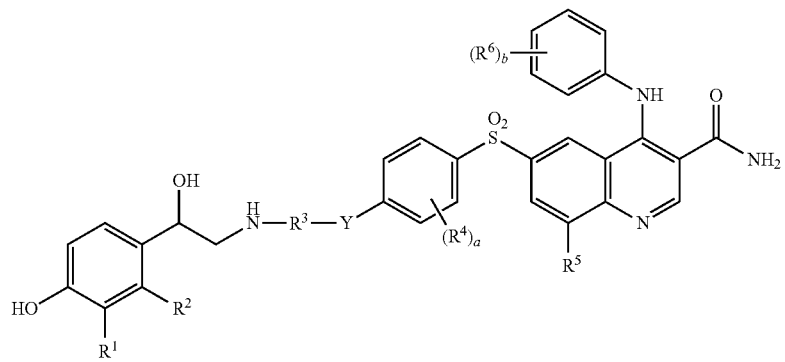

and pharmaceutically acceptable salts thereof wherein all variables are as defined herein, including particular and preferred embodiments of each variable.

In one embodiment, the compounds of the invention are defined wherein a is 0, 1 or 2, more particularly 0 or 1 and preferably 0. In those embodiments wherein a is 1, 2, 3 or 4, $R^4$ is selected from halo, alkyl, and $OR^7$. In one particular embodiment wherein a is 1, 2, 3 or 4, $R^4$ is selected from F, Cl, Br, methyl, ethyl, isopropyl, OH, $OCH_3$ and $OCH_2CH_3$.

In one embodiment, the compounds of the invention are defined wherein $R^5$ is alkyl, particularly $CH_3$.

In one embodiment, the compounds of the invention are defined wherein b is 1, 2 or 3, particularly 1 or 2. In one preferred embodiment b is 1.

In one embodiment, the compounds of the invention are defined wherein $R^6$ is selected from halo, alkyl, haloalkyl, $OR^7$, O-haloalkyl, $R^8$—$OR^7$, O—$R^8$—$OR^7$, C(O)alkyl, O—$R^8$—C(O)alkyl, $CON(R^7)_2$, $R^8$—$CON(R^7)_2$, $R^8$—N$(R^7)_2$, $N(R^7)C(O)$alkyl, $N(R^7)C(O)N(R^7)_2$, $N(R^7)SO_2$alkyl, $R^8$—$SO_2N(R^7)_2$, and CN. In one embodiment $R^6$ is selected from halo, alkyl, haloalkyl, $OR^7$, O-haloalkyl, $R^8$—$OR^7$, and CN. In one embodiment $R^6$ is selected from halo, alkyl, haloalkyl, $OR^7$, O-haloalkyl, and CN. In one particular embodiment $R^6$ is selected from F, Cl, Br, alkyl, haloalkyl, $OR^7$, O-haloalkyl, and CN. In one preferred embodiment $R^6$ is selected from F, Cl, Br, $CH_3$, $CH_2CH_3$, $CF_3$, OH, $OCH_3$, $OCH_2CH_3$, and CN. In one preferred embodiment $R^6$ is $OCH_3$.

In one embodiment, the compounds of the invention are defined wherein two $R^6$ on adjacent carbons, together with the phenyl to which they are bound form a bicyclic heterocyclic ring having 9 or 10 ring atoms wherein 1 or 2 ring atoms are selected from N, O and S and all other ring atoms are C. In one such embodiment, two $R^6$ on adjacent carbons, together with the phenyl to which they are bound form benzofuran.

In one embodiment, the compounds of the invention are defined wherein $R^7$ is H or $C_{1-4}$alkyl; more particularly H or $C_{1-3}$alkyl. In one embodiment $R^7$ is H or methyl.

Specific examples of compounds of Formula I set forth in the examples which follow. Preferred compounds of Formula I are selected from (R)-6-[[3-[[4-[5-[[2-Hydroxy-2-(8-hydroxy-2-oxo-1,2-dihydroquinolin-5-yl)ethyl]amino]pent-1-ynyl]phenyl]carbamoyl]phenyl]sulfonyl]-4-[(3-methoxyphenyl)amino]-8-methylquinoline-3-carboxamide

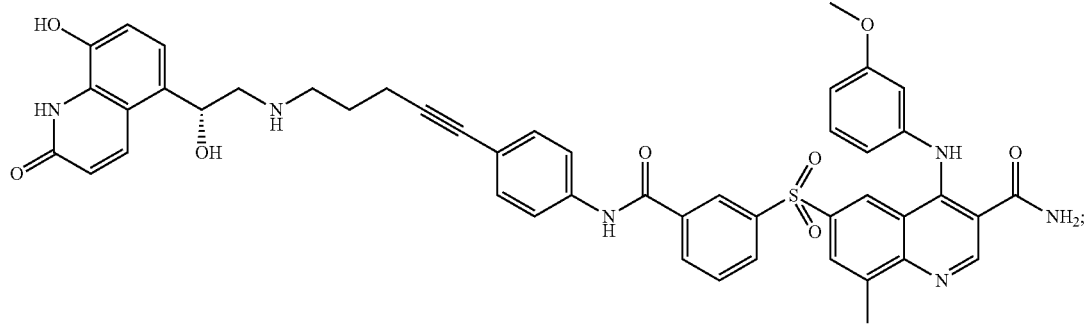 [SMILES: COc1cccc(Nc2c(C(N)=O)cnc3c(C)cc(S(=O)(=O)c4cccc(C(=O)Nc5ccc(C#CCCCNC[C@H](O)c6ccc(O)c7[nH]c(=O)ccc67)cc5)c4)cc23)c1]

(R)-6-[[3-[[6-[[2-(3-Formamido-4-hydroxyphenyl)-2-hydroxyethyl]amino]hexyl]carbamoyl]phenyl]sulfonyl]-4-[(3-methoxyphenyl)amino]-8-methylquinoline-3-carboxamide

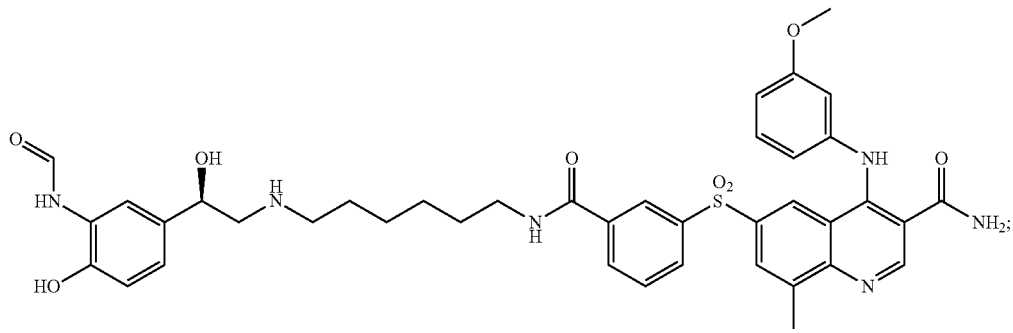 [SMILES: COc1cccc(Nc2c(C(N)=O)cnc3c(C)cc(S(=O)(=O)c4cccc(C(=O)NCCCCCCNC[C@H](O)c5ccc(O)c(NC=O)c5)c4)cc23)c1]

6-[3-[[4-[2-[[2-Hydroxy-2-(8-hydroxy-2-oxo-1,2-dihydroquinolin-5-yl)ethyl]amino]ethyl]piperazine-1-yl]carbonyl]benzenesulfonyl]-4-(3-methoxyphenylamino)-8-methylquinoline-3-carboxyamide

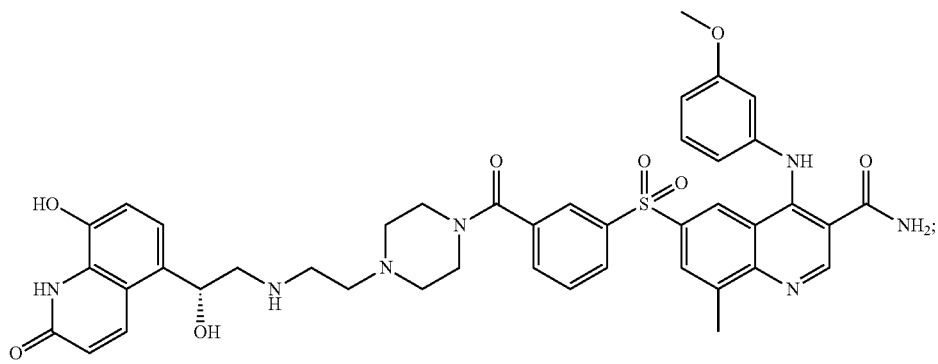 [SMILES: COc1cccc(Nc2c(C(N)=O)cnc3c(C)cc(S(=O)(=O)c4cccc(C(=O)N5CCN(CCNC[C@H](O)c6ccc(O)c7[nH]c(=O)ccc67)CC5)c4)cc23)c1]

(R)-6-[[3-[[4-[2-[[2-Hydroxy-2-(8-hydroxy-2-oxo-1,2-dihydroquinolin-5-yl)ethyl]amino]ethyl]phenyl]carbamoyl]phenyl]sulfonyl]-4-[(3-methoxyphenyl)amino]-8-methylquinoline-3-carboxamide

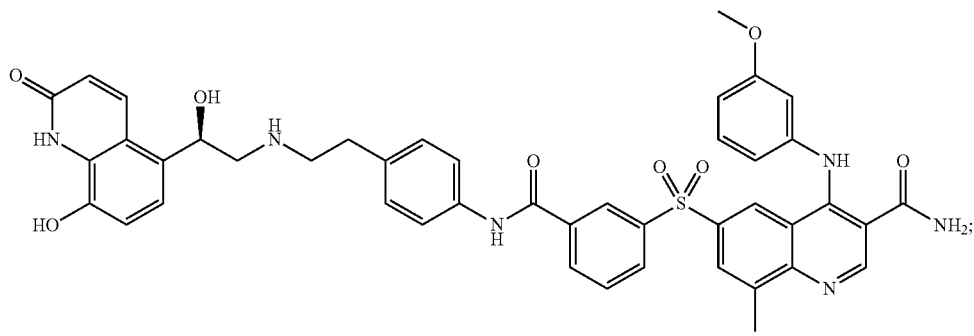 [SMILES: COc1cccc(Nc2c(C(N)=O)cnc3c(C)cc(S(=O)(=O)c4cccc(C(=O)Nc5ccc(CCNC[C@H](O)c6ccc(O)c7[nH]c(=O)ccc67)cc5)c4)cc23)c1]

and
6-[[3-[[3-[2-[[(R)-2-Hydroxy-2-(8-hydroxy-2-oxo-1,2-dihydroquinolin-5-yl)ethyl]amino]propyl]-N-methylbenzamido]methyl]phenyl]sulfonyl]-4-[(3-methoxyphenyl)amino]-8-methylquinoline-3-carboxamide

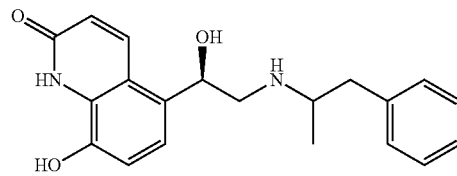
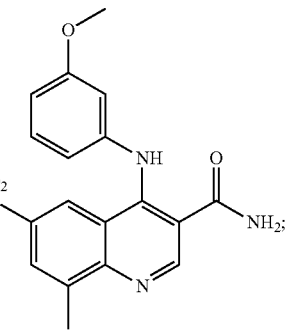

and pharmaceutically acceptable salts thereof.

The compounds of Formula I, may be in the form of a free base or a salt, particularly a pharmaceutically acceptable salt. For a review of pharmaceutically acceptable salts see Berge et al., *J. Pharma Sci.* (1977) 66:1-19.

Pharmaceutically acceptable salts formed from inorganic or organic acids include for example, hydrochloride, hydrobromide, hydroiodide, sulfate, bisulfate, nitrate, sulfamate, phosphate, hydrogen phosphate, acetate, trifluoroacetate, maleate, malate, fumarate, lactate, tartrate, citrate, formate, gluconate, succinate, pyruvate, tannate, ascorbate, palmitate, salicylate, stearate, phthalate, alginate, polyglutamate, oxalate, oxaloacetate, saccharate, benzoate, alkyl or aryl sulfonates (e.g., methanesulfonate, ethanesulfonate, benzenesulfonate, p-toluenesulfonate or naphthalenesulfonate) and isothionate; complexes formed with amino acids such as lysine, arginine, glutamic acid, glycine, serine, threonine, alanine, isoleucine, leucine and the like. The compounds of the invention may also be in the form of salts formed from elemental anions such as chlorine, bromine or iodine. For therapeutic use, salts of active ingredients of the compounds of Formula I will be pharmaceutically acceptable, i.e. they will be salts derived from a pharmaceutically acceptable acid. However, salts of acids which are not pharmaceutically acceptable may also find use, for example, in the preparation or purification of a pharmaceutically acceptable compound. Trifluoroacetate salts, for example, may find such use. All salts, whether or not derived from a pharmaceutically acceptable acid, are within the scope of the present invention. In one embodiment, the compounds of Formula I are in the form of the trifluoroacetate salt. In one embodiment, the compounds of Formula I are in the form of the hydrochloride salt.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space. "Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography. "Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York.

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species.

The term "tautomers" refers to a type of stereoisomers in which migration of a hydrogen atom results in two or more structures. The compounds of Formula I may exist in different tautomeric forms. One skilled in the art will recognize that amidines, amides, guanidines, ureas, thioureas, heterocycles and the like can exist in tautomeric forms. All possible tautomeric forms of the amidines, amides, guanidines, ureas, thioureas, heterocycles and the like of all of the embodiments of Formula I are within the scope of the instant invention. Tautomers exist in equilibrium and thus the depiction of a single tautomer in the formulas provided will be understood by those skilled in the art to refer equally to all possible tautomers.

It is to be noted that all enantiomers, diastereomers, and racemic mixtures, tautomers, polymorphs, pseudopolymorphs of compounds within the scope of Formula I and pharmaceutically acceptable salts thereof are embraced by the present invention. All mixtures of such enantiomers and diastereomers, including enantiomerically enriched mixtures and diastereomerically enriched mixtures are within the scope of the present invention. Enantionmerically enriched mixtures are mixtures of enantiomers wherein the ratio of the specified enantiomer to the alternative enantiomer is greater than 50:50. More particularly, an enantiomerically enriched mixture comprises at least about 75% of the specified enantiomer, and preferably at least about 85% of the specified enantiomer. In one embodiment, the enantiomerically enriched mixture is substantially free of the other enantiomer. Similarly, diastereomerically enriched mixtures are mixtures of diastereomers wherein the amount of the specified diastereomer is greater than the amount of each alternative diastereomer. More particularly, a diastereomerically enriched mixture comprises at least about 75% of the specified diastereomer, and preferably at least about 85% of the specified diastereomer. In one embodiment, the diastereomerically enriched mixture is substantially free of all other diastereomers.

For illustrative purposes, specific examples of enantiomers within the scope of the present invention include:

(R)-6-[[3-[[8-[[2-hydroxy-2-(8-hydroxy-2-oxo-1,2-dihydroquinolin-5-yl)ethyl]amino]octyl]carbamoyl]phenyl]sulfonyl]-4-[(3-methoxyphenyl)amino]-8-methylquinoline-3-carboxamide

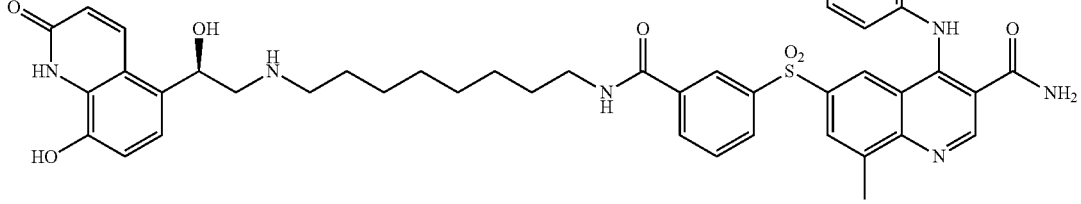

and
(S)-6-[[3-[[8-[[2-hydroxy-2-(8-hydroxy-2-o]sulfonyl xo-1,2-dihydroquinolin-5-yl)ethyl]amino]octyl]carbamoyl]phenyl]-4-[(3-methoxyphenyl)amino]-8-methylquinoline-3-carboxamide

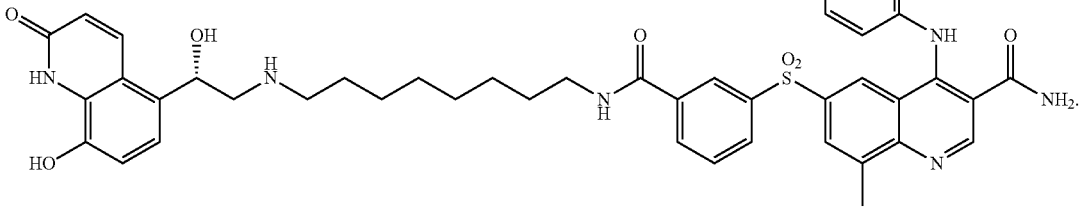

In one embodiment, the present invention provides an enantiomerically enriched mixture comprising (R)-6-[[3-[[4-[5-[[2-Hydroxy-2-(8-hydroxy-2-oxo-1,2-dihydroquinolin-5-yl)ethyl]amino]pent-1-ynyl]phenyl]carbamoyl]phenyl]sulfonyl]-4-[(3-methoxyphenyl)amino]-8-methylquinoline-3-carboxamide

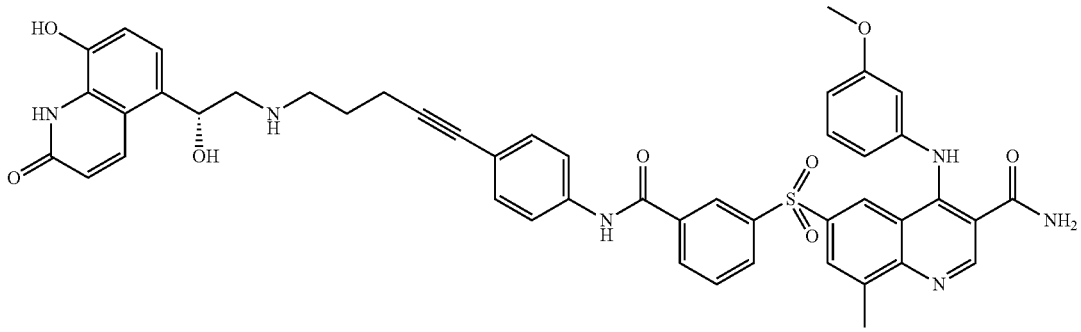 [SMILES: COc1cccc(Nc2c(C(N)=O)cnc3c(C)cc(S(=O)(=O)c4cccc(C(=O)Nc5ccc(C#CCCCNC[C@H](O)c6ccc(O)c7[nH]c(=O)ccc67)cc5)c4)cc23)c1]

or a pharmaceutically acceptable salt thereof, as the predominant isomer. A compound of Formula I and pharmaceutically acceptable salts thereof may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism also includes the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of Formula I and pharmaceutically acceptable salts thereof.

A compound of Formula I and pharmaceutically acceptable salts thereof may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of Formula I and pharmaceutically acceptable salts thereof.

The compounds of the invention may also be in the form of prodrugs. More specifically, the compounds may be present in the form of in vivo cleavable esters of the compounds of Formula I and salts of such esters. Examples of suitable esters include acetate, pivalate, tartrate, maleate, succinate and the like.

Uses

The compounds of the invention exhibit bifunctional activity as a dual pharmacophore phosphodiesterase 4 inhibitor (PDE4i), and beta agonist. Without being bound by any particular theory, it is believed that the compounds of the invention may function in vivo by reducing pulmonary inflammation (by elevation of cytosolic levels of 3',5'-cyclic adenosine monophosphate (cAMP) through inhibition of the PDE4 enzyme and potentially other pro-inflammatory mechanisms) and inducing bronchodilation (by the beta adrenergic receptor agonist moiety). There may also be further positive cooperative anti-inflammatory effects through simultaneous interaction of downstream signaling pathways via modulation of both targets with the same cell.

Local delivery of a single bi-functional compound which has dual activity as a PDE4i and beta agonist offers advantages over combination and conjunctive therapies. In particular, such bi-functional compounds may provide cooperative anti-inflammatory or bronchodilator effects though simultaneous modulation of the same pathways. Utilizing the bi-functional compounds of the present invention allows co-disposition in the same microenvironment which cannot be ensured with the individual drug compounds of combination or conjunctive therapy. In addition, such bi-functional compounds may provide reduced off-target effects leading to decreased risk of adverse events which may be associated with individual PDE4i or LABA compounds. If desired however, the dual active compounds of the present invention may nevertheless be combined with other pharmaceutical and non-pharmaceutical therapies which are conventionally employed in the treatment of respiratory diseases. Further detail regarding combination therapies utilizing the compounds of the present invention are described below.

As a consequence, the compounds of the invention are useful as medicaments, particularly for the treatment of clinical conditions for which a PDE4i or beta agonist may be indicated. Such conditions include the treatment of pulmonary inflammation or bronchoconstriction and a variety of respiratory diseases. For a review of potential therapeutic activities of PDE4i in the treatment of respiratory diseases see e.g., Kroegel & Foerster, Phosphdiesterase-4 inhibitors as a novel approach for the treatment of respiratory disease: cilomilast, *Expert Opin. Investig. Drugs* (2007) 16:109-124; Dastidar et al., Therapeutic benefit of PDE4 Inhibitors in inflammatory diseases, *Curr Opin Investig Drugs* (2007) 8:364-372; Krymskaya, et al., Phosphodiesterases regulate airway smooth muscle function in health and disease, *Curr. Top. Dev. Biol.* (2007) 79:61-74; and Spina, PDE4 inhibitors: current status, *Brit. J. Pharmacol.* 2008; 155:308-15.

In particular, the compounds of the invention are useful in methods of treating a variety of respiratory conditions such as diseases associated with reversible or irreversible airway obstruction, chronic obstructive pulmonary disease (COPD), including acute exacerbations of COPD, asthma, bronchiectasis (including bronchiectasis due to conditions other than cystic fibrosis), acute bronchitis, chronic bronchitis, post-viral cough, cystic fibrosis, emphysema, pneumonia, panbronchiolitis, and transplant-associated bronchiolitis, including lung- and bone marrow-transplant associated bronchiolitis, in a human in need thereof. The compounds of the invention may also be useful for treating ventilator-associated tracheobronchitis and/or preventing ventilator-associated pneumonia in ventilated patients. With respect to the treatment of acute exacerbations of COPD, the compounds of the invention are useful for reducing the frequency, severity or duration of acute exacerbation of COPD and/or for reducing the frequency, severity or duration of one of more symptoms of acute exacerbation of COPD.

All therapeutic uses and methods described herein are carried out by the step of administering an effective amount of a compound of the invention (a compound of Formula I or a pharmaceutically acceptable salt thereof) to a subject (typically mammal and preferably human) in need of treatment.

In one aspect, the present invention provides a method for the treatment of a condition in a mammal, such as a human, for which a PDE4i or a beta agonist is indicated.

The terms "treating" and "treatment", as used herein refers to reversing, alleviating, inhibiting the progress of, or preventing the disorder or condition or one or more symptoms of such disorder or condition.

In one embodiment the invention provides a method for the treatment of a respiratory disease. In one embodiment the invention provides a method for the treatment of a disease associated with reversible or irreversible airway obstruction in a mammal, particularly a human, in need thereof. In one particular embodiment the present invention provides a method for the treatment of COPD in a mammal, particularly a human in need thereof. In one particular embodiment the present invention provides a method for reducing the frequency, severity or duration of acute exacerbation of COPD or for the treatment of one or more symptoms of acute exacerbation of COPD in a mammal, particularly a human in need thereof. In one embodiment the invention provides a method for the treatment of asthma in a mammal, particularly a human, in need thereof. In one embodiment the invention provides a method for the treatment of bronchiectasis (including bronchiectasis due to conditions other than cystic fibrosis) in a mammal, particularly a human, in need thereof. In one embodiment the invention provides a method for the treatment of bronchitis, including acute and chronic bronchitis in a mammal, particularly a human, in need thereof. In one embodiment the invention provides a method for the treatment of post-viral cough in a mammal, particularly a human, in need thereof. In one embodiment the invention provides a method for the treatment of cystic fibrosis in a mammal, particularly a human, in need thereof. In one embodiment the invention provides a method for the treatment of emphysema in a mammal, particularly a human in need thereof. In one embodiment the invention provides a method for the treatment of pneumonia in a mammal, particularly a human in need thereof. In one embodiment the invention provides a method for the treatment of panbronchiolitis in a mammal, particularly a human in need thereof. In one embodiment the invention provides a method for the treatment of transplant-associated bronchiolitis, including lung- and bone marrow-transplant associated bronchiolitis in a mammal, particularly a human in need thereof. In one embodiment the invention provides a method for treating ventilator-associated tracheobronchitis and/or preventing ventilator-associated pneumonia in a ventilated human in need thereof. In one embodiment the invention provides a method for treating sinusitis in a mammal, particularly a human in need thereof.

There is also provided a compound of the invention for use in medical therapy, particularly for use in the treatment of condition in a mammal, such as a human, for which a PDE4i or beta agonist is indicated. In one embodiment the invention provides a method for the treatment of a respiratory disease. In one embodiment there is provided a compound of the invention for use in the treatment of a disease associated with reversible or irreversible airway obstruction in a mammal, particularly a human, in need thereof. In one particular embodiment there is provided a compound of the invention for use in the treatment of chronic obstructive pulmonary disease (COPD) in a mammal, particularly a human in need thereof. In one embodiment, there is provided a compound of the invention for use in reducing the frequency, severity or duration of acute exacerbation of COPD or for the treatment of one or more symptoms of acute exacerbation of COPD, in a mammal, particularly a human, in need thereof. In one embodiment there is provided a compound of the invention for use in the treatment of asthma in a mammal, particularly a human, in need thereof. In one embodiment there is provided a compound for use in the treatment of bronchiectasis, including bronchiectasis due to conditions other than cystic fibrosis, in a mammal, particularly a human, in need thereof. In one embodiment there is provided a compound for use in the treatment of bronchitis, including acute bronchitis and chronic bronchitis, in a mammal, particularly a human, in need thereof. In one embodiment there is provided a compound for use in the treatment of post-viral cough, in a mammal, particularly a human, in need thereof. In one embodiment there is provided a compound for use in the treatment of cystic fibrosis in a mammal, particularly a human in need thereof. In one embodiment there is provided a compound of the invention for use in the treatment of emphysema in a mammal, particularly a human, in need thereof. In one embodiment there is provided a compound of the invention for use in the treatment of pneumonia in a mammal, particularly a human, in need thereof. In one embodiment there is provided a compound of the invention for use in the treatment of panbronchiolitis or transplant-associated bronchiolitis, including lung- and bone marrow-transplant associated bronchiolitis in a mammal, particularly a human, in need thereof. In one embodiment there is provided a compound of the invention for use in the treatment of ventilator-associated tracheobronchitis or preventing ventilator-associated pneumonia in a ventilated human in need thereof. In one embodiment there is provided a compound of the invention for use in the treatment of sinusitis in a mammal, particularly a human, in need thereof.

The present invention also provides the use of a compound of the invention in the manufacture of a medicament for the treatment of a condition in a mammal, such as a human, for which a PDE4i or beta agonist is indicated. In one embodiment is provided the use of a compound of the invention in the manufacture of a medicament for the treatment of a respiratory disease. In one embodiment is provided the use of a compound of the invention in the manufacture of a medicament for the treatment of diseases associated with reversible or irreversible airway obstruction, chronic obstructive pulmonary disease (COPD), acute exacerbations of COPD, asthma, bronchiectasis (including bronchiectasis due to conditions other than cystic fibrosis), bronchitis (including acute bronchitis and chronic bronchitis), post-viral cough, cystic fibrosis, emphysema, pneumonia, panbronchiolitis, transplant-associated bronchiolitis, (including lung- and bone marrow-transplant associated bronchiolitis), ventilator-associated tracheobronchitis or preventing ventilator-associated pneumonia or treating sinusitis.

The term "effective amount", as used herein, is an amount of compound of the invention which is sufficient in the subject to which it is administered, to elicit the biological or medical response of a cell culture, tissue, system, or mammal (including human) that is being sought, for instance by a researcher or clinician. The term also includes within its scope, amounts effective to enhance normal physiological function. In one embodiment, the effective amount is the amount needed to provide a desired level of drug in the secretions and tissues of the airways and lungs, or alternatively, in the bloodstream of a subject to be treated to give an anticipated physiological response or desired biological effect when such a composition is administered by inhalation. For example, an effective amount of a compound of the invention for the treatment of a condition for which a PDE4i or beta agonist is indicated is sufficient in the subject to which it is administered to treat the particular condition. In one embodiment an effective amount is an amount of a compound of the invention which is sufficient for the treatment of COPD or cystic fibrosis in a human.

The precise effective amount of the compounds of the invention will depend on a number of factors including but not limited to the species, age and weight of the subject being treated, the precise condition requiring treatment and its severity, the bioavailability, potency, and other properties of the specific compound being administered, the nature of the formulation, the route of administration, and the delivery device, and will ultimately be at the discretion of the attendant physician or veterinarian. Further guidance with respect to appropriate dose may be found in considering conventional dosing of other PDE4i's such as cilomilast or roflumilast and other beta agonist's such as salmeterol, with due consideration also being given to any differences in potency between those compounds and the compounds of the present invention and that bi-functional nature of the compounds of the present invention.

An estimated dose administered topically to the airway surfaces of a subject (e.g., by inhalation) of a compound of the invention for treatment of a 70 kg human may be in the range of from about 20 to about 1000 micrograms. The selection of the specific dose for a patient will be determined by the attendant physician, clinician or veterinarian of ordinary skill in the art based upon a number of factors including those noted above. In one particular embodiment the dose of a compound of the invention for the treatment of a 70 kg human will be in the range of from about 50 to about 750 micrograms. In one preferred embodiment, the dose of a compound of the invention for the treatment of a 70 kg human will be in the range of from about 50 to about 750 micrograms. The foregoing suggested doses may be adjusted using conventional dose calculations if the compound is administered via a different route. Determination of an appropriate dose for administration by other routes is within the skill of those in the art in light of the foregoing description and the general knowledge in the art.

Delivery of an effective amount of a compound of the invention may entail delivery of a single dosage form or multiple unit doses which may be delivered contemporaneously or separate in time over a designated period, such as 24 hours. A dose of a compound of the invention (alone or in the form of a composition comprising the same) may be administered from one to ten times per day. Typically, a compound of the invention (alone or in the form of a composition comprising the same) will be administered four, three, two, or most preferably once per day (24 hours).

Compositions

While it is possible for a compound of the invention to be administered alone, it is preferable to present it in the form of a composition, particularly a pharmaceutical composition (formulation). Thus, in another aspect, the invention provides compositions, and particularly pharmaceutical compositions (such as an inhalable pharmaceutical composition) comprising a compound of the invention as an active ingredient, and a pharmaceutically acceptable excipient, diluent or carrier. The term "active ingredient" as employed herein refers to any compound of the invention or combination of two or more compounds of the invention in a pharmaceutical composition. The pharmaceutically acceptable excipient(s), diluent(s) or carrier(s) must be acceptable in the sense of being compatible with the other ingredients of the formulation and not deleterious to the recipient thereof. Generally, the pharmaceutically acceptable excipient(s), diluent(s) or carrier(s) employed in the pharmaceutical formulation are "non-toxic" meaning that it/they is/are deemed safe for consumption in the amount delivered in the formulation and "inert" meaning that it/they does/do not appreciable react with or result in an undesired effect on the therapeutic activity of the active ingredient(s).

Pharmaceutically acceptable excipients, diluents and carriers are conventional in the art and may be selected using conventional techniques, based upon the desired route of administration. See, REMINGTON'S, PHARMACEUTICAL SCIENCES, Lippincott Williams & Wilkins; $21^{st}$ Ed (May 1, 2005). Preferably, the pharmaceutically acceptable excipient(s), diluent(s) or carrier(s) are Generally Regarded As Safe (GRAS) according to the FDA.

Pharmaceutical compositions according to the invention include those suitable for topical administration and administration to the respiratory tract, including the nasal cavities and sinuses, oral and extrathoracic airways, and the lungs, including by use of aerosols which may be delivered by means of various types of dry powder inhalers, pressurized metered dose inhalers, softmist inhalers, nebulizers, or insufflators. The most suitable route of administration may depend upon, several factors including the patient and the condition or disorder being treated.

The formulations may be presented in unit dosage form or in bulk form as for example in the case of formulations to be metered by an inhaler and may be prepared by any of the methods well known in the art of pharmacy. Generally, the methods include the step of bringing the active ingredient into association with the carrier, diluent or excipient and optionally one or more accessory ingredients. In general the formulations are prepared by uniformly and intimately bringing into association the active ingredient with one or more liquid carriers, diluents or excipients or finely divided solid carriers, diluents or excipients, or both, and then, if necessary, shaping the product into the desired formulation.

In one preferred embodiment, the composition is an inhalable pharmaceutical composition which is suitable for inhalation and delivery to the endobronchial space. Typically, such composition is in the form of an aerosol comprising particles for delivery using a nebulizer, pressurized metered dose inhaler (MDI), softmist inhaler, or dry powder inhaler (DPI). The aerosol formulation used in the methods of the present invention may be a liquid (e.g., solution) suitable for administration by a nebulizer, softmist inhaler, or MDI, or a dry powder suitable for administration by an MDI or DPI.

Aerosols used to administer medicaments to the respiratory tract are typically polydisperse; that is they are comprised of particles of many different sizes. The particle size distribution is typically described by the Mass Median Aerodynamic Diameter (MMAD) and the Geometric Standard Deviation (GSD). For optimum drug delivery to the endobronchial space the MMAD is in the range from about 1 to about 10 μm and preferably from about 1 to about 5 μm, and the GSD is less than 3, and preferably less than about 2. Aerosols having a MMAD above 10 μm are generally too large when inhaled to reach the lungs. Aerosols with a GSD greater than about 3 are not preferred for lung delivery as they deliver a high percentage of the medicament to the oral cavity. To achieve these particle sizes in powder formulation, the particles of the active ingredient may be size reduced using conventional techniques such as micronisation or spray drying. Non-limiting examples of other processes or techniques that can be used to produce respirable particles include spray drying, precipitation, supercritical fluid, and freeze drying. The desired fraction may be separated out by air classification or sieving. In one embodiment, the particles will be crystalline. For liquid formulations, the particle size is determined by the selection of a particular model of nebulizer, softmist inhaler, or MDI.

Aerosol particle size distributions are determined using devices well known in the art. For example a multi-stage Anderson cascade impactor or other suitable method such as those specifically cited within the US Pharmacopoeia Chapter 601 as characterizing devices for aerosols emitted from metered-dose and dry powder inhalers.

Dry powder compositions for topical delivery to the lung by inhalation may be formulated without excipient or carrier and instead including only the active ingredients in a dry powder form having a suitable particle size for inhalation. Dry powder compositions may also contain a mix of the active ingredient and a suitable powder base (carrier/diluent/excipient substance) such as mono-, di- or poly-saccharides (e.g., lactose or starch). Lactose is typically the preferred excipient for dry powder formulations. When a solid excipient such as lactose is employed, generally the particle size of the excipient will be much greater than the active ingredient to aid the dispersion of the formulation in the inhaler.

Non-limiting examples of dry powder inhalers include reservoir multi-dose inhalers, pre-metered multi-dose inhalers, capsule-based inhalers and single-dose disposable inhalers. A reservoir inhaler contains a large number of doses (e.g. 60) in one container. Prior to inhalation, the patient actuates the inhaler which causes the inhaler to meter one dose of medicament from the reservoir and prepare it for inhalation. Examples of reservoir DPIs include but are not limited to the Turbohaler® by AstraZeneca and the ClickHaler® by Vectura. In a pre-metered multi-dose inhaler, each individual dose has been manufactured in a separate container, and actuation of the inhaler prior to inhalation causes a new dose of drug to be released from its container and prepared for inhalation. Examples of multidose DPI inhalers include but are not limited to Diskus® by GSK, Gyrohaler® by Vectura, and Prohaler® by Valois. During inhalation, the inspiratory flow of the patient accelerates the powder out of the device and into the oral cavity. For a capsule inhaler, the formulation is in a capsule and stored outside the inhaler. The patient puts a capsule in the inhaler, actuates the inhaler (punctures the capsule), then inhales. Examples include the Rotohaler™ (GlaxoSmithKline), Spinhaler™ (Novartis), HandiHaler™ (IB), TurboSpin™ (PH&T). With single-dose disposable inhalers, the patient actuates the inhaler to prepare it for inhalation, inhales, then disposes of the inhaler and packaging. Examples include the Twincer™ (U Groningen), One-Dose™ (GFE), and Manta Inhaler™ (Manta Devices).

Generally, dry powder inhalers utilize turbulent flow characteristics of the powder path to cause the excipient-drug aggregates to disperse, and the particles of active ingredient are deposited in the lungs. However, certain dry powder inhalers utilize a cyclone dispersion chamber to produce particles of the desired respirable size. In a cyclone dispersion chamber, the drug enters a coin shaped dispersion chamber tangentially so that the air path and drug move along the outer circular wall. As the drug formulation moves along this circular wall it bounces around and agglomerates are broken apart by impact forces. The air path spirals towards the center of the chamber exiting vertically. Particles that have small enough aerodynamic sizes can follow the air path and exit the chamber. In effect, the dispersion chamber works like a small jet mill. Depending on the specifics of the formulation, large lactose particles may be added to the formulation to aid in the dispersion through impact with the API particles.

The Twincer™ single-dose disposable inhaler appears to operate using a coin-shaped cyclone dispersion chamber referred to as an "air classifier." See, U.S. Published Patent Application No. 2006/0237010 to Rijksuniversiteit Groningen. Papers published by the University of Groningen, have stated that a 60 mg dose of pure micronized colistin sulfomethate could be effectively delivered as an inhalable dry powder utilizing this technology.

In preferred embodiments, the aerosol formulation is delivered as a dry powder using a dry powder inhaler wherein the particles emitted from the inhaler have an MMAD in the range of about 1 μm to about 5 μm and a GSD about less than 2.

Examples of suitable dry powder inhalers and dry powder dispersion devices for use in the delivery of compounds and compositions according to the present invention include but are not limited to those disclosed in U.S. Pat. No. 7,520,278; U.S. Pat. No. 7,322,354; U.S. Pat. No. 7,246,617; U.S. Pat. No. 7,231,920; U.S. Pat. No. 7,219,665; U.S. Pat. No. 7,207,330; U.S. Pat. No. 6,880,555; U.S. Pat. No. 5,522,385; U.S. Pat. No. 6,845,772; U.S. Pat. No. 6,637,431; U.S. Pat. No. 6,329,034; U.S. Pat. No. 5,458,135; U.S. Pat. No. 4,805,811; and U.S. Published Patent Application No. 2006/0237010. In one embodiment, the pharmaceutical formulation according to the invention is a dry powder for inhalation which is formulated for delivery by a Diskus®-type device. The Diskus® device comprises an elongate strip formed from a base sheet having a plurality of recesses spaced along its length and a lid sheet hermetically but peelably sealed thereto to define a plurality of containers, each container having therein an inhalable formulation containing a predetermined amount of active ingredient either alone or in admixture with one or more carriers or excipients (e.g., lactose) and/or other therapeutically active agents. Preferably, the strip is sufficiently flexible to be wound into a roll. The lid sheet and base sheet will preferably have leading end portions which are not sealed to one another and at least one of the leading end portions is constructed to be attached to a winding means. Also, preferably the hermetic seal between the base and lid sheets extends over their whole width. To prepare the dose for inhalation, the lid sheet may preferably be peeled from the base sheet in a longitudinal direction from a first end of the base sheet.

In one embodiment, the pharmaceutical formulation according to the invention is a dry powder for inhalation which is formulated for delivery using a single-dose disposable inhaler, and particularly the Twincer™ inhaler. The Twincer™ inhaler comprises a foil laminate blister with one or more recesses and a lid sheet hermetically but peelably sealed thereto to define one or more containers. Each container has therein an inhalable formulation containing a predetermined amount of active ingredient(s) either alone or in admixture with one or more carriers or excipeints (e.g., lactose). The lid sheet will preferably have a leading end portion which is constructed to project from the body of the inhaler. The patient would operate the device and thereby administer the aerosol formulation by 1) removing the outer packaging overwrap, 2) pulling the foil tab to uncover the drug in the blister and 3) inhaling the drug from the blister.

In another embodiment, the pharmaceutical formulation according to the invention is a dry powder for inhalation wherein the dry powder is formulated into microparticles as described in PCT Publication No. WO2009/015286 or WO2007/114881, both to NexBio. Such microparticles are generally formed by adding a counterion to a solution containing a compound of the invention in a solvent, adding an antisolvent to the solution; and gradually cooling the solution to a temperature below about 25° C., to form a composition containing microparticles comprising the compound. The microparticles comprising the compound may then be separated from the solution by any suitable means such as sedimentation, filtration or lyophillization. Suitable counterions, solvents and antisolvents for preparing microparticles of the compounds of the invention are described in WO2009/015286.

In another embodiment, a pharmaceutical composition according to the invention is delivered as a dry powder using a metered dose inhaler. Non-limiting examples of metered dose inhalers and devices include those disclosed in U.S. Pat. No. 5,261,538; U.S. Pat. No. 5,544,647; U.S. Pat. No. 5,622,163; U.S. Pat. No. 4,955,371; U.S. Pat. No. 3,565,070; U.S. Pat. No. 3,361,306 and U.S. Pat. No. 6,116,234 and U.S. Pat. No. 7,108,159. In a preferred embodiment, a compound of the invention is delivered as a dry powder using a metered dose inhaler wherein the emitted particles have an MMAD that is in the range of about 1 μm to about 5 μm and a GSD that is less than about 2.

Liquid aerosol formulations for delivery to the endobronchial space or lung by inhalation may for example be formulated as aqueous solutions or suspensions or as aerosols delivered from pressurized packs, such as metered dose inhalers, with the use of suitable liquefied propellants, softmist inhalers, or nebulizers. Such aerosol compositions suitable for inhalation can be either a suspension or a solution and generally contain the active ingredient(s) together with a pharmaceutically acceptable carrier or diluent (e.g., water (distilled or sterile), saline, hypertonic saline, or ethanol) and optionally one or more other therapeutically active agents.

Aerosol compositions for delivery by pressurized metered dose inhalers typically further comprise a pharmaceutically acceptable propellant. Examples of such propellants include fluorocarbon or hydrogen-containing chlorofluorocarbon or mixtures thereof, particularly hydrofluoroalkanes, e.g., dichlorodifluoromethane, trichlorofluoromethane, dichlorotetrafluoroethane, especially 1,1,1,2-tetrafluoroethane, 1,1, 1,2,3,3,3-heptafluoro-n-propane or a mixture thereof. The aerosol composition may be excipient free or may optionally contain additional formulation excipients well known in the art such as surfactants e.g., oleic acid or lecithin and cosolvents e.g., ethanol. Pressurized formulations will generally be retained in a canister (e.g., an aluminum canister) closed with a valve (e.g., a metering valve) and fitted into an actuator provided with a mouthpiece.

In another embodiment, a pharmaceutical composition according to the invention is delivered as a liquid using a metered dose inhaler. Non-limiting examples of metered dose inhalers and devices include those disclosed in U.S. Pat. Nos. 6,253,762, 6,413,497, 7,601,336, 7,481,995, 6,743,413, and 7,105,152. In a preferred embodiment, a compound of the invention is delivered as a dry powder using a metered dose inhaler wherein the emitted particles have an MMAD that is in the range of about 1 µm to about 5 µm and a GSD that is less than about 2.

In one embodiment the aerosol formulation is suitable for aerosolization by a jet nebulizer, or ultrasonic nebulizer including static and vibrating porous plate nebulizers. Liquid aerosol formulations for nebulization may be generated by solubilizing or reconstituting a solid particle formulation or may be formulated with an aqueous vehicle with the addition of agents such as acid or alkali, buffer salts, and isotonicity adjusting agents. They may be sterilized by in-process techniques such as filtration, or terminal processes such as heating in an autoclave or gamma irradiation. They may also be presented in non-sterile form.

Patients can be sensitive to the pH, osmolality, and ionic content of a nebulized solution. Therefore these parameters should be adjusted to be compatible with the active ingredient and tolerable to patients. The most preferred solution or suspension of active ingredient will contain a chloride concentration >30 mM at pH 4.5-8.0 and an osmolality of from about 800-1600 mOsm/kg. The pH of the solution can be controlled by either titration with common acids (hydrochloric acid or sulfuric acid, for example) or bases (sodium hydroxide, for example) or via the use of buffers. Commonly used buffers include citrate buffers, acetate buffers, and phosphate buffers. Buffer strengths can range from 2 mM to 50 mM.

Such formulations may be administered using commercially available nebulizers or other atomizer that can break the formulation into particles or droplets suitable for deposition in the respiratory tract. Non-limiting examples of nebulizers which may be employed for the aerosol delivery of a composition of the invention include pneumatic jet nebulizers, vented or breath enhanced jet nebulizers, or ultrasonic nebulizers including static or vibrating porous plate nebulizers.

A jet nebulizer utilizes a high velocity stream of air blasting up through a column of water to generate droplets. Particles unsuitable for inhalation impact on walls or aerodynamic baffles. A vented or breath enhanced nebulizer works in essentially the same way as a jet nebulizer except that inhaled air passes through the primary droplet generation area to increase the output rate of the nebulizer while the patient inhales.

In an ultrasonic nebulizer, vibration of a piezoelectric crystal creates surface instabilities in the drug reservoir that cause droplets to be formed. In porous plate nebulizers pressure fields generated by sonic energy force liquid through the mesh pores where it breaks into droplets by Rayleigh breakup. The sonic energy may be supplied by a vibrating horn or plate driven by a piezoelectric crystal, or by the mesh itself vibrating. Non-limiting examples of atomizers include any single or twin fluid atomizer or nozzle that produces droplets of an appropriate size. A single fluid atomizer works by forcing a liquid through one or more holes, where the jet of liquid breaks up into droplets. Twin fluid atomizers work by either forcing both a gas and liquid through one or more holes, or by impinging a jet of liquid against another jet of either liquid or gas. The choice of nebulizer which aerosolizes the aerosol formulation is important in the administration of the active ingredient(s). Different nebulizers have differing efficiencies based their design and operation principle and are sensitive to the physical and chemical properties of the formulation. For example, two formulations with different surface tensions may have different particle size distributions. Additionally, formulation properties such as pH, osmolality, and permeant ion content can affect tolerability of the medication, so preferred embodiments conform to certain ranges of these properties. In a preferred embodiment, the formulation for nebulization is delivered to the endobronchial space as an aerosol having an MMAD between about 1 μm and about 5 μm and a GSD less than 2 using an appropriate nebulizer. To be optimally effective and to avoid upper respiratory and systemic side effects, the aerosol should not have a MMAD greater than about 5 μm and should not have a GSD greater than about 2. If an aerosol has an MMAD larger than about 5 μm or a GSD greater than about 2 a large percentage of the dose may be deposited in the upper airways decreasing the amount of drug delivered to the site of inflammation and bronchoconstriction in the lower respiratory tract. If the MMAD of the aerosol is smaller than about 1 μm then a large percentage of the particles may remain suspended in the inhaled air and may then be exhaled during expiration.

The compounds of the invention may also be administered by transbronchoscopic lavage.

Compositions designed for nasal administration include aerosols, solutions, suspensions, sprays, mists and drops. Aerosolable formulations for nasal administration may be formulated in much the same ways as aerosolable formulations for inhalation with the condition that particles of non-respirable size will be preferred in formulations for nasal administration. Typically, particles of about 5 microns in size, up to the size of visible droplets may be employed. Thus, for nasal administration, a particle size in the range of 10-500 μm may be used to ensure retention in the nasal cavity.

In another aspect, the invention provides a method for treating a respiratory disease in a human in need thereof, comprising administering to the human a pharmaceutical composition comprising a compound of the invention, wherein the compound is administered in an effective amount. In one preferred embodiment, the method comprises administering the pharmaceutical composition as an inhalable composition comprising from about 20 to about 1000 micrograms of a compound of the invention.

In another aspect, the invention provides a method of treating any one of: a disease associated with reversible or irreversible airway obstruction, chronic obstructive pulmonary disease (COPD), asthma, bronchiectasis (including bronchiectasis due to conditions other than cystic fibrosis), acute bronchitis, chronic bronchitis, post-viral cough, cystic fibrosis, emphysema, pneumonia, panbronchiolitis, transplant-associate bronchiolitis, and ventilator-associated tracheobronchitis or preventing ventilator-associated pneumonia, or treating sinusitis in a human in need thereof, comprising administering to the human a pharmaceutical composition comprising a compound of the invention, wherein the compound is administered in an effective amount. In one preferred embodiment, the method comprises administering the pharmaceutical composition as an inhalable composition comprising from about 20 to about 1000 micrograms of a compound of the invention.

Preferred unit dosage formulations for the compounds of the invention are those containing an effective amount of the active ingredient or an appropriate fraction thereof.

It should be understood that in addition to the ingredients particularly mentioned above, the formulations of this invention may include other agents conventional in the art having regard to the type of formulation in question.

The compositions of the present invention may be formulated for immediate, controlled or sustained release as desired for the particular condition being treated and the desired route of administration. Because the free base of a compound is generally less soluble in aqueous solutions than the salt, compositions comprising a free base of a compound of Formula I may be employed to provide more sustained release of active agent delivered by inhalation to the lungs. An active agent present in the lungs in particulate form which has not dissolved into solution is not available to induce a physiological response, but serves as a depot of bioavailable drug which gradually dissolves into solution. As another example, a formulation may employ both a free base and salt form of a compound of the invention to provide both immediate release and sustained release of the active ingredient for dissolution into the mucus secretions of, for example, the nose.

Combinations

The compounds of the invention may be formulated and/or used in combination with other therapeutically active agents. Examples of other therapeutically active agents which may be formulated or used in combination with the compounds of the invention include but are not limited to anti-inflammatory agents, anticholinergic agents, peroxisome proliferator-activated receptor (PPAR) gamma agonists, PPAR delta agonists, epithelial sodium channel blockers (ENaC blockers), kinase inhibitors (e.g. p38 MAPK, PI3K, JNK, ERK, IKK2), anti-infective agents, and antihistamines.

The present invention thus provides, as another aspect, a composition comprising an effective amount of a compound of the invention and one or more other therapeutically active agents selected from anti-inflammatory agents, anticholinergic agents, P2Y2 receptor agonists, PPAR gamma agonists, PPAR delta agonists, ENaC blockers, kinase inhibitors (e.g. p38 MAPK, PI3K, JNK, ERK, IKK2), antiinfective agents, and antihistamines. Use of the compounds of the invention in combination with one or more other therapeutically active agents may lower the dose of the compound of the invention that is required to treat the respiratory disease, thereby reducing the potential for undesired side-effects attributable to systemically absorbed beta agonists.

Suitable anti-inflammatory agents for use in combination with the compounds of the invention include corticosteroids and non-steroidal anti-inflammatory drugs (NSAIDs), particularly phosphodiesterase (PDE) inhibitors. Examples of corticosteroids for use in the present invention include oral or inhaled corticosteroids or prodrugs thereof. Specific examples include but are not limited to ciclesonide, desisobutyryl-ciclesonide, budesonide, flunisolide, mometasone and esters thereof (e.g., mometasone furoate), fluticasone propionate, fluticasone furoate, beclomethasone, methyl prednisolone, prednisolone, dexamethasone, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, beclomethasone esters (e.g., the 17-propionate ester or the 17,21-dipropionate ester, fluoromethyl ester, triamcinolone acetonide, rofleponide, or any combination or subset thereof. Preferred corticosteroids for formulation or use in combination with the compounds of the invention are selected from ciclesonide, desisobutyryl-ciclesonide, budesonide, mometasone, fluticasone propionate, and fluticasone furoate, or any combination or subset thereof.

NSAIDs for use in the present invention include but are not limited to sodium cromoglycate, nedocromil sodium, phosphodiesterase (PDE) inhibitors (e.g., theophylline, aminophylline, PDE4 inhibitors, mixed PDE3/PDE4 inhibitors or mixed PDE4/PDE7 inhibitors), leukotriene receptor antagonists, inhibitors of leukotriene synthesis (e.g., 5 LO and FLAP inhibitors), nitric oxide synthase (iNOS) inhibitors, protease inhibitors (e.g., tryptase inhibitors, neutrophil elastase inhibitors, and metalloprotease inhibitors) β2-integrin antagonists and adenosine receptor agonists or antagonists (e.g., adenosine 2a agonists), cytokine antagonists (e.g., chemokine antagonists) or inhibitors of cytokine synthesis (e.g., prostaglandin D2 or CRTh2 receptor antagonists).

The PDE4 inhibitor, mixed PDE3/PDE4 inhibitor or mixed PDE4/PDE7 inhibitor may be any compound that is known to inhibit the PDE4 enzyme or which is discovered to act as a PDE4 inhibitor, and which are selective PDE4 inhibitors (i.e., compounds which do not appreciably inhibit other members of the PDE family). Examples of specific PDE4 inhibitors for formulation and use in combination with the compounds of the present invention include but are not limited to roflumilast, pumafentrine, arofylline, cilomilast, tofimilast, oglemilast, tolafentrine, piclamilast, ibudilast, apremilast, 2-[4-[6,7-diethoxy-2,3-bis(hydroxymethyl)-1-naphthalenyl]-2-pyridinyl]-4-(3-pyridinyl)-1(2H)-phthalazinone (T2585), N-(3,5-dichloro-4-pyridinyl)-1-[(4-fluorophenyl)methyl]-5-hydroxy-α-oxo-1H-indole-3-acetamide (AWD-12-281), 4-[(2R)-2-[3-(cyclopentyloxy)-4-methoxyphenyl]-2-phenylethyl]pyridine (CDP-840), 2-[4-[[[[2-(1,3-benzodioxol-5-yloxy)-3-pyridinyl]carbonyl]amino]methyl]-3-fluorophenoxy]-(2R)-propanoic acid (CP-671305), N-(4,6-dimethyl-2-pyrimidinyl)-4-[4,5,6,7-tetrahydro-2-(4-methoxy-3-methylphenyl)-5-(4-methyl-1-piperazinyl)-1H-indol-1-yl] benzenesulfonamide, (2E)-2-butenedioate (YM-393059), 9-[(2-fluorophenyl)methyl]-N-methyl-2-(trifluoromethyl)-9H-purin-6-amine (NCS-613), N-(2,5-dichloro-3-pyridinyl)-8-methoxy-5-quinolinecarboxamide (D-4418), N-[(3R)-9-amino-3,4,6,7-tetrahydro-4-oxo-1-phenylpyrrolo[3,2,1-][1,4]benzodiazepin-3-yl]-3H-purin-6-amine (PD-168787), 3-[[3-(cyclopentyloxy)-4-methoxyphenyl]methyl]-N-ethyl-8-(1-methylethyl)-3H-purin-6-amine hydrochloride (V-11294A), N-(3,5-dichloro-1-oxido-4-pyridinyl)-8-methoxy-2-(trifluoromethyl)-5-quinolinecarboxamide (Sch351591), 5-[3-(cyclopentyloxy)-4-methoxyphenyl]-3-[(3-methylphenyl)methyl]-(3S,5S)-2-piperidinone (HT-0712), 5-[2-[(1R,4R)-4-amino-1-[3-(cyclopentyloxy)-4-methoxyphenyl]cyclohexyl]ethynyl]-pyrimidine-2-amine, 6-[3-(dimethylcarbamoyl) phenylsulfonyl]-4-(3-methoxyphenylamino)-8-methylquinoline-3-carboxamide (GSK-256066), cis-[4-cyano-4-(3-cyclopropylmethoxy-4-difluoromethoxyphenyl) cyclohexan-1-ol], and 4-[6,7-diethoxy-2,3-bis(hydroxymethyl)-1-naphthalenyl]-1-(2-methoxyethyl)-2 (1H)-pyridinone (T-440), and any combination or subset thereof.

Leukotriene antagonists and inhibitors of leukotriene synthesis include zafirlukast, montelukast sodium, zileuton, and pranlukast.

Anticholinergic agents for formulation or use in combination with the compounds of the invention include but are not limited to muscarinic receptor antagonists, particularly including pan antagonists and antagonists of the $M_3$ receptors. Exemplary compounds include the alkaloids of the belladonna plants, such as atropine, scopolamine, homatropine, hyoscyamine, and the various forms including salts thereof (e.g., anhydrous atropine, atropine sulfate, atropine oxide or HCl, methylatropine nitrate, homatropine hydrobromide, homatropine methyl bromide, hyoscyamine hydrobromide, hyoscyamine sulfate, scopolamine hydrobromide, scopolamine methyl bromide), or any combination or subset thereof.

Additional anticholinergics for formulation and use in combination with the methantheline, propantheline bromide, anisotropine methyl bromide or Valpin 50, aclidinium bromide, glycopyrrolate (Robinul), isopropamide iodide, mepenzolate bromide, tridihexethyl chloride, hexocyclium methylsulfate, cyclopentolate HCl, tropicamide, trihexyphenidyl CCl, pirenzepine, telenzepine, and methoctramine, or any combination or subset thereof.

Preferred anticholinergics for formulation and use in combination with the compounds of the invention include ipratropium (bromide), oxitropium (bromide) and tiotropium (bromide), or any combination or subset thereof.

Examples of ENaC receptor blockers for formulation and use in combination with the compounds of the invention include but are not limited to amiloride and derivatives thereof such as those compounds described in U.S. Pat. No. 6,858,615, and PCT Publication Nos. WO2003/070182, WO2004/073629, WO2005/018644, WO2006/022935, WO2007/018640, and WO2007/146869, all to Parion Sciences, Inc.

Examples of kinase inhibitors include inhibitors of NFkB, PI3K (phosphatidylinositol 3-kinase) (CAL-263 (oral), Trial trove and Calistoga web site), p38-MAP kinase (SB-681323 (oral); Singh et al., *J Clin Pharmacol.* 2010 January; 50(1): 94-100).

Antiinfective agents for formulation and use in combination with the compounds of the invention include antivirals and antibiotics. Examples of suitable antivirals include Tamiflu® and Relenza®. Examples of suitable antibiotics include but are not limited to aztreonam (arginine or lysine), fosfomycin, and aminoglycosides such as tobramycin, or any combination or subset thereof.

Antihistamines (i.e., H1-receptor antagonists) for formulation and use in combination with the compounds of the invention include but are not limited to:

ethanolamines such as diphenhydramine HCl, carbinoxamine maleate, doxylamine, clemastine fumarate, and dimenhydrinate;

ethylenediamines such as pyrilamine maleate (metpyramine), tripelennamine HCl, tripelennamine citrate, and antazoline;

alkylamines such as pheniramine, chlorpheniramine, bromopheniramine, dexchlorpheniramine, triprolidine and acrivastine;

pyridines such as methapyrilene, piperazines such as hydroxyzine HCl, hydroxyzine pamoate, cyclizine HCl, cyclizine lactate, meclizine HCl and cetirizine HCl;

piperidines such as astemisole, levocabastine HCl, loratadine, descarboethoxy loratadine, terfenadine, and fexofenadine HCl;

tri- and tetracyclics such as promethazine, chlorpromethazine trimeprazine and azatadine; and azelastine HCl, or any combination or subset thereof.

In the above-described methods of treatment and uses, a compound of the invention may be employed alone, or in combination with one or more other therapeutically active agents. Typically, any therapeutically active agent that has a therapeutic effect in the disease or condition being treated with the compound of the invention may be utilized in combination with the compounds of the invention, provided that the particular therapeutically active agent is compatible with therapy employing a compound of the invention. Typical therapeutically active agents which are suitable for use in combination with the compounds of the invention include agents described above.

In one preferred embodiment, the compounds of the invention are used in combination with one or more anti-inflammatory agents, particularly PDE4i or an inhaled corticosteroid. In one preferred embodiment, the compounds of the invention are used in combination with one or more anticholinergics, particularly muscarinic (M3) receptor antagonists.

In another aspect, the invention provides methods for treatment and uses as described above, which comprise administering an effective amount of a compound of the invention and at least one other therapeutically active agent. The compounds of the invention and at least one additional therapeutically active agent may be employed in combination concomitantly or sequentially in any therapeutically appropriate combination. The administration of a compound of the invention with one or more other therapeutically active agents may be by administration concomitantly in 1) a unitary pharmaceutical composition, such as the compositions described above, or 2) separate pharmaceutical compositions each including one or more of the component active ingredients. The components of the combination may be administered separately in a sequential manner wherein the compound of the invention is administered first and the other therapeutically active agent is administered second or vice versa.

When a compound of the invention is used in combination with another therapeutically active agent, the dose of each compound may differ from that when the compound of the invention is used alone. Appropriate doses will be readily determined by one of ordinary skill in the art. The appropriate dose of the compound of the invention, the other therapeutically active agent(s) and the relative timings of administration will be selected in order to achieve the desired combined therapeutic effect, and are within the expertise and discretion of the attendant physician, clinician or veterinarian.

Synthetic Processes

The present invention also provides processes for preparing the compounds of the invention and to the synthetic intermediates useful in such processes, as described in detail below.

Certain abbreviations and acronyms are used in describing the synthetic processes and experimental details. Although most of these would be understood by one skilled in the art, the following table contains a list of many of these abbreviations and acronyms.

| Abbreviation | Meaning |
| --- | --- |
| AIBN | azobisisobutyronitrile |
| Bn | benzyl |
| Boc | tert-butoxycarbonyl |
| (Boc)$_2$O | di-tert-butyldicarbonate |
| BOP | benzotriazole-1-yl-oxy-tris-(dimethylamino)-phosphonium hexafluorophosphate |
| Cbz | Carbobenzyloxy |
| DCC | N,N'-dicyclohexylcarbodiimide |

| Abbreviation | Meaning |
|---|---|
| DCE | dichloroethane |
| DCM | dichloromethane |
| DIEA | N,N-diisopropylethylamine |
| DME | dimethoxyethane |
| DMF | dimethylformamide |
| DMSO | dimethylsulfoxide |
| Et | ethyl |
| EtOAc | ethyl acetate |
| EtOH | ethanol |
| $Et_3N$ and TEA | triethylamine |
| ESI | electrospray ionization |
| g | gram(s) |
| h | hour(s) |
| $H_2$ | hydrogen gas |
| HATU | 2-(1H-7-Azabenzotriazol-1-yl)-1,1,3,3-tetramethyl uronium hexafluorophosphate |
| HPLC | High performance liquid chromatography |
| IBX | 2-iodobenzoic acid |
| iPrOH | Isopropyl alcohol |
| LAH | lithium aluminum hydride |
| M | Molar |
| mg | milligram(s) |
| Me | methyl |
| MeOH | methanol |
| m/z or m/e | mass to charge ratio |
| $MH^+$ | mass plus 1 |
| $MH^-$ | mass minus 1 |
| MIC | minimal inhibitory concentration |
| min | minute(s) |
| ml | milliliter(s) |
| mmol | millimole(s) |
| MS or ms | mass spectrum |
| MsCl | methanesulfonyl chloride, mesyl chloride |
| Ms | methanesulfonate; mesylate |
| N | Normal |
| $NaBH(OAc)_3$ | sodium triacetoxy borohydride |
| $NaCNBH_3$ | sodium cyanoborohydride |
| $NaN_3$ | sodium azide |
| NMP | N-methyl-2-piperidinone |
| PDC | Pyridinium dichromate |
| $Pd(OH)_2/C$ | Palladium hydroxide on carbon |
| Ph | phenyl |
| PMP | 1,2,2,6,6-pentamethylpiperidine |
| $PPh_3$ | triphenylphosphine |
| $PtO_2$ | Platinum oxide |
| Py | Pyridyl or pyridine |
| rt or r.t. | room temperature (aka ambient temperature) |
| t-Bu | tert-butyl |
| TBAF | tetrabutylammoniumfluoride |
| TBS | tert-butyldimethylsilyl |
| TBSCl | tert-butyldimethylsilyl chloride |
| TFA | trifluoroacetic acid |
| THF | tetrahydrofuran |
| TLC or tlc | thin layer chromatography |
| δ | parts per million down field from tetramethylsilane |

In the following synthetic processes, it may be desirable for the preparation of certain compounds of the invention to install protecting groups on reactive sites of the intermediate. One skilled in the art will readily be able to determine the desirability of using protecting groups, suitable protecting groups to employ based on the compounds and reaction conditions and methods for the installation and removal of such protecting groups. Suitable protecting groups include TBS, Bn, and Boc. Conventional techniques for installing and removing such protecting groups may be employed in the instant reaction as well.

A general procedure to prepare compounds of the invention is shown in Scheme 1 below.

Scheme 1

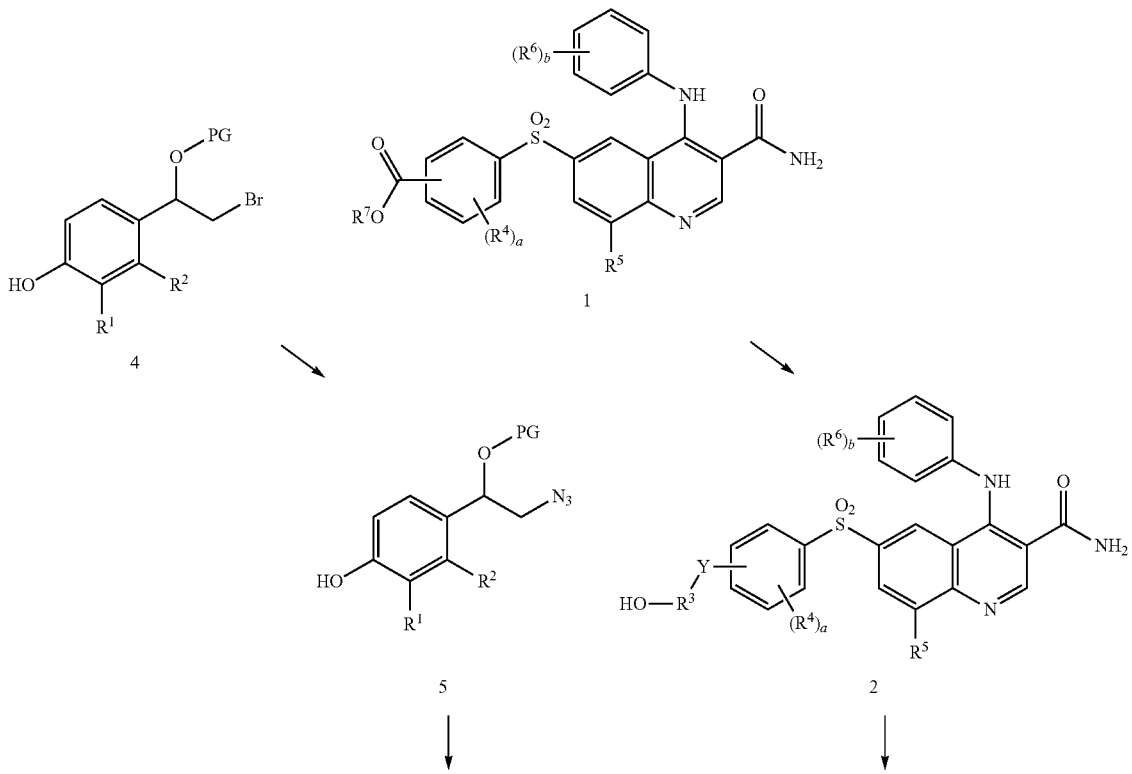

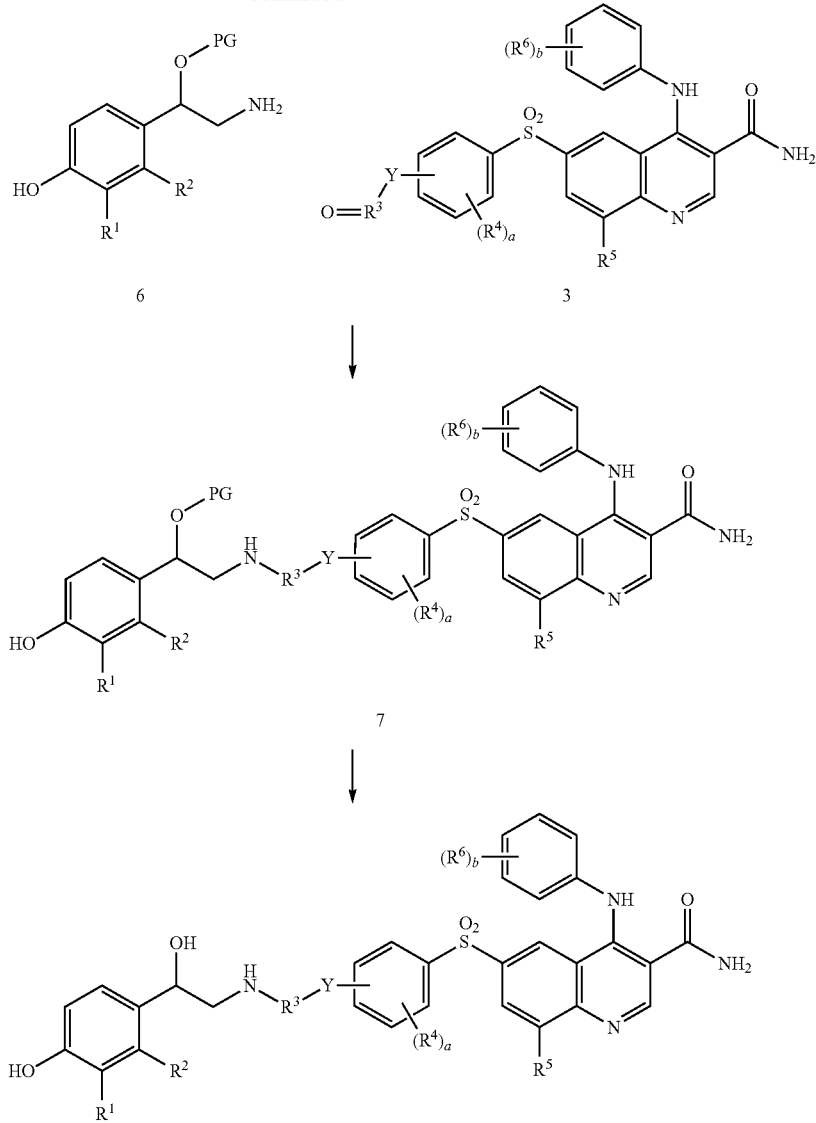

wherein:
R[7] on compound 1 is H
Y is C(O), OC(O), or N(R[7])C(O);
PG is a suitable protecting group, such as H or TBS; and all other variables are as defined above.

Generally, one process for preparing compounds of the invention comprises the steps of:
a) reductive alkylation of a Compound 3 or a salt thereof with a Compound 6 or a salt thereof to prepare a Compound 7 or a salt thereof; and
b) optionally deprotecting the Compound 7 or a salt thereof, to prepare a compound of Formula I or a salt thereof.

Coupling of compound 1 (wherein R[7] is H) with an amine under standard conditions, such as for example, HATU couplings, mixed anhydrides, DCC couplings, and the like, gives the amide Compound 2. Compound 1 is known in the literature and the amine is either commercially available or synthesized by standard means including those described above. Compound 2 is oxidized under standard conditions (Dess-Martin, PDC, Swern) to give the corresponding carbonyl compound 3.

Compound 4, which is known in the literature, is converted to compound 5, by treatment with NaN$_3$ in an appropriate solvent, such as DMF at an elevated temperature, between about 50 to about 120° C. Compound 5 may be reduced to the corresponding amine compound 6 under standard hydrogenation conditions, such as Pd on carbon at atmospheric pressure for between 1 and 24 h.

The amine compound 6 is coupled with compound 3 under reductive alkylation conditions, such as NaCNBH$_3$ or NaBH(OAc)$_3$ in an alcoholic solvent to give the corresponding compound 7. Compound 7 is converted to the compounds of the invention by removal of any protecting group. A t-butyldimethylsilyl protecting group was often used and in those cases, deprotection was accomplished using conventional techniques, such as deprotection with TBAF.

As will be readily appreciated by those skilled in the art, the foregoing process may also be carried out using salt forms of the intermediate Compounds 1-7 or alternatively, a compound of formula I may be prepared and then converted to the desired salt form using conventional salt formation techniques.

If a protected carbonyl is available to form R³, the compound may be prepared as shown in Scheme 2.

Scheme 2

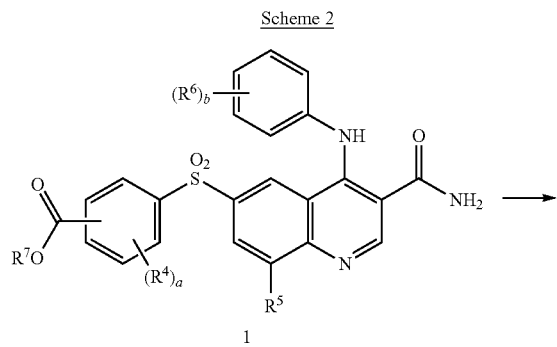

1

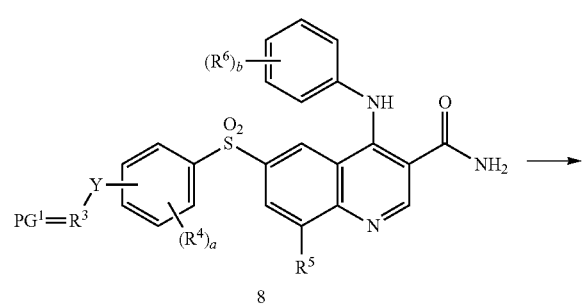

8

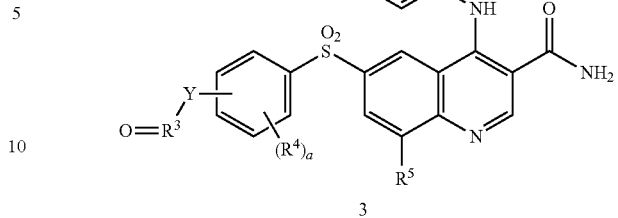

3 wherein:
R⁷ on compound 1 is H;
Y is C(O), OC(O), or N(R⁷)C(O);
PG¹ is a suitable carbonyl protecting group, such as dioxolane, acetal or ketal; and all other variables are as defined above.

According to Scheme 2, coupling of compound 1 (wherein R⁷ is H) with an amine under standard conditions, such as HATU couplings, mixed anhydrides, DCC couplings, and the like, gives the corresponding amide compound 8. Deprotection of compound 8 gives the corresponding carbonyl compound 3. Compound 8 may be deprotected using conventional deprotection techniques, dependent on the protecting group used.

In another embodiment, compounds of the invention may be prepared by displacement of a leaving group as shown in Scheme 3.

Scheme 3

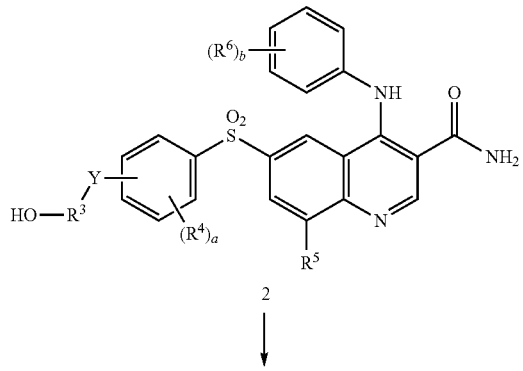

2

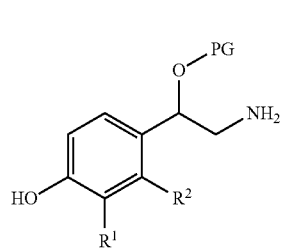

6

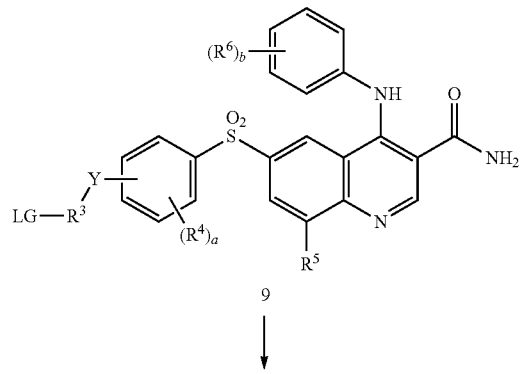

9

-continued

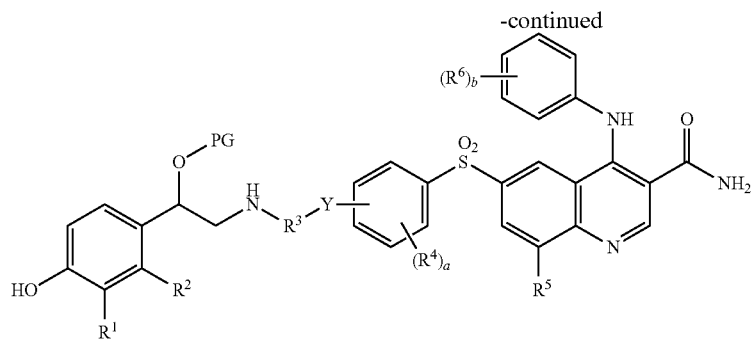

7 wherein:
PG is a suitable protecting group, such as H or TBS;
LG is a suitable leaving group such as Br, Cl, I, O-Ms, O-triflate;
and all other variables are as defined above.

Generally, this process for preparing compounds of the invention comprises the steps of:
a) coupling a compound 9 or a salt thereof with a compound 6 or a salt thereof to prepare a compound 7 or a salt thereof; and
b) optionally deprotecting the Compound 7 or a salt thereof, to prepare a compound of Formula I or a salt thereof.

More specifically, according to this embodiment, the alcohol in compound 2 may be converted to a suitable leaving group under standard conditions to give compound 9. For example, conversion of the alcohol of compound 2 to a mesylate may occur through treatment of compound 2 with MsCl and an appropriate base, such as TEA or pyridine in an appropriate solvent such as $CH_2Cl_2$ at ambient temperature. Alternatively, conversion of the alcohol of compound 2 to a bromide may occur under standard conditions such as $CBr_4$ and $PPh_3$. Compound 9 is then coupled with compound 6 at elevated temperatures, such as about 50 to about 150 C, in an appropriate solvent such as DMSO or DMF with an appropriate base such as $K_2CO_3$, DIEA or PMP, to give compound 7. Compound 7 may then be deprotected to provide compounds of Formula I as described above in Scheme 1.

In another embodiment, compounds of formula I wherein Y is $C(O)N(R^7)CH_2$, may be prepared from alternate intermediate compounds 2' and 3' as shown in Scheme 4.

Scheme 4

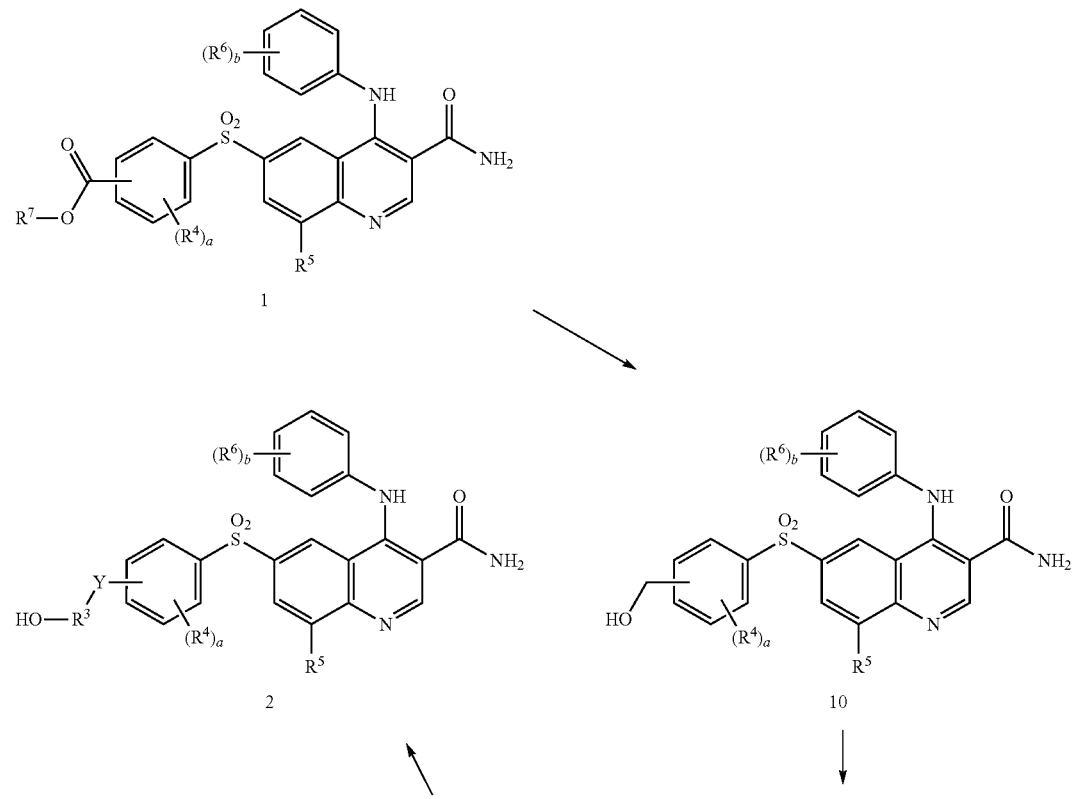

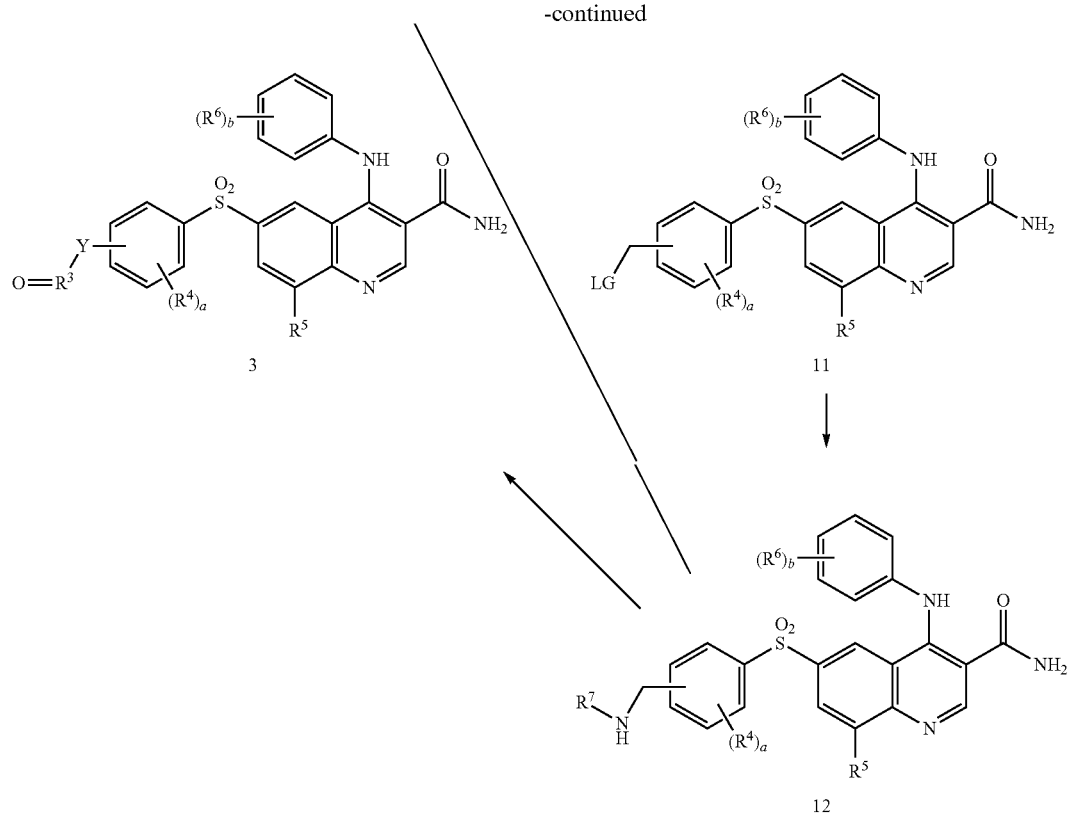

wherein:
R⁷ on compound 1 is alkyl and R⁷ on compound 12 is H or alkyl;
Y is C(O)N(R⁷)CH₂;
LG is a suitable leaving group such as Br, Cl, I, O-Ms, O-triflate,
and all other variables are as defined above.

More specifically, according to this embodiment, the ester in Compound 1 may be converted to an alcohol 10. Conversion of the alcohol to a suitable leaving group under standard conditions to give compound 11. For example, conversion of the alcohol of compound 10 to a mesylate may occur through treatment of compound 10 with MsCl and pyridine in an appropriate solvent such as CH₂Cl₂ at ambient temperature. Alternatively, conversion of the alcohol of compound 10 to a bromide may occur under standard conditions such as CBr₄ and PPh₃. Compound 11 may than be reacted with an amine, R⁷NH₂, where R⁷ is H or alkyl, to give compound 12. Alternatively, compound 11 may be reacted with azide at elevated temperatures, such as about 50 to about 150 C, in an appropriate solvent such as DMSO or DMF, and subsequently reduced with H₂ and an appropriate catalyst such as Pd/C in an appropriate alcohol solvent to give compound 12, where R⁷ is H. Compound 12 may then be reacted with an appropriate acid or reactive acid species to provide compound 2 in the manner as described above in Scheme 1 for the conversion of compound 1 to compound 2.

In another embodiment, intermediate compounds 7 may be prepared in an inverse fashion by displacement of a halide on the latent β-agonist moiety with an amine as shown in Scheme 5.

Scheme 5

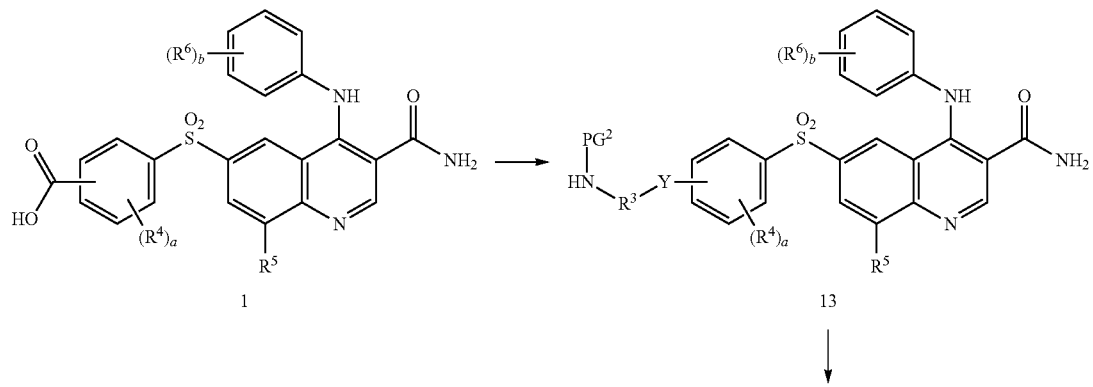

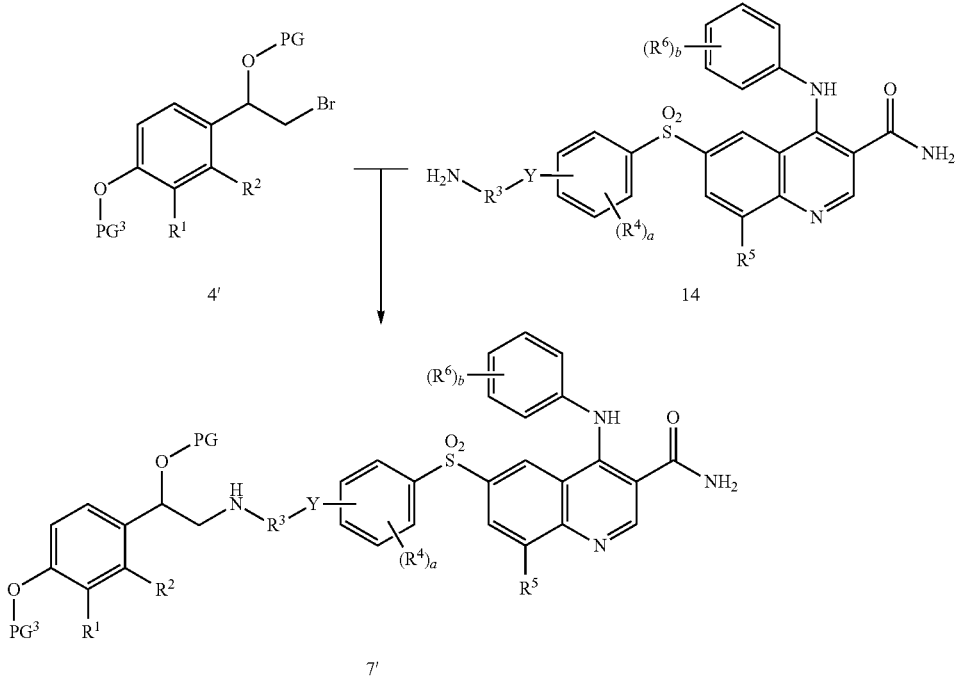

wherein:
PG is H or TBS;
PG² is a suitable protecting group such as Boc or Cbz;
PG³ is H or benzyl;
and all other variables are as defined above.

Additionally, according to this embodiment, the acid in compound 1 may be coupled to a mono-protected diamine, which are commercially available or known, to produce compound 13. Appropriate protecting groups include Boc or Cbz. The protecting group may be removed under standard conditions to give Compound 14. Reaction of compound 14 with the protected bromide 4 at elevated temperatures, such as about 50 to about 150° C., in an appropriate solvent such as DMSO or DMF to give a protected version of compound 7, i.e. 7'.

In another embodiment, compounds of formula I wherein Y is C(O)N(R⁷) or N(R⁷)C(O)N(R⁷), may be prepared by converting the acid compound 1 to the corresponding aniline (compound 15) and further conversion of the aniline compound 15 to the desired intermediate compound 2 or compound 8 according to Scheme 6.

Scheme 6

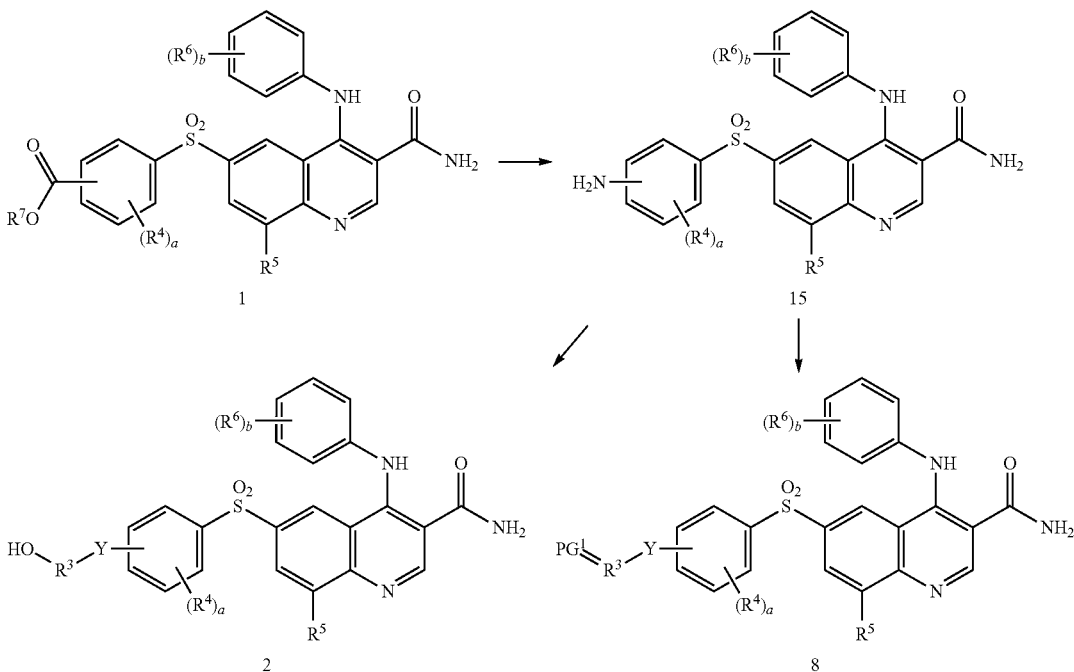

wherein:
R⁷ on compound 1 is H;
Y is C(O)NH or N(R⁷)C(O)NH;
and all other variables are as defined above.

More specifically, according to this embodiment, the acid in compound 1 (wherein R⁷ is H) may be converted to the corresponding amine compound 15. For example, conversion may occur by treatment of the acid 1 with diphenylphosphorylazide, a suitable base, such as TEA or DIEA, in a suitable solvent, such as t-butanol at an elevated temperature, such as 40° C. to reflux to produce the t-butyl carbamate. Deprotection under standard conditions such as TFA in DCM or HCl in MeOH at temperatures between −20° and room temperature will give compound 15. Compound 15 may then be reacted as compound 12 was above in scheme 4 with an appropriate acid or reactive acid species to provide compounds 2 or 8 above where Y is CONH. Alternatively, coupling of the aniline compound 15 with a phosgene equivalent, such as carbonyldiimidazole or 4-nitrophenylochloroformate at low temperature, between −78° C. and 0° C., gives an activated species, which can be subsequently reacted with an appropriately substituted amine at higher temperature, between rt and 100° C., to give compounds 2 or 8, where Y is N(R⁷)C(O)NH.

As will be apparent to those skilled in the art, substituted anilines of compound 15 may also be utilized to prepare compounds 2 or 8, and ultimately compounds of Formula I wherein Y is C(O)N(R⁷) or N(R⁷)C(O)N(R⁷) and R⁷ is other than H.

In another embodiment, intermediate compounds 18 may be prepared by addition of thiol on compound 16 followed by oxidation as shown in Scheme 7.

Scheme 7

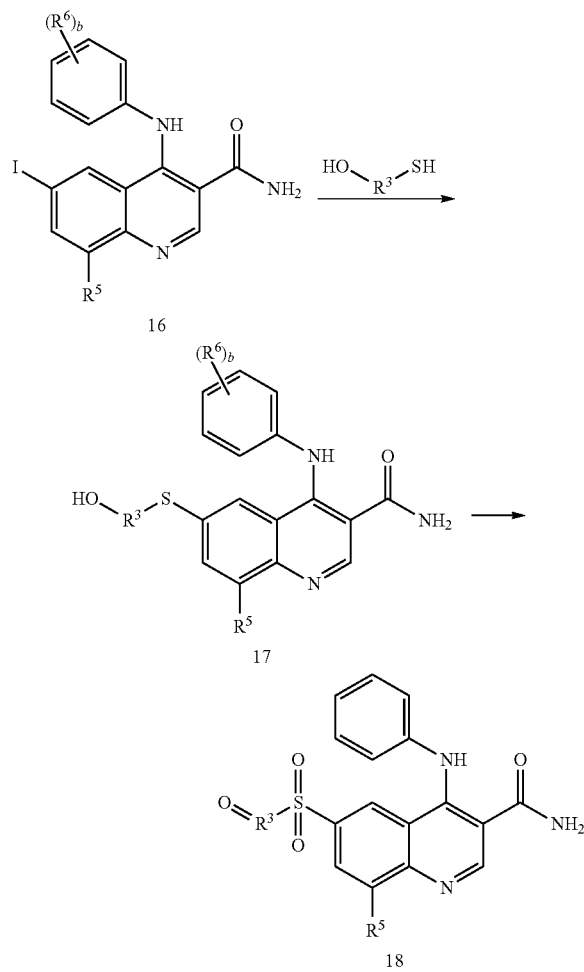

wherein:
R⁵ is CH₃ and R⁶ is OCH₃ on compound 16;
and all other variables are as defined above.

According to Scheme 7, coupling of compound 16 with an alkyl thiol under palladium catalysis gives the corresponding thioether compound 17. Oxidation with Oxone affords the corresponding sulfone which is then oxidized under standard conditions (Dess-Martin, PDC, Swern) to give the corresponding carbonyl compound 18.

The order of steps in the foregoing reactions is not critical to the practice of the present invention and the steps may be carried out in any suitable order according to the knowledge of those skilled in the art, to provide the compounds of formula I.

The foregoing detailed description may be further understood from the following examples, which are presented for the purposes of illustration only and are not intended to limit the scope of the invention. The invention is defined solely by the claims which follow. In the following examples, compounds are named using standard IUPAC naming principles where possible. The naming convention employed for the novel compounds are exemplified by Examples below.

EXAMPLES

Intermediate 1: (R)-5-[2-Azido-1-[(tert-butyldimethylsilyl)oxy]ethyl]-8-(benzyloxy)quinolin-2(1H)-one

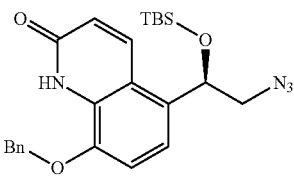

NaN₃ (266 mg, 4.1 mmol) was added to a stirring solution of (R)-8-(benzyloxy)-5-[2-bromo-1-[(tert-butyldimethylsilyl)oxy]ethyl]quinolin-2(1H)-one (1 g, 2.05 mmol) in DMF (20 mL) at rt and warmed to 80° C. for 3 h. The resulting solution was poured into H₂O (80 mL) and extracted with EtOAc (3×50 mL). The combined organic layers were washed with H₂O (2×100 mL), brine (100 mL), dried over Na₂SO₄ (s), and concentrated to give the title compound (1.37 g) as yellow solid. The compound was used with no further purification. ES/MS calcd. for C₂₄H₃₁N₄O₃Si⁺ 451.2. Found m/z=451.3 (M+H)⁺.

Intermediate 2: (R)-5-[2-Amino-1-[(tert-butyldimethylsily]oxy]ethyl]-8-hydroxyquinolin-2(1H)-one

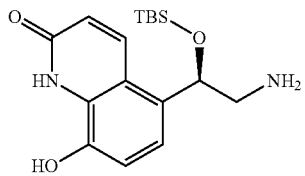

Intermediate 1 (1.37 g) was dissolved in MeOH (20 mL) and Pd(OH)₂/C (20% w/w, 288 mg, 0.41 mmol) was added. Nitrogen gas was bubbled through the solution for 5 min. The resulting suspension was attached to a balloon filled with H₂ and stirred over night. The reaction mixture was filtered through celite and concentrated to give a brown oil (1.208 g). Chromatography (9:1, CH₂Cl₂/MeOH, 0.1% Et₃N) afforded the title compound (597 mg, 87% 2 steps) as a light yellow solid. ES/MS calcd. for $C_{17}H_{27}N_2O_3Si^+$ 335.2. Found m/z=335.2 (M+H)$^+$.

Intermediate 3: (R)-8-(benzyloxy)-5-(1-((tert-butyldimethylsilyl)oxy)-2-(methylamino)ethyl)quinolin-2(1H)-one

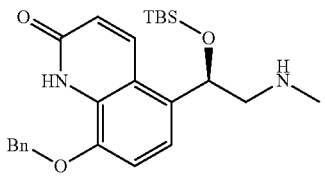

A solution of (R)-8-(benzyloxy)-5-(2-bromo-1-(tert-butyldimethylsilyloxy)ethyl)quinolin-2(1H)-one (1.5 g, 3.1 mmol) in methylamine/tetrahydrofuran (2.0 M, 16 mL, 32 mmol) was heated in a sealed tube at 100° C. (oil bath) for 3 days. After allowing the mixture to cool to room temperature, it was concentrated and purified via automated flash silica gel chromatography, using a 25 g Silicycle SiliSep flash column (dichloromethane/methanol/ammonium hydroxide). Concentration of the desired fractions under reduced pressure provided the title compound. ES/MS calcd. for $C_{25}H_{35}N_2O_3Si^+$ 439.2. Found m/z=439.3 (M+H)$^+$.

Intermediate 4: (R)-5-(1-((tert-butyldimethylsilyl)oxy)-2-(methylamino)ethyl)-8-hydroxyquinolin-2(1H)-one

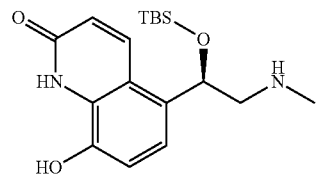

Intermediate 3 was dissolved in MeOH (25 mL) and Pd/C (10% w/w, 100 mg) was added. The resulting suspension was attached to a balloon filled with H$_2$ and stirred for 7 hours. The reaction mixture was filtered through Celite diatomaceous earth and concentrated to give provide the title compound as a hard foam. ES/MS calcd. for $C_{18}H_{29}N_2O_3Si^+$ 349.2. Found m/z=349.2 (M+H)$^+$.

Intermediate 5: (R)-5-(2-Azido-1-hydroxyethyl)-8-(benzyloxy)quinolin-2(1H)-one

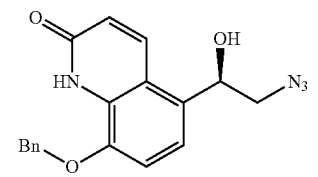 [SMILES: [N-]=[N+]=NC[C@H](O)c1ccc(OCc2ccccc2)c2[nH]c(=O)ccc12]

A 1.0 M (THF) solution of TBAF (0.443 mL, 0.443 mmol) was added to a stirring solution of Intermediate 1 (200 mg, 0.443 mmol) in THF (4 mL) at rt. The resulting mixture was stirred over night then concentrated. Chromatography (1:3, Hexanes/EtOAc) afforded the title compound (137 mg, 92%) as an off-white solid. ES/MS calcd. for $C_{18}H_{17}N_4O_3^+$ 337.1. Found m/z=337.2 (M+H)$^+$.

Intermediate 6: (R)-5-(2-Amino-1-hydroxyethyl)-8-hydroxyquinolin-2(1H)-one

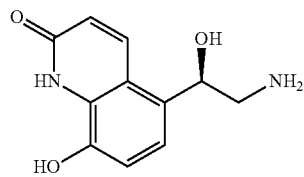 [SMILES: NC[C@H](O)c1ccc(O)c2[nH]c(=O)ccc12]

The title compound was synthesized in a manner analogous to that described for Intermediate 2, using Intermediate 5 as a substrate. ES/MS calcd. for $C_{11}H_{13}N_2O_3^+$ 221.1. Found m/z=221.2 (M+H)$^+$.

Intermediate 7: (R)-1-[4-(Benzyloxy)-3-[[(tert-butyldimethylsilyl)oxy]methyl]-phenyl]-2-bromoethanol

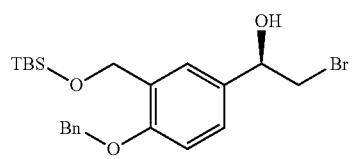

TBSCl (5 g, 33.2 mmol) and imidazole (3.7 g, 55.4 mmol) were added to a stirring solution of (R)-1-[4-(benzyloxy)-3-(hydroxymethyl)phenyl]-2-bromoethanol (10 g, 27.7 mmol) in CH$_2$Cl$_2$ (200 mL) at rt. The resulting suspension was stirred for 1 h then quenched with H$_2$O (200 mL). The aqueous layer was extracted with CH$_2$Cl$_2$ (3×100 mL). The combined organic layer was washed with brine (300 mL), dried over Na$_2$SO$_4$ (s), and concentrated to give the title compound (13.9 g) as a clear oil. The compound was used with no further purification. ES/MS calcd. for $C_{22}H_{31}BrNaO_3Si^+$ 473.1. Found m/z=473.1 (M+Na)$^+$.

Intermediate 8: (R)-2-Azido-1-[4-(benzyloxy)-3-[[(tert-butyldimethylsilyl)oxy]-methyl]phenyl]ethanol

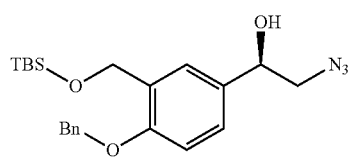

The title compound was synthesized in a manner analogous to that described for Intermediate 1, using Intermediate 7 in place of (R)-8-benzyloxy)-5-(2-bromo-1-((tert-butyldimethylsilyl)oxy)ethyl)quinolin-2(1H)-one. ES/MS calcd. for $C_{22}H_{31}N_3NaO_3Si^+$ 436.2. Found m/z=436.2 (M+Na)$^+$.

Intermediate 9: (R)-4-(2-Amino-1-hydroxyethyl)-2-[[(tert-butyldimethylsilyl)oxy]methyl]phenol

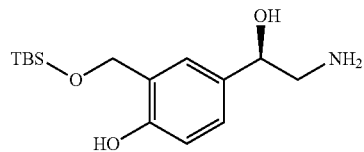

The title compound was synthesized in a manner analogous to that described for Intermediate 2, using Intermediate 8 as a substrate. ES/MS calcd. for $C_{15}H_{27}NNaO_3Si^+$ 320.2. Found m/z=320.2 (M+Na)$^+$.

Intermediate 10: (R)—N-[2-(Benzyloxy)-5-(2-bromo-1-hydroxyethyl)phenyl]formamide

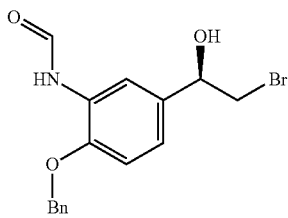 [SMILES: O=CNc1cc([C@@H](O)CBr)ccc1OCc1ccccc1]

(R)-1-[4-(Benzyloxy)-3-nitrophenyl]-2-bromoethanol (0.2 g, 5.7 mmol) in THF:toluene (1:1, 5 mL) was reacted with PtO$_2$ (1% w/w) on a Parr shaker at 45 psi at rt overnight. The next morning the PtO$_2$ was removed by filtration over celite. The filtered solution was cooled to 0° C. and a solution of acetic anhydride (0.161 mL, 0.569 mmol) and formic acid (0.043 mL, 1.140 mmol) was added dropwise to a stirred solution. After 30 min the reaction was warmed to rt and stirred for 2 h. The reaction mixture was concentrated to near dryness and water was added. The aqueous layer was extracted with EtOAc (3×25 mL). The combined organic layers were washed with NaHCO$_3$, brine, dried over Na$_2$SO$_4$ (s), and concentrated. Chromatography (1:1 Hexanes/EtOAc) gave the title compound (156 mg, 78% 2 steps). ES/MS calcd. $C_{16}H_{17}BrNO_3^+$ 350.0. Found m/z=350 (M+H)$^+$.

Intermediate 11: (R)—N-[5-(2-Azido-1-hydroxyethyl)-2-(benzyloxy)phenyl]formamide

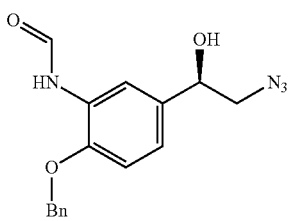 [SMILES: [N-]=[N+]=NC[C@H](O)c1ccc(OCc2ccccc2)c(NC=O)c1]

The title compound was synthesized in a manner analogous to that described for Intermediate 1, using Intermediate 10 as a substrate. ES/MS calcd. $C_{16}H_{17}N_4O_3^+$ 313.1. Found m/z=313 (M+H)$^+$.

Intermediate 12: (R)—N-[5-[2-Azido-1-[(tert-butyldimethylsilyl)oxy]ethyl]-2-(benzyloxy)phenyl]formamide

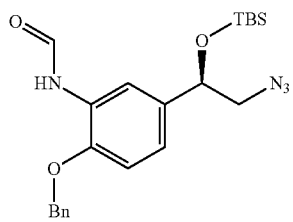

The title compound was synthesized in a manner analogous to that described for Intermediate 7, using Intermediate 11 in place of (R)-4-(2-bromo-1-hydroxyethyl)-2-(hydroxymethyl)phenol. ES/MS calcd. $C_{22}H_{31}N_4O_3Si^+$ 427.2. Found m/z=427 (M+H)$^+$.

Intermediate 13: (R)—N-(5-[2-Amino-1-[(tert-butyldimethylsilyl)oxy]ethyl]-2-hydroxyphenyl]formamide

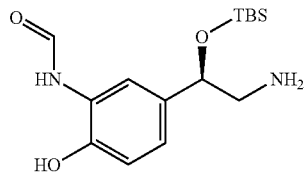

The title compound was synthesized in a manner analogous to that described for Intermediate 2, using Intermediate 12 in place of Intermediate 1. ES/MS calcd. $C_{15}H_{27}N_2O_3Si^+$ 311.2. Found m/z=311 (M+H)$^+$ Intermediate 14: (R)-1-[3-Amino-4-(benzyloxy)phenyl]-2-bromoethanol

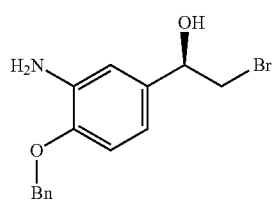 [SMILES: Nc1cc([C@@H](O)CBr)ccc1OCc1ccccc1]

(R)-1-[4-(Benzyloxy)-3-nitrophenyl]-2-bromoethanol (0.200 g, 0.569 mmol) in 1:1 THF:toluene (5 mL) was reacted with PtO$_2$ (1% w/w) on a Parr shaker at 45 psi at rt overnight. The next morning the PtO$_2$ was removed by filtration over celite. The product was concentrated to give the title compound. ES/MS calcd. for $C_{15}H_{17}BrNO_2^+$ 322.0. Found m/z=322 (M+H)$^+$.

Intermediate 15: (R)-1-(3-Amino-4-(benzyloxy)phenyl)-2-azidoethanol

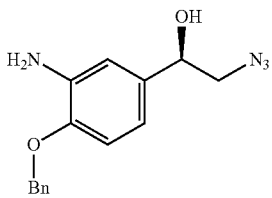 [SMILES: [N-]=[N+]=NC[C@H](O)c1ccc(OCc2ccccc2)c(N)c1]

The title compound was synthesized in a manner analogous to that described for Intermediate 1, using Intermediate 14 in place of (R)-8-(benzyloxy)-5-[2-bromo-1-[(tert-butyldimethylsily)oxy]ethyl]quinolin-2(1H)-one. ES/MS calcd. for $C_{15}H_{17}N_4O_2^+$ 285.1. Found m/z=285 (M+H)$^+$.

Intermediate 16: of (R)-8-(Benzyloxy)-5-[2-bromo-1-[(tert-butyldimethylsilyl)oxy]ethyl]quinolin-2(1H)-one

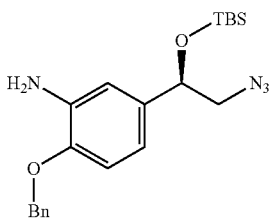

The title compound was synthesized in a manner analogous to that described for Intermediate 7, using Intermediate 15 in place of (R)-4-(2-bromo-1-hydroxyethyl)-2-(hydroxymethyl)phenol. ES/MS calcd. for $C_{21}H_{31}N_4O_2Si^+$ 399.2. Found m/z=399 (M+H)$^{4"}$.

Intermediate 17: (R)—N-[5-[2-Azido-1-[(tert-butyldimethylsilyl)oxy]ethyl]-2-(benzyloxy)phenyl]methanesulfonamide

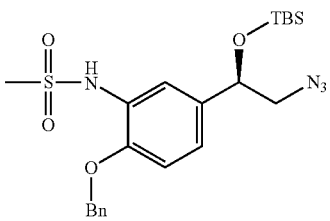

Methanesulfonyl chloride (0.044 mL, 0.569 mmol) was added to a stirring solution of Intermediate 16 (275 mg, 0.569 mmol) in pyridine (10 mL) at 0° C. The resulting mixture was warmed to rt and monitored for completeness by LC/MS. An additional 1 equivalent of methanesulfonyl chloride was added after 1 h followed by an additional 0.5 equivalent after another h for a total of 2.5 equivalents. After an additional 1 h, water (50 mL) was added and stirred at rt for 2 h. The aqueous was extracted with $CH_2Cl_2$ (4×25 mL). The combined organic layers were washed with satd. $NaHCO_3$, brine, dried over $Na_2SO_4$ (s), and concentrated. Chromatography (1:1 Hexanes/EtOAc) afforded the title compound (197 mg, 72%, 3 steps). ES/MS calcd. for $C_{22}H_{33}N_4O_4SSi^+$ 477.2. Found m/z=477 (M+H)$^+$ Intermediate 18: (R)—N-[5-[2-Amino-1-[(tert-butyldimethylsily)oxy]ethyl]-2-hydroxyphenyl]methanesulfonamide

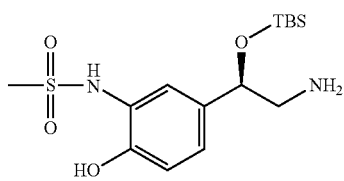

The title compound was synthesized in a manner analogous to that described for Intermediate 2, using Intermediate 17 in place of Intermediate 1. The compound was used with no further purification. ES/MS calcd. for $C_{15}H_{29}N_2O_4SSi^+$ 361.2. Found m/z=361 (M+H)$^+$.

Intermediate 19: ((6-bromohexyl)oxy)(tert-butyl)dimethylsilane

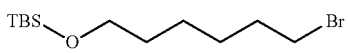

Imidazole (1.1 g, 16.56 mmol) and TBS-Cl (1.37 g, 9.11 mmol) were added to a stirring solution of 6-bromohexanol (1.5 g, 8.28 mmol) in $CH_2Cl_2$ (80 mL). The resulting mixture was stirred over night then quenched with $H_2O$ (100 mL). The aqueous layer was extracted with $CH_2Cl_2$ (3×50 mL). The combined organic layers were washed with brine, dried over $Na_2SO_4$, and concentrated to give the title compound (2.6 g) as clear oil. The compound was used with no further purification.

Intermediate 20: tert-Butyl (6-hydroxyhexyl)carbamate

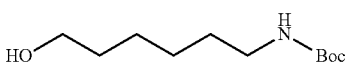 [SMILES: CC(C)(C)OC(=O)NCCCCCCO]

6-Aminohexan-1-ol (250 mg, 2.135 mmol) was combined with (Boc)$_2$O (0.512 g, 2.348 mmol) and $K_2CO_3$ (0.590 g, 4.27 mmol) in 1:1 dioxane:water (10 mL) and stirred at rt overnight. The solution was concentrated, water added, and extracted with EtOAc. The organic phased was then washed with saturated $NaHCO_3$, saturated NaCl, dried over $Na_2SO_4$, and concentrated to give the title compound. The product was carried through to the next step without purification; ES/MS calcd. for $C_{11}H_{24}NO_3^+$ 218.2. Found m/z=218 (M+H)$^+$.

Intermediate 21: 6-(Methylamino)hexan-1-ol

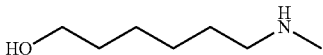

Intermediate 20 (2.14 mmol) was added to a stirring solution at 0° C. containing 95% LAH (0.426 g, 10.68 mmol) in 10 mL of anhydrous THF. This mixture was then heated to 80° C. and allowed to reflux for 3 h. After 3 h the reaction was cooled to 0° C. and water (0.426 mL), 20% (w/v) NaOH (0.426 mL), and water (1.215 mL) were added sequentially. This was stirred for 15 min at rt then MgSO$_4$ was added and stirred for another 30 min. The mixture was filtered through celite, washed with THF, and concentrated to give the title compound. The compound was used with no further purification. ES/MS calcd. for $C_7H_{18}NO^+$ 132.1. Found m/z=132 (M+H)$^+$.

Intermediate 22: 1-benzyl-4-((6-((tert-butyldimethylsilyl)oxy)hexyl)oxy)piperidine

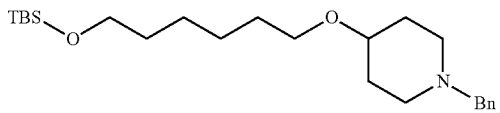

Solid NaH (60% w/w in mineral oil, 352 mg, 4.6 mmol) was added to a stirring solution of 1-Benzyl-4-hydroxypiperidine (841 mg, 4.4 mmol) in DMF (50 mL) at 0° C. The resulting suspension was stirred for 5 min then Intermediate 19 (2.6 g, 8.8 mmol) was added. The reaction mixture was warmed to rt then heated to 70° C. over night. The resulting solution was cooled then pour into H$_2$O (100 mL) and extracted with EtOAc (3×50 mL). The combined organic layers were washed with H$_2$O (100 mL), brine (100 mL), dried over Na$_2$SO$_4$, and concentrated to give crude either 2.96 g as yellow oil. Chromatography (1:3, hexanes/EtOAc) afforded the title compound (157 mg, 8%) as clear oil. ES/MS calcd for $C_{24}H_{44}NO_2Si^+$ 406.3. Found m/z=406.3 (M+H)$^+$.

Intermediate 23: 4-((6-((tert-butyldimethylsily)oxy)hexyl)oxy)piperidine

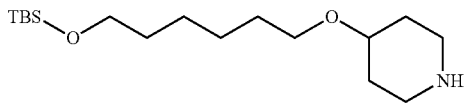

Intermediate 22 (157 mg, 0.387 mmol) was dissolved in MeOH (5 mL) then added 10% (w/w) Pd/C (41 mg, 0.0387 mmol). The reaction vessel was attached to 3-way valve with balloon containing hydrogen gas. The vessel was evacuated 3 times then back flushed with hydrogen. The resulting suspension was stirred overnight, filtered, and concentrated to give the title compound (120 mg) as clear oil. The compound was used with no further purification. ES/MS calcd for $C_{17}H_{38}NO_2Si^+$ 316.3. Found m/z=316.3 (M+H)$^+$.

Intermediate 24: benzyl 4-(6-((tert-butyldimethylsilyl)oxy)hexyl)piperazine-1-carboxylate

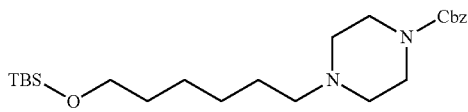

Intermediate 19 (2.6 g, 8.8 mmol) was added to a stirring solution of benzyl piperazine-1-carboxylate (1.1 mL, 5.87 mmol) in CH$_3$CN (80 mL). The reaction mixture was refluxed over night, cooled, and quenched with satd. NaHCO$_3$ (100 mL). The aqueous layer was extracted with EtOAc (3×50 mL) and the combined organic layers were washed with brine, dried over Na$_2$SO$_4$, concentrated to give the crude (3.8 g) as opaque oil. The chromatography (1:3, hexanes/EtOAc) afforded the title compound (1.78 g, 70%) as clear oil. ES/MS calcd. for $C_{24}H_{43}N_2O_3Si^+$ 435.3. Found m/z=435.2 (M+H)$^+$.

Intermediate 25: 1-(6-((tert-butyldimethylsilyl)oxy)hexyl)piperazine

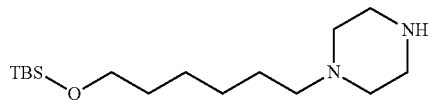

The title compound was synthesized in a manner analogous to that described for Intermediate 23, using Intermediate 24 as a substrate. ES/MS calcd. for $C_{16}H_{37}N_2OSi^+$ 301.3. Found m/z=301.3 (M+H)$^+$.

Intermediate 26: 6-(but-3-yn-1-yloxy)hexyl acetate

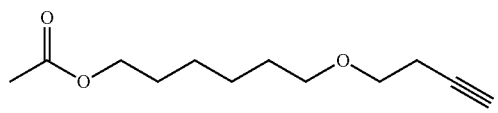

A solution of 1-bromo-6-(but-3-ynyloxy)hexane (1.5 g, 6.4 mmol, prepared according to Procopiou, P. et al. J Med Chem 2009 52(8), 2280-2288) was taken up in DMF (25 mL) and treated with tetra-n-butylammonium acetate (2.9 g, 9.7 mmol). The mixture was stirred overnight at room temperature and then concentrated under reduced pressure. The residue was partitioned between water and diethyl ether. The aqueous phase was extracted thrice with diethyl ether. The combined extracts were washed once each with water and saturated aqueous sodium chloride solution, dried over anhydrous magnesium sulfate, and concentrated under reduced pressure to provide the title compound as a clear, colorless liquid.

Intermediate 27: tert-Butyl 4-aminophenethylcarbamate

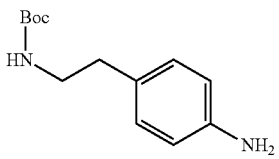

Di-tert-butyl-dicarbonate (1.60 g, 7.34 mmol) was added to a solution of 2-(4-aminophenyl)ethylamine (1.00 g, 7.34 mmol) in EtOAc (20 mL) at rt. After stirring for 18 h, the reaction was washed with 10% NaHCO$_3$ and concentrated in vacuo to give a yellow semi-crystalline waxy solid, 1.74 g. $^1$H NMR (400 MHz, DMSO-d$_6$) δ 6.79-6.82 (m, 2H), 6.77 (br t, J=5.4 Hz, 1H), 6.46-6.49 (m, 2H), 4.83 (s, 2H), 2.99-3.05 (m, 2H), 2.47-2.51 (m, 2H), 1.37 (s, 9H). ES/MS calcd. for C$_{13}$H$_{20}$N$_2$NaO$_2$ 259.1. Found m/z 259.1 (M+Na)$^+$.

Intermediate 28: tert-Butyl 4-(2-(methylamino)ethoxy)phenethylcarbamate

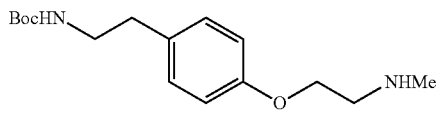 [SMILES: CNCCOc1ccc(CCNC(=O)OC(C)(C)C)cc1]

To a solution of N-Boc-tyramine (750 mg, 3.16 mmol) and triphenylphosphine (1.655 g, 6.308 mmol) in THF (30 mL) was added 2-(methylamino)ethanol (0.38 mL, 4.75 mmol) followed by DIAD (1.25 mL, 6.31 mmol). After stirring at room temperature for 72 h, the reaction mixture was concentrated under reduced pressure. The residue was purified by column chromatography on silica gel (gradient elution 1:20 to 1:3 MeOH/DCM) to afford the title compound (407 mg, 44%) as an oily white solid. ES/MS calcd. for C$_{16}$H$_{27}$N$_2$O$_3^+$ 295.2. Found m/z=295.2 (M+H)$^+$.

Intermediate 29: methyl 4-(4'-amino-[1,1'-biphenyl]-4-yl)butanoate

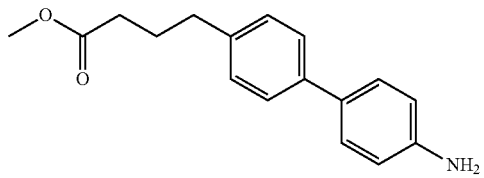 [SMILES: COC(=O)CCCc1ccc(-c2ccc(N)cc2)cc1]

Solid 4-(4,4,5,5-tetramethyl-1,3,2-dioxaborolan-2-yl)aniline (158 mg, 0.723 mmol) and Pd(PPh$_3$)$_4$ (38 mg, 0.033 mmol) were added to a solution of methyl 4-(4-iodophenyl) butanoate (200 mg, 0.657 mmol) in dimethoxyethane/2M Na$_2$CO$_3$ (3 mL, 2:1) at rt. The resulting mixture was degassed with argon gas then heated at 110° C. using microwave for 30 min. The reaction mixture was diluted with EtOAc (10 mL) then washed with H$_2$O (10 mL), brine (10 mL), dried over Na$_2$SO$_4$, and concentrated to give crude (294 mg) as brown oil. Chromatography (9:1, CH$_2$Cl$_2$/MeOH) afforded the title compound (146 mg, 82%) as a light yellow solid. ES/MS calcd. for C$_{17}$H$_{20}$NO$_2^+$ 270.2. Found m/z=270.2 (M+H)$^+$.

Intermediate 30: methyl 4-(3'-amino-[1,1'-biphenyl]-4-yl)butanoate

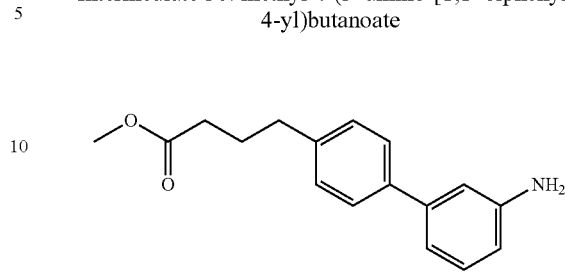

The title compound was synthesized in a manner analogous to that described for Intermediate 29, using (3-aminophenyl)boronic acid as in place of 4-(4,4,5,5-tetramethyl-1,3,2-dioxaborolan-2-yl)aniline ES/MS calcd. for C$_{17}$H$_{20}$NO$_2^+$ 270.2. Found m/z=270.2 (M+H)$^+$.

Intermediate 31: 5-(4-Aminophenyl)pent-4-yn-1-ol

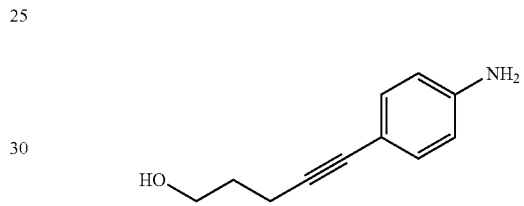

4-Iodoaniline (10 g, 45 mmol), palladium on carbon (2.86 g, 1.35 mmol, 5% w/w), PPh$_3$ (1.4 g, 5.4 mmol), CuI (513 mg, 2.7 mmol), and K$_2$CO$_3$ (15 g, 5.4 mmol) were added to DME (50 mL) and H$_2$O (50 mL). The mixture is degassed while stirring by bubbling nitrogen vigorously into the solution. Pent-4-yn-1-ol (10.5 mL, 114 mmol) was added by syringe. The mixture was heated at 85° C. After cooling, water (100 mL) and EtOAc (200 mL) were added. The mixture was extracted with EtOAc. The organic layer and the water layer were independently neutralized with 1N HCl. The aqueous layer was extracted with EtOAc and the combined organic layers dried over MgSO$_4$. The material was concentrated by rotary evaporation and the oil was purified by chromatography (gradient 10-100% EtOAc/Hex) to give the title compound as a dark oil (6 g, 76%). $^1$H NMR (400 MHz, CDCl3) δ 7.19 (dd, 2H, J=8.9, 1.5 Hz), 6.58 (dd, 2H, J=8.9, 1.5 Hz), 3.85 (t, 2H, J=8.0 Hz), 3.75 (brs, 2H), 2.55 (t, 2H, J=8.0 Hz), 1.86 (m, 2H); ES/MS calcd. for C$_{11}$H$_{14}$NO$^+$ 176.1. Found m/z=176.1 (M+H)$^+$.

Intermediate 32: 2,2,2-trifluoro-N-(4-iodophenyl)acetamide

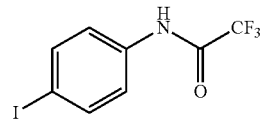 [SMILES: O=C(Nc1ccc(I)cc1)C(F)(F)F]

4-iodoaniline (0.250 g, 1.147 mmol) in 5 mL of anhydrous THF was cold to 0° C. and then TFA Anhydride (2.294 mmol, 0.482 g, 0.319 mL) was added drop wise over 5 minutes. The mixture was allowed to react at 0° C. for 15 minutes then warmed to room temperature and reacted for another 40 minutes. The reaction was worked up by concentrating off the solvent and TFA. Then placed on high-vac over night. ES/MS calcd. for $C_8H_5F_3INO$ 314.9. Found m/z=316 (M+H)$^+$.

Intermediate 33: 2,2,2-trifluoro-N-(4-iodophenyl)-N-methylacetamide

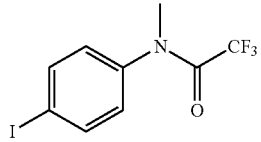

Intermediate 32 (1.0 g, 3.175 mmol) in 20 mL of acetone was combined with $CH_3I$ (6.350 mmol, 0.901 g, 0.395 mL) and $K_2CO_3$ (6.350 mmol, 0.876 g) then refluxed at 80° C. for 2 hours. The reaction was worked up quenching the reaction with 1× saturated $NaHCO_3$, extracted 4×25 mL EtOAc then washed 1× water, 1× saturated NaCl, dried over $Na_2SO_4$, then concentrated. The product was carried through without purification. ES/MS calcd. for $C_9H_7F_3INO$ 328.95. Found m/z=330 (M+H)$^+$.

Intermediate 34: 2,2,2-trifluoro-N-(4-iodo-2-methylphenyl)acetamide

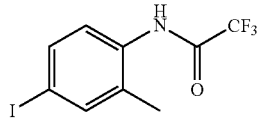

Title compound was synthesized in a manner analogous to Intermediate 32 using 4-iodo-2-methylaniline as a substrate. ES/MS calcd. for $C_9H_7F_3INO$ 328.95. Found m/z=330 (M+H)$^+$.

Intermediate 35: 2,2,2-trifluoro-N-(4-iodo-3-methylphenyl)acetamide

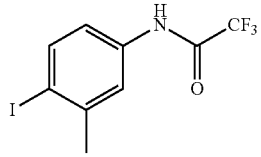

The title compound was synthesized in a manner analogous to that described in Intermediate 32, using 4-iodo-3-methylaniline as a substrate. ES/MS calcd. for $C_9H_7F_3INO$ 328.95. Found m/z=330 (M+H)$^+$.

Intermediate 36: 2,2,2-trifluoro-N-(4-(5-hydroxypent-1-yn-1-yl)phenyl)-N-methylacetamide

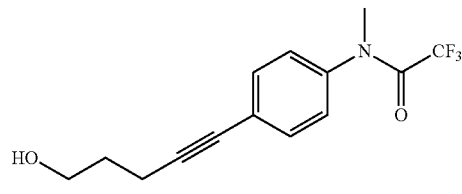 [SMILES: CN(C(=O)C(F)(F)F)c1ccc(C#CCCCO)cc1]

Intermediate 33 (0.377 g, 1.147 mmol) in 10 mL of TEA was combined with $PdCl_2(PPh_3)_2$ (0.02294 mmol, 0.016 g) the mixture was then degassed using $N_2$ for 5 minutes. Then CuI (0.01147 mmol, 0.002 g) and Pent-4-yn-1-ol (1.147 mmol, 0.115 g) then reacted at 50° C. for 4 hours. The reaction was worked up quenching the reaction with 1× saturated $NaHCO_3$, extracted 4×25 ml EtOAc then washed 1× water, 1× saturated NaCl, dried over $Na_2SO_4$, then concentrated. The product was purified 0-75% EtOAc in Hexanes over 20 min on silica. ES/MS calcd. for $C_{14}H_{14}F_3NO_2$ 285.1. Found m/z=286 (M+H)$^+$.

Intermediate 37: 2,2,2-trifluoro-N-(4-(5-hydroxypent-1-yn-1-yl)-2-methylphenyl)acetamide

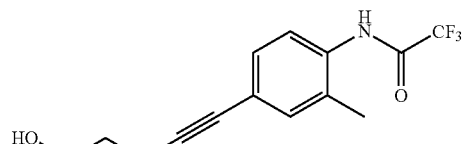

Title compound was synthesized in a manner analogous to Intermediate 36 using Intermediate 34 in place of Intermediate 33. ES/MS calcd. for $C_{14}H_{14}F_3NO_2$ 285.1. Found m/z=286 (M+H)$^+$.

Intermediate 38: 2,2,2-trifluoro-N-(4-(5-hydroxypent-1-vn-1-yl)-3-methylphenyl)acetamide

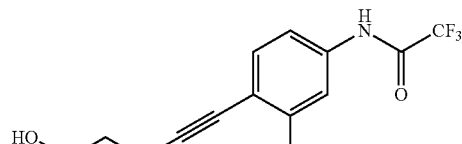

The title compound was synthesized in a manner analogous to that described in Intermediate 36, using Intermediate 35 in place of Intermediate 33. ES/MS calcd. for $C_{14}H_{14}F_3NO_2$ 285.1. Found m/z=286 (M+H)$^+$.

Intermediate 39: 2,2,2-trifluoro-N-(4-(6-hydroxyhex-1-yn-1-yl)phenyl)acetamide

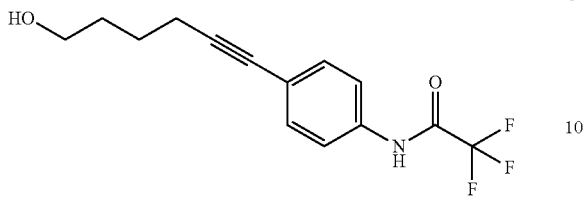

A solution of Intermediate 32 (2.7 g, 8.5 mmol, prepared according to Melissaris, A. P. and Litt, M. H. J Org Chem 1994, 59, 5818-5821) in DMF (26 mL) was treated successively with tetra-n-butylammonium acetate (3.8 g, 13 mmol) and palladium (II) acetate (57 mg, 0.26 mmol). The mixture was degassed with nitrogen and then treated with 5-hexyn-1-ol (0.93 mL, 8.5 mmol). After four hours of stirring at room temperature, additional quantities of the following reagents were added: tetra-n-butylammonium acetate (1 g), palladium (II) acetate (57 mg), and 5-hexyn-1-ol (1 mL). After stirring overnight at room temperature, the mixture was partitioned between diethyl ether and water. The aqueous phase was extracted four times with diethyl ether. The combined organic extracts were washed twice with water and once with saturated aqueous sodium chloride solution before drying over anhydrous magnesium sulfate, filtration and concentration under reduced pressure to provide the title compound as brown syrup that partially solidified under vacuum. ES/MS calcd. for $C_{14}H_{15}F_3NO_2^+$: 286.1. Found m/z=286.2 (M+H)$^+$

Intermediate 40: N-(4-(5-bromopent-1-yn-1-yl)phenyl)-2,2,2-trifluoroacetamide

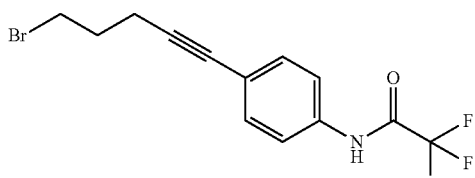

A solution of N-(4-(5-chloropent-1-ynyl)phenyl)-2,2,2-trifluoroacetamide (10 mmol, prepared analogously to Intermediate 39, employing 5-chloropentyne in place of 5-hexyn-1-ol) in 3-pentanone (200 mL) was treated with lithium bromide (10 eq, 100 mmol). The mixture was heated to reflux for 16 hours, followed by concentration to dryness under reduced pressure. The residue was taken up in ethyl acetate and washed with water. The concentrated organic phase was taken up again in 3-pentanone (200 mL) and heated to reflux for four hours in the presence of lithium bromide (10 eq, 100 mmol). The mixture was concentrated to dryness under reduced pressure. The residue was partitioned between ethyl acetate and water. The organic phase was washed with saturated aqueous sodium chloride solution, dried over anhydrous magnesium sulfate, filtered, and concentrated to dryness under reduced pressure. The crude product was purified via automated flash silica gel chromatography, using a 40 g Silicycle SiliSep flash column (hexanes/ethyl acetate). Concentration of the desired fractions under reduced pressure provided the title compound as an off-white solid. ES/MS calcd. for $C_{13}H_{12}BrF_3NO^+$ 334.0. Found m/z=334.1 (M+H)$^+$.

Intermediate 41: 1-(5-chloropent-1-yn-1-yl)-4-nitrobenzene

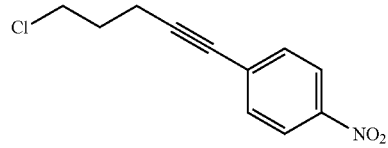 [SMILES: O=[N+]([O-])c1ccc(C#CCCCCl)cc1]

A mixture of 4-iodonitrobenzene (25 g, 100 mmol), dichlorobis(triphenylphosphine)palladium(II) (0.30 g, 0.43 mmol) and copper (I) iodide (0.18 g, 0.95 mmol) in tetrahydrofuran (300 mL) and triethylamine (150 mL) was degassed under Argon for 10 minutes. The mixture was then heated to 55° C. and treated with 5-chloropentyne (12 mL, 110 mmol) via syringe. After 30 minutes of stirring, additional quantities of dichlorobis(triphenylphosphine)palladium(II) (0.10 g) and 5-chloropentyne (1 mL) were added. After another 30 minutes of stirring, the mixture was allowed to cool to room temperature and then was filtered through a pad of Celite diatomaceous earth. The filtrate was concentrated to dryness under reduced pressure to provide 1-(5-chloropent-1-ynyl)-4-nitrobenzene, which was carried on without further purification. ES/MS calcd. for $C_{11}H_{11}ClNO_2^+$ 224.1. Found m/z=224.2 (M+H)$^+$.

Intermediate 42: 1-(5-bromopent-1-yn-1-yl)-4-nitrobenzene

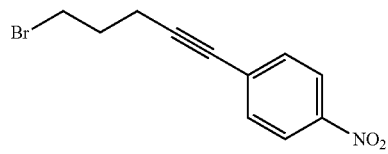 [SMILES: O=[N+]([O-])c1ccc(C#CCCCBr)cc1]

The title compound was synthesized in a manner analogous to that described for Intermediate 40, using Intermediate 41 as a substrate. ES/MS calcd. for $C_{11}H_{11}BrNO_2^+$ 268.0. Found m/z=268.1 (M+H)$^+$.

Intermediate 43: 1-(4-aminophenyl)-5-bromopentan-1-one

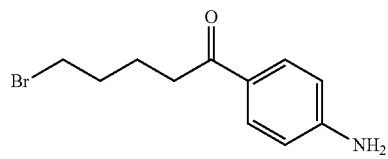 [SMILES: Nc1ccc(C(=O)CCCCBr)cc1]

A mixture of Intermediate 42 (200 mmol) was dissolved in a mixture of N-methylpyrrolidine/dichloromethane (1:1, 800 mL) and treated with tin (II) chloride dehydrate (218, 960 mmol) in 30 g portions. The exothermic reaction mixture was cooled in an ice-water bath. Following completion of the tin chloride addition, the cooling bath was removed and the mixture was allowed to regain room temperature. After 45 minutes of stirring, the mixture was quenched by adding it portion-wise to a mixture of ice and concentrated ammonium hydroxide solution. The slurry was filtered through a fritted glass funnel, washing with dichloromethane. The filtrates were concentrated under reduced pressure and diluted with diethyl ether. This organic phase was washed four times with water and once with a saturated aqueous sodium chloride solution, dried over anhydrous magnesium sulfate, filtered, and concentrated to dryness under reduced pressure. The residue was triturated with ethyl acetate. The solid was collected by filtration through a ceramic frit, washed with ethyl acetate, and dried under vacuum to provide the title compound. Subsequent crops of the title compound were recovered from the concentrated ethyl acetate filtrate. ES/MS calcd. for $C_{11}H_{15}BrNO^+$ 258.0. Found m/z=258.1 $(M+H)^+$.

Intermediate 44: N-(4-(5-bromopentanoyl)phenyl)-2,2,2-trifluoroacetamide

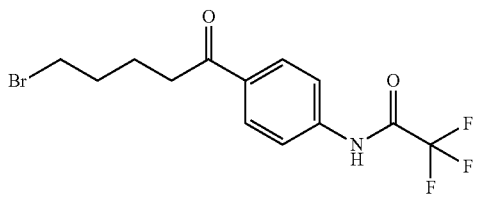 [SMILES: O=C(CCCCBr)c1ccc(NC(=O)C(F)(F)F)cc1]

The title compound was synthesized in a manner analogous to that described for Intermediate 32, using Intermediate 43 as a substrate. ES/MS calcd. for $C_{13}H_{14}BrF_3NO_2^+$ 352.0. Found m/z=352.1 $(M+H)^+$.

Intermediate 45: N-(4-(2-(4-bromobutyl)-1,3-dithiolan-2-yl)phenyl)-2,2,2-trifluoroacetamide

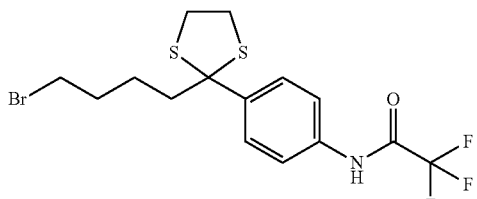

1,2-Ethanedithiol (1.0 mL, 12 mmol), followed by boron trifluoride diethyl etherate (2.0 mL, 16 mmol) was added to a solution of Intermediate 44 (2.9 g, 8.2 mmol) in dichloromethane (30 mL). After one hour of stirring at room temperature, the mixture was poured into an aqueous solution of sodium hydrogen carbonate. The resulting aqueous phase was extracted thrice with dichloromethane and the combined extracts were concentrated under reduced pressure to give a liquid, which after automated flash silica gel chromatography (ethyl acetate/hexanes), provided to title compound. ES/MS calcd. for $C_{15}H_{18}BrF_3NOS_2^+$ 428.0. Found m/z=428.1 $(M+H)^+$.

Intermediate 46: 5-(3-nitrophenyl)pent-4-yn-1-ol

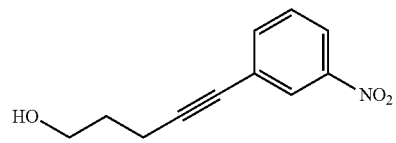 [SMILES: O=[N+]([O-])c1cccc(C#CCCCO)c1]

The title compound was synthesized in a manner analogous to that described for Intermediate 39, using 3-iodonitrobenzene as a substrate. ES/MS calcd. for $C_{11}H_{12}NO_3^+$ 206.1. Found m/z=206.2 $(M+H)^+$.

Intermediate 47: 5-(3-aminophenyl)pent-4-yn-1-ol

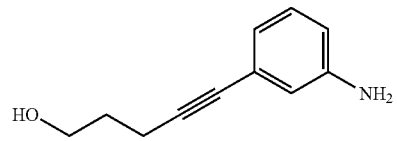 [SMILES: Nc1cccc(C#CCCCO)c1]

A solution of Intermediate 46 (16 mmol) in ethanol (80 mL) was treated successively with 10% aqueous hydrochloric acid solution (4 mL) and iron powder and then was lowered in to a 95° C. oil bath. After 90 minutes of reflux heating, the mixture was deemed complete by LC/MS analysis and was filtered while hot through a pad of Celite diatomaceous earth, eluting with methanol. The filtrate was concentrated to dryness under reduced pressure. The residue was purified via automated flash silica gel chromatography, using a 40 g Silicycle SiliSep flash column (hexanes/ethyl acetate). Concentration of the desired fractions under reduced pressure provided the title compound. ES/MS calcd. for $C_{11}H_{14}NO^+$ 176.1. Found m/z=176.2 $(M+H)^+$.

Intermediate 48: 6-(4-aminophenyl)hex-5-yn-1-ol

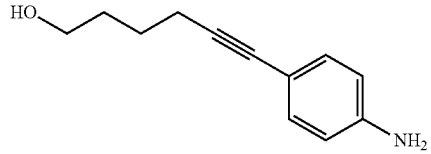 [SMILES: Nc1ccc(C#CCCCCO)cc1]

A solution of Intermediate 39 (8.5 mmol) in IPA (20 mL) was added to a 100° C. solution of potassium hydroxide (1.4 g, 26 mmol) in IPA (150 mL). The mixture was henceforth heated to reflux for 3.5 hours before being concentrated to drying under reduced pressure. The residue was partitioned between water and dichloromethane. The aqueous phase was extracted three times with dichloromethane. The combined extracts were concentrated to dryness under reduced pressure, and the resulting residue was purified via automated flash silica gel chromatography, using a 25 g Silicycle SiliSep flash column (hexanes/ethyl acetate). Concentration of the desired fractions under reduced pressure provided the title compound as a pale blond oil. ES/MS calcd. for $C_{12}H_{16}NO^+$: 190.1. Found m/z=190.2 $(M+H)^+$

Intermediate 49: 5-(4-(methylamino)phenyl)pent-4-yn-1-ol

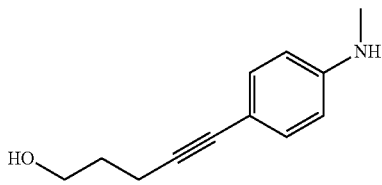

Intermediate 36 (0.221 g, 0.7752 mmol) was reacted with $K_2CO_3$ (0.7752 mmol, 0.107 g) in 12 mL of 2:1 MeOH:Water at room temperature overnight. The reaction was worked up quenching the reaction with 1× saturated $NaHCO_3$, extracted 4×25 ml EtOAc then washed 1× water, 1× saturated NaCl, dried over $Na_2SO_4$, then concentrated. The product was purified 0-10% MeOH in DCM over 15 min on TEA silica 12 g. ES/MS calcd. for $C_{12}H_{15}NO$ 189.1. Found m/z=190 (M+H)$^+$.

Intermediate 50: 5-(4-amino-3-methylphenyl)pent-4-yn-1-ol

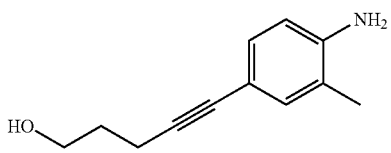

Title compound was synthesized in a manner analogous to Intermediate 49 using Intermediate 37 as a substrate. ES/MS calcd. for $C_{12}H_{15}NO$ 189.1 found m/z=190 (M+H)$^+$.

Intermediate 51: 5-(4-amino-2-methylphenyl)pent-4-yn-1-ol

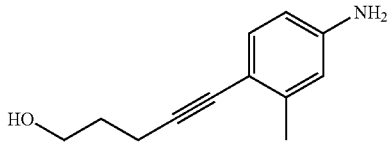

The title compound was synthesized in a manner analogous to that described in Intermediate 49, using Intermediate 38 as a substrate. ES/MS calcd. for $C_{12}H_{15}NO$ 189.1. Found m/z=190 (M+H)$^+$.

Intermediate 52: 1-(4-((6-bromohexyl)oxy)butyl)-4-nitrobenzene

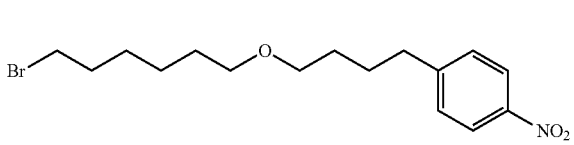 [SMILES: O=[N+]([O-])c1ccc(CCCCOCCCCCCBr)cc1]

A stirred mixture of 4-(4-nitrophenyl)butan-1-ol (2.0 g, 10 mmol), tetra-n-butylammomium hydrogen sulfate (0.17 g, 0.5 mmol), and 1,6-dibromohexane (3.2 mL, 20 mmol) in dichloromethane (10 mL) was treated with aqueous sodium hydroxide solution (10 M, 1 mL). The reaction mixture was stirred for 6 days at room temperature. The organic and aqueous phases were separated. The aqueous phase was extracted thrice with dichloromethane. The combined organics were washed with water, dried over anhydrous magnesium sulfate, filtered, and concentrated under reduced pressure. The crude residue was purified via automated flash silica gel chromatography, using a 40 g Silicycle SiliSep flash column (hexanes/ethyl acetate). Concentration of the desired fractions under reduced pressure provided the title compound as pale straw-colored oil (0.72 g, 20%). ES/MS calcd. for $C_{16}H_{25}BrNO_3^+$ 358.1. Found m/z=358.2 (M+H)$^+$.

Intermediate 53: 1-(2((6-bromohexyl)oxy)ethyl)-4-nitrobenzene

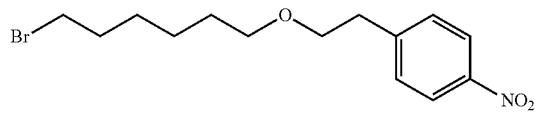 [SMILES: O=[N+]([O-])c1ccc(CCOCCCCCCBr)cc1]

The title compound was synthesized in a manner analogous to that described for Intermediate 52, using 2-(4-nitrophenyl)ethanol in place of 4-(4-nitrophenyl)butan-1-ol. ES/MS calcd. for $C_{14}H_{21}BrNO_3^+$ 330.1. Found m/z=330.1 (M+H)$^+$.

Intermediate 54: 6-((4-(4-(2,2,2-trifluoro-N-methylacetamido)phenyl)but-3-yn-1-yl)oxy)hexyl acetate

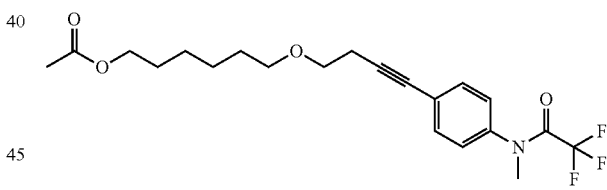

The title compound was synthesized in a manner analogous to that described for Intermediate 36, using Intermediate 26 in place of Intermediate 33. ES/MS calcd. for $C_{21}H_{27}F_3NO_4^+$ 414.2. Found m/z=414.3 (M+H)$^+$.

Intermediate 55: 6-(4-(4-(2,2,2-trifluoro-N-methylacetamido)phenyl)butoxy)hexyl acetate

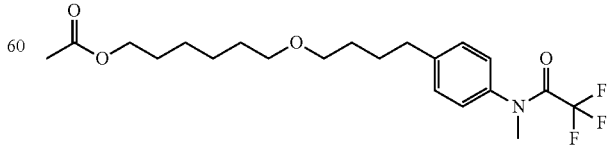

A solution of Intermediate 54 (1.2 g, 2.9 mmol) in methanol was treated with palladium on carbon (10% w/w, 50 mg).

Mixture was shaken under 50 psi of hydrogen gas for two hours and then filtered through a pad of Celite diatomaceous earth. The filtrate was concentrated under reduced pressure to provide the title compound as an oil (1.2 g, 100%). ES/MS calcd. for $C_{21}H_{31}F_3NO_4^+$ 418.2. Found m/z=418.3 (M+H)$^+$.

Intermediate 56: 6-(4-(4-(methylamino)phenyl)butoxy)hexan-1-ol

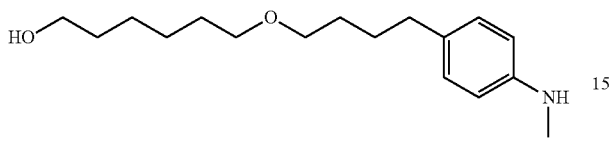

The title compound was synthesized in a manner analogous to that described for Intermediate 49, using Intermediate 55 as a substrate. ES/MS calcd. for $C_{17}H_{30}NO_2^+$ 280.2. Found m/z=280.3 (M+H)$^+$.

Intermediate 57: 4-(4-((6-((tert-butyldimethylsily)oxy)hexyl)oxy)butyl)-N-methylaniline

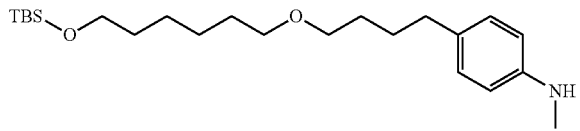

A solution of Intermediate 56 (0.92 g, 3.3 mmol) in dichloromethane was treated successively with tert-butyldimethylsilyl chloride (0.75 g, 5.0 mmol), DMAP (50 mg), and triethylamine (1.4 mL, 10 mmol). After a few minutes, additional quantities of tert-butyldimethylsilyl chloride (0.75 g, 5.0 mmol) and triethylamine (1 mL) were added. The mixture was filtered through a pad of Celite and concentrated. The residue was purified via automated flash silica gel chromatography, using a 40 g Silicycle SiliSep flash column (hexanes/ethyl acetate). Concentration of the desired fractions under reduced pressure provided the title compound as clear, colorless syrup (0.99 g, 76%). ES/MS calcd. for $C_{23}H_{44}NO_2Si^+$ 394.3. Found m/z=394.4 (M+H)$^+$.

Intermediate 58: 6-((11-hydroxyundecyl)thio)-4-((3-methoxyphenyl)amino)-8-methylquinoline-3-carboxamide

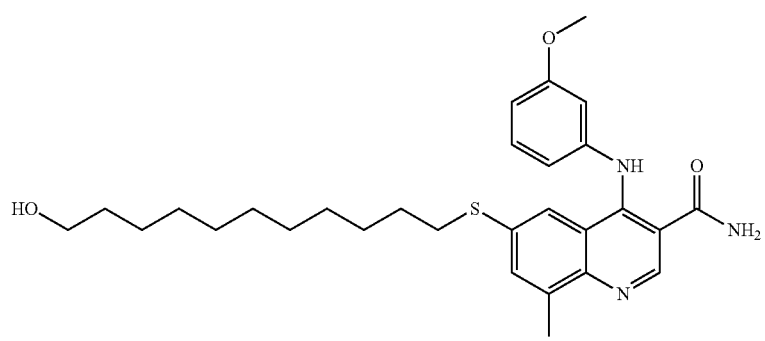 [SMILES: COc1cccc(Nc2c(C(N)=O)cnc3c(C)cc(SCCCCCCCCCCCO)cc23)c1]

The title compound was synthesized in a manner analogous to that described in Org. Lett. 2004, 6(24), 4587-4590. To a round bottom flask were added 6-iodo-4-((3-methoxyphenyl)amino)-8-methylquinoline-3-carboxamide (1.0 g, 2.31 mmol), dry dioxane (23 mL) and i-Pr$_2$NEt (0.81 mL, 4.62 mmol). Catalytic Pd$_2$(dba)$_3$ (63 mg, 0.07 mmol), Xantphos (80 mg, 0.14 mmol) and 11-mercapto-1-undecanol (494 mg, 2.42 mmol) were then added. The mixture was evacuated and backfilled with nitrogen (3 cycles). The mixture was heated to reflux for 2 h (HPLC confirmed the completion of the reaction). The reaction mixture was then allowed to reach ambient temperature followed by filtration and concentration. The crude product was used without further purification for the next step. ES/MS calcd. for $C_{29}H_{40}N_3O_3S^+$ 510.3. Found m/z=510.4 (M+H)$^+$.

Intermediate 59: 6-((3-bromophenyl)thio)-4-((3-methoxyphenyl)amino)-8-methylquinoline-3-carboxamide

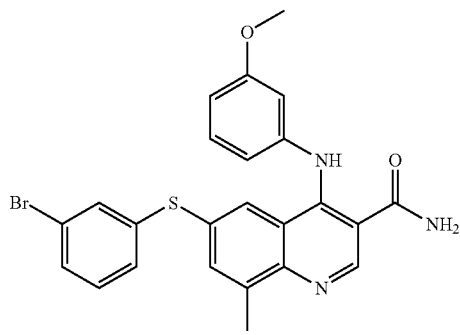 [SMILES: COc1cccc(Nc2c(C(N)=O)cnc3c(C)cc(Sc4cccc(Br)c4)cc23)c1]

The title compound was synthesized in a manner analogous to that described for Intermediate 58, using 3-bromothiophenol in place of 11-mercapto-1-undecanol. ES/MS calcd. for $C_{24}H_{21}BrN_3O_2S^+$ 494.1. Found m/z=494.1 (M+H)$^+$.

Intermediate 60: 6-((4-bromophenyl)thio)-4-((3-methoxyphenyl)amino)-8-methylquinoline-3-carboxamide

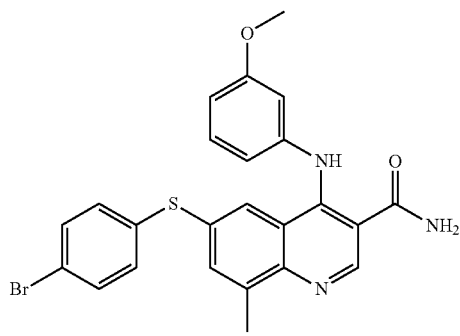 [SMILES: COc1cccc(Nc2c(C(N)=O)cnc3c(C)cc(Sc4ccc(Br)cc4)cc23)c1]

The title compound was synthesized in a manner analogous to that described for Intermediate 59, using 4-bromothiophenol in place of 11-mercapto-1-undecanol. ES/MS calcd. for $C_{24}H_{21}BrN_3O_2S^+$ 494.1. Found m/z=494.1 (M+H)$^+$

Intermediate 61: 6-((11-hydroxyundecyl)sulfonyl)-4-((3-methoxyphenyl)amino)-8-methylquinoline-3-carboxamide

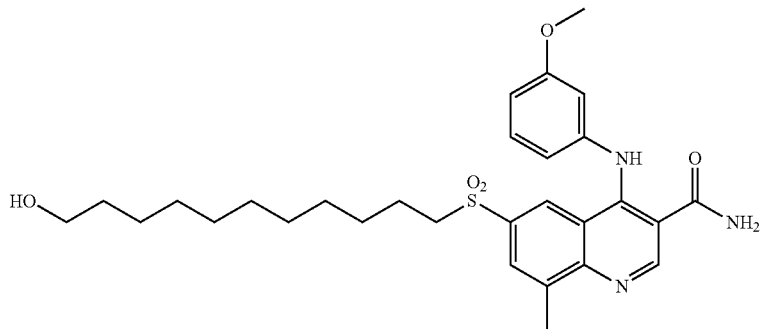 [SMILES: COc1cccc(Nc2c(C(N)=O)cnc3c(C)cc(S(=O)(=O)CCCCCCCCCCCO)cc23)c1]

To a solution of Intermediate 58 (2.31 mmol) in DMF (15 mL) was added Oxone (2.8 g). The reaction mixture was stirred at room temperature for 3 days then poured into 10% $Na_2SO_3$. Chloroform was added, the phases were separated and the aqueous phase was extracted twice with chloroform. The organic layers were combined, washed once with brine, dried over anhydrous magnesium sulfate and evaporated under reduced pressure. The crude product was purified by flash column chromatography (0-10% MeOH in dichloromethane) to give the title compound (434 mg, 35% for 2 steps). ES/MS calcd. for $C_{29}H_{40}N_3O_5S^+$ 542.3. Found m/z=542.4 (M+H)$^+$.

Intermediate 62: 6-((3-bromophenyl)sulfonyl)-4-((3-methoxyphenyl)amino)-8-methylquinoline-3-carboxamide

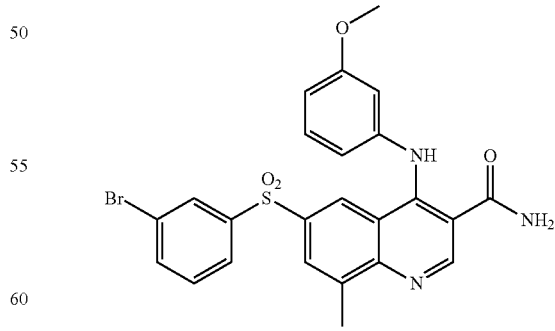

The title compound was synthesized in a manner analogous to that described for Intermediate 61, using Intermediate 59 as a substrate. ES/MS calcd. for $C_{24}H_2BrN_3O_4S^+$ 526.0. Found m/z=526.1 (M+H)$^+$.

Intermediate 63: 6-((4-bromophenyl)sulfonyl)-4-((3-methoxyphenyl)amino)-8-methylquinoline-3-carboxamide

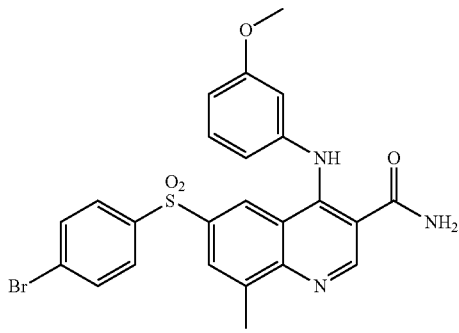 [SMILES: COc1cccc(Nc2c(C(N)=O)cnc3c(C)cc(S(=O)(=O)c4ccc(Br)cc4)cc23)c1]

The title compound was synthesized in a manner analogous to that described for Intermediate 61, using Intermediate 60 as a substrate. ES/MS calcd. for $C_{24}H_{21}BrN_3O_4S^+$ 526.0. Found m/z=526.1 (M+H)$^+$.

Intermediate 64: 6-((4'-(hydroxymethyl)-[1,1'-biphenyl]-3-yl)sulfonyl)-4-((3-methoxyphenyl)amino)-8-methylquinoline-3-carboxamide

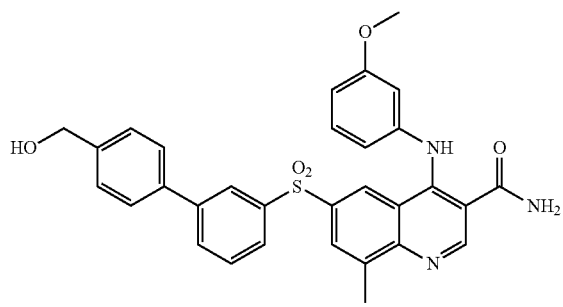 [SMILES: COc1cccc(Nc2c(C(N)=O)cnc3c(C)cc(S(=O)(=O)c4cccc(-c5ccc(CO)cc5)c4)cc23)c1]

To a suspension of Intermediate 62 (0.95 mmol) and 4-(hydroxymethyl)phenylboronic acid (290 mg, 1.90 mmol) in DME (10 mL) at room temperature was added 2 M Na$_2$CO$_3$ (1.4 mL, 2.85 mmol) and PdCl$_2$(PPh$_3$)$_2$ (33 mg, 0.005 mmol). The reaction mixture was stirred at reflux for 2 h and then cooled to room temperature. After the addition of 60 mL of chloroform, a white precipitate formed which was collected by filtration. The crude product was purified by flash column chromatography (0-15% MeOH in dichloromethane) to give the title compound (357 mg, 68% for 3 steps). ES/MS calcd. for $C_{31}H_{28}N_3O_5S^+$ 554.2. Found m/z=554.3 (M+H)$^+$.

Intermediate 65: 6-((4'-(hydroxymethyl)-[1,1'-biphenyl]-4-yl)sulfonyl)-4-((3-methoxyphenyl)amino)-8-methylquinoline-3-carboxamide

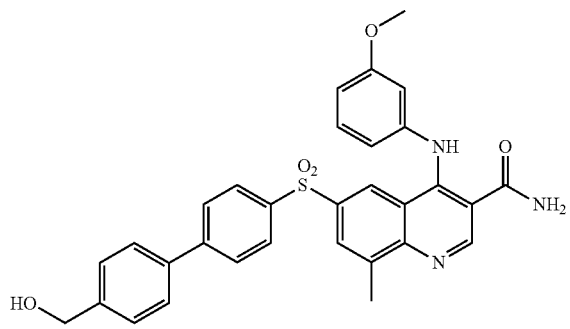 [SMILES: COc1cccc(Nc2c(C(N)=O)cnc3c(C)cc(S(=O)(=O)c4ccc(-c5ccc(CO)cc5)cc4)cc23)c1]

The title compound was synthesized in a manner analogous to that described for Intermediate 64, using Intermediate 63 (1.38 mmol) as substrate. The crude product was triturated in 15 mL of ethyl acetate for 10 min. After cooling to room temperature, the suspension was recovered by filtration and washed with ethyl acetate to give the title compound as a yellowish solid (591 mg, 77% for 3 steps). ES/MS calcd. for $C_{31}H_{28}N_3O_5S^+$ 554.2. Found m/z=554.3 (M+H)$^+$.

Intermediate 66: 6-((4'-(3-hydroxypropyl)-[1,1'-biphenyl]-4-yl)sulfonyl)-4-((3-methoxyphenyl)amino)-8-methylquinoline-3-carboxamide

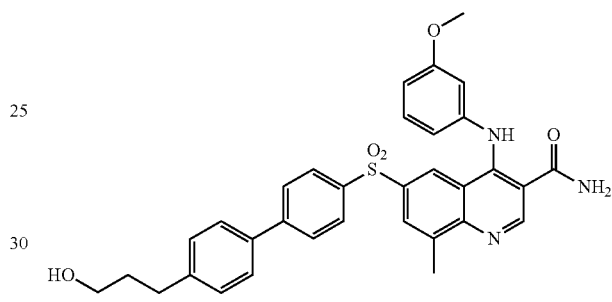

The title compound was synthesized in a manner analogous to that described for Intermediate 65, using 4-(3-hydroxypropyl)phenylboronic acid in place of 4-(hydroxymethyl)phenylboronic acid. ES/MS calcd. for $C_{33}H_{32}N_3O_5S^+$ 582.2. Found m/z=582.3 (M+H)$^+$.

Intermediate 67: 6-((4'-(3-hydroxypropyl)-(1,1'-biphenyl]-3-yl)sulfonyl)-4-((3-methoxyphenyl)amino)-8-methylquinoline-3-carboxamide

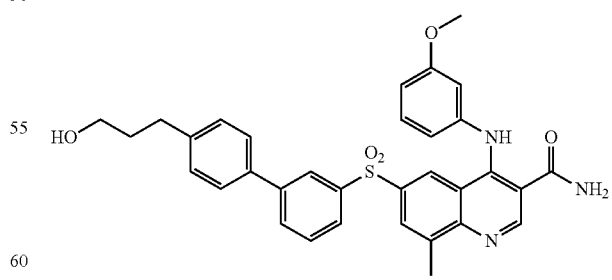

The title compound was synthesized in a manner analogous to that described for Intermediate 64, using 4-(3-hydroxypropyl)phenylboronic acid in place of 4-(hydroxymethyl)phenylboronic acid. ES/MS calcd. for $C_{33}H_{32}N_3O_5S^+$ 582.2. Found m/z=582.3 (M+H)$^+$.

Intermediate 68: 6-((4'-(5-hydroxypentyl)-(1,1'-biphenyl]-4-yl)sulfonyl)-4-((3-methoxyphenyl)amino)-8-methylquinoline-3-carboxamide

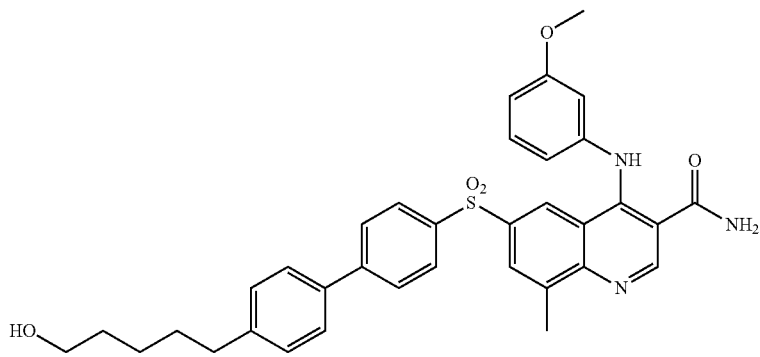 [SMILES: COc1cccc(Nc2c(C(N)=O)cnc3c(C)cc(S(=O)(=O)c4ccc(-c5ccc(CCCCCO)cc5)cc4)cc23)c1]

The title compound was synthesized in a manner analogous to that described for Intermediate 65, using 3-[4-(4,4,5,5-tetramethyl-[1,3,2]dioxaborolan-2-yl)-phenyl]pentan-1-ol in place of 4-(hydroxymethyl)phenylboronic acid. ES/MS calcd. for $C_{35}H_{36}N_3O_5S^+$ 610.2. Found m/z=610.3 (M+H)$^+$.

Intermediate 69: 6-((4'-(5-hydroxypentyl)-(1,1'-biphenyl]-3-yl)sulfonyl)-4-((3-methoxyphenyl)amino)-8-methylquinoline-3-carboxamide

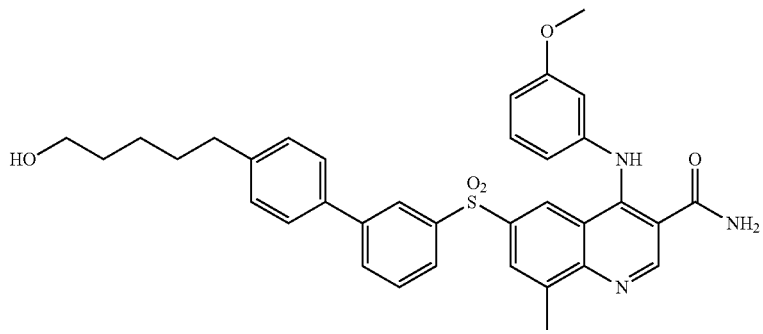 [SMILES: COc1cccc(Nc2c(C(N)=O)cnc3c(C)cc(S(=O)(=O)c4cccc(-c5ccc(CCCCCO)cc5)c4)cc23)c1]

The title compound was synthesized in a manner analogous to that described for Intermediate 64, using 4-(5-hydroxypentyl)phenylboronic acid in place of 4-(hydroxymethyl)phenylboronic acid. ES/MS calcd. for $C_{35}H_{36}N_3O_5S^+$ 610.2. Found m/z=610.3 (M+H)$^+$.

Intermediate 70: 6-[[3-[(8-Hydroxyoctyl)carbamoyl]phenyl]sulfonyl]-4-[(3-methoxyphenyl)amino]-8-methylquinoline-3-carboxamide

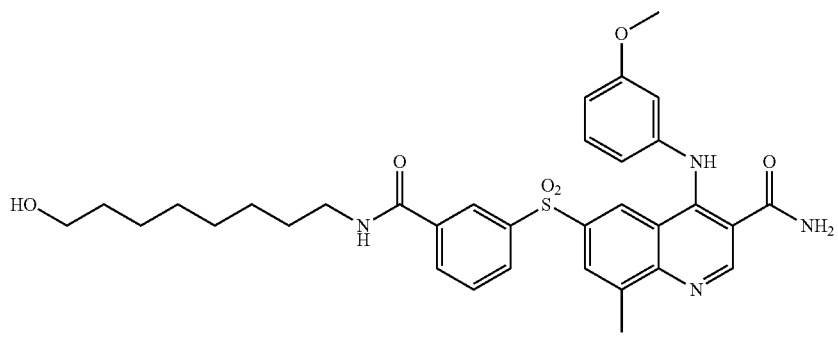 [SMILES: COc1cccc(Nc2c(C(N)=O)cnc3c(C)cc(S(=O)(=O)c4cccc(C(=O)NCCCCCCCCO)c4)cc23)c1]

HATU (116 mg, 0.305 mmol) and DIEA (0.106 mL, 0.61 mmol) were added to a stirring solution of 3-[[3-carbamoyl-4-[(3-methoxyphenyl)amino]-8-methylquinolin-6-yl]sulfonyl]benzoic acid (100 mg, 0.203 mmol) in DMF (2 mL) at rt. After 5 min 8-aminooctanol (0.35 mL, 0.244 mmol) was added and the resulting solution was stirred for an additional 1 h. The reaction mixture was poured into 10% (w/v) citric acid (50 mL) and the aqueous layer was extracted with EtOAc (3×30 mL). The combined organic layers were washed with H$_2$O (2×100 mL), brine (100 mL), dried over Na$_2$SO$_4$ (s), and concentrated to give a brown semi-solid (129 mg). Chromatography (9:1, CH$_2$Cl$_2$/MeOH, 0.1% Et$_3$N) afforded the title compound (120 mg, 95%) as a yellow solid. ES/MS calcd. for C$_{33}$H$_{39}$N$_4$O$_6$Si$^+$ 619.3. Found m/z=619.3 (M+H)$^+$.

Intermediate 71: 6-[[3-[(6-Hydroxyhexyl)carbamoyl]phenyl]sulfonyl]-4-[(3-methoxyphenyl)amino]-8-methylquinoline-3-carboxamide

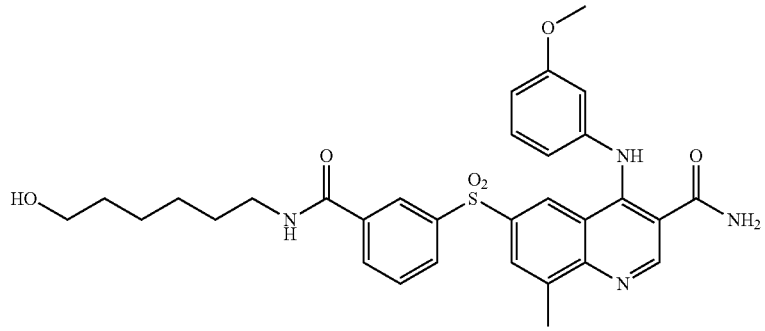 [SMILES: COc1cccc(Nc2c(C(N)=O)cnc3c(C)cc(S(=O)(=O)c4cccc(C(=O)NCCCCCCO)c4)cc23)c1]

The title compound was synthesized in a manner analogous to that described for Intermediate 70, using 6-aminohexanol in place of 8-aminooctanol. ES/MS calcd. for C$_{31}$H$_{35}$N$_4$O$_6$S$^+$ 591.2. Found m/z=591.3 (M+H)$^+$.

Intermediate 72: 6-[[3-[[4-(5-Hydroxypent-1-yn-1-yl)phenyl]carbamoyl]phenyl]sulfonyl]-4-[(3-methoxyphenyl)amino]-8-methylquinoline-3-carboxamide

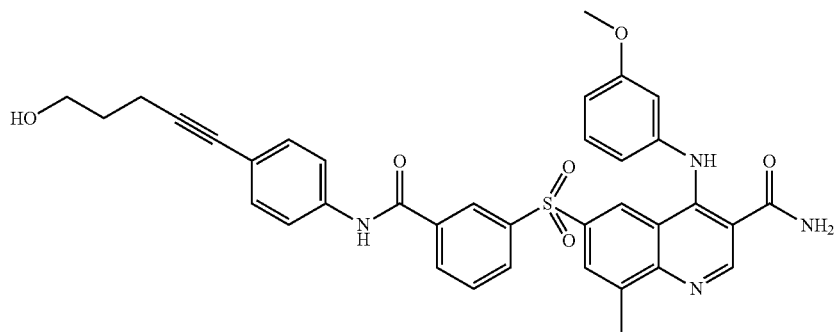 [SMILES: COc1cccc(Nc2c(C(N)=O)cnc3c(C)cc(S(=O)(=O)c4cccc(C(=O)Nc5ccc(C#CCCCO)cc5)c4)cc23)c1]

The title compound was synthesized in a manner analogous to that described for Intermediate 70, using Intermediate 31 in place of 8-aminooctanol. ES/MS calcd. for C$_{36}$H$_{33}$N$_4$O$_6$S$^+$ 649.2. Found m/z=649.3 (M+H)$^+$.

Intermediate 73: 6-((3-((4-(5-hydroxypent-1-yn-1-yl)phenyl)(methyl)carbamoyl)phenyl)sulfonyl)-4-((3-methoxyphenyl)amino)-8-methylquinoline-3-carboxamide

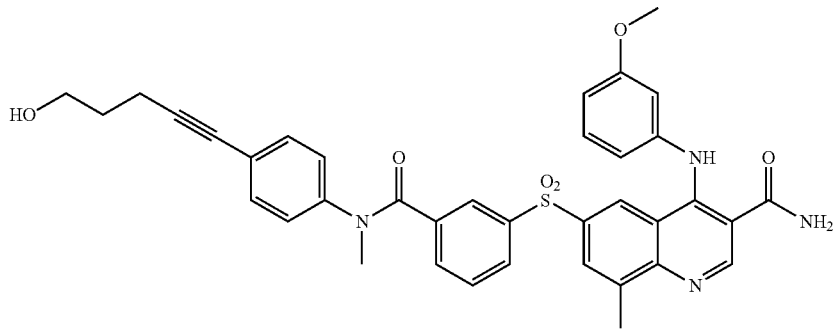 [SMILES: COc1cccc(Nc2c(C(N)=O)cnc3c(C)cc(S(=O)(=O)c4cccc(C(=O)N(C)c5ccc(C#CCCCO)cc5)c4)cc23)c1]

Title compound was synthesized in a manner analogous to Intermediate 70 using Intermediate 49 in place of 8-aminooctanol. ES/MS calcd. for $C_{37}H_{34}N_4O_6S$ 662.2. Found m/z=663 (M+H)⁺.

Intermediate 74: 6-((3-((4-(5-hydroxypent-1-yn-1-yl)-2-methylphenyl)carbamoyl)phenyl)sulfonyl)-4-((3-methoxyphenyl)amino)-8-methylquinoline-3-carboxamide

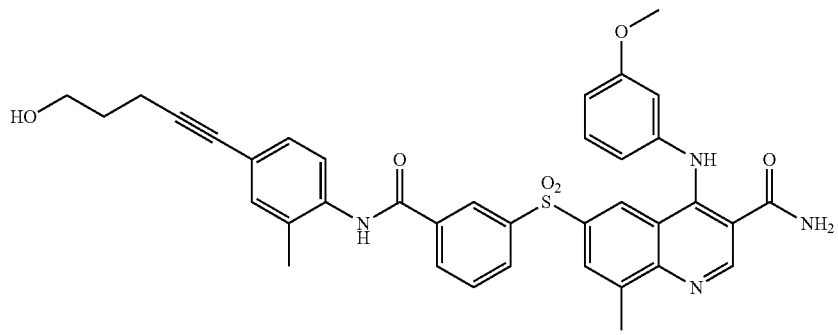 [SMILES: COc1cccc(Nc2c(C(N)=O)cnc3c(C)cc(S(=O)(=O)c4cccc(C(=O)Nc5ccc(C#CCCCO)cc5C)c4)cc23)c1]

Title compound was synthesized in a manner analogous to Intermediate 70 using Intermediate 50 in place of 8-aminooctanol. ES/MS calcd. for $C_{37}H_{34}N_4O_6S$ 662.2. Found m/z=663 (M+H)⁺.

Intermediate 75: 6-((3-((4-(5-hydroxypent-1-yn-1-yl)-3-methylphenyl)carbamoyl)phenyl)sulfonyl)-4-((3-methoxyphenyl)amino)-8-methylquinoline-3-carboxamide

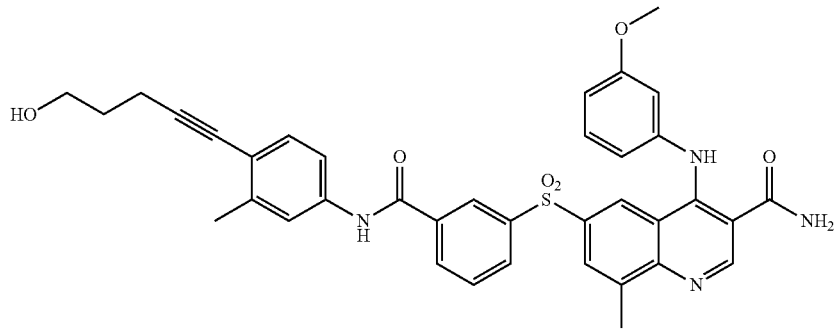 [SMILES: COc1cccc(Nc2c(C(N)=O)cnc3c(C)cc(S(=O)(=O)c4cccc(C(=O)Nc5ccc(C#CCCCO)c(C)c5)c4)cc23)c1]

The title compound was synthesized in a manner analogous to that described in Intermediate 70, using Intermediate 51 in place of Intermediate 70. ES/MS calcd. for $C_{37}H_{34}N_4O_6S$ 662.2. Found m/z=663 (M+H)⁺.

Intermediate 76: 6-((3-((4-(6-hydroxyhex-1-yn-1-yl)phenyl)carbamoyl)phenyl)sulfonyl)-4-((3-methoxyphenyl)amino)-8-methylquinoline-3-carboxamide

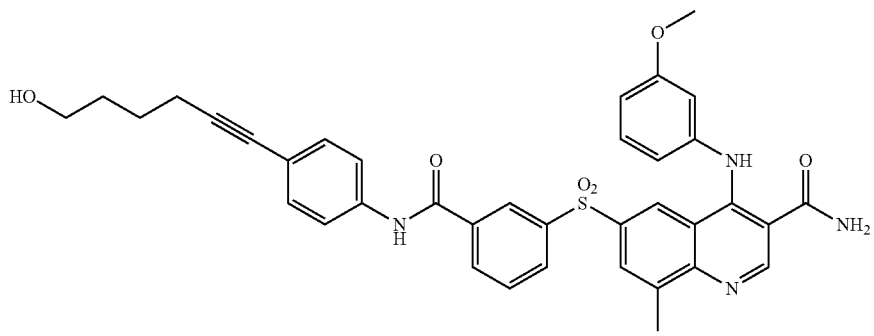 [SMILES: COc1cccc(Nc2c(C(N)=O)cnc3c(C)cc(S(=O)(=O)c4cccc(C(=O)Nc5ccc(C#CCCCCO)cc5)c4)cc23)c1]

The title compound was synthesized in a manner analogous to that described for Intermediate 70, using Intermediate 48 in place of 8-aminooctanol. ES/MS calcd. for $C_{37}H_{35}N_4O_6S^+$ 663.2. Found m/z=663.3 (M+H)$^+$.

Intermediate 77: 6-((3-((3-(5-hydroxypent-1-yn-1-yl)phenyl)carbamoyl)phenyl)sulfonyl)-4-((3-methoxyphenyl)amino)-8-methylquinoline-3-carboxamide

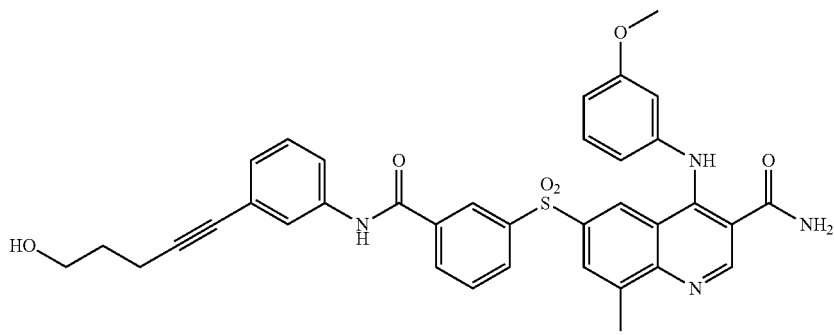 [SMILES: COc1cccc(Nc2c(C(N)=O)cnc3c(C)cc(S(=O)(=O)c4cccc(C(=O)Nc5cccc(C#CCCCO)c5)c4)cc23)c1]

The title compound was synthesized in a manner analogous to that described for Intermediate 70, using Intermediate 47 in place of 8-aminooctanol. ES/MS calcd. for $C_{36}H_{33}N_4O_6S^+$ 649.2. Found m/z=649.3 (M+H)$^+$.

Intermediate 78: 6-((3-((4-(4-((6-((tert-butyldimethylsilyl)oxy)hexyl)oxy)butyl)phenyl)(methyl)carbamoyl)phenyl)sulfonyl)-4-((3-methoxyphenyl)amino)-8-methylquinoline-3-carboxamide

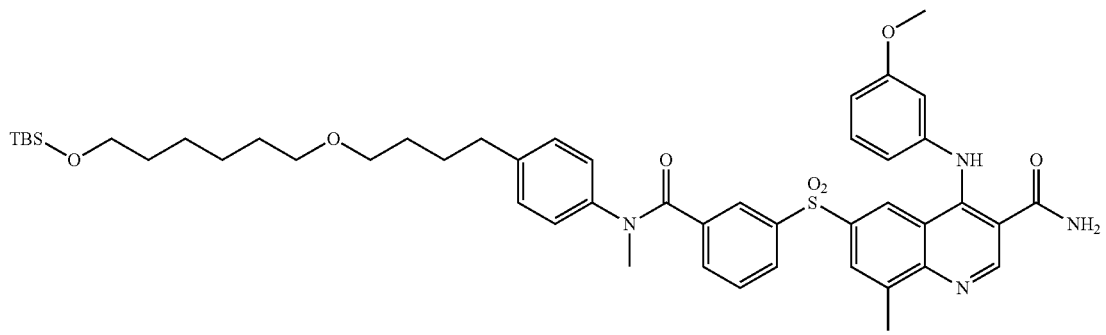

The title compound was synthesized in a manner analogous to that described for Intermediate 70, using Intermediate 57 in place of 8-aminooctanol. ES/MS calcd. for $C_{48}H_{63}N_4O_7SSi^+$ 867.4. Found m/z=867.6 (M+H)$^+$.

Intermediate 79: 6-((3-((4-(4-((6-hydroxyhexyl)oxy)butyl)phenyl)(methyl)carbamoyl)phenyl)sulfonyl)-4-((3-methoxyphenyl)amino)-8-methylquinoline-3-carboxamide

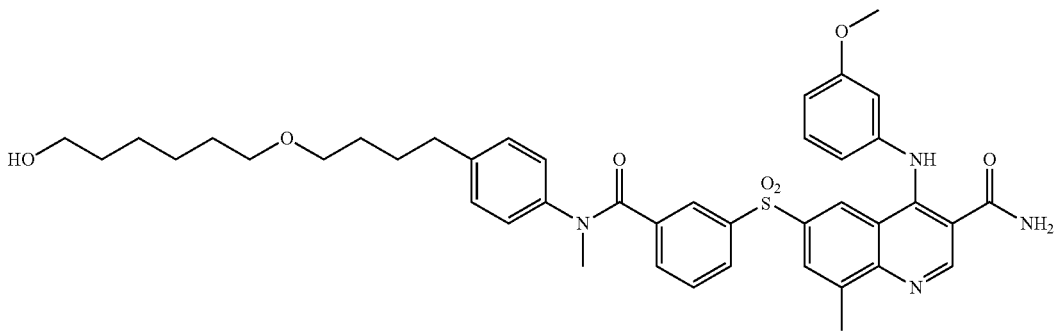 [SMILES: COc1cccc(Nc2c(C(N)=O)cnc3c(C)cc(S(=O)(=O)c4cccc(C(=O)N(C)c5ccc(CCCCOCCCCCCO)cc5)c4)cc23)c1]

The title compound was synthesized in a manner analogous to that described for Intermediate 5, using Intermediate 78 as a substrate. ES/MS calcd. for $C_{42}H_{49}N_4O_7S^+$ 753.3. Found m/z=753.4 (M+H)$^+$.

Intermediate 80: 6-[[3-[[6-Hydroxyhexyl)(methyl)carbamoyl]phenyl]sulfonyl]-4-[(3-methoxyphenyl)amino]-8-methylquinoline-3-carboxamide

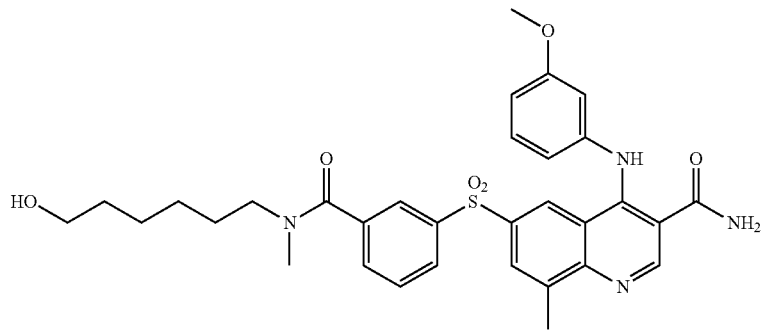 [SMILES: COc1cccc(Nc2c(C(N)=O)cnc3c(C)cc(S(=O)(=O)c4cccc(C(=O)N(C)CCCCCCO)c4)cc23)c1]

The title compound was synthesized in a manner analogous to that described for Intermediate 70, using Intermediate 21 in place of 8-aminooctanol. ES/MS calcd. for $C_{32}H_{37}N_4O_6S^+$ 605.2. Found m/z=605 (M+H)$^+$.

Intermediate 81: 6-((3-((4'-(hydroxymethyl)-[1,1'-biphenyl]-4-yl)carbamoyl)phenyl)sulfonyl)-4-((3-methoxyphenyl)amino)-8-methylquinoline-3-carboxamide

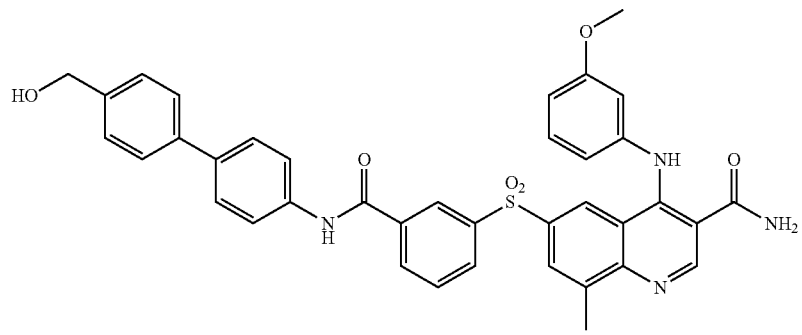 [SMILES: COc1cccc(Nc2c(C(N)=O)cnc3c(C)cc(S(=O)(=O)c4cccc(C(=O)Nc5ccc(-c6ccc(CO)cc6)cc5)c4)cc23)c1]

The title compound was synthesized in a manner analogous to that described for Intermediate 70, using (4'-amino-[1,1'-biphenyl]-4-yl)methanol in place of 8-aminooctanol. ES/MS calcd. for $C_{38}H_{33}N_4O_6S^+$ 673.2. Found m/z=673.2 (M+H)$^+$.

Intermediate 82: tert-Butyl 4-[3-[[3-carbamoyl-4-[(3-methoxyphenyl)amino]-8-methylquinolin-6-yl]sulfonyl]benzamido]phenethylcarbamate

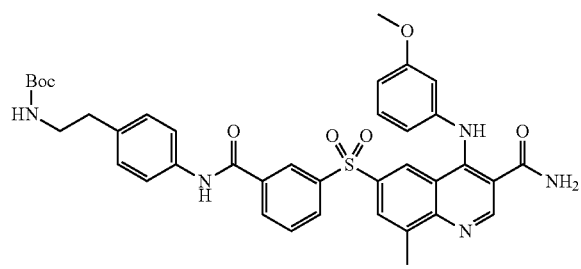 [SMILES: COc1cccc(Nc2c(C(N)=O)cnc3c(C)cc(S(=O)(=O)c4cccc(C(=O)Nc5ccc(CCNC(=O)OC(C)(C)C)cc5)c4)cc23)c1]

The title compound was synthesized in a manner analogous to that described for Intermediate 70, using Intermediate 27 in place of 8-aminooctanol. $^1$H NMR (400 MHz, DMSO-d$_6$) δ 10.80 (s, 1H), 10.46 (s, 1H), 9.09 (s, 1H), 8.25-8.39 (m, 3H), 8.21 (d, J=7.9 Hz, 1H), 8.04 (s, 1H), 7.87 (d, J=8.0 Hz, 1H), 7.72-7.80 (m, 2H), 7.69 (d, J=8.4 Hz, 2H), 7.20 (d, J=8.4 Hz, 2H), 7.11 (t, J=8.0 Hz, 1H), 6.88 (t, J=5.4 Hz, 1H), 6.60-6.68 (m, 2H), 6.52 (d, J=8.3 Hz, 1H), 3.60 (s, 3H), 3.08-3.18 (m, 2H), 2.65-2.73 (m, 5H), 1.40 (s, 9H); ES/MS calcd. for $C_{38}H_{40}N_6O_7S^+$ 710.3. Found m/z=710.3 (M+H)$^+$.

Intermediate 83: tert-butyl 4-(2-(3-((3-carbamoyl-4-((3-methoxyphenyl)amino)-8-methylquinolin-6-yl)sulfonyl)-N-methylbenzamido)ethoxy)phenethylcarbamate

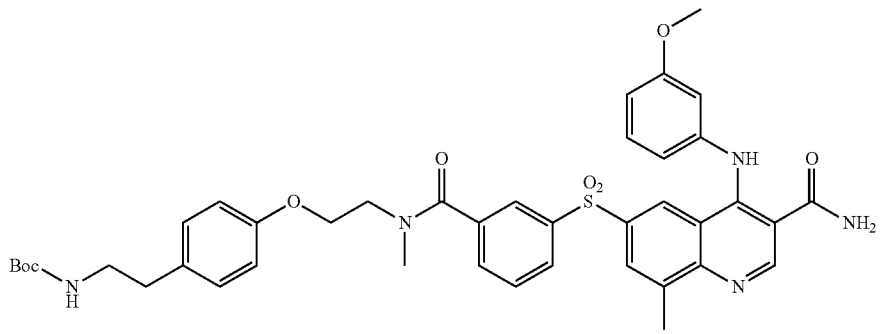 [SMILES: COc1cccc(Nc2c(C(N)=O)cnc3c(C)cc(S(=O)(=O)c4cccc(C(=O)N(C)CCOc5ccc(CCNC(=O)OC(C)(C)C)cc5)c4)cc23)c1]

The title compound was synthesized in a manner analogous to that described for Intermediate 70, using Intermediate 28 in place of 8-aminooctanol. ES/MS calcd. for $C_{41}H_{46}N_5O_8S^+$ 768.3. Found m/z=768.3 (M+H)$^+$.

Intermediate 84: 6-((3-(4-((6-((tert-butyldimethylsilyl)oxy)hexyl)oxy)piperidine-1-carbonyl)phenyl)sulfonyl)-4-((3-methoxyphenyl)amino)-8-methylquinoline-3-carboxamide

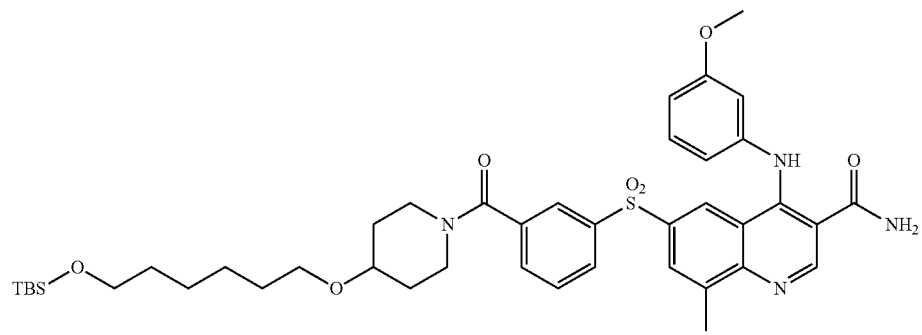

The title compound was synthesized in a manner analogous to that described for Intermediate 70, using Intermediate 23 in place of 8-aminooctanol. ES/MS calcd. for $C_{42}H_{57}N_4O_7SSi^+$ 789.4. Found m/z=789.3 (M+H)$^+$.

Intermediate 85: 6-((3-(4-(6-((tert-butyldimethylsilyl)oxy)hexyl)piperazine-1-carbonyl)phenyl)sulfonyl)-4-((3-methoxyphenyl)amino)-8-methylquinoline-3-carboxamide

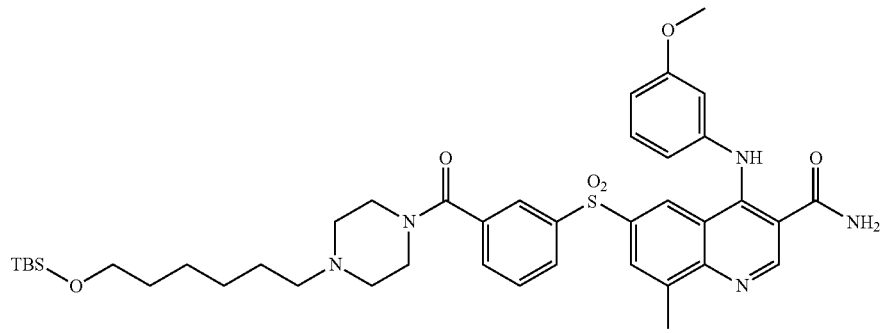

The title compound was synthesized in a manner analogous to that described for Intermediate 70, using Intermediate 25 in place of 8-aminooctanol. ES/MS calcd. for $C_{41}H_{56}N_5O_6SSi^+$ 774.4. Found m/z=774.5 (M+H)$^+$.

Intermediate 86: methyl 4-(4'-(3-((3-carbamoyl-4-((3-methoxyphenyl)amino)-8-methylquinolin-6-yl)sulfonyl)benzamido)-[1,1'-biphenyl]-4-yl)butanoate

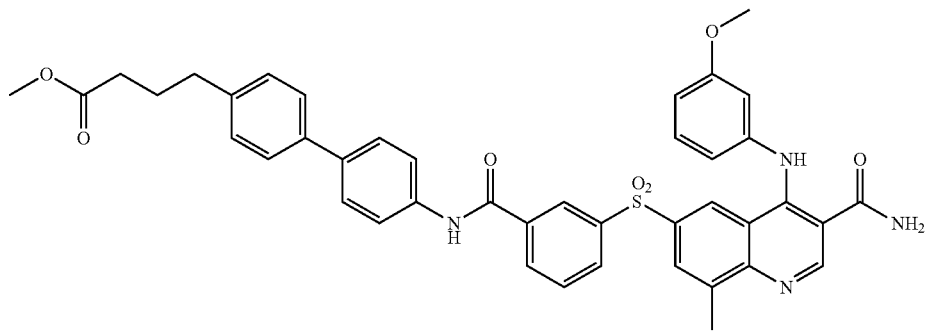 [SMILES: COC(=O)CCCc1ccc(-c2ccc(NC(=O)c3cccc(S(=O)(=O)c4cc(C)c5ncc(C(N)=O)c(Nc6cccc(OC)c6)c5c4)c3)cc2)cc1]

The title compound was synthesized in a manner analogous to that described for Intermediate 70, using Intermediate 29 in place of 8-aminooctanol. ES/MS calcd. for $C_{42}H_{39}N_4O_7S^+$ 743.3. Found m/z=743.4 (M+H)$^+$.

Intermediate 87: methyl 4-(3'-(3-((3-carbamoyl-4-((3-methoxyphenyl)amino)-8-methylquinolin-6-yl)sulfonyl)benzamido)-[1,1'-biphenyl]-4-yl)butanoate

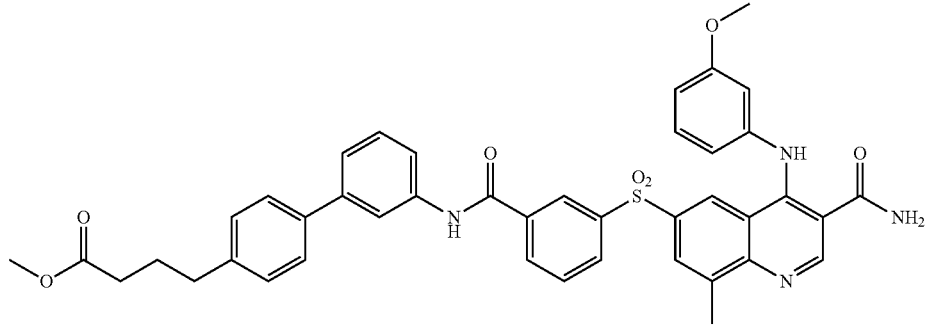 [SMILES: COC(=O)CCCc1ccc(-c2cccc(NC(=O)c3cccc(S(=O)(=O)c4cc(C)c5ncc(C(N)=O)c(Nc6cccc(OC)c6)c5c4)c3)c2)cc1]

The title compound was synthesized in a manner analogous to that described for Intermediate 70, using Intermediate 30 in place of 8-aminooctanol. ES/MS calcd. for $C_{42}H_{39}N_4O_7S^+$ 743.3. Found m/z=743.4 (M+H)$^+$.

Intermediate 88: 6-((3-(4-((6-hydroxyhexyl)oxy)piperidine-1-carbonyl)phenyl)sulfonyl)-4-((3-methoxyphenyl)amino)-8-methylquinoline-3-carboxamide

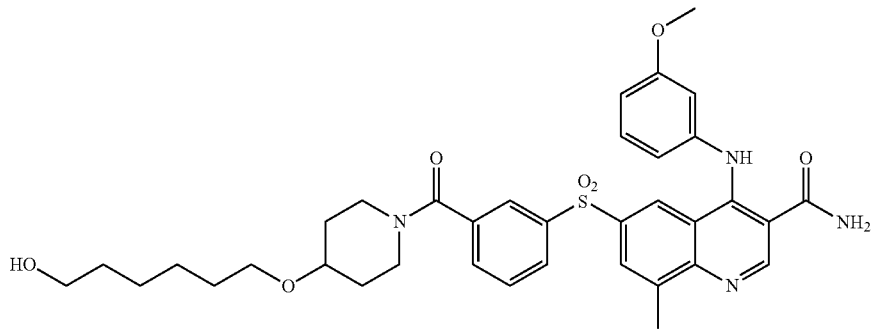 [SMILES: COc1cccc(Nc2c(C(N)=O)cnc3c(C)cc(S(=O)(=O)c4cccc(C(=O)N5CCC(OCCCCCCO)CC5)c4)cc23)c1]

The title compound was synthesized in a manner analogous to that described for Intermediate 5, using Intermediate 84 as a substrate. ES/MS calcd. for $C_{36}H_{43}N_4O_7S^+$ 675.3. Found m/z=675.2 (M+H)$^+$.

Intermediate 89: 6-((3-(4-(6-hydroxyhexyl)piperazine-1-carbonyl)phenyl)sulfonyl)-4-((3-methoxyphenyl)amino)-8-methylquinoline-3-carboxamide

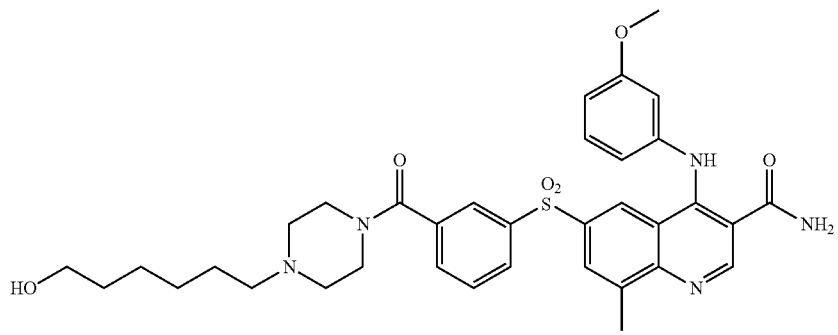 [SMILES: COc1cccc(Nc2c(C(N)=O)cnc3c(C)cc(S(=O)(=O)c4cccc(C(=O)N5CCN(CCCCCCO)CC5)c4)cc23)c1]

The title compound was synthesized in a manner analogous to that described for Intermediate 5, using Intermediate 85 as a substrate. ES/MS calcd. for $C_{35}H_{42}N_5O_6S^+$ 660.3. Found m/z=660.3 (M+H)$^+$.

Intermediate 90: 6-((3-((4'-(4-hydroxybutyl)-[1,1'-biphenyl]-4-yl)carbamoyl)phenyl)sulfonyl)-4-((3-methoxyphenyl)amino)-8-methylquinoline-3-carboxamide

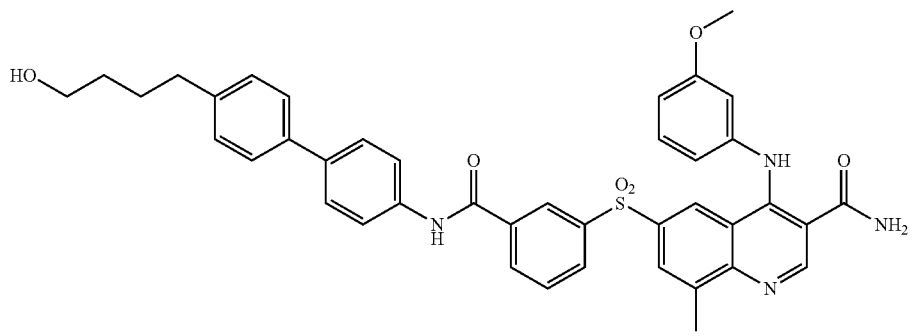 [SMILES: COc1cccc(Nc2c(C(N)=O)cnc3c(C)cc(S(=O)(=O)c4cccc(C(=O)Nc5ccc(-c6ccc(CCCCO)cc6)cc5)c4)cc23)c1]

Solid LiAlH$_4$ (29 mg, 0.713 mmol) was added to a stirring solution of Intermediate 86 (265 mg, 0.357 mmol) in THF (5 mL) at 0° C. After stirring for an hour H$_2$O (0.029 mL), 15% (w/v) NaOH (0.029 mL), and H$_2$O (0.087 mL) were added in order then stirred for additional 1 h. The resulting suspension was diluted with EtOAc (10 mL) and the organic layer was washed with H$_2$O (15 mL), brine (15 mL), dried over Na$_2$SO$_4$, and concentrated to give crude alcohol (224 mg) as yellow solid. Chromatography (9:1, CH$_2$Cl$_2$/MeOH) afforded the title compound (110 mg, 43%) as yellow solid. ES/MS calcd. for C$_{41}$H$_{39}$N$_4$O$_6$S$^+$ 715.3. Found m/z=715.4 (M+H)$^+$.

Intermediate 91: 6-((3-((4'-(4-hydroxybutyl)-(1,1'-biphenyl]-3-yl)carbamoyl)phenyl)sulfonyl)-4-((3-methoxyphenyl)amino)-8-methylquinoline-3-carboxamide

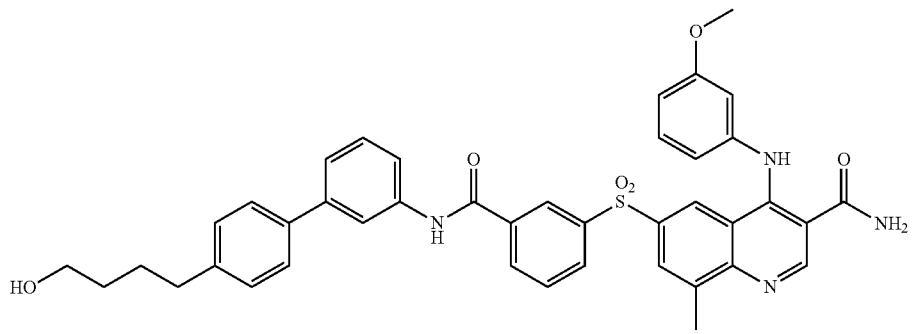 [SMILES: COc1cccc(Nc2c(C(N)=O)cnc3c(C)cc(S(=O)(=O)c4cccc(C(=O)Nc5cccc(-c6ccc(CCCCO)cc6)c5)c4)cc23)c1]

The title compound was synthesized in a manner analogous to that described for Intermediate 90, using Intermediate 87 as a substrate. ES/MS calcd. for C$_{41}$H$_{39}$N$_4$O$_6$S$^+$ 715.3. Found m/z=715.4 (M+H)$^+$.

Intermediate 92: 6-[[3-[[4-(5-Hydroxypentyl)phenyl]carbamoyl]phenyl]sulfonyl]-4-((3-methoxyphenyl)amino]-8-methylquinoline-3-carboxamide

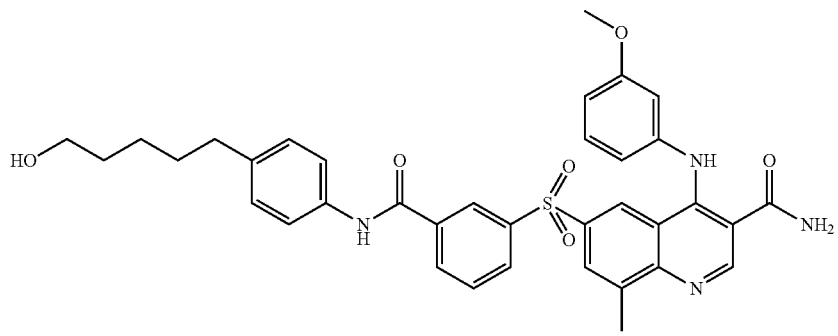 [SMILES: COc1cccc(Nc2c(C(N)=O)cnc3c(C)cc(S(=O)(=O)c4cccc(C(=O)Nc5ccc(CCCCCO)cc5)c4)cc23)c1]

Pd(OH)$_2$ (20% on activated carbon, 250 mg) was added to a solution of Intermediate 72 (250 mg, 0.38 mmol) in MeOH/THF (1:1) (10 mL). The solution was hydrogenated via balloon for 5 h. The Pd was filtered through a plug of celite. The filtrate was then concentrated in vacuo to afford the title compound as a yellow solid (260 mg). ES/MS calcd. for C$_{36}$H$_{37}$N$_4$O$_6$S$^+$ 653.2. Found m/z=653.3 (M+H)$^+$.

Intermediate 93: 6-[3-[[4-(2-Hydroxyethyl)piperazin-1-yl]carbonyl]-benzenesulfonyl]-4-(3-methoxyphenylamino)-8-methylquinoline-3-carboxyamide

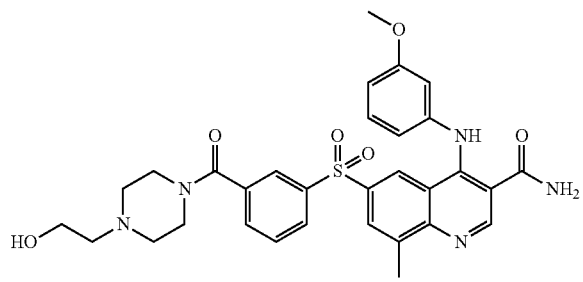 [SMILES: COc1cccc(Nc2c(C(N)=O)cnc3c(C)cc(S(=O)(=O)c4cccc(C(=O)N5CCN(CCO)CC5)c4)cc23)c1]

To a mixture of 2-(piperazin-1-yl)ethanol (160 mg, 1.22 mmol), 3-[3-carbamoyl-4-(3-methoxyphenylamino)-8-methylquinoline-6-sulfonyl]benzoic acid (500 mg, 1.02 mmol), and BOP (540 mg, 1.22 mmol) in 3 mL DMF, TEA (0.34 mL, 3.06 mmol) was added at rt. The reaction mixture was stirred over night. Water was added, and the precipitate was collected by filtration. The filter cake was washed with $CH_2Cl_2$, and dried, giving the title compound. ES/MS calcd. for $C_{31}H_{34}N_5O_6S^+$ 604.2. Found m/z=604.2 (M+H)$^+$.

Intermediate 94: 6-[[3-[[4-(2-Aminoethyl)phenyl]carbamoyl]phenyl]sulfonyl]-4-[(3-methoxyphenyl)amino]-8-methylquinoline-3-carboxamide

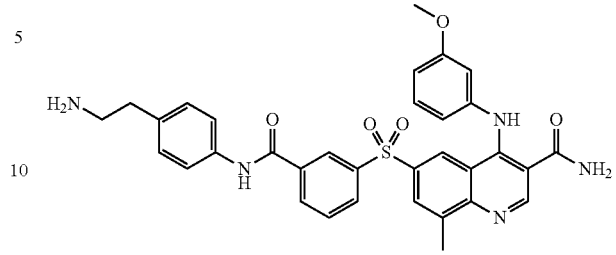

TFA (0.5 mL) was added dropwise to a suspension of Intermediate 82 (382 mg, 0.538 mmol) in $CH_2Cl_2$ (5 mL) at rt. After stirring for 5 h, the reaction was concentrated in vacuo to give a brown residue. A portion was treated with silica-carbonate resin and used in the following step without further purification. ES/MS calcd. for $C_{33}H_{32}N_5O_5S^+$ 610.2. Found m/z=610.2 (M+H)$^+$.

Intermediate 95: 6-((3-((2-(4-(2-aminoethyl)phenoxy)ethyl)(methyl)carbamoyl)phenyl)sulfonyl)-4-((3-methoxyphenyl)amino)-8-methylquinoline-3-carboxamide

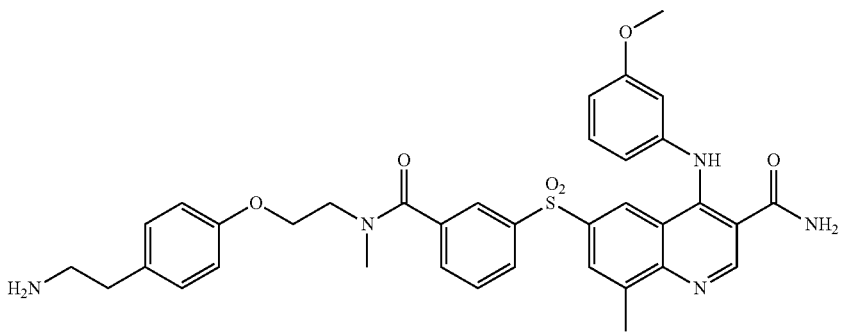 [SMILES: COc1cccc(Nc2c(C(N)=O)cnc3c(C)cc(S(=O)(=O)c4cccc(C(=O)N(C)CCOc5ccc(CCN)cc5)c4)cc23)c1]

The title compound was synthesized in a manner analogous to that described for Intermediate 94, using Intermediate 83 as a substrate. ES/MS calcd for $C_{36}H_{38}N_5O_6S^+$ 668.25. Found m/z=668.2 (M+H)$^+$.

Intermediate 96: 4-((3-methoxyphenyl)amino)-8-methyl-6-((3-(piperazine-1-carbonyl)phenyl)sulfonyl)quinoline-3-carboxamide

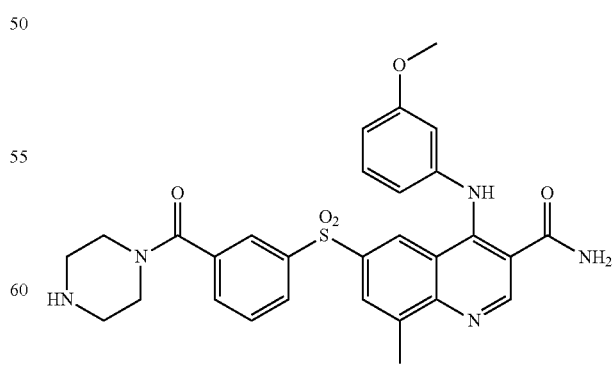

The title compound was synthesized in a manner analogous to that described for Intermediate 70, using piperazine in place of 8-aminooctanol. ES/MS calcd. for $C_{29}H_{30}N_5O_5S^+$ 560.2. Found m/z=560.2 (M+H)$^+$.

Intermediate 97: 4-((3-methoxyphenyl)amino)-8-methyl-6-((3-(4-(3-(2-oxopropyl)benzoyl)piperazine-1-carbonyl)phenyl)sulfonyl)quinoline-3-carboxamide

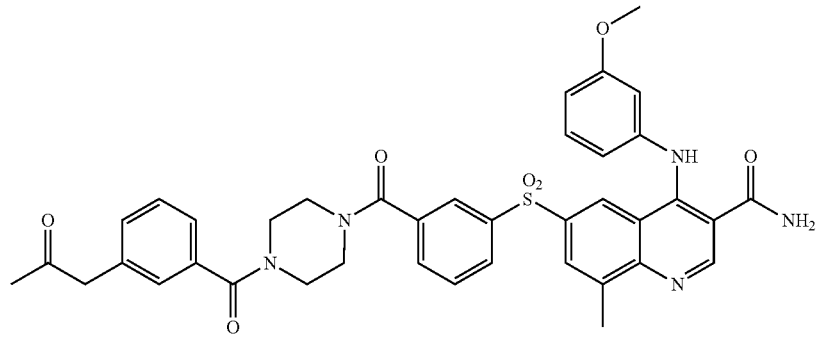 [SMILES: COc1cccc(Nc2c(C(N)=O)cnc3c(C)cc(S(=O)(=O)c4cccc(C(=O)N5CCN(C(=O)c6cccc(CC(C)=O)c6)CC5)c4)cc23)c1]

HATU (82 mg, 0.217 mmol), DIEA (0.103 mL, 0.59 mmol), and 3-(2-oxopropyl)benzoic acid (39 mg, 0.217 mmol) were added to a stirring solution of Intermediate 96 (110 mg, 0.197 mmol) in DMF (2 mL) at rt. The reaction mixture was stirred for 40 min then pour into $H_2O$ (50 mL). The resulting precipitate was filtered, washed with $H_2O$, and dried to give crude di-amide (256 mg). Chromatography (9:1, $CH_2Cl_2$/MeOH) afforded the title compound (85 mg, 64%) as a yellow solid. ES/MS calcd. for $C_{39}H_{38}N_5O_7S^+$ 720.3. Found m/z=720.2 $(M+H)^+$.

Intermediate 98: 6-((3-((3-(5-bromopent-1-yn-1-yl)phenyl)carbamoyl)phenyl)sulfonyl)-4-((3-methoxyphenyl)amino)-8-methylquinoline-3-carboxamide

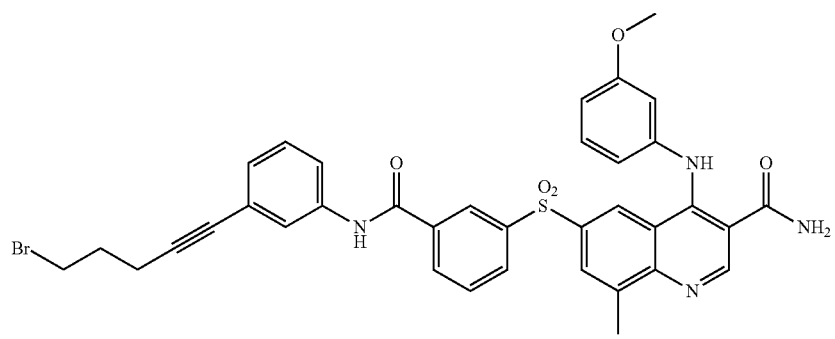 [SMILES: COc1cccc(Nc2c(C(N)=O)cnc3c(C)cc(S(=O)(=O)c4cccc(C(=O)Nc5cccc(C#CCCCBr)c5)c4)cc23)c1]

A suspension of Intermediate 77 (0.65 g, 1.0 mmol) and carbon tetrabromide (1.0 g, 3.0 mmol) in dichloromethane (14 mL) was sonicated for 5 minutes and then cooled in an ice-water bath. Following the addition, via syringe, of a triphenylphosphine (0.52 g, 2.0 mmol) solution in tetrahydrofuran, the cooling bath was removed, allowing the mixture to stir overnight at room temperature. The mixture was quenched with ethanol and concentrated to foam under reduced pressure. The foam was taken up in tetrahydrofuran (15 mL) and treated as before with carbon tetrabromide (3.0 mmol) and triphenylphosphine (2.0 mmol). After stirring overnight at room temperature, the mixture was concentrated under reduced pressure. The crude material was again taken up in tetrahydrofuran (15 mL) and treated as before with carbon tetrabromide (3.0 mmol) and triphenylphosphine (2.0 mmol). After stirring overnight at room temperature, the mixture was concentrated under reduced pressure. The residue was taken up a suspension in acetone and filtered. The concentrated filtrate was purified via automated flash silica gel chromatography, using a 40 g Silicycle SiliSep flash column (hexanes/ethyl acetate). Concentration of the desired fractions under reduced pressure provided the title compound as straw-colored foam (0.35 g, 48%). ES/MS calcd. for $C_{36}H_{32}BrN_4O_5S^+$ 711.1. Found m/z=711.2 $(M+H)^+$.

Intermediate 99: 6-((3-((4-(4-((6-bromohexyl)oxy) butyl)phenyl)(methyl)carbamoyl)phenyl)sulfonyl)-4-((3-methoxyphenyl)amino)-8-methylquinoline-3-carboxamide

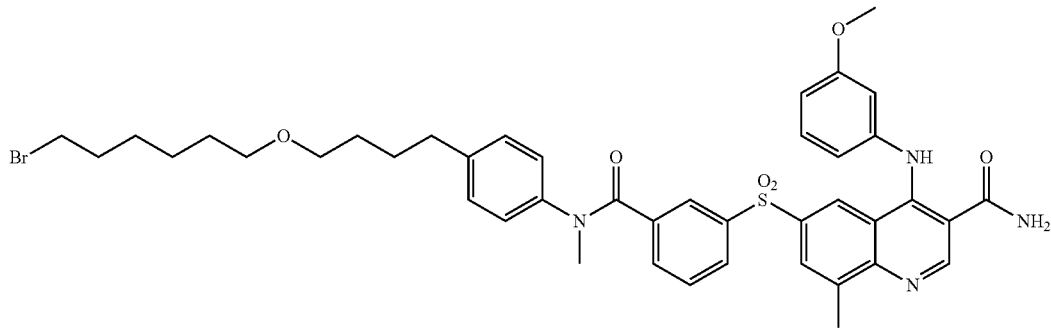 [SMILES: COc1cccc(Nc2c(C(N)=O)cnc3c(C)cc(S(=O)(=O)c4cccc(C(=O)N(C)c5ccc(CCCCOCCCCCCBr)cc5)c4)cc23)c1]

The title compound was synthesized in a manner analogous to that described for Intermediate 98, using Intermediate 79 in place of Intermediate 77. ES/MS calcd. for $C_{42}H_{48}BrN_4O_6S^+$ 815.3. Found m/z=815.4 $(M+H)^+$.

Intermediate 100: (R)-methyl 3-(2-((2-(8-(benzyloxy)-2-oxo-1,2-dihydroquinolin-5-yl)-2-((tert-butyldimethylsilyl)oxy)ethyl)amino)-2-methylpropyl)benzoate

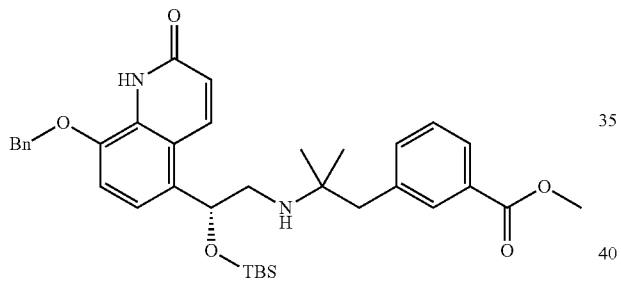

Methyl 3-(2-amino-2-methylpropyl)benzoate (1 g, 4.82 mmol) was added to (R)-8-(benzyloxy)-5-(2-bromo-1-((tert-butyldimethylsilyl)oxy)ethyl)quinolin-2(1H)-one (1.57 g, 3.22 mmol) neat. The resulting mixture was heated to 95° C. for 3 d then cooled. Chromatography (1:3, hexanes/EtOAc) afforded the title compound (970 mg, 49%) as light yellow oil. ES/MS calcd. for $C_{36}H_{47}N_2O_5Si^+$ 615.3. Found m/z=615.3 $(M+H)^+$.

Intermediate 101: (R)-3-(2-((2-(8-(benzyloxy)-2-oxo-1,2-dihydroquinolin-5-yl)-2-((tert-butyldimethylsilyl)oxy)ethyl)amino)-2-methylpropyl)benzoic acid

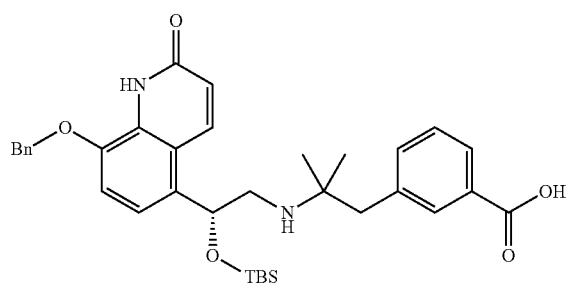

Solid LiOH (370 mg, 15.4 mmol) was added to a stirring solution of Intermediate 100 (950 mg, 1.55 mmol) in THF/MeOH/H₂O (15 mL, 3/1/1) at rt. The reaction mixture was stirred over night then pH was adjusted to 1 with 1 N HCl. The aqueous layer was extracted with EtOAc and the combined organic layers were washed with brine, dried over Na₂SO₄, and concentrated to give crude acid (1.09 g) as yellow solid. Recrystallization (CH₂Cl₂/Et₂O) afforded the title compound (830 mg, 89%) as off white solid. ES/MS calcd. for $C_{35}H_{45}N_2O_5Si^+$ 601.3. Found m/z=601.3 $(M+H)^+$.

Intermediate 102: (R)—N-(4-(5-((2-((tert-butyldimethylsilyl)oxy)-2-(8-hydroxy-2-oxo-1,2-dihydroquinolin-5-yl)ethyl)(methyl)amino)pent-1-yn-1-yl)phenyl)-2,2,2-trifluoroacetamide

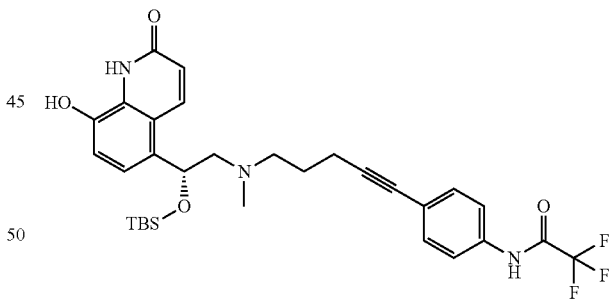

A mixture of Intermediate 40 (0.30 g, 0.90 mmol) and Intermediate 4 (375 mg, 1.1 mmol) in DMF (5 mL) was treated with N,N-diisopropylethylamine (0.47 mL, 2.7 mmol) and catalytic tetra-n-butylammonium iodide (100 mg). The mixture was heated for 3 days in a 55° C. oil bath. The mixture was concentrated under reduced pressure and purified via automated flash silica gel chromatography, using a 12 g Silicycle SiliSep flash column (dichloromethane/methanol/ammonium hydroxide). Concentration of the desired fractions under reduced pressure provided the title compound. ES/MS calcd. for $C_{31}H_{39}F_3N_3O_4Si^+$ 602.3. Found m/z=602.4 $(M+H)^+$.

Intermediate 103: (R)-5-(2-((5-(4-aminophenyl)pent-4-yn-1-yl)(methyl)amino)-1-((tert-butyldimethylsilyl)oxy)ethyl)-8-hydroxyquinolin-2(1H)-one

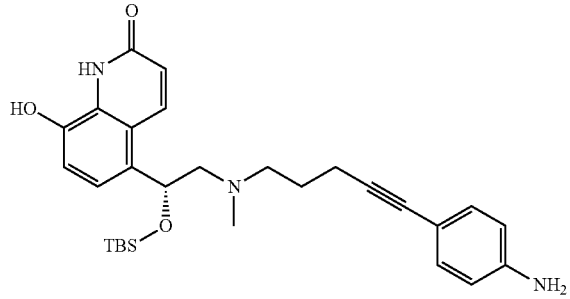

The title compound was synthesized in a manner analogous to that described for Intermediate 49, using instead Intermediate 102 as a substrate. ES/MS calcd. for $C_{29}H_{40}N_3O_3Si^+$ 506.3. Found m/z=506.4 (M+H)$^+$.

Intermediate 104: (R)—N-(4-(2-(4-((2-((tert-butyldimethylsilyl)oxy)-2-(8-hydroxy-2-oxo-1,2-dihydroquinolin-5-yl)ethyl)amino)butyl)-1,3-dithiolan-2-yl)phenyl)-2,2,2-trifluoroacetamide

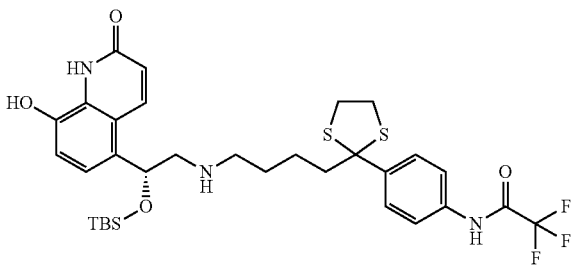

The title compound was synthesized in a manner analogous to that described for Intermediate 102, using Intermediate 45 in place of Intermediate 98. ES/MS calcd. for $C_{32}H_{43}F_3N_3O_4S_2Si^+$ 682.2. Found m/z=682.4 (M+H)$^+$.

Intermediate 105: (R)-tert-butyl (4-(2-(4-aminophenyl)-1,3-dithiolan-2-yl)butyl)(2-((tert-butyldimethylsilyl)oxy)-2-(8-hydroxy-2-oxo-1,2-dihydroquinolin-5-yl)ethyl)carbamate

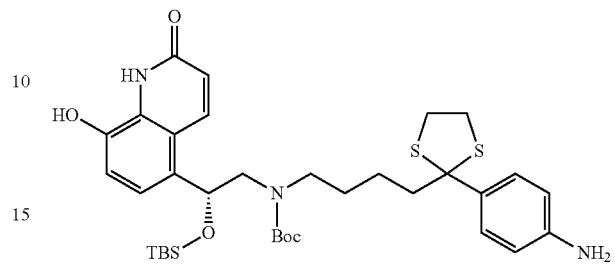

A solution of Intermediate 104 (0.41 g, 0.60 mmol) in tetrahydrofuran (5 mL) was treated with di-tert-butyldicarbonate (0.39 g, 1.8 mmol), triethylamine (0.25 mL, 1.8 mmol) and N,N-dimethylaminopyridine (DMAP, 50 mg). The reaction mixture was stirred overnight at room temperature and then concentrated to dryness under reduced pressure. The residue was taken up in acetone (5 mL) and treated with aqueous sodium hydroxide solution (1 N, 2 mL). The mixture was stirred in a 40° C. oil bath and was then concentrated under reduced pressure. MeOH (5 mL) was added and the mixture was heated for 2 days in a 40° C. oil bath. The mixture was concentrated under reduced pressure and the mixture was partitioned between 1 N aqueous hydrochloric acid solution and dichloromethane. The aqueous phase was basified to pH 10 with concentrated aqueous ammonium hydroxide solution and was then extracted three times with dichloromethane. The combined organics were washed with water, dried over anhydrous magnesium sulfate, filtered, and concentrated under reduced pressure. The residue was purified via automated flash silica gel chromatography, using a 25 g Silicycle SiliSep flash column (dichloromethane/methanol/ammonium hydroxide). Concentration of the desired fractions under reduced pressure provided the title compound as white foam.

ES/MS calcd. for $C_{35}H_{52}N_3O_5S_2Si^+$ 686.3. Found m/z=498.2 (M-TBS-t-Bu+H)$^+$.

Intermediate 106: (R)-8-hydroxy-5-(2,2,3,3-tetramethyl-18-(4-nitrophenyl)-4,14-dioxa-7-aza-3-silaoctadecan-5-yl)quinolin-2(1H)-one

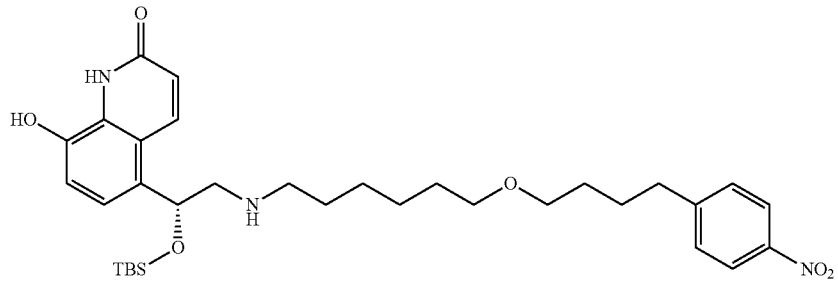

The title compound was synthesized in a manner analogous to that described for Intermediate 102, using Intermediate 52 in place of Intermediate 45. ES/MS calcd. for $C_{33}H_{50}N_3O_6Si^+$ 612.4. Found m/z=612.5 (M+H)$^+$.

Intermediate 107: (R)-tert-butyl (2-(8-((tert-butoxy-carbonyl)oxy)-2-oxo-1,2-dihydroquinolin-5-yl)-2-((tert-butyldimethylsilyl)oxy)ethyl)(6-(4-(4-nitrophenyl)butoxy)hexyl)carbamate

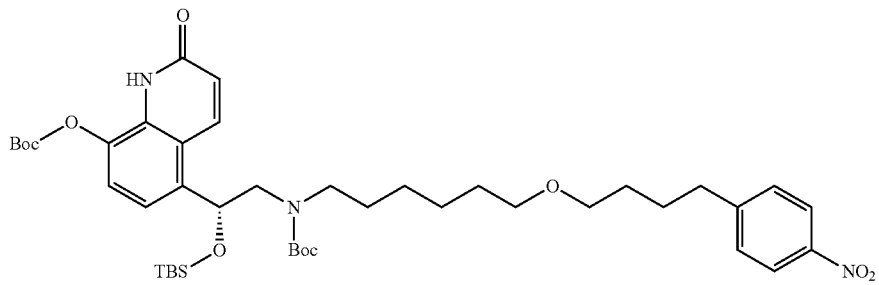

A solution of Intermediate 106 (0.53 g, 0.87 mmol) in dichloromethane (5 mL) was treated with di-tert-butyldicarbonate (0.57 g, 2.6 mmol), triethylamine (0.61 mL, 4.4 mmol) and N,N-dimethylaminopyridine (DMAP, 20 mg). The reaction mixture was stirred overnight at room temperature and then concentrated to dryness under reduced pressure. The residue was purified via automated flash silica gel chromatography, using a 25 g Silicycle SiliSep flash column (hexanes/ethyl acetate). Concentration of the desired fractions under reduced pressure provided the title compound as clear, colorless oil, which turned into a white foam under reduced pressure. ES/MS calcd. for $C_{43}H_{66}N_3O_{10}Si^+$ 812.5. Found m/z=812.6 $(M+H)^+$.

Intermediate 108: (R)-tert-butyl (6-(4-(4-aminophenyl)butoxy)hexyl)(2-(8-((tert-butoxycarbonyl)oxy)-2-oxo-1,2-dihydroquinolin-5-yl)-2-((tert-butyldimethylsilyl)oxy)ethyl)carbamate

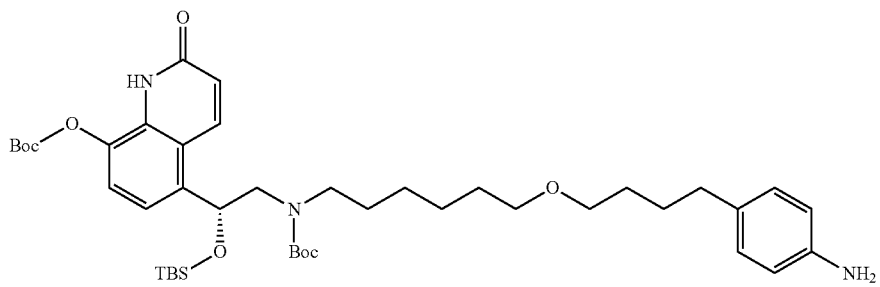

A suspension of Pd/C (10% w/w, 15 mg) and Intermediate 107 (0.25 g, 0.31 mmol) in MeOH (4 mL) was stirred under a balloon of hydrogen gas for 30 minutes, followed by filtration of the mixture through a pad of Celite diatomaceous earth, and concentration under reduced pressure. The title compound was provided as a white foam (0.13 g, 54%). ES/MS calcd. for $C_{43}H_{68}N_3O_8Si^+$ 782.5. Found m/z=782.6 $(M+H)^+$.

Intermediate 109: (R)-8-hydroxy-5-(2,2,3,3-tetramethyl-16-(4-nitrophenyl)-4,14-dioxa-7-aza-3-silahexadecan-5-yl)quinolin-2(1H)-one

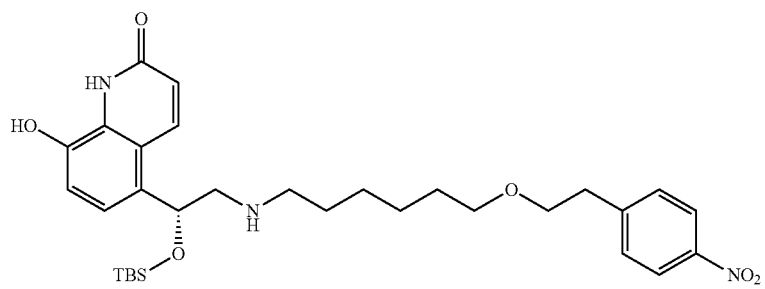

The title compound was synthesized in a manner analogous to that described for Intermediate 106, using Intermediate 53 in place of Intermediate 52. ES/MS calcd. for $C_{31}H_{46}N_3O_6Si^+$ 584.3. Found m/z=584.4 $(M+H)^+$.

Intermediate 110: (R)-tert-butyl (2-(8-((tert-butoxy-carbonyl)oxy)-2-oxo-1,2-dihydroquinolin-5-yl)-2-((tert-butyldimethylsilyl)oxy)ethyl)(6-(4-nitro-phenethoxy)hexyl)carbamate

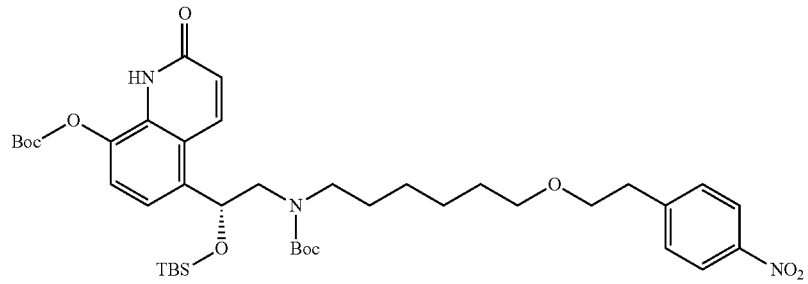

The title compound was synthesized in a manner analogous to that described for Intermediate 107, using Intermediate 109 as a substrate. ES/MS calcd. for $C_{41}H_{62}N_3O_{10}Si^+$ 784.4. Found m/z=784.5 (M+H)$^+$.

Intermediate 111: (R)-tert-butyl (6-(4-aminopheneth-oxy)hexyl)(2-(8-((tert-butoxycarbonyl)oxy)-2-oxo-1,2-dihydroquinolin-5-yl)-2-((tert-butyldimethylsilyl)oxy)ethyl)carbamate

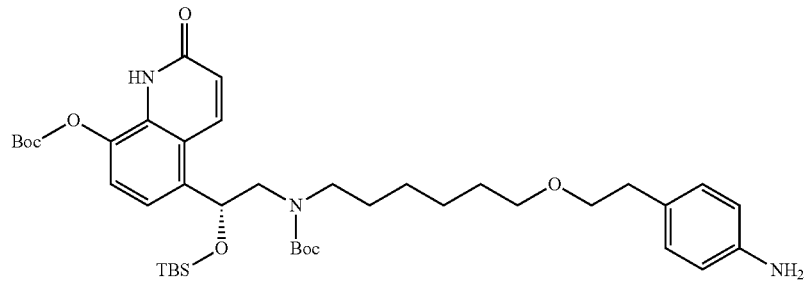

A solution of Intermediate 110 (0.38 mmol) in methanol (9 mL) was treated with iron (III) chloride hexahydrate (10 mg) and decolorizing charcoal (100 mg). While the mixture was being heated to reflux, hydrazine monohydrate (1.0 mL) was added dropwise via syringe. After two hours of heating at reflux, the mixture was allowed to cool and was filtered through a pad of Celite diatomaceous earth. The filtrate was concentrated to dryness under reduced pressure and the residue was purified via automated flash silica gel chromatography, using a 12 g Silicycle SiliSep flash column (dichloromethane/methanol/ammonium hydroxide). Concentration of the desired fractions under reduced pressure provided the title compound (0.14 g, 56%) as a black foam. ES/MS calcd. for $C_{36}H_{56}N_3O_6Si^+$ 654.4. Found m/z=654.5 (M+H)$^+$.

Intermediate 112: 4-[(3-Methoxyphenyl)amino]-8-methyl-6-[[3-[(8-oxooctyl)carbamoyl]phenyl]sulfonyl]quinoline-3-carboxamide

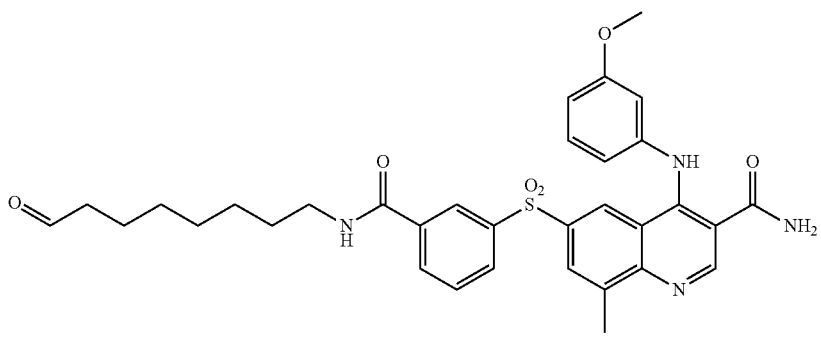 [SMILES: COc1cccc(Nc2c(C(N)=O)cnc3c(C)cc(S(=O)(=O)c4cccc(C(=O)NCCCCCCCC=O)c4)cc23)c1]

Dess-Martin reagent (105 mg, 0.249 mmol) was added to a stirring solution of Intermediate 70 (77 mg, 0.124 mmol) in DMF (2 mL) at rt. The resulting solution was stirred for 3 h and poured into satd. NaHCO$_3$ (50 mL). The precipitate was filtered, washed with H$_2$O, and dried to give the title compound (70 mg) as a yellow solid. The compound was used with no further purification. ES/MS calcd. for $C_{33}H_{37}N_4O_6S^+$ 617.2. Found m/z=617.3 (M+H)$^+$.

Intermediate 113: 4-](3-Methoxyphenyl)amino]-8-methyl-6-[[3-[(6-oxohexyl)carbamoyl]phenyl]sulfonyl]quinoline-3-carboxamide

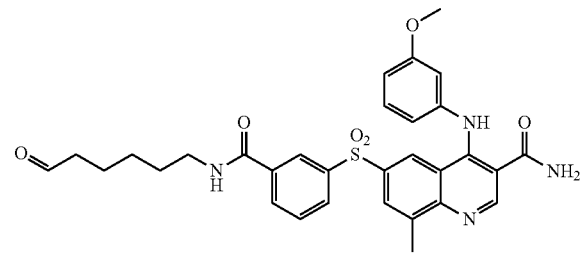 [SMILES: COc1cccc(Nc2c(C(N)=O)cnc3c(C)cc(S(=O)(=O)c4cccc(C(=O)NCCCCCC=O)c4)cc23)c1]

The title compound was synthesized in a manner analogous to that described for Intermediate 112, using Intermediate 71 as a substrate. ES/MS calcd. for $C_{31}H_{33}N_4O_6S^+$ 589.2 found m/z=589.2 (M+H)$^+$.

Intermediate 114: 4-[(3-Methoxyphenyl)amino]-8-methyl-6-[[3-[methyl(6-oxohexyl)carbamoyl]phenyl]sulfonyl]quinoline-3-carboxamide

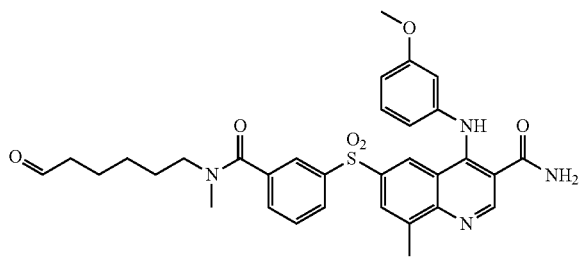 [SMILES: COc1cccc(Nc2c(C(N)=O)cnc3c(C)cc(S(=O)(=O)c4cccc(C(=O)N(C)CCCCCC=O)c4)cc23)c1]

The title compound was synthesized in a manner analogous to that described for Intermediate 112, using Intermediate 80 as a substrate. ES/MS calcd. for $C_{32}H_{35}N_4O_6S^+$ 603.2. Found m/z=603 (M+H)$^+$.

Intermediate 115: 4-[(3-Methoxyphenyl)amino]-8-methyl-6-[[3-[[4-(5-oxopent-1-yn-1-yl)phenyl]carbamoyl]phenyl]sulfonyl]quinoline-3-carboxamide

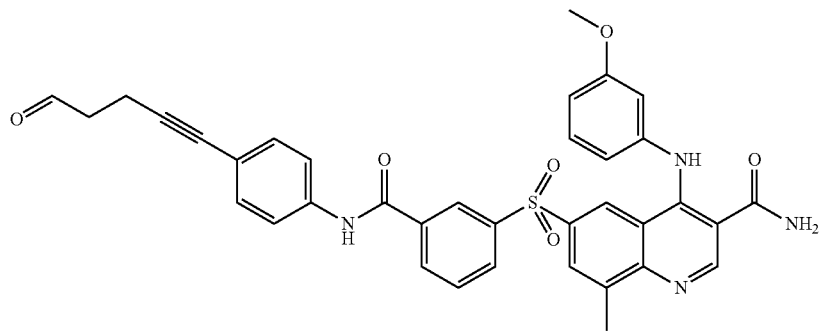 [SMILES: COc1cccc(Nc2c(C(N)=O)cnc3c(C)cc(S(=O)(=O)c4cccc(C(=O)Nc5ccc(C#CCCC=O)cc5)c4)cc23)c1]

The title compound was synthesized in a manner analogous to that described for Intermediate 112 using Intermediate 72 as a substrate. ES/MS calcd. for $C_{36}H_{31}N_4O_6S^+$ 647.2. Found m/z=647.6 (M+H)$^+$.

Intermediate 116: 4-((3-methoxyphenyl)amino)-8-methyl-6-((3-(methyl(4-(5-oxopent-1-yn-1-yl)phenyl)carbamoyl)phenyl)sulfonyl)quinoline-3-carboxamide

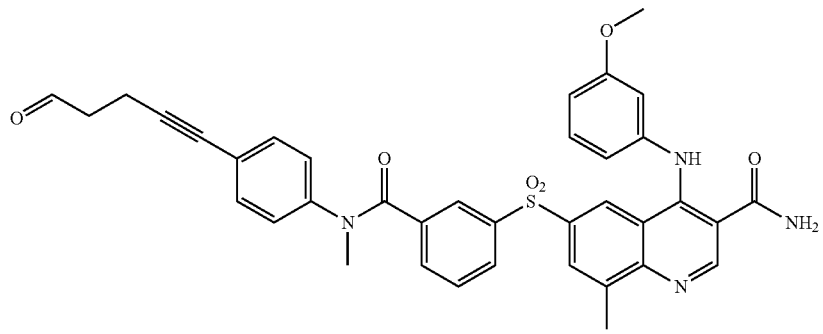 [SMILES: COc1cccc(Nc2c(C(N)=O)cnc3c(C)cc(S(=O)(=O)c4cccc(C(=O)N(C)c5ccc(C#CCCC=O)cc5)c4)cc23)c1]

Title compound was synthesized in a manner analogous to Intermediate 112 using Intermediate 73 as a substrate. ES/MS calcd. for $C_{37}H_{32}N_4O_6S$ 660.2. Found m/z=661 (M+H)$^+$.

Intermediate 117: 4-((3-methoxyphenyl)amino)-8-methyl-6-((3-((2-methyl-4-(5-oxopent-1-yn-1-yl)phenyl)carbamoyl)phenyl)sulfonyl)quinoline-3-carboxamide

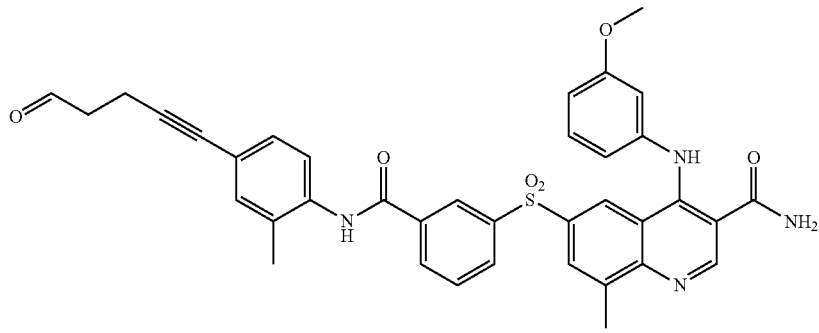 [SMILES: COc1cccc(Nc2c(C(N)=O)cnc3c(C)cc(S(=O)(=O)c4cccc(C(=O)Nc5ccc(C#CCCC=O)cc5C)c4)cc23)c1]

Title compound was synthesized in a manner analogous to Intermediate 112 using Intermediate 74 as a substrate. ES/MS calcd. for $C_{37}H_{32}N_4O_6S$ 660.2. Found m/z=661 (M+H)$^+$.

Intermediate 118: 4-((3-methoxyphenyl)amino)-8-methyl-6-((3-((3-methyl-4-(5-oxopent-1-yn-1-yl)phenyl)carbamoyl)phenyl)sulfonyl)quinoline-3-carboxamide

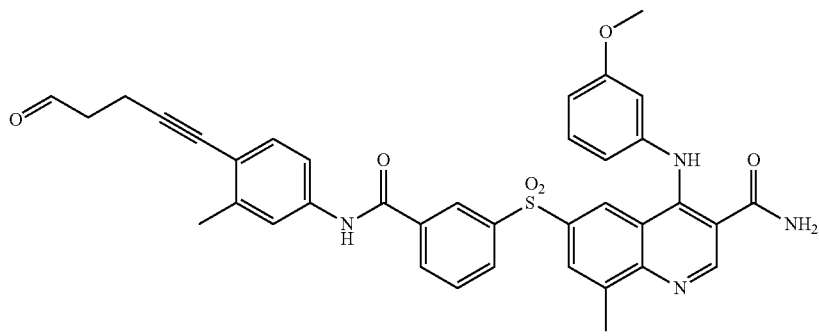 [SMILES: COc1cccc(Nc2c(C(N)=O)cnc3c(C)cc(S(=O)(=O)c4cccc(C(=O)Nc5ccc(C#CCCC=O)c(C)c5)c4)cc23)c1]

The title compound was synthesized in a manner analogous to that described in Intermediate 112, using Intermediate 75 as a substrate. ES/MS calcd. for $C_{37}H_{32}N_4O_6S$ 660.2. Found m/z=661 (M+H)$^+$.

Intermediate 119: 4-((3-methoxyphenyl)amino)-8-methyl-6-((3-((4-(6-oxohex-1-yn-1-yl)phenyl)carbamoyl)phenyl)sulfonyl)quinoline-3-carboxamide

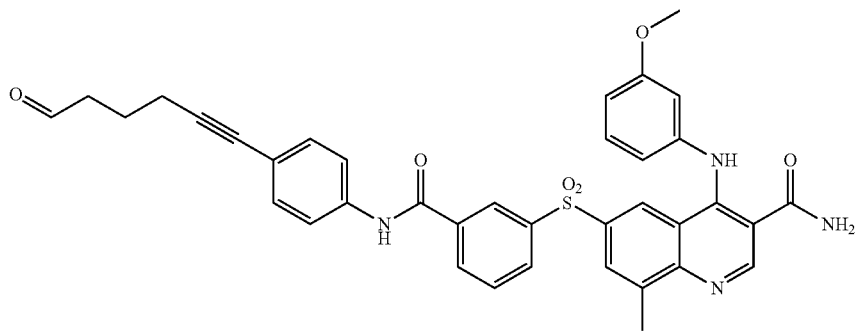 [SMILES: COc1cccc(Nc2c(C(N)=O)cnc3c(C)cc(S(=O)(=O)c4cccc(C(=O)Nc5ccc(C#CCCCC=O)cc5)c4)cc23)c1]

The title compound was synthesized in a manner analogous to that described for Intermediate 112, using instead Intermediate 76 as substrate. ES/MS calcd. for $C_{37}H_{33}N_4O_6S^+$ 661.2. Found m/z=663.1 (M+H)$^+$.

Intermediate 120: 4-[(3-Methoxyphenyl)amino]-8-methyl-6-[[3-[[4-(5-oxopentyl)phenyl]carbamoyl]phenyl]sulfonyl]quinoline-3-carboxamide

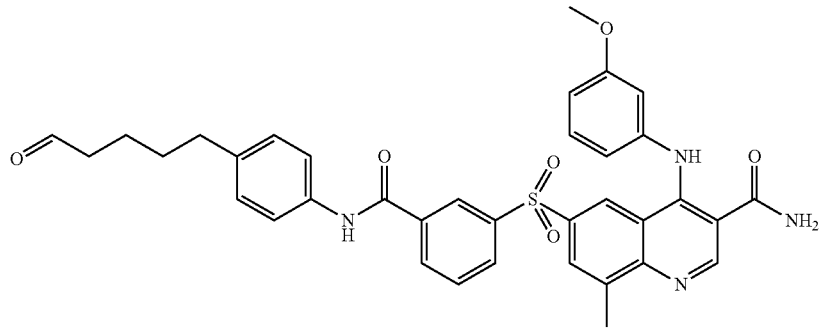 [SMILES: COc1cccc(Nc2c(C(N)=O)cnc3c(C)cc(S(=O)(=O)c4cccc(C(=O)Nc5ccc(CCCCC=O)cc5)c4)cc23)c1]

The title compound was synthesized in a manner analogous to that described for Intermediate 112 using Intermediate 92 as a substrate. ES/MS calcd. for $C_{36}H_{35}N_4O_6S^+$ 651.2. Found m/z=651.3 (M+H)$^+$.

Intermediate 121: 4-((3-methoxyphenyl)amino)-8-methyl-6-((3-(4-((6-oxohexyl)oxy)piperidine-1-carbonyl)phenyl)sulfonyl)quinoline-3-carboxamide

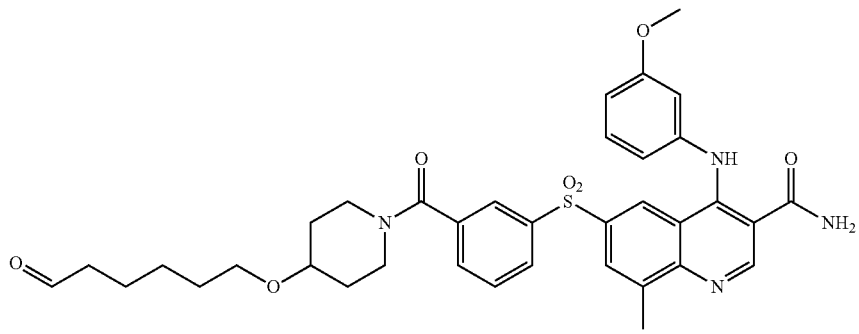 [SMILES: COc1cccc(Nc2c(C(N)=O)cnc3c(C)cc(S(=O)(=O)c4cccc(C(=O)N5CCC(OCCCCCC=O)CC5)c4)cc23)c1]

The title compound was synthesized in a manner analogous to that described for Intermediate 112, using Intermediate 88 as a substrate. ES/MS calcd. for $C_{36}H_{41}N_4O_7S^+$ 673.3. Found m/z=673.3 (M+H)$^+$.

Intermediate 122: 4-((3-methoxyphenyl)amino)-8-methyl-6-((3-(4-(6-oxohexyl)piperazine-1-carbonyl)phenyl)sulfonyl)quinoline-3-carboxamide

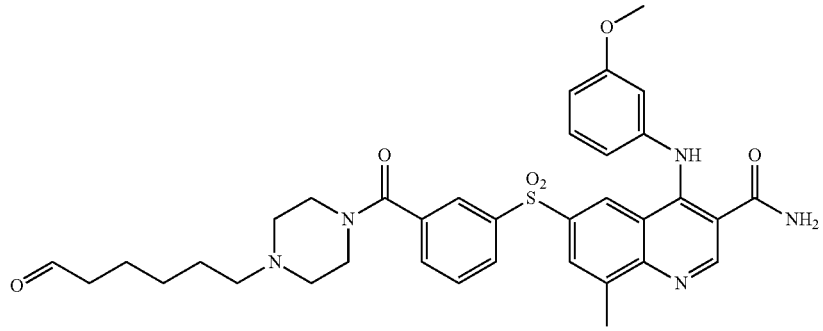 [SMILES: COc1cccc(Nc2c(C(N)=O)cnc3c(C)cc(S(=O)(=O)c4cccc(C(=O)N5CCN(CCCCCC=O)CC5)c4)cc23)c1]

The title compound was synthesized in a manner analogous to that described for Intermediate 112, using Intermediate 89 as a substrate. ES/MS calcd. for $C_{35}H_{40}N_5O_6S^+$ 658.3. Found m/z=658.3 (M+H)$^+$.

Intermediate 123: 6-((3-((4'-formyl-[1,1-biphenyl]-4-yl)carbamoyl)phenyl)sulfonyl)-4-((3-methoxyphenyl)amino)-8-methylquinoline-3-carboxamide

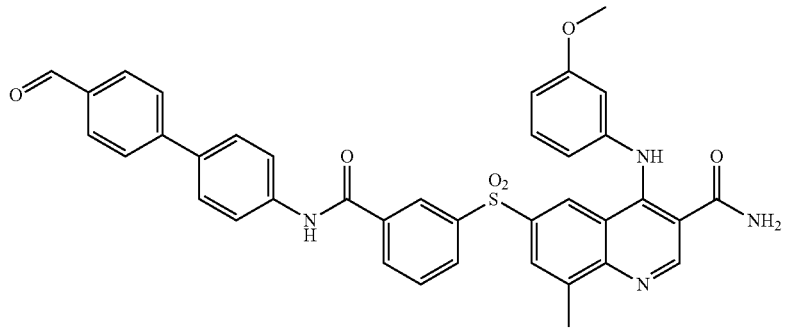 [SMILES: COc1cccc(Nc2c(C(N)=O)cnc3c(C)cc(S(=O)(=O)c4cccc(C(=O)Nc5ccc(-c6ccc(C=O)cc6)cc5)c4)cc23)c1]

The title compound was synthesized in a manner analogous to that described for Intermediate 112, using Intermediate 81 as a substrate. ES/MS calcd. for $C_{38}H_{31}N_4O_6S^+$ 671.2. Found m/z=671.2 (M+H)$^+$.

Intermediate 124: 4-((3-methoxyphenyl)amino)-8-methyl-6-((3-((4'-(4-oxobutyl)-(1,1-biphenyl]-4-yl)carbamoyl)phenyl)sulfonyl)quinoline-3-carboxamide

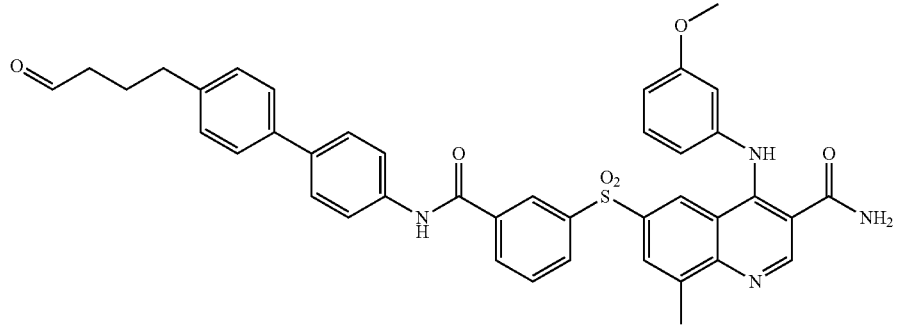 [SMILES: COc1cccc(Nc2c(C(N)=O)cnc3c(C)cc(S(=O)(=O)c4cccc(C(=O)Nc5ccc(-c6ccc(CCCC=O)cc6)cc5)c4)cc23)c1]

The title compound was synthesized in a manner analogous to that described for Intermediate 112, using IBX in place of Dess-Martin reagent and Intermediate 90 as a substrate. ES/MS calcd. for $C_{41}H_{37}N_4O_6S^+$ 713.2. Found m/z=713.3 (M+H)$^+$.

Intermediate 125: 4-((3-methoxyphenyl)amino)-8-methyl-6-((3-((4'-(4-oxobutyl)-[1,1'-biphenyl]-3-yl)carbamoyl)phenyl)sulfonyl)quinoline-3-carboxamide

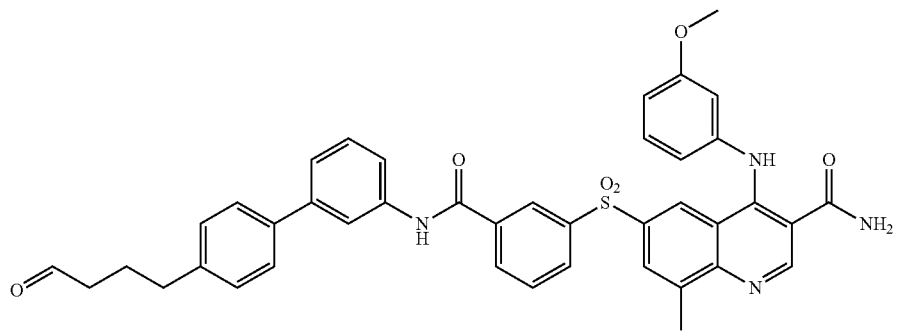 [SMILES: COc1cccc(Nc2c(C(N)=O)cnc3c(C)cc(S(=O)(=O)c4cccc(C(=O)Nc5cccc(-c6ccc(CCCC=O)cc6)c5)c4)cc23)c1]

The title compound was synthesized in a manner analogous to that described for Intermediate 124, using Intermediate 91 as a substrate. ES/MS calcd. for $C_{41}H_{37}N_4O_6S^+$ 713.2. Found m/z=713.4 (M−H)$^+$.

Intermediate 126: 4-((3-methoxyphenyl)amino)-8-methyl-6-((11-oxoundecyl)sulfonyl)quinoline-3-carboxamide

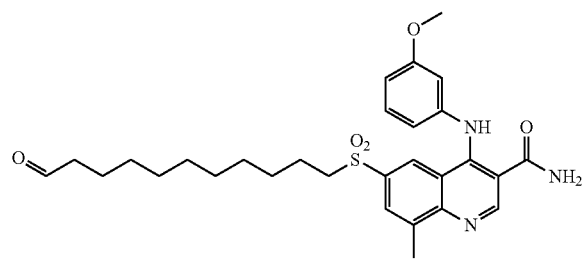 [SMILES: COc1cccc(Nc2c(C(N)=O)cnc3c(C)cc(S(=O)(=O)CCCCCCCCCCC=O)cc23)c1]

The title compound was synthesized in a manner analogous to that described for Intermediate 112, using Intermediate 61 as a substrate. ES/MS calcd. for $C_{29}H_{38}N_3O_5S^+$ 540.3. Found m/z=540.4 (M+H)$^+$.

Intermediate 127: 6-((4'-formyl-[1,1'-biphenyl]-3-yl)sulfonyl)-4-((3-methoxyphenyl)amino)-8-methylquinoline-3-carboxamide

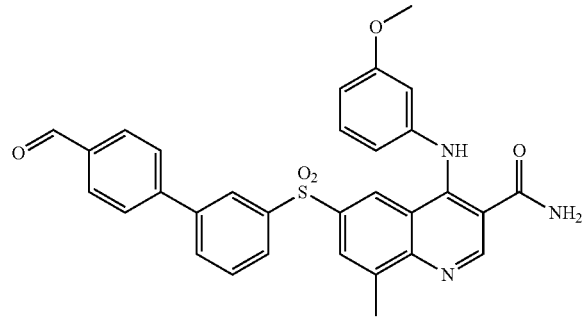 [SMILES: COc1cccc(Nc2c(C(N)=O)cnc3c(C)cc(S(=O)(=O)c4cccc(-c5ccc(C=O)cc5)c4)cc23)c1]

The title compound was synthesized in a manner analogous to that described for Intermediate 112, using Intermediate 64 as a substrate. ES/MS calcd. for $C_{31}H_{26}N_3O_5S^+$ 552.2. Found m/z=552.3 (M+H)$^+$.

Intermediate 128: 6-((4'-formyl-[1,1'-biphenyl]-4-yl)sulfonyl)-4-((3-methoxyphenyl)amino)-8-methylquinoline-3-carboxamide

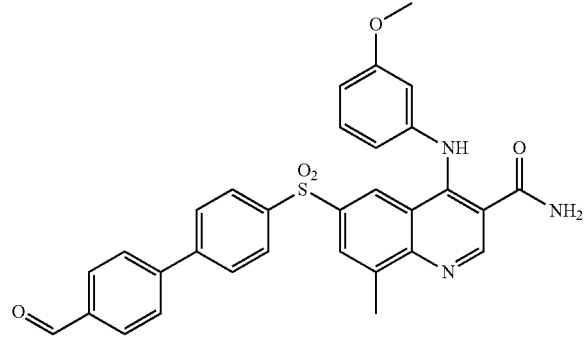 [SMILES: COc1cccc(Nc2c(C(N)=O)cnc3c(C)cc(S(=O)(=O)c4ccc(-c5ccc(C=O)cc5)cc4)cc23)c1]

The title compound was synthesized in a manner analogous to that described for Intermediate 112, using Intermediate 65 as a substrate. ES/MS calcd. for $C_{31}H_{26}N_3O_5S^+$ 552.2. Found m/z=552.2 (M+H)$^+$.

Intermediate 129: 4-((3-methoxyphenyl)amino)-8-methyl-6-((4'-(3-oxopropyl)-[1,1'-biphenyl]-4-yl)sulfonyl)quinoline-3-carboxamide

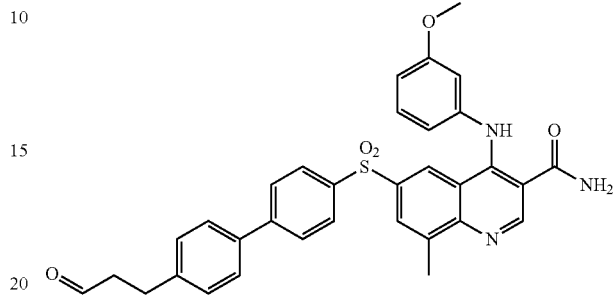

The title compound was synthesized in a manner analogous to that described for Intermediate 124, using Intermediate 66 as a substrate. ES/MS calcd. for $C_{33}H_{30}N_3O_5S^+$ 580.2. Found m/z=580.3 (M+H)$^+$.

Intermediate 130: 4-((3-methoxyphenyl)amino)-8-methyl-6-((4'-(3-oxopropyl)-[1,1'-biphenyl]-3-yl)sulfonyl)quinoline-3-carboxamide

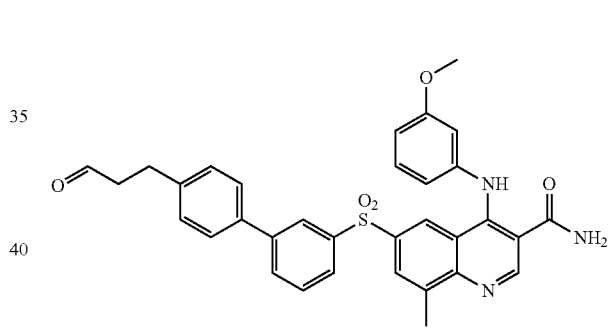

The title compound was synthesized in a manner analogous to that described for Intermediate 124, using Intermediate 67 as substrate. ES/MS calcd. for $C_{33}H_{30}N_3O_5S^+$ 580.2. Found m/z=580.3 (M+H)$^+$.

Intermediate 131: 4-((3-methoxyphenyl)amino)-8-methyl-6-((4'-(5-oxopentyl)-[1,1'-biphenyl]-4-yl)sulfonyl)quinoline-3-carboxamide

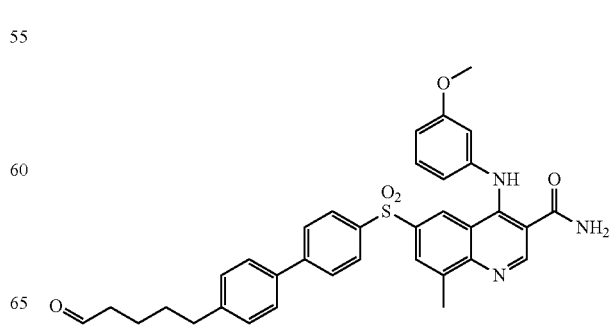

The title compound was synthesized in a manner analogous to that described for Intermediate 124, using Intermediate 68 as substrate. ES/MS calcd. for $C_{35}H_{34}N_3O_5S^+$ 608.2. Found m/z=608.3 (M+H)$^+$.

Intermediate 132: 4-((3-methoxyphenyl)amino)-8-methyl-6-((4'-(5-oxopentyl)-[1,1'-biphenyl]-3-yl)sulfonyl)quinoline-3-carboxamide

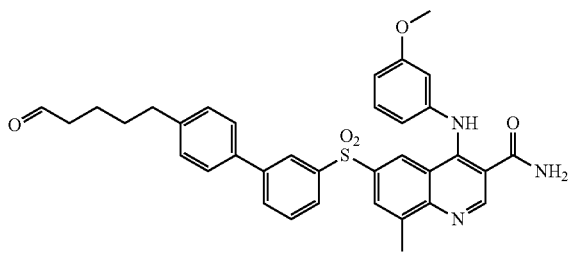 [SMILES: COc1cccc(Nc2c(C(N)=O)cnc3c(C)cc(S(=O)(=O)c4cccc(-c5ccc(CCCCC=O)cc5)c4)cc23)c1]

The title compound was synthesized in a manner analogous to that described for Intermediate 124, using Intermediate 69 as a substrate. ES/MS calcd. for $C_{35}H_{34}N_3O_5S^+$ 608.2. Found m/z=608.3 (M+H$^+$).

Intermediate 133: 4-((3-Methoxyphenyl)amino)-8-methyl-6-((3-(4-oxopiperidine-1-carbonyl)phenyl)sulfonyl)quinoline-3-carboxamide

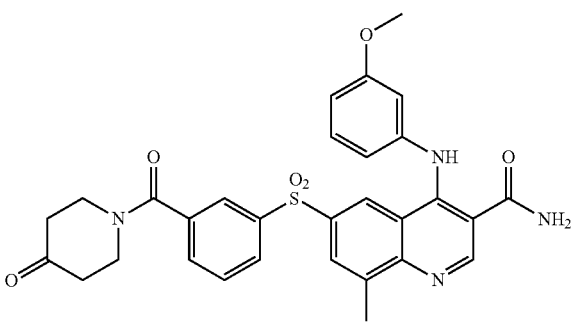 [SMILES: COc1cccc(Nc2c(C(N)=O)cnc3c(C)cc(S(=O)(=O)c4cccc(C(=O)N5CCC(=O)CC5)c4)cc23)c1]

HATU (348 mg, 0.915 mmol) and DIEA (0.319 mL, 1.83 mmol) were added to a stirring solution of 3-[[3-carbamoyl-4-[(3-methoxyphenyl)amino]-8-methylquinolin-6-yl]sulfonyl]benzoic acid (300 mg, 0.61 mmol) in DMF (6 mL) at rt. After 5 min. 1,4-dioxa-8-azaspiro[4.5]decane (0.156 mL, 1.22 mmol) was added and the resulting solution was stirred for an additional 1.5 h. The reaction mixture was poured into H$_2$O (50 mL) and filtered. The filter cake was washed with H$_2$O then dried to give a yellow solid. To the solid dissolved in THF (6 mL) was added 5 N HCl (1.22 mL, 6.1 mmol). The reaction mixture was heated to 50° C. and stirred over night. The resulting mixture was cooled to rt, and diluted with EtOAc (20 mL). The organic layer was washed with said. NaHCO$_3$ (20 mL), H$_2$O (20 mL), brine (20 mL), dried over Na$_2$SO$_4$ (s), then concentrated to give the title compound (361 mg) as a yellow solid. The compound was used with no further purification. ES/MS calcd. for $C_{30}H_{29}N_4O_6S^+$ 573.2. Found m/z=573.2 (M+H)$^+$.

Intermediate 134: 6-[[3-(Hydroxymethyl)phenyl]sulfonyl]-4-[(3-methoxyphenyl)amino]-8-methylquinoline-3-carboxamide

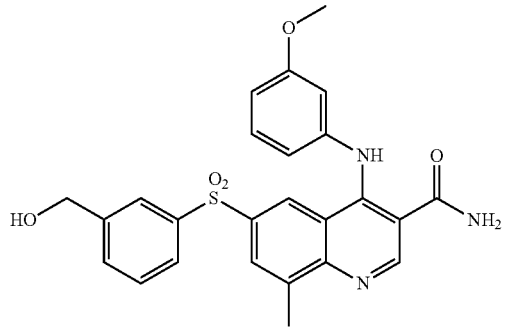

LAH (158 mg, 3.96 mmol) was added to a stirring solution of methyl 3-[[3-carbamoyl-4-[(3-methoxyphenyl)amino]-8-methylquinolin-6-yl]sulfonyl]benzoate (500 mg, 0.99 mmol) in THF (10 mL) at 0° C. After stirring for 20 min, H$_2$O (0.158 mL), 15% (w/v) NaOH (0.158 mL), and H$_2$O (0.474 mL) were added sequentially. The resulting suspension was stirred for 1 h then the precipitate was filtered, washed with water (20 mL), and dried to give the title compound (330 mg) as a yellow solid. The compound was used with no further purification. ES/MS calcd. for $C_{25}H_{24}N_3O_5S^+$ 478.1. Found m/z=478.1 (M+H)$^+$.

Intermediate 135: 3-[[3-Carbamoyl-4-[(3-methoxyphenyl)amino]-8-methylquinolin-6-yl]sulfonyl]benzyl methanesulfonate

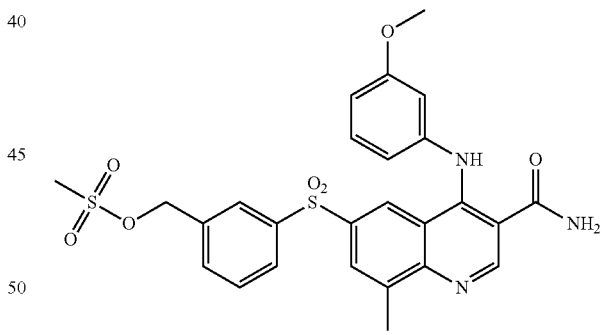

Methanesulfonyl chloride (0.06 mL, 1.474 mmol) and DIEA (0.243 mL, 1.394 mmol) were added to a stirring solution of Intermediate 134 (330 mg, 0.697 mmol) at rt. The reaction was monitored by LC/MS and additional methanesulfonyl chloride (0.06 mL, 1.474 mmol) and DIEA (0.243 mL, 1.394 mmol) were added after 3 h. The resulting reaction mixture was stirred for an additional 1 h then quenched with satd. NaHCO$_3$ (50 mL). The aqueous layer was extracted with CH$_2$Cl$_2$ (3×20 mL). The combined organic layers were washed with H$_2$O (100 mL), brine (100 mL), dried over Na$_2$SO$_4$ (s), and concentrated to give the title compound (460 mg) as a yellow solid. The compound was used with no further purification. ES/MS calcd. for $C_{26}H_{26}N_3O_7S_2^+$ 556.1. Found m/z=556.1 (M+H)$^+$.

Intermediate 136: 4-[(3-Methoxyphenyl)amino)-8-methyl-6-[[3-[(methylamino)methyl]phenyl]sulfonyl]quinoline-3-carboxamide

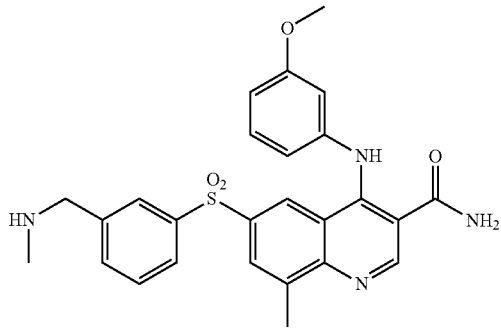 [SMILES: COc1cccc(Nc2c(C(N)=O)cnc3c(C)cc(S(=O)(=O)c4cccc(CO)c4)cc23)c1]

Methyl amine (2 M in THF, 4.1 mL, 8.28 mmol) was added to a stirring solution of Intermediate 135 (460 mg, 0.828 mmol) in THF (10 mL) at rt. The reaction mixture was warmed to 60° C. and stirred over night. The resulting solution was cooled to rt then diluted with $H_2O$ (50 mL). The aqueous layer was extracted with EtOAc (3×30 mL). The combined organic layers were washed with $H_2O$ (50 mL), brine (50 mL), dried over $Na_2SO_4$ (s), and concentrated to give a yellow solid (380 mg). Chromatography (9:1, $CH_2Cl_2$/MeOH, 0.2% $Et_3N$) afforded the title compound (135 mg, 33%) as a light yellow solid. ES/MS calcd. for $C_{26}H_{27}N_4O_4S^+$ 491.2. Found m/z=491.2 $(M+H)^+$.

Intermediate 137: 4-[(3-Methoxyphenyl)amino]-8-methyl-6-[[3-[[3-(2-oxopropyl)phenylcarbonyl(methyl)amino]methyl]phenyl]sulfonyl]quinoline-3-carboxamide

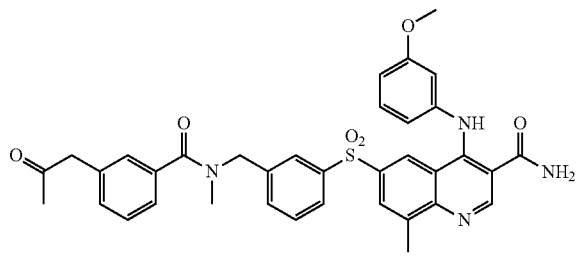 [SMILES: COc1cccc(Nc2c(C(N)=O)cnc3c(C)cc(S(=O)(=O)c4cccc(CN(C)C(=O)c5cccc(CC(C)=O)c5)c4)cc23)c1]

3-(2-Oxopropyl)benzoic acid (33 mg, 0.185 mmol) and DIEA (0.097 mL, 0.555 mmol) were added to a stirring solution of Intermediate 136 (100 mg, 0.204 mmol) in DMF (2 mL) at rt. The reaction mixture was stirred for 5 min and HATU (78 mg, 0.204 mmol) was added. The resulting solution was stirred for 3 h then poured into $H_2O$ (50 mL). The precipitate was filtered, washed with $H_2O$ (30 mL), and dried to give the title compound (106 mg) as a yellow solid. ES/MS calcd for $C_{36}H_{35}N_4O_6S^+$ 651.2. Found m/z=651.4 $(M+H)^+$.

Intermediate 138: Methanesulfonic acid 2-[4-[3-[3-carbamoyl-4-(3-methoxyphenylamino)-8-methylquinoline-6-sulfonyl]benzoyl]piperazin-1-yl]ethyl ester

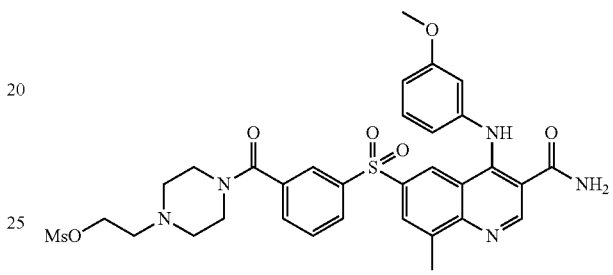

To a solution of Intermediate 93 (410 mg, 0.68 mmol) in $CH_2Cl_2$ at 0° C., MsCl (105 µL, 1.36 mmol) was added, followed by TEA (284 µL, 2.0 mmol). The reaction mixture was stirred for 30 min, and poured into 0.5 N HCl (aq). The aqueous phase was washed with $CH_2Cl_2$, then made basic with $NaHCO_3$ (aq) to pH~8 and extracted with $CH_2Cl_2$. The combined organic phases were washed with brine, dried, and concentrated to give the title compound. ES/MS calcd. for $C_{32}H_{36}N_5O_8S_2^+$ 682.2. Found m/z=682.3 $(M+H)^+$.

Intermediate 139: 6-[3-[4-[2-[2-(tert-Butyldimethylsilanyloxy)-2-(8-hydroxy-2-oxo-1,2-dihydroquinolin-5-yl)ethylamino]ethyl]piperazine-1-carbonyl]benzenesulfonyl]-4-(3-methoxy-phenylamino)-8-methylquinoline-3-carboxamide

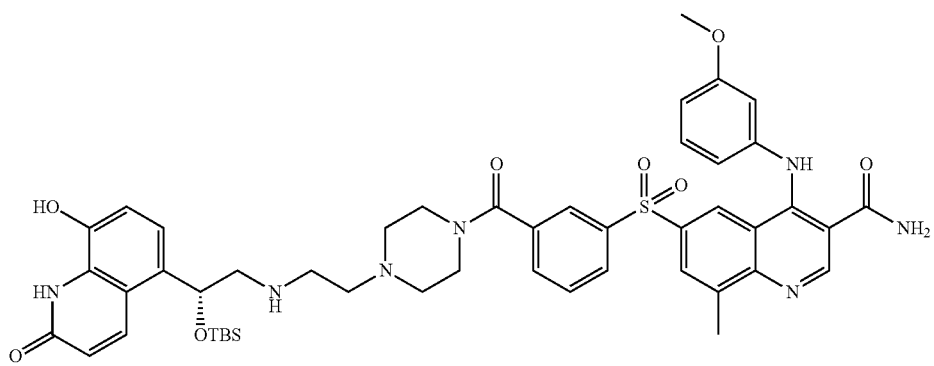 [SMILES: COc1cccc(Nc2c(C(N)=O)cnc3c(C)cc(S(=O)(=O)c4cccc(C(=O)N5CCN(CCNC[C@H](O[Si](C)(C)C(C)(C)C)c6ccc(O)c7[nH]c(=O)ccc67)CC5)c4)cc23)c1]

To a solution of Intermediate 138 (360 mg, 0.53 mmol) and Intermediate 2 (209 mg, 0.53 mmol) in 3 mL DMSO, DIEA (276 µL, 1.59 mmol) was added at 50° C. The reaction mixture was stirred for 1 h and water was added. The solid was collected by filtration and purified with prep HPLC to give the title compound. ES/MS calcd. for $C_{48}H_{58}N_7O_8SSi^+$ 920.4. Found m/z=920.3 $(M+H)^+$.

Intermediate 140: (R)-6-[[3-[[4-[2-[[2-[8-(Benzy-loxy)-2-oxo-1,2-dihydroquinolin-5-yl]-2-[(tert-bu-tyldimethylsilyl)oxy]ethyl]amino]ethyl]phenyl]car-bamoyl]-phenyl]sulfonyl]-4-[(3-methoxyphenyl)amino]-8-methylquinoline-3-carboxamide

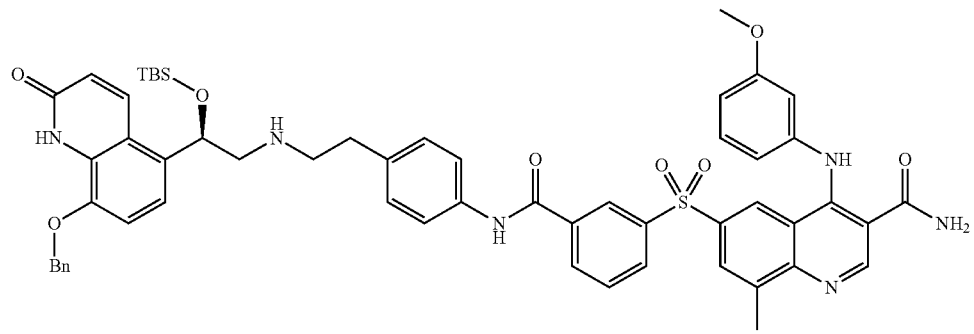

Intermediate 94 (206 mg, 0.258 mmol) was combined with (R)-8-(benzyloxy)-5-[2-bromo-1-[(tert-butyldimethylsilyl)oxy]ethyl]quinolin-2(1H)-one (115 mg, 0.235 mmol), sodium iodide (20 mg, 0.133 mmol), and $K_2CO_3$ (97 mg, 0.705 mmol) in a mixture of anhydrous acetonitrile (1.0 mL) and anhydrous DMF (0.5 mL) and was heated to 100° C. in a microwave for 2 h. The reaction was poured into $H_2O$ and extracted repeatedly into EtOAc. Flash chromatography (0-15% MeOH/$CH_2Cl_2$) gave the title compound as a yellow solid, 98 mg. $^1$H NMR (400 MHz, DMSO-$d_6$) δ 10.81 (s, 1H), 10.54 (br s, 1H), 10.45 (s, 1H), 9.09 (s, 1H), 8.36 (d, J=1.7 Hz, 1H), 8.29-8.34 (m, 2H), 8.27 (d, J=10.0 Hz, 1H), 8.21 (dt, J=7.8, 1.3 Hz, 1H), 8.02-8.05 (m, 1H), 7.85-7.89 (m, 1H), 7.78 (br s, 1H), 7.75 (t, J=7.9 Hz, 1H), 7.67 (d, J=8.4 Hz, 2H), 7.54-7.58 (m, 2H), 7.33-7.40 (m, 2H), 7.27-7.33 (m, 1H), 7.14-7.20 (m, 3H), 7.11 (t, J=8.1 Hz, 1H), 7.09 (d, J=8.3 Hz, 1H), 6.62-6.68 (m, 2H), 6.54 (d, J=9.9 Hz, 1H), 6.50-6.54 (m, 1H), 5.26 (s, 2H), 5.09-5.17 (m, 1H), 3.60 (s, 3H), 2.72-2.86 (m, 3H), 2.71 (s, 3H), 2.59-2.68 (m, 3H), 0.78 (s, 9H), 0.00 (s, 3H), −0.21 (s, 3H). ES/MS calcd. for $C_{57}H_{61}N_6O_8SSi^+$ 1017.4. Found m/z=1017.5 (M+H$^+$).

Intermediate 141: (R)-6-((3-((2-(4-(2-((2-(8-(benzy-loxy)-2-oxo-1,2-dihydroquinolin-5-yl)-2-((tert-bu-tyldimethylsilyl)oxy)ethyl)amino)ethyl)phenoxy)ethyl)(methyl)carbamoyl)phenyl)sulfonyl)-4-((3-methoxyphenyl)amino)-8-methylquinoline-3-carboxamide

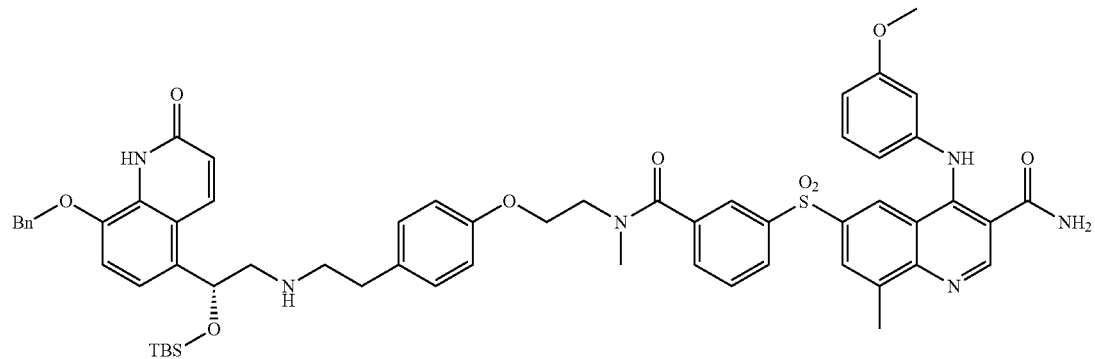

The title compound was synthesized in a manner analogous to that described for Intermediate 140, using Intermediate 95 in place of Intermediate 94. ES/MS calcd for $C_{60}H_{67}N_6O_9SSi^+$ 1075.45. Found m/z=1075.4 (M+H)$^+$.

Intermediate 142: (R)-6-((3-(4-(3-(2-((2-(8-(benzyloxy)-2-oxo-1,2-dihydroquinolin-5-yl)-2-((tert-butyldimethylsilyl)oxy)ethyl)amino)-2-methylpropyl)benzoyl)piperazine-1-carbonyl)phenyl)sulfonyl)-4-((3-methoxyphenyl)amino)-8-methylquinoline-3-carboxamide

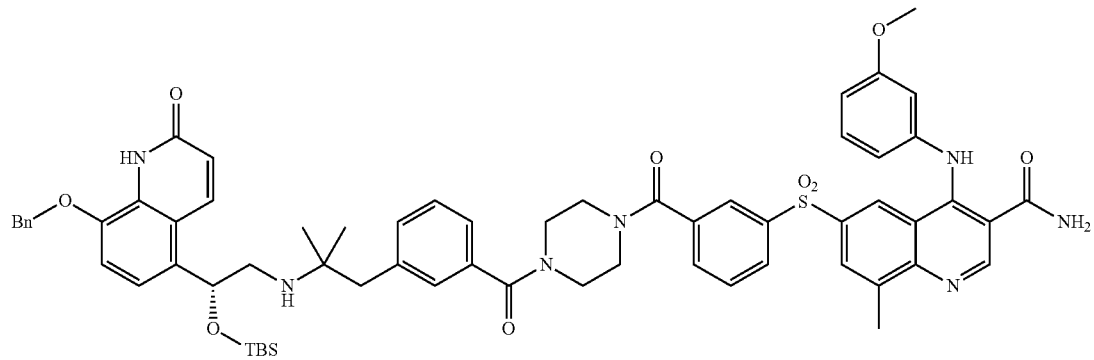

The title compound was synthesized in a manner analogous to that described for Intermediate 97, using Intermediate 101 in place of 3-(2-oxopropyl)benzoic acid. ES/MS calcd. for $C_{64}H_{72}N_7O_9SSi^+$ 1142.5. Found m/z=1142.5 (M+H)$^+$.

Intermediate 143: (R)-6-((3-((3-(2-((2-(8-(benzyloxy)-2-oxo-1,2-dihydroquinolin-5-yl)-2-((tert-butyldimethylsilyl)oxy)ethyl)amino)-2-methylpropyl)-N-methylbenzamido)methyl)phenyl)sulfonyl)-4-((3-methoxyphenyl)amino)-8-methylquinoline-3-carboxamide

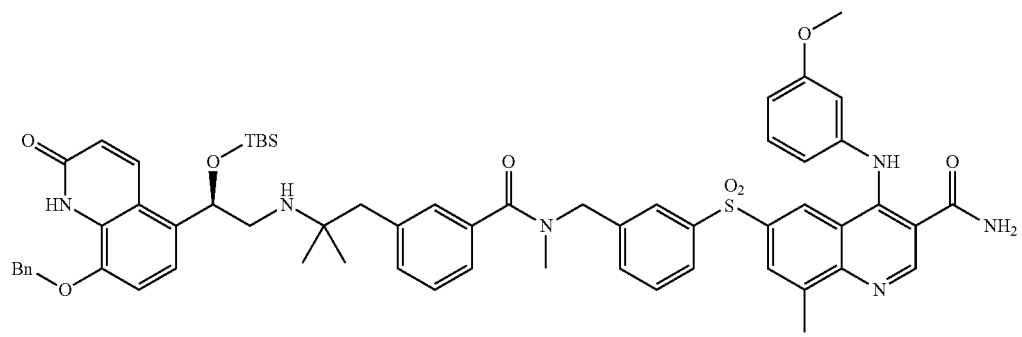

The title compound was synthesized in a manner analogous to that described for Intermediate 142, using Intermediate 136 in place of Intermediate 96. ES/MS calcd. for $C_{61}H_{68}N_6NaO_8SSi^+$ 1095.5. Found m/z=1095.4 (M+Na)$^+$.

Intermediate 144: (R)-6-[[3-[[4-[2-[[2-[8-(Benzyloxy)-2-oxo-1,2-dihydroquinolin-5-yl]-2-hydroxyethyl]amino]ethyl]phenyl]carbamoyl]phenyl]sulfonyl]-4-[(3-methoxyphenyl)amino]-8-methylquinoline-3-carboxamide

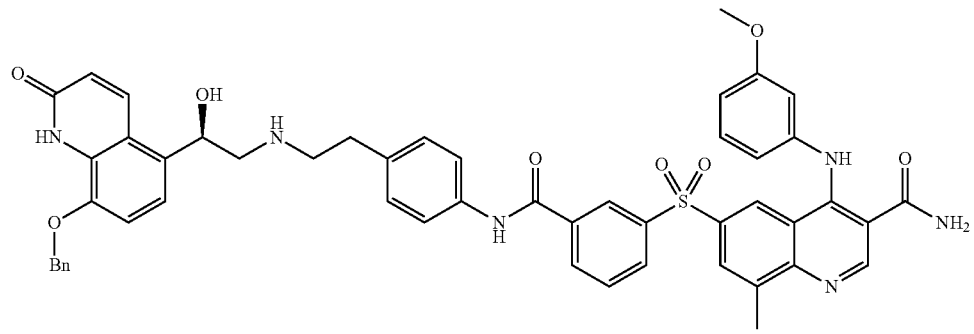 [SMILES: COc1cccc(Nc2c(C(N)=O)cnc3c(C)cc(S(=O)(=O)c4cccc(C(=O)Nc5ccc(CCNC[C@H](O)c6ccc(OCc7ccccc7)c7[nH]c(=O)ccc67)cc5)c4)cc23)c1]

Intermediate 140 (135 mg, 0.133 mmol) was combined with TBAF (1M/THF, 0.4 mL) and acetic acid (23 μL) in anhydrous acetonitrile (0.2 mL) and allowed to stir at rt. After 18 h, the reaction was concentrated in vacuo to a brown oil, which was suspended in H$_2$O. The solid was filtered and washed with H$_2$O and hexane, then dried to give the title compound as a yellow solid, 124 mg, which was used in the next step without further purification. $^1$H NMR (400 MHz, DMSO-d$_6$) δ 10.80 (s, 1H), 10.46 (s, 1H), 9.09 (s, 1H), 8.37 (s, 1H), 8.32 (s, 1H), 8.30 (br s, 1H), 8.16-8.24 (m, 2H), 8.03 (s, 1H), 7.86 (d, J=7.9 Hz, 1H), 7.77 (br s, 1H), 7.76 (dd, J=7.6, 15.6 Hz, 1H), 7.66 (d, J=8.3 Hz, 2H), 7.55 (d, J=7.6 Hz, 2H), 7.32-7.41 (m, 2H), 7.26-7.32 (m, 1H), 7.07-7.23 (m, 5H), 6.61-6.69 (m, 2H), 6.49-6.59 (m, 2H), 5.28 (s, 2H), 5.03 (t, J=6.1 Hz, 1H), 3.60 (s, 3H), 3.15-3.19 (m, 2H), 2.70 (s, 3H), 2.62-2.81 (m, 7H). ES/MS calcd. for C$_{51}$H$_{47}$N$_6$O$_8$S$^+$ 903.3. Found m/z=903.3 (M+H$^+$).

Intermediate 145: (R)-6-((3-((2-(4-(2-((2-(((tert-butyldimethylsilyl)oxy)-2-(8-hydroxy-2-oxo-1,2-dihydroquinolin-5-yl)ethyl)amino)ethyl)phenoxy)ethyl)(methyl)carbamoyl)phenyl)sulfonyl)-4-((3-methoxyphenyl)amino)-8-methylquinoline-3-carboxamide A solution of Intermediate 141 (0.3769 g, 0.3505 mmol) in MeOH (7 mL) was degassed by bubbling N$_2$ through the solution for approximately 10 minutes. The solution was cooled to 0° C. and Pd/C (0.3850 g of 10 wt %) was added slowly. The reaction flask was purged and filled with H$_2$ 3× before stirring under H$_2$ (1 atm, balloon). The reaction mixture was warmed to room temperature and reaction progress was monitored by LC-MS. After 72 h, the reaction mixture was filtered through a pad of Celite. The filter cake was washed with 1:1 DCM/MeOH. The filtrate was concentrated and the residue was dissolved in 3:1 MeOH/EtOAc. The solution was degassed and cooled as described above; Pd/C (0.311 g of 10 wt %) was added and the mixture was placed under H$_2$ atmosphere as described above. Reaction progress was monitored by LC-MS. After 24 h, the reaction mixture was filtered through a pad of Celite and the filtrate was concentrated under reduced pressure. The residue was purified by column chromatography on silica gel (gradient elution 1:19 to 1:3 MeOH/DCM) to yield the title compound (0.155 g, 45%) as a yellow solid. ES/MS calcd for C$_{53}$H$_{61}$N$_6$O$_9$SSi$^+$ 985.4. Found m/z=985.5 (M+H)$^+$.

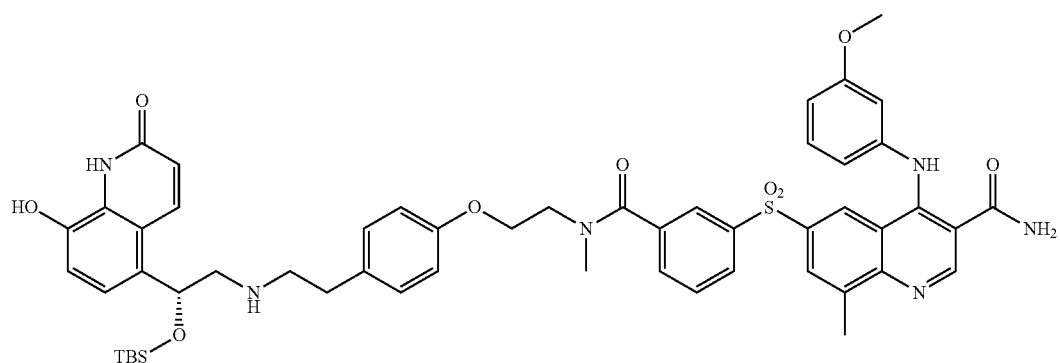

Intermediate 146: (R)-6-((3-(4-(3-(2-((2-(8-(benzyloxy)-2-oxo-1,2-dihydroquinolin-5-yl)-2-hydroxyethyl)amino)-2-methylpropyl)benzoyl)piperazine-1-carbonyl)phenyl)sulfonyl)-4-((3-methoxyphenyl)amino)-8-methylquinoline-3-carboxamide

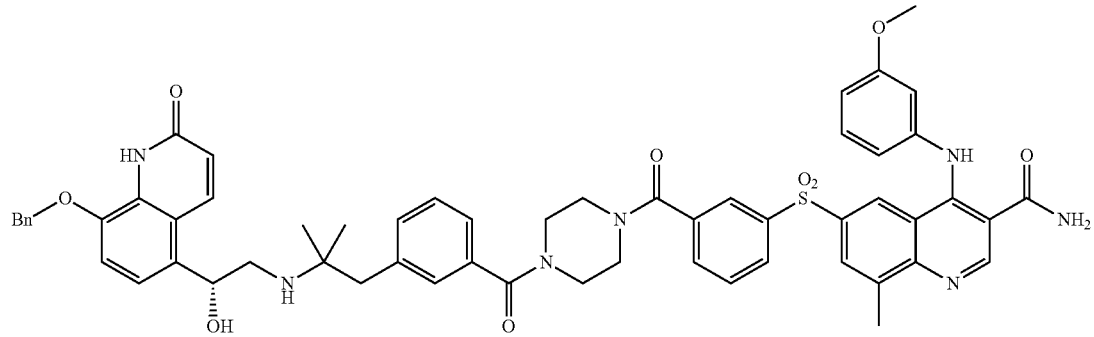 [SMILES: COc1cccc(Nc2c(C(N)=O)cnc3c(C)cc(S(=O)(=O)c4cccc(C(=O)N5CCN(C(=O)c6cccc(CC(C)(C)NC[C@H](O)c7ccc(OCc8ccccc8)c8[nH]c(=O)ccc78)c6)CC5)c4)cc23)c1]

The title compound was synthesized in a manner analogous to that described for Intermediate 144, using Intermediate 142 as a substrate. ES/MS calcd. for $C_{58}H_{58}N_7O_9S^+$ 1028.4. Found m/z=1028.3 (M+H)$^+$.

Intermediate 147: (R)-6-((3-((3-(2-((2-(8-(benzyloxy)-2-oxo-1,2-dihydroquinolin-5-yl)-2-hydroxyethyl)amino)-2-methylpropyl)-N-methylbenzamido)methyl)phenyl)sulfonyl)-4-((3-methoxyphenyl)amino)-8-methylquinoline-3-carboxamide

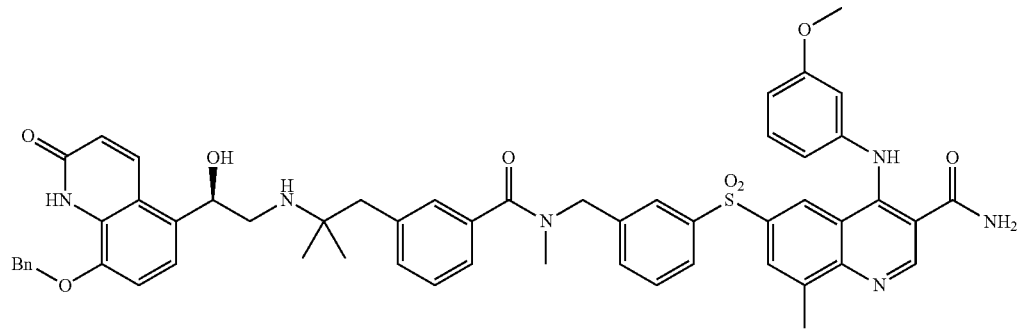 [SMILES: COc1cccc(Nc2c(C(N)=O)cnc3c(C)cc(S(=O)(=O)c4cccc(CN(C)C(=O)c5cccc(CC(C)(C)NC[C@H](O)c6ccc(OCc7ccccc7)c7[nH]c(=O)ccc67)c5)c4)cc23)c1]

The title compound was synthesized in a manner analogous to that described for Intermediate 144, using Intermediate 143 as a substrate. ES/MS calcd. for $C_{55}H_{54}N_6NaO_8S^+$ 981.4. Found m/z=981.4 (M+Na)$^+$.

Intermediate 148: (R)-6-[[3-[[8-[[2-[(tert-Butyldimethylsilyl)oxy]-2-(8-hydroxy-2-oxo-1,2-dihydroquinolin-5-yl]ethyl]amino]octyl]carbamoyl]phenyl]sulfonyl]-4-[(3-methoxyphenyl)amino]-8-methylquinoline-3-carboxamide

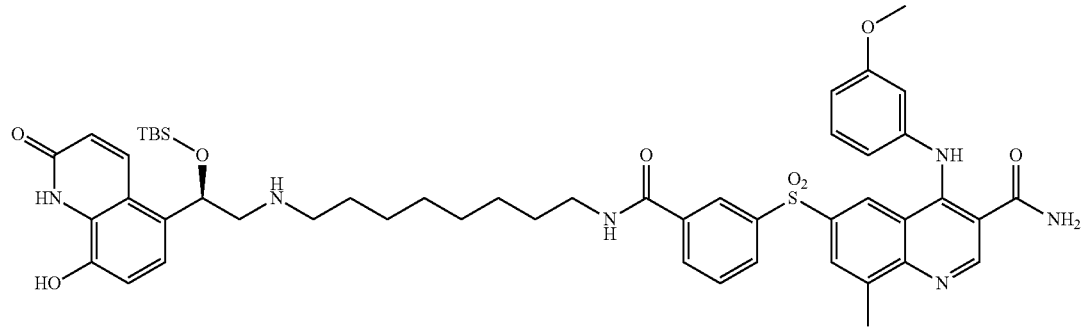

Glacial acetic acid (0.005 mL, 0.089 mmol) and Intermediate 2 (50 mg, 0.149 mmol) were added to a stirring solution of Intermediate 112 (55 mg, 0.089 mmol) in DMF (2 mL) at rt. The resulting solution was stirred for 3 h, then NaBH(OAc)$_3$ (57 mg, 0.267 mmol) was added in portions. The reaction mixture was stirred over night then poured into said. NaHCO$_3$ (40 mL). The precipitate was filtered, washed with H$_2$O (50 mL), and dried to give the title compound (76 mg) as a yellow solid. The compound was used with no further purification. ES/MS calcd. for $C_{50}H_{63}N_6O_8SSi^+$ 935.4. Found m/z=935.4 (M+H$^+$).

Intermediate 149: (R)-6-[[3-[[6-[[2-[tert-Butyldimethylsilyl)oxy]-2-(8-hydroxy-2-oxo-1,2-dihydroquinolin-5-yl)ethyl]amino]hexyl]carbamoyl]phenyl]sulfonyl]-4-[(3-methoxyphenyl)amino]-8-methylquinoline-3-carboxamide

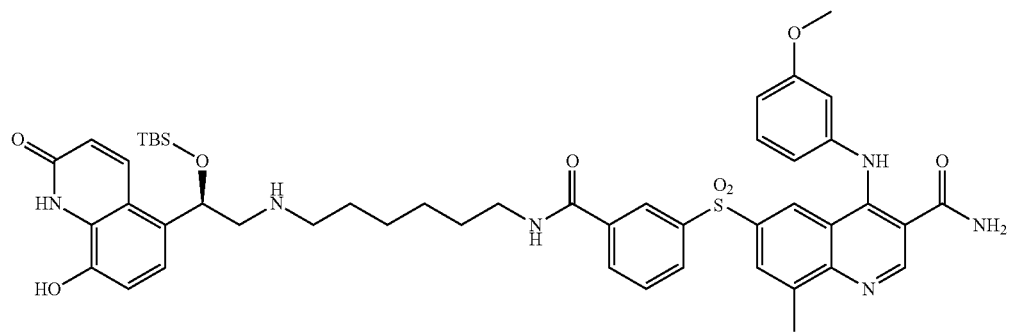

The title compound was synthesized in a manner analogous to that described for Intermediate 148, using Intermediate 113 in place of Intermediate 112. ES/MS calcd. for $C_{48}H_{59}N_6O_8SSi^+$ 907.4. Found m/z=907.4 (M+H$^+$).

Intermediate 150: (R)-6-[[3-[[4-[[2-[(Tert-Butyldimethylsilyl)oxy]-2-(8-hydroxy-2-oxo-1,2-dihydroquinolin-5-yl)ethyl]amino]piperidin-1-yl]carbonyl]phenyl]sulfonyl]-4-[(3-methoxyphenyl)amino]-8-methylquinoline-3-carboxamide

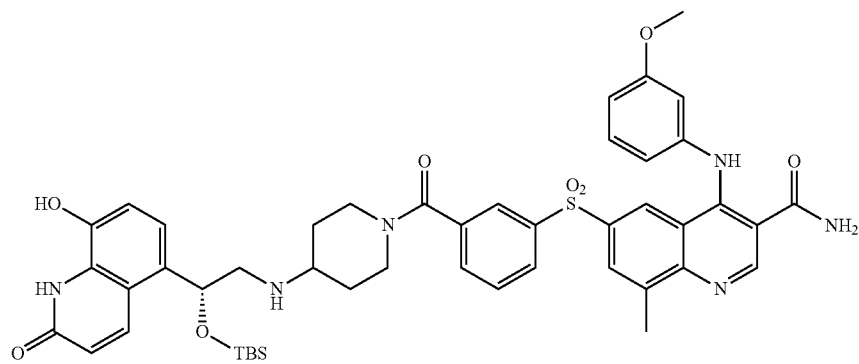

The title compound was synthesized in a manner analogous to that described for Intermediate 148, using Intermediate 133 in place of Intermediate 112. ES/MS calcd. for $C_{47}H_{55}N_6O_8SSi^+$ 891.4. Found m/z=891.4 (M+H$^+$).

Intermediate 151: (R)-6-((3-((4'-(4-((2-((tert-butyldimethylsilyl)oxy)-2-(5-hydroxy-3-oxo-3,4-dihydro-2H-benzo[b][1,4]oxazin-8-yl)ethyl)amino)butyl)-[1,1'-biphenyl]-4-yl)carbamoyl)phenyl)sulfonyl)-4-((3-methoxyphenyl)amino)-8-methylquinoline-3-carboxamide

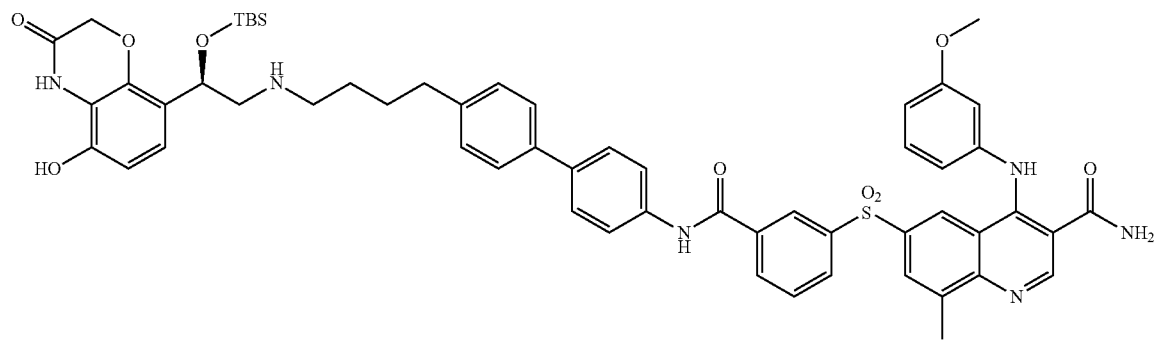

The title compound was synthesized in a manner analogous to that described for Intermediate 148, using (R)-8-(2-amino-1-((tert-butyldimethylsilyl)oxy)ethyl)-5-hydroxy-2H-benzo[b][1,4]oxazin-3(4H)-one in place of Intermediate 2 and Intermediate 124 in place of Intermediate 112. ES/MS calcd. for $C_{57}H_{63}N_6O_9SSi^+$ 1035.4. Found m/z=1035.6 (M+H)$^+$.

Intermediate 152: (R)-6-((3-((4'-(4-((2-((tert-butyldimethylsilyl)oxy)-2-(5-hydroxy-3-oxo-3,4-dihydro-2H-benzo[b][1,4]oxazin-8-yl)ethyl)amino)butyl)-[1,1'-biphenyl]-3-yl)carbamoyl)phenyl)sulfonyl)-4-((3-methoxyphenyl)amino)-8-methylquinoline-3-carboxamide

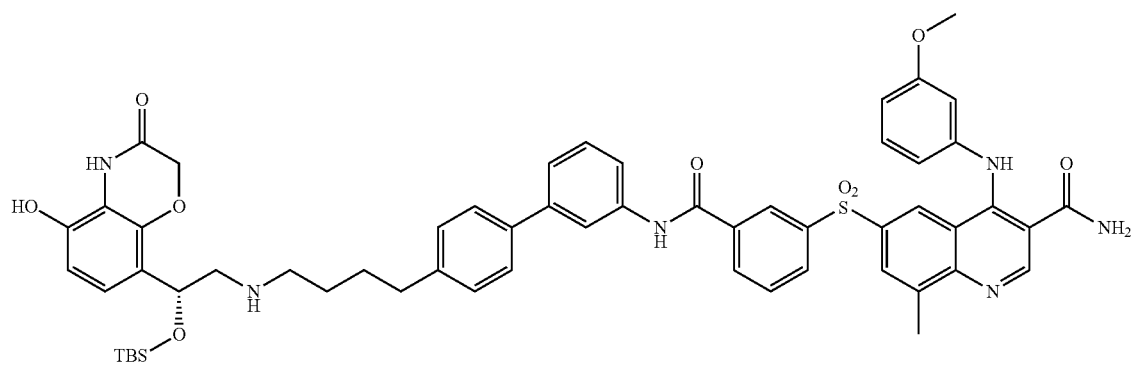

The title compound was synthesized in a manner analogous to that described for Intermediate 148, using Intermediate 125 in place of Intermediate 124. ES/MS calcd. for $C_{57}H_{63}N_6O_9SSi^+$ 1035.4. Found m/z=1035.6 (M+H)$^+$.

Intermediate 153: (R)-6-[[3-[[4-[5-[[2-[(tert-Butyldimethylsilyl)oxy]-2-(8-hydroxy-2-oxo-1,2-dihydroquinolin-5-yl)ethyl]amino]pent-1-ynyl]phenyl]carbamoyl]phenyl]-sulfonyl]-4-[(3-methoxyphenyl)amino]-8-methylquinoline-3-carboxamide

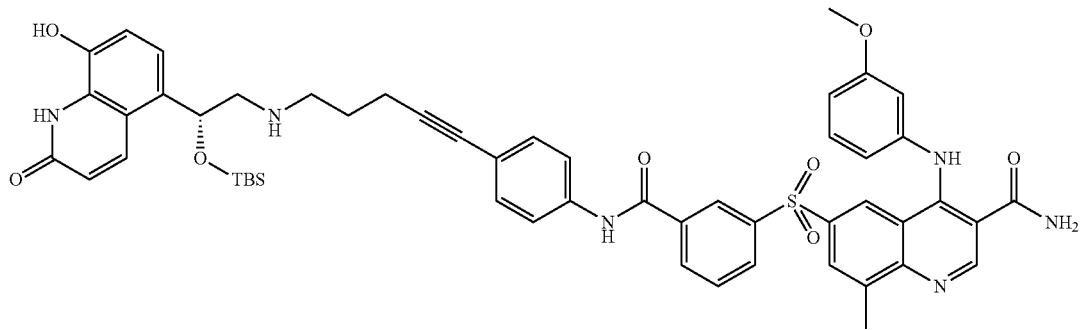

The title compound was synthesized in a manner analogous to that described for Intermediate 148, using Intermediate 115 in place of Intermediate 112. ES/MS calcd. for $C_{53}H_{57}N_6O_8SSi^+$ 965.4. Found m/z=965.4 (M+H)$^+$.

Intermediate 154: (R)-6-((3-((4-(5-((2-((tert-butyldimethylsilyl)oxy)-2-(8-hydroxy-2-oxo-1,2-dihydroquinolin-5-yl)ethyl)amino)pent-1-yn-1-yl)-2-methylphenyl)carbamoyl)phenyl)sulfonyl)-4-((3-methoxyphenyl)amino)-8-methylquinoline-3-carboxamide

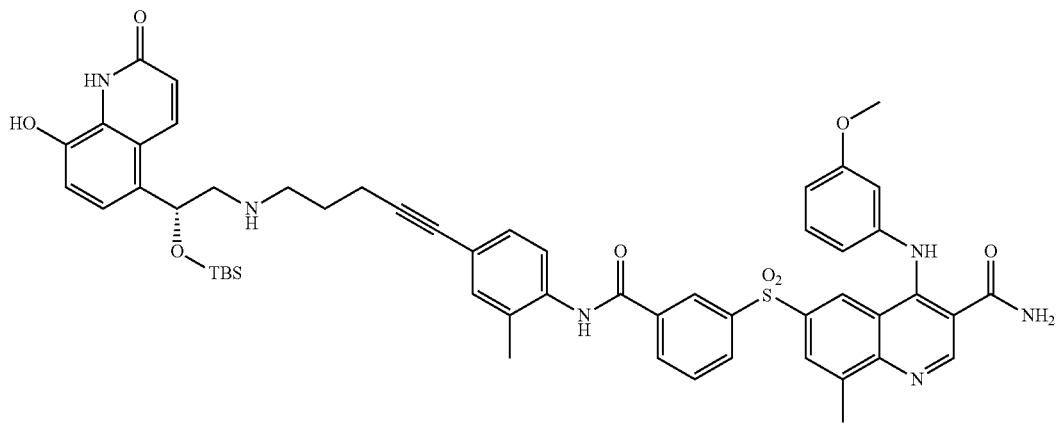

The title compound was synthesized in a manner analogous to that described in Intermediate 148, using Intermediate 117 in place of Intermediate 112. ES/MS calcd. for $C_{52}H_{56}N_6O_9SSi$ 978.4. Found m/z=979 (M+H)$^+$.

Intermediate 155: (R)-6-((3-((4-(6-((2-((tert-butyldimethylsilyl)oxy)-2-(8-hydroxy-2-oxo-1,2-dihydroquinolin-5-yl)ethyl)amino)hex-1-yn-1-yl)phenyl)carbamoyl)phenyl)sulfonyl)-4-((3-methoxyphenyl)amino)-8-methylquinoline-3-carboxamide

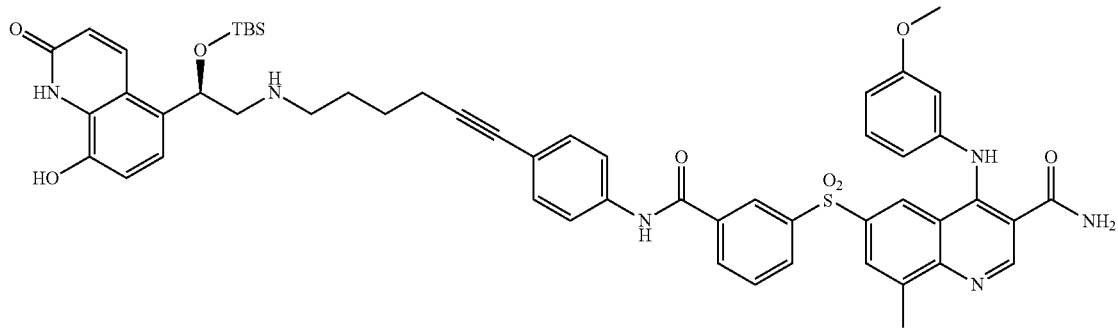

The title compound was synthesized in a manner analogous to that described for Intermediate 148, using instead Intermediate 119 in place of Intermediate 112. ES/MS calcd. for $C_{54}H_{59}N_6O_8SSi^+$ 979.4. Found m/z=979.5 (M+H)$^+$.

Intermediate 156: (R)-6-((3-((4-(5-((2-((tert-butyldimethylsilyl)oxy)-2-(8-hydroxy-2-oxo-1,2-dihydroquinolin-5-yl)ethyl)(methyl)amino)pent-1-yn-1-yl)phenyl)carbamoyl)phenyl)sulfonyl)-4-((3-methoxyphenyl)amino)-8-methylquinoline-3-carboxamide

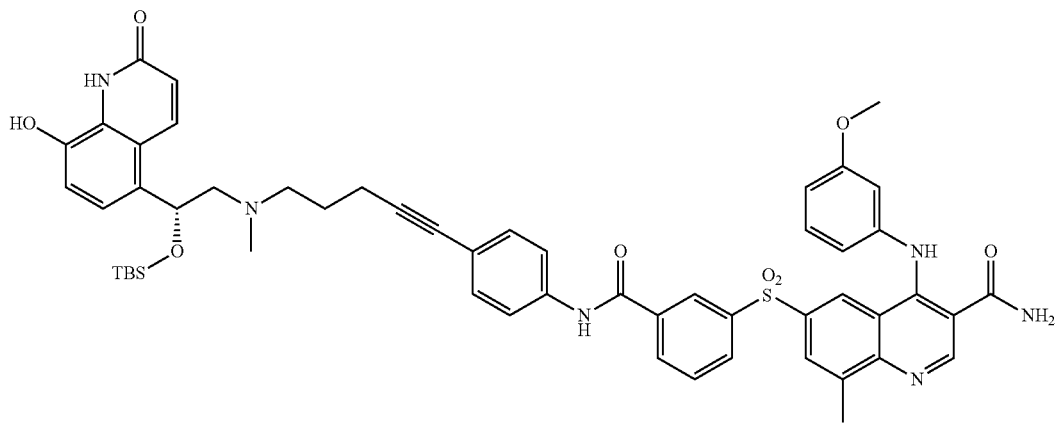

The title compound was synthesized in a manner analogous to that described for Intermediate 70, using Intermediate 103 in place of 8-aminooctanol. ES/MS calcd. for $C_{54}H_{59}N_6O_8SSi^+$ 979.4. Found m/z=979.6 (M+H)$^+$.

Intermediate 157: (R)-6-((3-((3-(5-((2-((tert-butyldimethylsilyl)oxy)-2-(8-hydroxy-2-oxo-1,2-dihydroquinolin-5-yl)ethyl)amino)pent-1-yn-1-yl)phenyl)carbamoyl)phenyl)sulfonyl)-4-((3-methoxyphenyl)amino)-8-methylquinoline-3-carboxamide

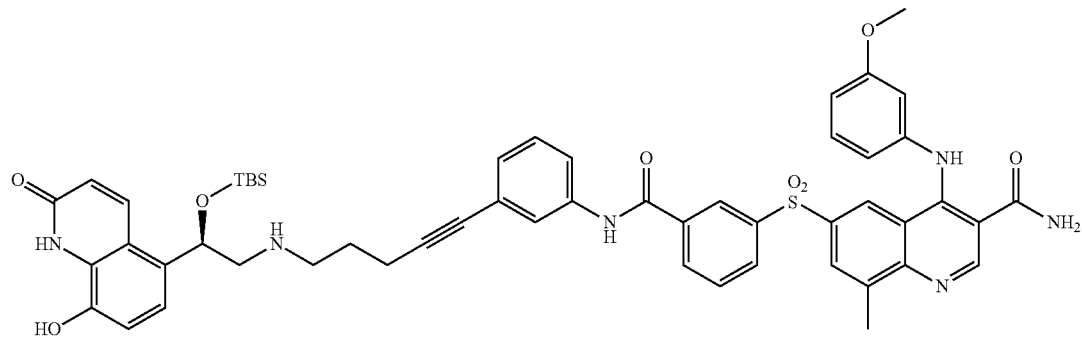

A mixture of Intermediate 98 (0.35 g, 0.48 mmol) and Intermediate 2 (0.24 g, 0.72 mmol) in DMF (4.5 mL) was treated with N,N-diisopropylethylamine (0.25 mL) and catalytic potassium iodide (50 mg). The mixture was heated for 19 hours in a 55° C. oil bath. The mixture was concentrated under reduced pressure and purified via automated flash silica gel chromatography, using a 25 g Silicycle SiliSep flash column (dichloromethane/methanol/ammonium hydroxide). Concentration of the desired fractions under reduced pressure provided the title compound as a yellow solid (0.28 g, 61%). ES/MS calcd. for $C_{53}H_{57}N_6O_8SSi^+$ 965.4. Found m/z=965.5 (M+H)$^+$.

Intermediate 158: (R)-tert-butyl (2-((tert-butyldimethylsilyl)oxy)-2-(8-hydroxy-2-oxo-1,2-dihydroquinolin-5-yl)ethyl)(4-(2-(4-(3-((3-carbamoyl-4-((3-methoxyphenyl)amino)-8-methylquinolin-6-yl)sulfonyl)benzamido)phenyl)-1,3-dithiolan-2-yl)butyl)carbamate

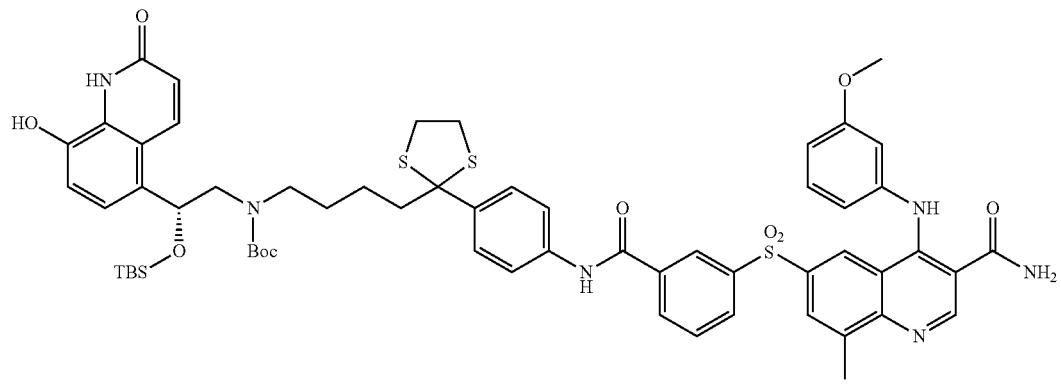

DMAP (20 mg), HATU (110 mg, 0.29 mmol) and DIEA (0.15 mL, 0.87 mmol) were added to a stirring mixture of 3-[[3-carbamoyl-4-[(3-methoxyphenyl)amino]-8-methylquinolin-6-yl]sulfonyl]benzoic acid (144 mg, 0.29 mmol) and Intermediate 105 (0.18 g, 0.35 mmol) in NMP (3 mL). The reaction mixture was stirred overnight in an 80° C. oil bath and then purified by reverse-phase high performance liquid chromatography (RP-HPLC, acetonitrile/water/0.1% TFA) to provide, after concentration, the title compound as a dark yellow solid (90 mg, 27%). ES/MS calcd. for $C_{60}H_{71}N_6O_{10}S_3Si^+$ 1159.4. Found m/z=1159.6 (M+H)$^+$.

Intermediate 159: (R)-tert-butyl (2-(8-((tert-butoxy-carbonyl)oxy)-2-oxo-1,2-dihydroquinolin-5-yl)-2-((tert-butyldimethylsilyl)oxy)ethyl)(6-(4-(4-(3-((3-carbamoyl-4-((3-methoxyphenyl)amino)-8-methylquinolin-6-yl)sulfonyl)benzamido)phenyl)butoxy)hexyl)carbamate

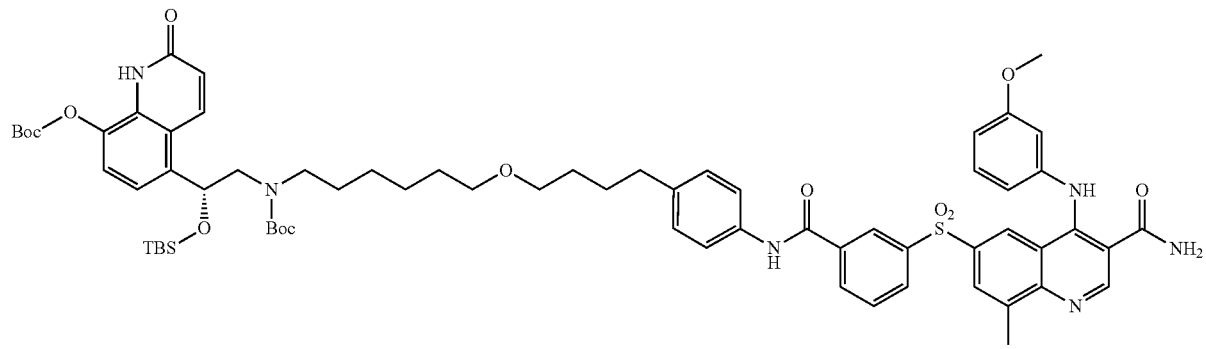

The title compound was synthesized in a manner analogous to that described for Intermediate 70, using Intermediate 108 in place of 8-aminooctanol. ES/MS calcd. for $C_{68}H_{87}N_6O_{13}SSi^+$ 1255.6. Found m/z=1256 (M+H)$^+$.

Intermediate 160: (R)-tert-butyl (2-(8-((tert-butoxy-carbonyl)oxy)-2-oxo-1,2-dihydroquinolin-5-yl)-2-((tert-butyldimethylsilyl)oxy)ethyl)(6-(4-(3-((3-carbamoyl-4-((3-methoxyphenyl)amino)-8-methylquinolin-6-yl)sulfonyl)benzamido)phenethoxy)hexyl)carbamate

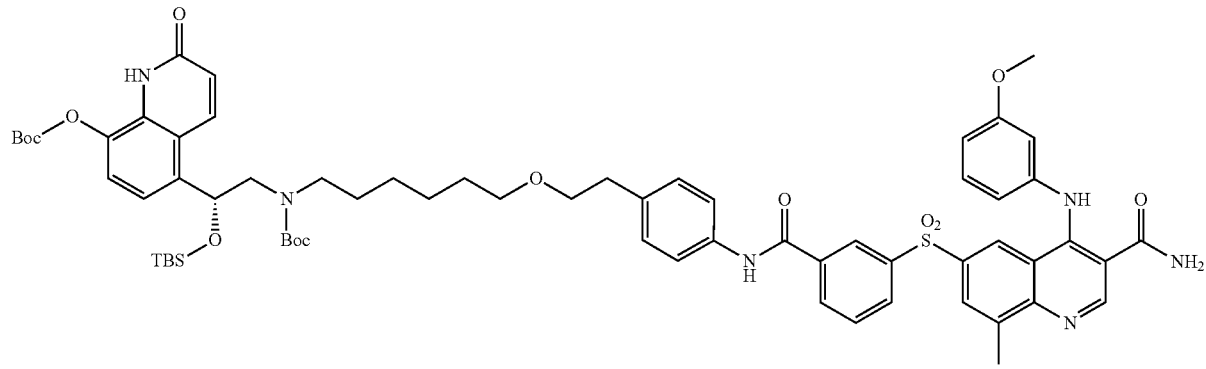

The title compound was synthesized in a manner analogous to that described for Intermediate 70, using Intermediate 111 in place of 8-aminooctanol. ES/MS calcd. for $C_{61}H_{75}N_6O_{11}SSi^+$ 1127.5. Found m/z=1127.7 (M+H)$^+$.

Intermediate 161: (R)-6-((3-((4-(5-(8-hydroxy-2-oxo-1,2-dihydroquinolin-5-yl)-2,2,3,3-tetramethyl-4,14-dioxa-7-aza-3-silaoctadecan-18-yl)phenyl)(methyl)carbamoyl)phenyl)sulfonyl)-4-((3-methoxyphenyl)amino)-8-methylquinoline-3-carboxamide

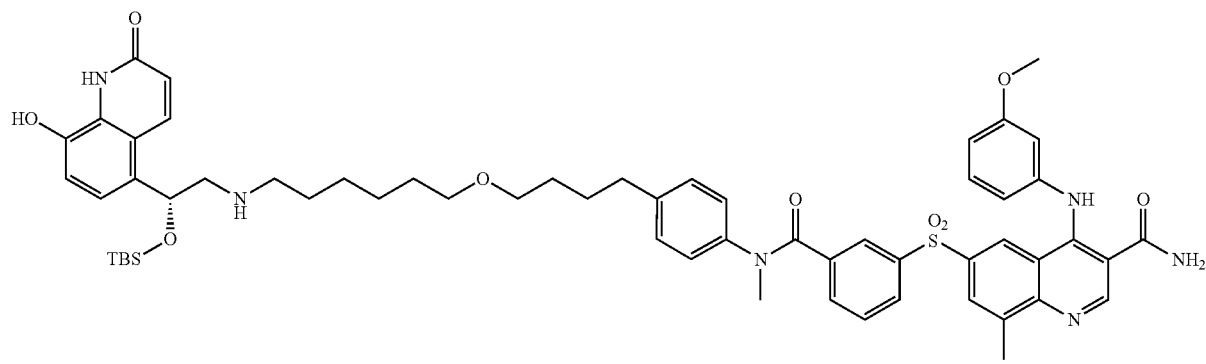

The title compound was synthesized in a manner analogous to that described for Intermediate 157, using Intermediate 99 in place of Intermediate 98. ES/MS calcd. for $C_{54}H_{73}BrN_6O_9SSi^+$ 1069.5. Found m/z=1069.7 (M+H)$^+$.

Intermediate 162: (R)-6-((3-((4-(5-((2-((tert-butyldimethylsilyl)oxy)-2-(5-hydroxy-3-oxo-3,4-dihydro-2H-benzo[b][1,4]oxazin-8-yl)ethyl)amino)pent-1-yn-1-yl)-2-methylphenyl)carbamoyl)phenyl)sulfonyl)-4-((3-methoxyphenyl)amino)-8-methylquinoline-3-carboxamide

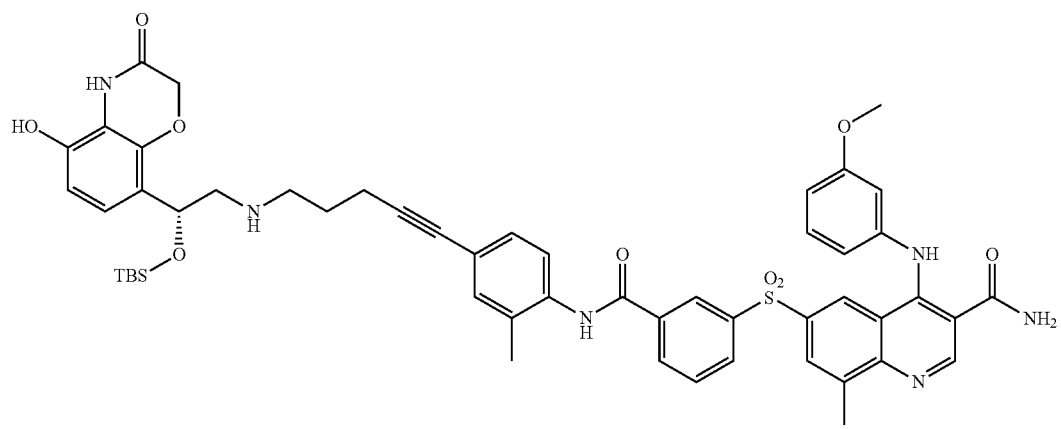

The title compound was synthesized in a manner analogous to that described in Intermediate 151, using Intermediate 117 in place of Intermediate 124. ES/MS calcd. for $C_{53}H_{58}N_6O_9SSi$ 982.4. Found m/z=983 (M+H)$^+$.

Intermediate 163: (R)-6-((3-((4-(5-((2-((tert-butyldimethylsilyl)oxy)-2-(5-hydroxy-3-oxo-3,4-dihydro-2H-benzo[b][1,4]oxazin-8-yl)ethyl)amino)pent-1-yn-1-yl)-3-methylphenyl)carbamoyl)phenyl)sulfonyl))-4-((3-methoxyphenyl)amino)-8-methylquinoline-3-carboxamide

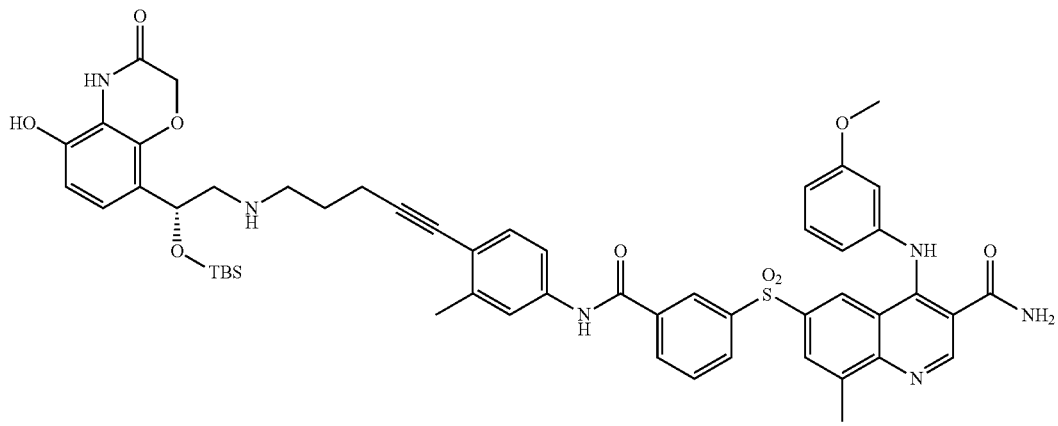

The title compound was synthesized in a manner analogous to that described in Intermediate 151, using Intermediate 118 in place of Intermediate 124. ES/MS calcd. for $C_{53}H_{58}N_6O_9SSi$ 982.4. Found m/z=983 (M+H)$^+$.

Intermediate 164: (R)-6-((3-((6-((2-((tert-butyldimethylsilyl)oxy)-2-(6-hydroxy-3-oxo-3,4-dihydro-2H-benzo[b]1,4]oxazin-8-yl)ethyl)amino)hexyl)carbamoyl)phenyl)sulfonyl)-4-((3-methoxyphenyl)amino)-8-methylquinoline-3-carboxamide

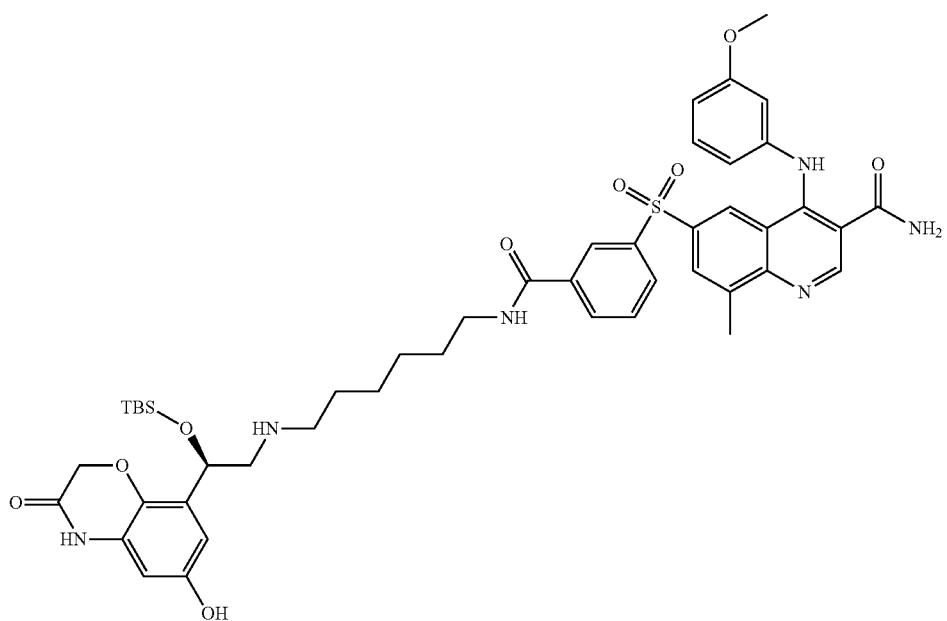

The title compound was synthesized in a manner analogous to that described for Intermediate 149, using (R)-8-(2-amino-1-((tert-butyldimethylsilyl)oxy)ethyl)-6-hydroxy-2H-benzo[b][1,4]oxazin-3(4H)-one in place of Intermediate 2. ES/MS calcd. for $C_{47}H_{59}N_6O_9SSi^+$ 911.4. Found m/z=911.5 (M+H)$^+$ Intermediate 165: (R)-6-((3-((4-(5-((2-((tert-butyldimethylsilyl)oxy)-2-(6-hydroxy-3-oxo-3,4-dihydro-2H-benzo[b][1,4]oxazin-8-yl)ethyl)amino)pent-1-yn-1-yl)phenyl)carbamoyl)phenyl)sulfonyl)-4-((3-methoxyphenyl)amino)-8-methylquinoline-3-carboxamide

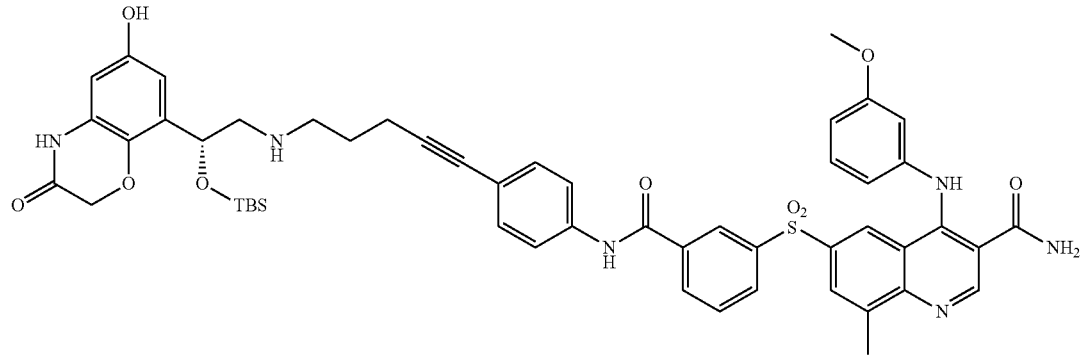

The title compound was synthesized in a manner analogous to that described for Intermediate 153, using (R)-8-(2-amino-1-((tert-butyldimethylsilyl)oxy)ethyl)-6-hydroxy-2H-benzo[b][1,4]oxazin-3(4H)-one in place of Intermediate 2. ES/MS calcd. for $C_{52}H_{57}N_6O_9SSi^+$ 969.4. Found m/z=969.5 (M+H)$^+$.

Intermediate 166: (R)-6-[[3-[[4-[5-[[2-[3-[[(tert-Butyldimethylsilyl)oxy]methyl]-4-hydroxyphenyl]-2-hydroxyethyl]amino]pentyl]phenyl]carbamoyl]phenyl]sulfonyl]-4-[(3-methoxyphenyl)amino]-8-methylquinoline-3-carboxamide

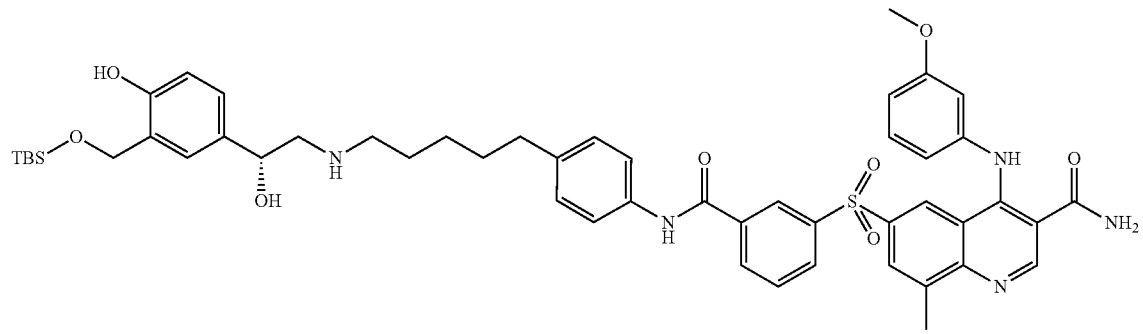

The title compound was synthesized in a manner analogous to that described for Intermediate 148, using Intermediate 9 in place of Intermediate 2 and Intermediate 120 in place of Intermediate 112. ES/MS calcd. for $C_{51}H_{62}N_5O_8SSi^+$ 932.40. Found m/z=932.4 (M+H)$^+$.

Intermediate 167: (R)-6-[[3-[[6-[[2-[(tert-Butyldimethylsilyl)oxy]-2-(3-formamido-4-hydroxyphenyl)ethyl]amino]hexyl]carbamoyl]phenyl]sulfonyl]-4-((3-methoxyphenyl)amino]-8-methylquinoline-3-carboxamide

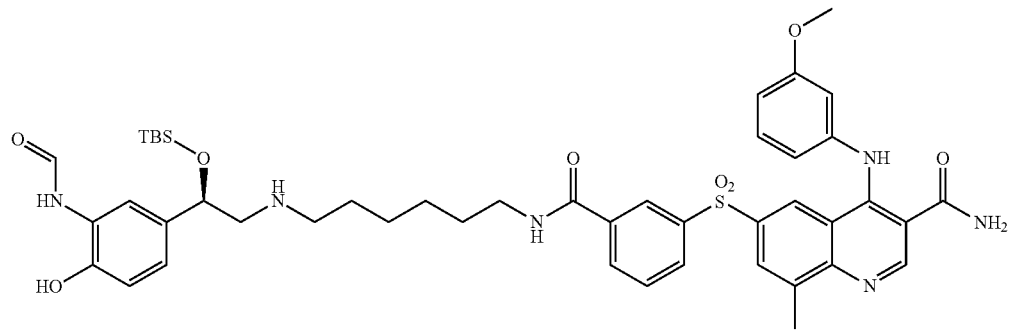

The title compound was synthesized in a manner analogous to that described for Intermediate 149, using Intermediate 13 in place of Intermediate 2. ES/MS calcd. for $C_{46}H_{59}N_6O_8SSi^+$ 883.4. Found m/z=883 (M+H)$^+$.

Intermediate 168: (R)-6-((3-((6-((2-((tert-butyldimethylsilyl)oxy)-2-(3-formamido-4-hydroxyphenyl)ethyl)amino)hexyl)(methyl)carbamoyl)phenyl)sulfonyl)-4-((3-methoxyphenyl)amino)-8-methylquinoline-3-carboxamide

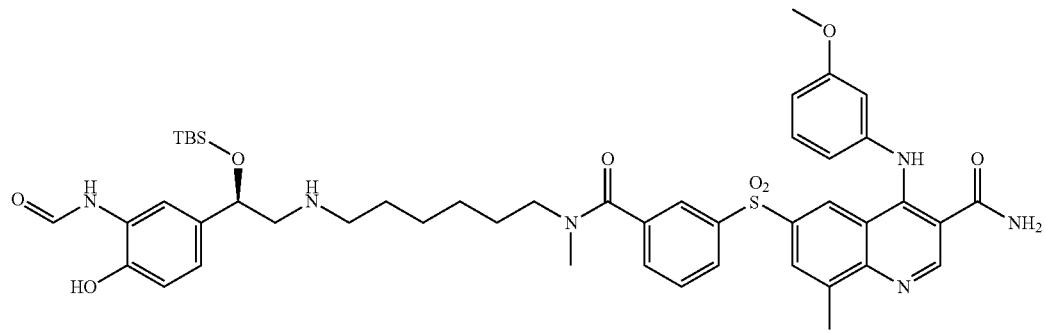

The title compound was synthesized in a manner analogous to that described in Intermediate 167, using Intermediate 114 in place of Intermediate 113. ES/MS calcd. $C_{47}H_{60}N_6O_8SSi$ 896.4. Found m/z=897 (M+H)$^+$.

Intermediate 169: (R)-6-((3-((6-((2-((tert-butyldimethylsilyl)oxy)-2-(5-hydroxy-3-oxo-3,4-dihydro-2H-benzo[b][1,4]oxazin-8-yl)ethyl)amino)hexyl)(methyl)carbamoyl)phenyl)sulfonyl)-4-((3-methoxyphenyl)amino)-8-methylquinoline-3-carboxamide

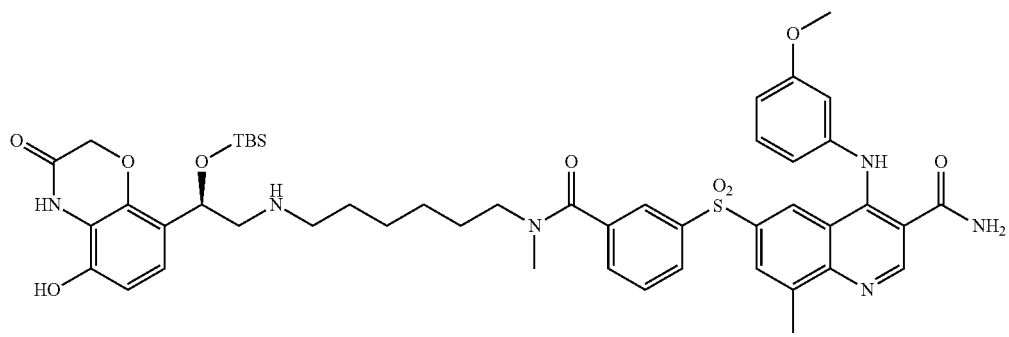

The title compound was synthesized in a manner analogous to that described in Intermediate 151, using Intermediate 114 in place of Intermediate 124. ES/MS calcd. $C_{48}H_{60}N_6O_9SSi$ 942.4. Found m/z=925 (M+H)$^+$.

Intermediate 170: (R)-6-((3-((6-((2-(((tert-butyldimethylsilyl)oxy)-2-(5-hydroxy-3-oxo-3,4-dihydro-2H-benzo[b][1,4]oxazin-8-yl)ethyl)amino)hexyl)carbamoyl)phenyl)sulfonyl)-4-((3-methoxyphenyl)amino)-8-methylquinoline-3-carboxamide

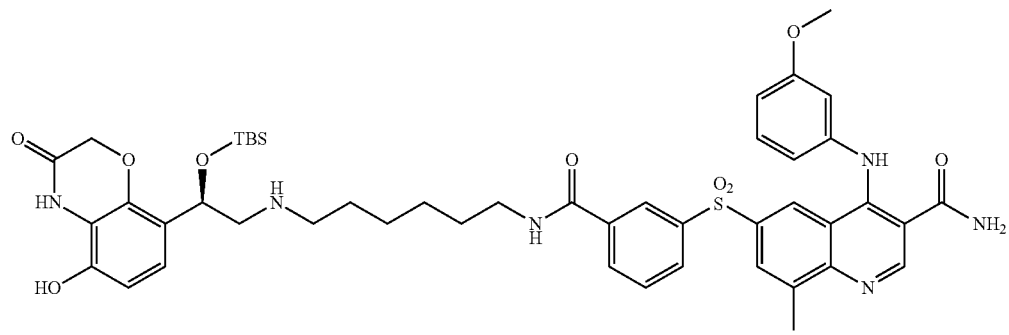

The title compound was synthesized in a manner analogous to that described in Intermediate 151, using Intermediate 113 in place of Intermediate 124. ES/MS calcd. for $C_{47}H_{58}N_6O_9SSi$ 910.4. Found m/z=911 (M+H)$^+$.

Intermediate 171: (R)-6-[[3-[[4-[5-[[2-[(tert-Butyldimethylsilyl)oxy]-2-(3-formamido-4-hydroxyphenyl)ethyl]amino]pent-1-ynyl]phenyl]carbamoyl]phenyl]sulfonyl]-4-[(3-methoxyphenyl)amino]-8-methylquinoline-3-carboxamide

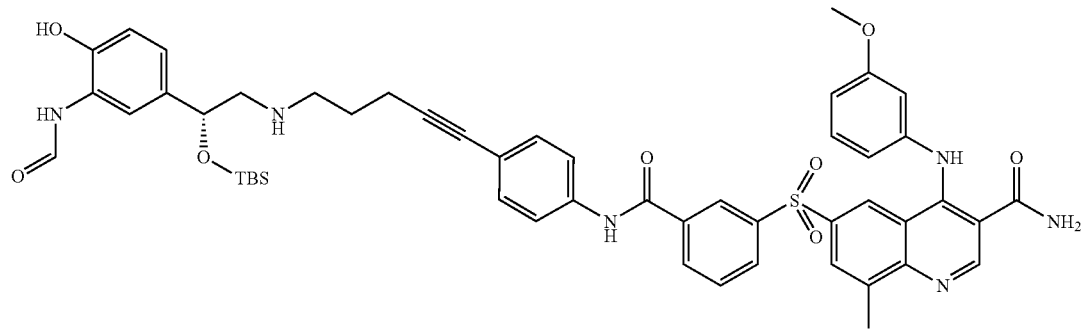

The title compound was synthesized in a manner analogous to that described for Intermediate 153, using Intermediate 13 in place of Intermediate 2. ES/MS calcd. $C_{51}H_{57}N_6O_8SSi^+$ 941.4. Found m/z=941 (M+H)$^+$.

Intermediate 172: (R)-6-((3-((4-(5-((2-((tert-butyldimethylsilyl)oxy)-2-(5-hydroxy-3-oxo-3,4-dihydro-2H-benzo[b][1,4]oxazin-8-yl)ethyl)amino)pent-1-yn-1-yl)phenyl)carbamoyl)phenyl)sulfonyl)-4-((3-methoxyphenyl)amino)-8-methylquinoline-3-carboxamide

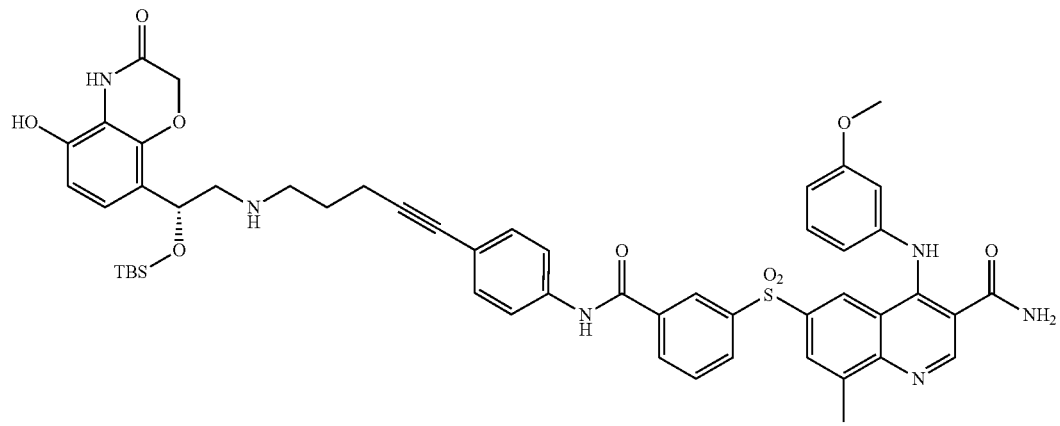

The title compound was synthesized in a manner analogous to that described in Intermediate 151, using Intermediate 115 in place of Intermediate 124. ES/MS calcd. for $C_{52}H_{56}N_6O_9SSi$ 968.4. Found m/z=969 (M+H)$^+$.

Intermediate 173: (R)-6-[[3-[[6-[[2-[3-[[(tert-Butyldimethylsilyl)oxy]methyl]-4-hydroxyphenyl]-2-hydroxyethyl]amino]hexyl]carbamoyl]phenyl]sulfonyl]-4-[(3-methoxyphenyl)amino]-8-methylquinoline-3-carboxamide

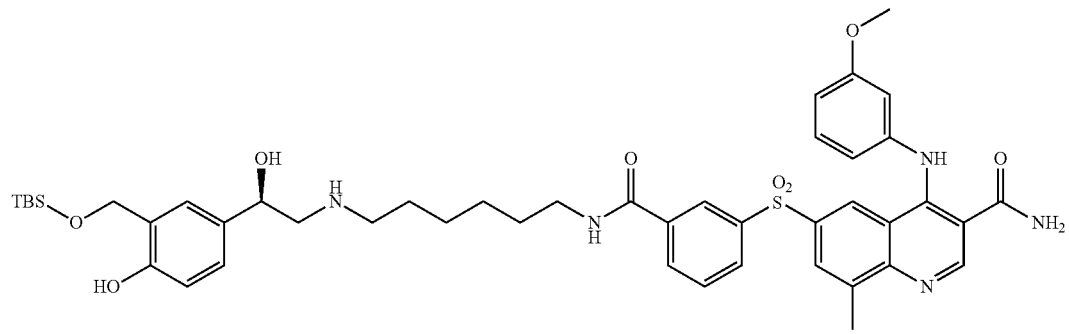

The title compound was synthesized in a manner analogous to that described for Intermediate 149, using Intermediate 9 in place of Intermediate 2. ES/MS calcd. for $C_{46}H_{60}H_5O_8SSi^+$ 870.4. Found m/z=870 (M+H)$^+$ Intermediate 174: (R)-6-[[3-[[4-[[2-[3-[[(tert-Butyldimethylsilyl)oxy]methyl]-4-hydroxyphenyl]-2-hydroxyethyl]amino]piperidine-1-yl]-carbonyl]phenyl]sulfonyl]-4-[(3-methoxyphenyl)amino]-8-methylquinoline-3-carboxamide

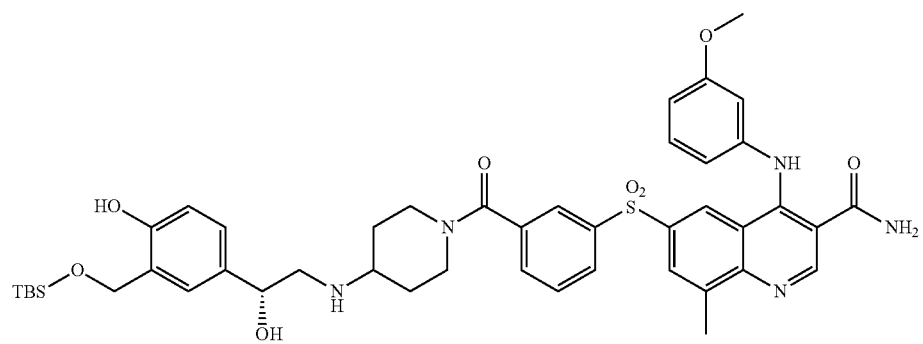

The title compound was synthesized in a manner analogous to that described for Intermediate 150, using Intermediate 9 in place of Intermediate 2. ES/MS calcd. for $C_{45}H_{56}N_5O_8SSi^+$ 854.4. Found m/z=854 (M+H)$^+$.

Intermediate 175: (R)-6-[[3-[[6-[[2-[(tert-Butyldimethylsilyl)oxy]-2-(4-hydroxy-3-(methylsulfonamido)phenyl]ethyl]amino]hexyl]carbamoyl]phenyl]sulfonyl]-4-[(3-methoxyphenyl)amino]-8-methylquinoline-3-carboxamide

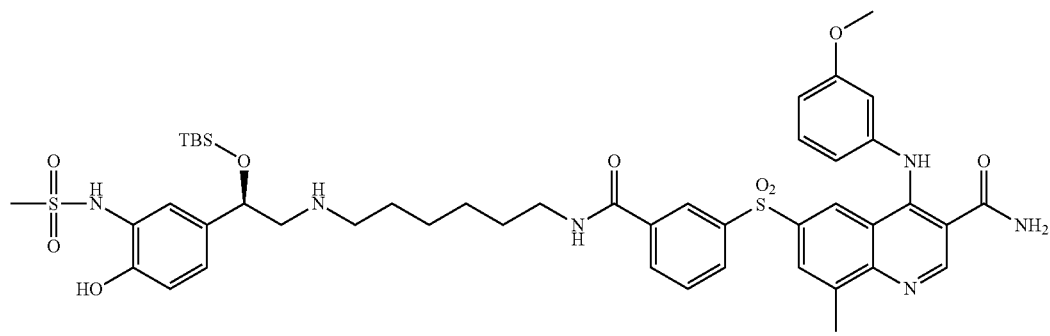

The title compound was synthesized in a manner analogous to that described for Intermediate 149, using Intermediate 18 in place of Intermediate 2. ES/MS calcd. for $C_{46}H_{61}N_6O_9S_2Si^+$ 933.4. Found m/z=933 (M+H)$^+$.

Intermediate 176: (R)-6-[[3-[[6-[[2-[3-[[(tert-Butyldimethylsilyl)oxy]methyl]-4-hydroxyphenyl]-2-hydroxyethyl]amino]hexyl](methyl)carbamoyl]phenyl]sulfonyl]-4-([(3-methoxyphenyl)amino]-8-methylquinoline-3-carboxamide

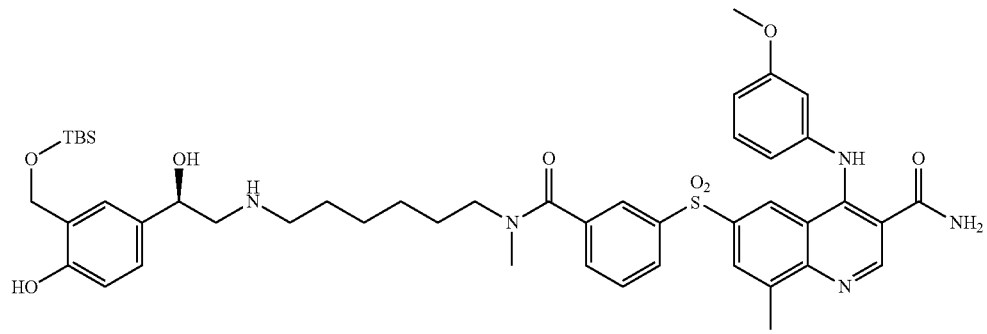

The title compound was synthesized in a manner analogous to that described for Intermediate 173, using Intermediate 114 in place of Intermediate 113. ES/MS calcd. for $C_{47}H_{62}N_5O_8SSi^+$ 884.4. Found m/z=884 (M+H)$^+$.

Intermediate 177: (R)-6-((11-((2-(((tert-butyldimethylsilyl)oxy)-2-(6-hydroxy-3-oxo-3,4-dihydro-2H-benzo[b][1,4]oxazin-8-yl)ethyl)amino)undecyl)sulfonyl)-4-((3-methoxyphenyl)amino)-8-methylquinoline-3-carboxamide

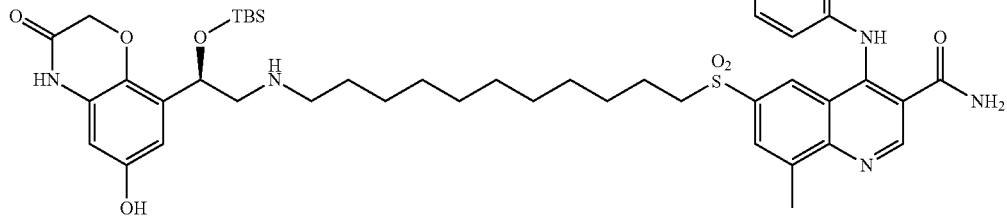

The title compound was synthesized in a manner analogous to that described for Intermediate 148, using (R)-8-(2-amino-1-((tert-butyldimethylsilyl)oxy)ethyl)-6-hydroxy-2H-benzo[b][1,4]oxazin-3(4H)-one in place of Intermediate 2 and Intermediate 126 in place of Intermediate 112. ES/MS calcd. for $C_{45}H_{64}N_5O_8SSi^+$ 862.4. Found m/z=862.6 (M+H)$^+$.

Intermediate 178: (R)-6-((4'-(3-((2-(((tert-butyldimethylsilyl)oxy)-2-(5-hydroxy-3-oxo-3,4-dihydro-2H-benzo[b][1,4]oxazin-8-yl)ethyl)amino)propyl)-[1,1'-biphenyl]-4-yl)sulfonyl)-4-((3-methoxyphenyl)amino)-8-methylquinoline-3-carboxamide

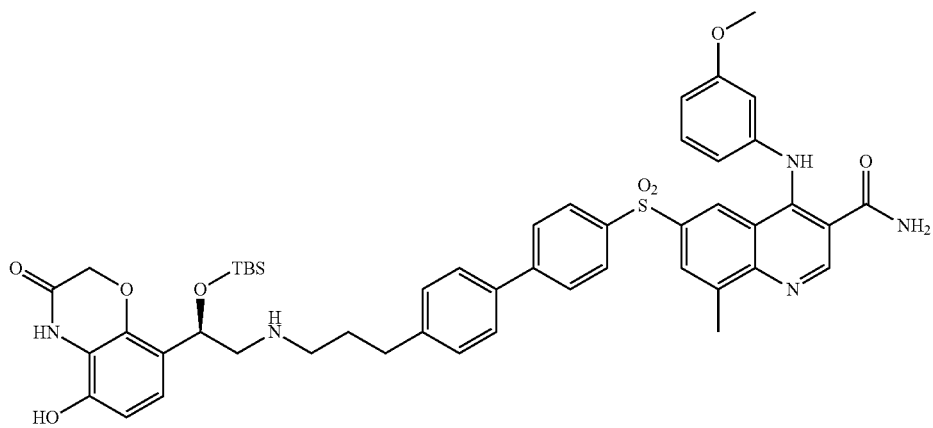

The title compound was synthesized in a manner analogous to that described for Intermediate 125, using Intermediate 129 in place of Intermediate 91. ES/MS calcd. for $C_{49}H_{56}N_5O_8SSi^+$ 902.4. Found m/z=902.5 (M+H)$^+$.

Intermediate 179: (R)-6-((4'-(3-((2-((tert-butyldimethylsilyl)oxy)-2-(5-hydroxy-3-oxo-3,4-dihydro-2H-benzo[b][1,4]oxazin-8-yl)ethyl)amino)propyl)-[1,1'-biphenyl]-3-yl)sulfonyl)-4-((3-methoxyphenyl)amino)-8-methylquinoline-3-carboxamide

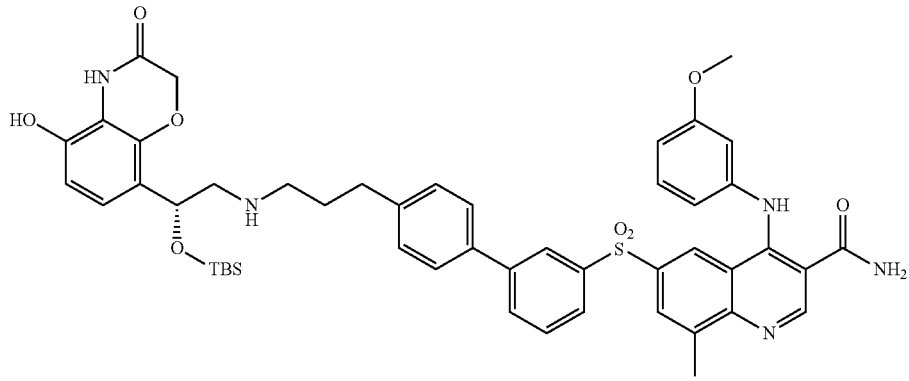

The title compound was synthesized in a manner analogous to that described for Intermediate 125, using Intermediate 130 in place of Intermediate 91. ES/MS calcd. for $C_{49}H_{56}N_5O_8SSi^+$ 902.4. Found m/z=902.5 (M+H)$^+$.

Intermediate 180: (R)-6-((4''-(5-((2-((tert-butyldimethylsilyl)oxy)-2-(5-hydroxy-3-oxo-3,4-dihydro-2H-benzo[b][1,4]oxazin-8-yl)ethyl)amino)pentyl)-1,1-biphenyl]-4-yl)sulfonyl)-4-((3-methoxyphenyl)amino)-8-methylquinoline-3-carboxamide

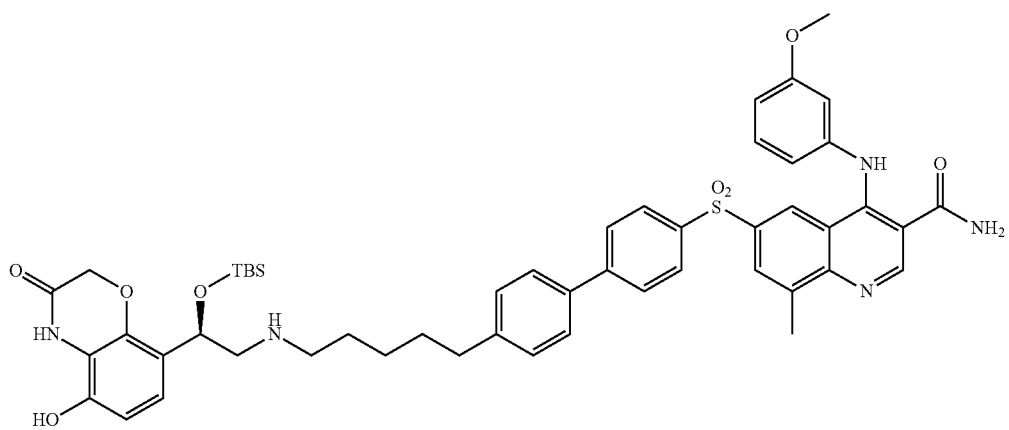

The title compound was synthesized in a manner analogous to that described for Intermediate 125, using Intermediate 131 in place of Intermediate 91. The crude product was purified by PREP-HPLC to give the title compound as a TFA-salt which was used as this for the next step. ES/MS calcd. for $O_{51}H_{60}N_5O_8SSi^+$ 930.4. Found m/z=930.5 (M+H)$^+$.

Intermediate 181: (R)-6-((4'-(5-((2-((tert-butyldimethylsilyl)oxy)-2-(5-hydroxy-3-oxo-3,4-dihydro-2H-benzo[b][1,4]oxazin-8-yl)ethyl)amino)pentyl)-(1,1'-biphenyl]-3-yl)sulfonyl)-4-((3-methoxyphenyl)amino)-8-methylquinoline-3-carboxamide

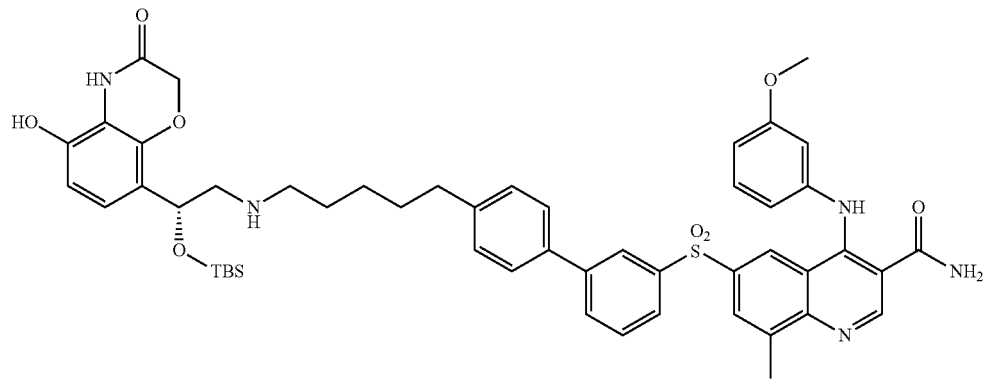

The title compound was synthesized in a manner analogous to that described for Intermediate 125, using Intermediate 132 in place of Intermediate 91. ES/MS calcd. for $C_{51}H_{60}N_5O_8SSi^+$ 930.4. Found m/z=930.5 $(M+H)^+$.

Example 1

(R)-6-[[3-[[8-[[2-Hydroxy-2-(8-hydroxy-2-oxo-1,2-dihydroquinolin-5-yl)ethyl]amino]octyl]carbamoyl]phenyl]sulfonyl]-4-[(3-methoxyphenyl)amino]-8-methylquinoline-3-carboxamide

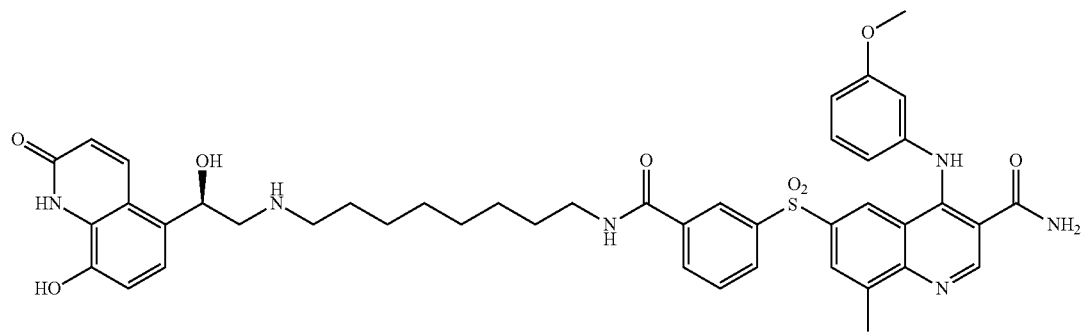 [SMILES: COc1cccc(Nc2c(C(N)=O)cnc3c(C)cc(S(=O)(=O)c4cccc(C(=O)NCCCCCCCCNC[C@H](O)c5ccc(O)c6[nH]c(=O)ccc56)c4)cc23)c1]

A solution of TBAF (1.0 M in THF, 0.244 mL, 0.244 mmol) was added to a stirring solution of Intermediate 148 (76 mg, 0.0813 mmol) in THF (2 mL) at rt. After stirring overnight, glacial acetic acid (0.023 mL, 0.407 mmol) was added and stirred for an additional 16 h. The reaction mixture was concentrated and purified by PREP-HPLC to give the title compound (19 mg).

$^1$H NMR (400 MHz, DMSO-d6) δ 11.90 (m, 1H), 11.18 (m, 1H), 10.49 (m, 2H), 9.33 (brs, 1H), 9.03 (s, 1H), 8.92 (s, 1H), 8.75 (t, 1H, J=5.7 Hz), 8.35-8.06 (m, 4H), 7.90-7.55 (m, 2H), 7.30-7.13 (m, 2H), 6.98 (d, 1H, J=8.1 Hz), 6.76 (dd, 1H, J=2.2, 8.2 Hz), 6.70 (m, 1H), 6.58 (m, 2H), 6.14 (m, 1H), 5.33 (m, 1H), 3.64 (s, 3H), 3.28 (dd, 2H, J=6.7, 13.1 Hz), 3.15-2.89 (m, 2H), 2.74 (m, 3H), 2.54 (s, 3H), 1.73-1.26 (s, 12H); ES/MS calcd. for $C_{44}H_{49}N_6O_8S^+$ 821.2. Found m/z=821.3 $(M+H)^+$.

Example 2

(R)-6-[[3-[[6-[[2-Hydroxy-2-(8-hydroxy-2-oxo-1,2-dihydroquinolin-5-yl)ethyl]amino]hexyl]carbamoyl]phenyl]sulfonyl]-4-((3-methoxyphenyl)amino)-8-methylquinoline-3-carboxamide

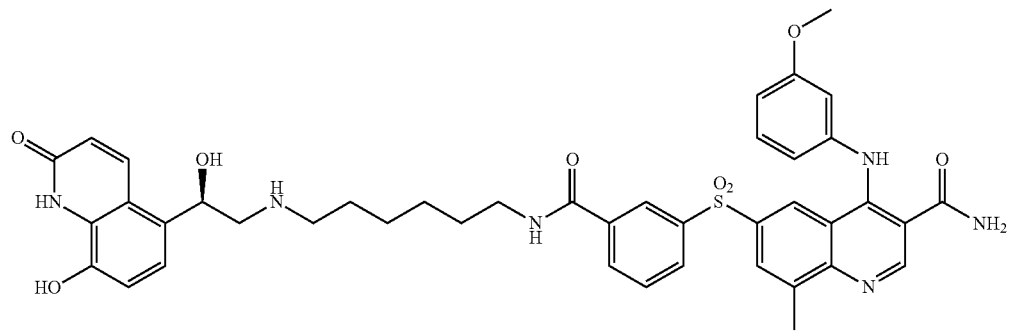 [SMILES: COc1cccc(Nc2c(C(N)=O)cnc3c(C)cc(S(=O)(=O)c4cccc(C(=O)NCCCCCCNC[C@H](O)c5ccc(O)c6[nH]c(=O)ccc56)c4)cc23)c1]

The title compound was synthesized in a manner analogous to that described for Example 1, using Intermediate 149 as a substrate.

$^1$H NMR (400 MHz, DMSO-d6) δ 11.90 (m, 1H), 10.93 (m, 1H), 10.50 (m, 2H), 9.07 (m, 1H), 8.92 (m, 1H), 8.80 (m, 1H), 8.64-7.67 (m, 12H), 7.17 (m, 1H), 6.99 (d, 1H, J=7.9), 6.73 (m, 1H), 6.60 (m, 2H), 6.13 (brs, 1H), 5.30 (m, 1H), 3.65 (s, 3H), 3.31 (m, 2H), 3.02 (m, 3H), 2.72 (m, 2H), 1.69-1.26 (m, 8H); ES/MS calcd. for $C_{42}H_{45}N_6O_8S^+$ 793.3. Found m/z=793.3 (M+H)$^+$.

Example 3

(R)-6-[[3-[[4-[[2-Hydroxy-2-(8-hydroxy-2-oxo-1,2-dihydroquinolin-5-yl)ethyl]amino]piperidine-1-yl]carbonyl)phenyl]sulfonyl]-4-[(3-methoxyphenyl)amino]-8-methylquinoline-3-carboxamide

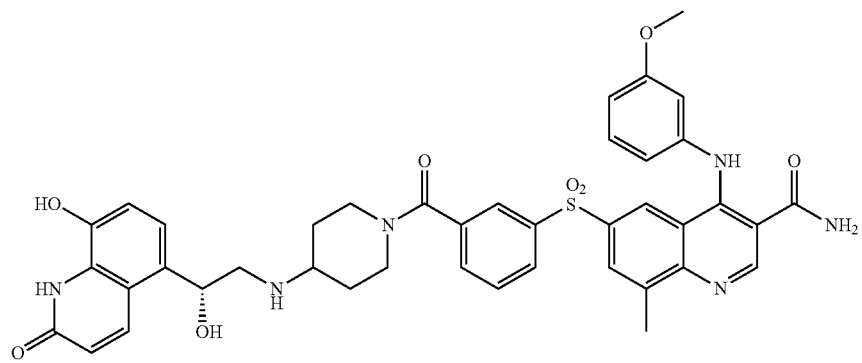 [SMILES: COc1cccc(Nc2c(C(N)=O)cnc3c(C)cc(S(=O)(=O)c4cccc(C(=O)N5CCC(NC[C@H](O)c6ccc(O)c7[nH]c(=O)ccc67)CC5)c4)cc23)c1]

The title compound was synthesized in a manner analogous to that described for Example 1 using Intermediate 150 as a substrate, but with no addition of glacial acetic acid.

$^1$H NMR (400 MHz, DMSO-d6) δ 11.13 (brs, 1H), 10.51 (brs, 1H), 9.05 (s, 1H), 8.78 (m, 2H), 8.38 (m, 2H), 8.05 (m, 2H), 7.75 (m, 3H), 7.18 (m, 2H), 6.99 (d, 1H, J=8.2 Hz), 6.72 (m, 2H), 6.61 (m, 2H), 6.20 (brs, 2H), 5.33 (m, 1H), 4.54 (m, 1H), 3.68 (s, 3H), 3.54-2.75 (m, 7H), 2.70 (s, 3H), 2.05 (m, 2H), 1.52 (m, 2H); ES/MS calcd. for $C_{41}H_{41}N_6O_8S^+$ 777.3. Found m/z=777.3 (M+H)$^+$.

Example 4

(R)-6-[[3-[[4-[5-[[2-Hydroxy-2-(8-hydroxy-2-oxo-1,2-dihydroquinolin-5-yl)ethyl]amino]pent-1-ynyl]-phenyl]carbamoyl]phenyl]sulfonyl]-4-[(3-methoxyphenyl)amino]-8-methylquinoline-3-carboxamide 2,2,2-trifluoroacetate

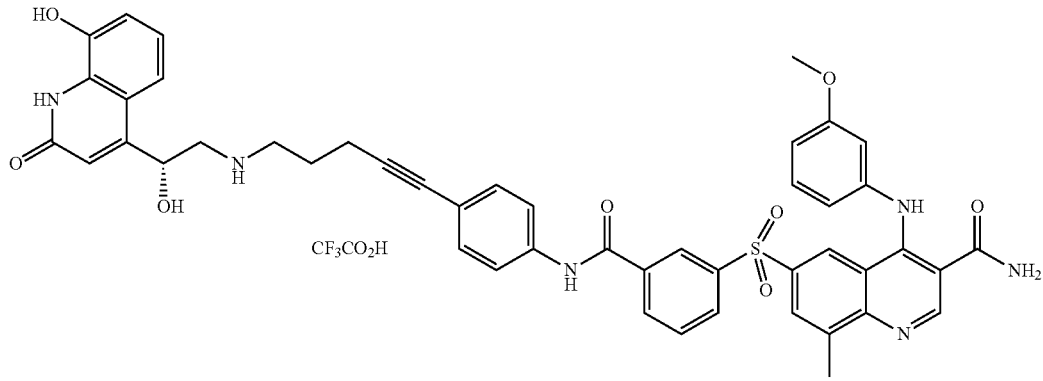 [SMILES: COc1cccc(Nc2c(C(N)=O)cnc3c(C)cc(S(=O)(=O)c4cccc(C(=O)Nc5ccc(C#CCCCNC[C@H](O)c6cc(=O)[nH]c7c(O)cccc67)cc5)c4)cc23)c1 ; "CF3CO2H"]

The title compound was prepared in a manner analogous to that described for Intermediate 148 using Intermediate 6 in place of Intermediate 2 and Intermediate 115 in place of Intermediate 112.

$^1$H NMR (400 MHz, DMSO-d6) δ11.07-10.91 (m, 1H), 10.68-10.59 (m, 1H), 10.56-10.46 (m, 2H), 9.07 (s, 1H), 8.72-8.52 (m, 2H), 8.43-8.26 (m, 3H), 8.26-8.12 (m, 2H), 8.11-8.02 (m, 1H), 7.79 (d, 4H, J=8.85 Hz), 7.43 (d, 2H, J=8.74 Hz), 7.22-7.06 (m, 2H), 7.04-6.93 (m, 1H), 6.72-6.63 (m, 2H), 6.63-6.51 (m, 2H), 6.24-6.12 (m, 1H), 5.33-5.25 (m, 1H), 3.60 (s, 3H), 3.18-3.08 (m, 4H), 2.71 (s, 3H), 2.54 (s, 2H), 2.00-1.87 (m, 2H); ES/MS calcd. for $C_{47}H_{43}N_6O_8S^+$ 851.3. Found m/z=851.3 (M+H)$^+$.

Example 5

(R)-6-[[3-[[4-[5-[[2-Hydroxy-2-(8-hydroxy-2-oxo-1,2-dihydroquinolin-5-yl)ethyl]amino]pent-1-ynyl]phenyl]carbamoyl]phenyl]sulfonyl]-4-[(3-methoxyphenyl)amino]-8-methylquinoline-3-carboxamide

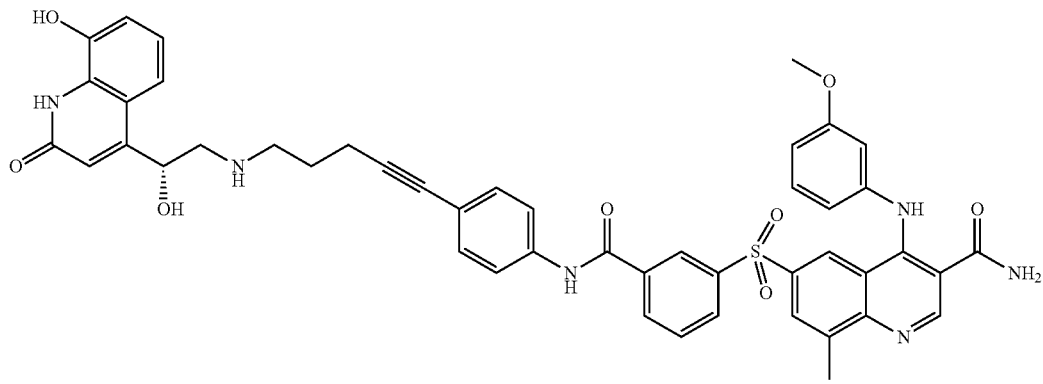 [SMILES: COc1cccc(Nc2c(C(N)=O)cnc3c(C)cc(S(=O)(=O)c4cccc(C(=O)Nc5ccc(C#CCCCNC[C@H](O)c6cc(=O)[nH]c7c(O)cccc67)cc5)c4)cc23)c1]

TBAF (1.0 M) (1.036 mL, 1.036 mmol) was added to a solution of Intermediate 153 (500 mg, 0.518 mmol), and acetic acid (0.5 mL) in THF (15 mL). The solution was stirred overnight at rt. After which time 7N MeOH/NH$_4$ was added to neutralize the acidic mixture. All solvents were removed in vacuo and the resultant solid was suspended in MeOH (30 mL) and filtered. The solid was treated with a mixture of MeOH/water (1:1) (40 mL) and sonicated for 5 min.

The remaining solid was filtered, washed with MeOH (20 mL), and dried under high vacuum to afford the title compound as a yellow solid (221 mg).

$^1$H NMR (400 MHz, DMSO-d6) δ ppm 10.77 (s, 1H), 10.59 (s, 1H), 9.06 (s, 1H), 8.34 (d, 1H, J=1.74 Hz), 8.28 (s, 2H), 8.17 (t, 2H, J=8.51 Hz), 8.03-7.98 (m, 1H), 7.88-7.82 (m, 1H), 7.73 (t, 4H, J=8.08 Hz), 7.37 (d, 2H, J=8.71 Hz), 7.06 (m, 2H), 6.89 (d, 1H, J=8.12 Hz), 6.61 (dd, 2H, J=8.52, 1.64 Hz), 6.49 (dd, 2H, J=13.94, 5.62 Hz), 5.05-4.99 (m, 1H), 3.57 (s, 3H), 2.69 (m, 6H), 2.43 (t, 2H J=6.98 Hz), 1.71-1.61 (m, 2H); ES/MS calcd. for $C_{47}H_{43}N_6O_8S^+$ 851.3. Found m/z=851.3 (M+H)$^+$; CHN Analysis: Calcd for $C_{47}H_{46}N_6O_8S \cdot 2H_2O$, MW=886.30, C=63.64%; H=5.23%; N=9.48%. Found C=63.50%, H=4.75%, N=8.98%.

Example 6

(R)-6-[[3-[[4-[5-[[2-Hydroxy-2-(8-hydroxy-2-oxo-1,2-dihydroquinolin-5-yl)ethyl]amino]pent-1-ynyl]phenyl]-carbamoyl]phenyl]sulfonyl]-4-[(3-methoxyphenyl)amino]-8-methylquinoline-3-carboxamide hydrochloride

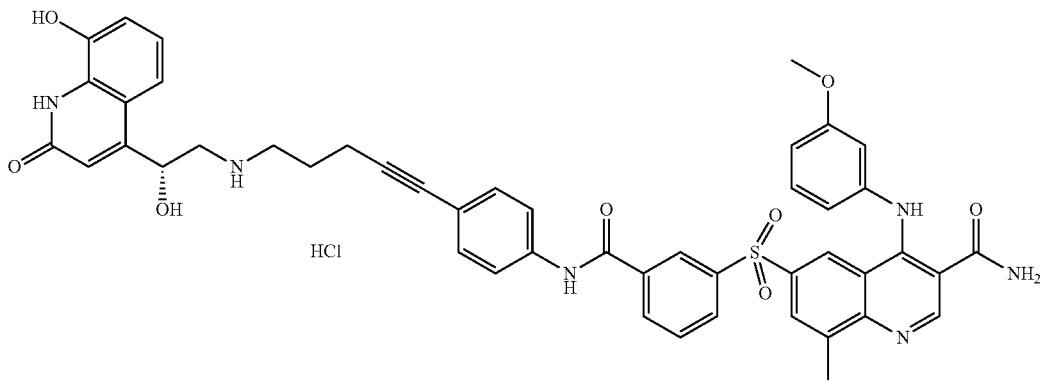 [SMILES: COc1cccc(Nc2c(C(N)=O)cnc3c(C)cc(S(=O)(=O)c4cccc(C(=O)Nc5ccc(C#CCCCNC[C@H](O)c6cc(=O)[nH]c7c(O)cccc67)cc5)c4)cc23)c1 ; Cl]

Example 4 was exchanged to the hydrochloride salt with the use of Dowex exchange resin.

$^1$H NMR (400 MHz, DMSO-d6) δ ppm 11.07-10.91 (m, 1H), 10.68-10.59 (m, 1H), 10.56-10.46 (m, 2H), 9.07 (s, 1H), 8.72-8.52 (m, 2H), 8.43-8.26 (m, 3H), 8.26-8.12 (m, 2H), 8.11-8.02 (m, 1H), 7.79 (d, 4H, J=8.85 Hz), 7.43 (d, 2H, J=8.74 Hz), 7.22-7.06 (m, 2H), 7.04-6.93 (m, 1H), 6.72-6.63 (m, 2H), 6.63-6.51 (m, 2H), 6.24-6.12 (m, 1H), 5.33-5.25 (m, 1H), 3.60 (s, 3H), 3.18-3.08 (m, 4H), 2.71 (s, 3H), 2.54 (s, 2H), 2.00-1.87 (m, 2H); ES/MS calcd. for $C_{47}H_{43}N_6O_8S^+$ 851.3. Found m/z=851.3 (M+H)$^+$.

Example 7

(R)-6-((3-((4-(6-((2-hydroxy-2-(8-hydroxy-2-oxo-1,2-dihydroquinolin-5-yl)ethyl)amino)hex-1-yn-1-yl)phenyl)carbamoyl)phenyl)sulfonyl)-4-((3-methoxyphenyl)amino)-8-methylquinoline-3-carboxamide

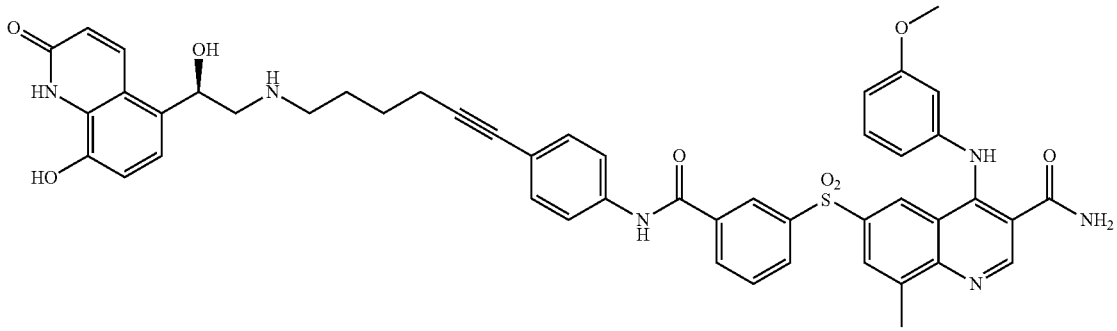 [SMILES: COc1cccc(Nc2c(C(N)=O)cnc3c(C)cc(S(=O)(=O)c4cccc(C(=O)Nc5ccc(C#CCCCCNC[C@H](O)c6ccc(O)c7[nH]c(=O)ccc67)cc5)c4)cc23)c1]

The title compound was synthesized in a manner analogous to that described for Example 1, using instead Intermediate 155 as substrate.

¹H NMR (400 MHz, dmso-d6) δ 11.25 (s, 1H), 10.64 (s, 1H), 10.50 (m, 2H), 9.03 (s, 1H), 8.57 (m, 2H), 8.43 (s, 1H), 8.36 (s, 1H), 8.32 (m, 1H), 8.22 (d, J=7.9 Hz, 1H), 8.18-8.10 (m, 2H), 7.92 (d, J=7.9 Hz, 1H), 7.86-7.73 (m, 3H), 7.47-7.36 (m, 2H), 7.17 (t, J=8.4 Hz, 2H), 6.98 (d, J=8.2 Hz, 1H), 6.72 (m, 2H), 6.60 (m, 2H), 6.15 (bs, 1H), 5.31 (m, 1H), 4.80 (bs, 1H), 3.60 (s, 3H), 3.46-2.77 (m, 4H), 2.50-2.45 (m, 2H), 2.71 (s, 3H), 1.84-1.74 (m, 2H), 1.62-1.54 (m, 2H);

ES/MS calcd. for $C_{48}H_{45}N_6O_8S^+$ 865.3. Found m/z=865.4 $(M+H)^+$.

Example 8

(R)-6-((3-((4-(5-((2-hydroxy-2-(8-hydroxy-2-oxo-1,2-dihydroquinolin-5-yl)ethyl)(methyl)amino)pent-1-yn-1-yl)phenyl)carbamoyl)phenyl)sulfonyl)-4-((3-methoxyphenyl)amino)-8-methylquinoline-3-carboxamide

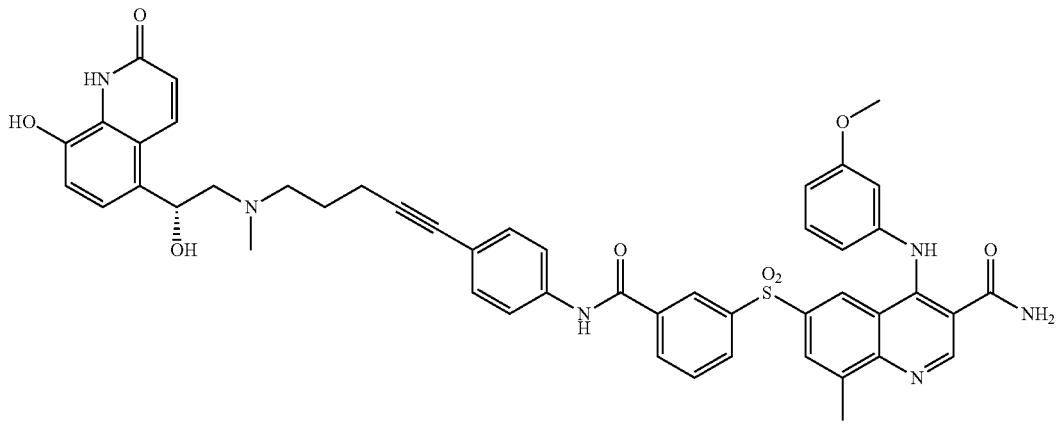 [SMILES: COc1cccc(Nc2c(C(N)=O)cnc3c(C)cc(S(=O)(=O)c4cccc(C(=O)Nc5ccc(C#CCCCN(C)C[C@H](O)c6ccc(O)c7[nH]c(=O)ccc67)cc5)c4)cc23)c1]

The title compound was synthesized in a manner analogous to that described for Example 1, using Intermediate 156 as a substrate.

¹H NMR (400 MHz, DMSO-d6) δ 10.79 (s, 1H), 10.61 (s, 1H), 10.34-10.25 (m, 2H), 9.09 (s, 1H), 8.39-8.28 (m, 3H), 8.23-8.16 (m, 2H), 8.05-8.02 (m, 1H), 7.87 (m, 1H), 7.81-7.74 (m, 4H), 7.39 (d, 2H, J=8.4 Hz), 7.13-7.08 (m, 2H), 6.92 (d, 1H, J=8.0 Hz), 6.67-6.61 (m, 2H), 6.54-6.47 (m, 2H), 5.10 (m, 1H), 3.60 (s, 3H), 2.71 (s, 3H), 2.67-2.59 (m, 5H), 2.39-2.27 (m, 4H), 1.69-1.58 (m, 2H);

ES/MS calcd. for $C_{48}H_{45}N_6O_8S^+$ 865.3. Found m/z=865.4 $(M+H)^+$.

Example 9

(R)-6-((3-((3-(5-((2-hydroxy-2-(8-hydroxy-2-oxo-1,2-dihydroquinolin-5-yl)ethyl)amino)pent-1-yn-1-yl)phenyl)carbamoyl)phenyl)sulfonyl)-4-((3-methoxyphenyl)amino)-8-methylquinoline-3-carboxamide

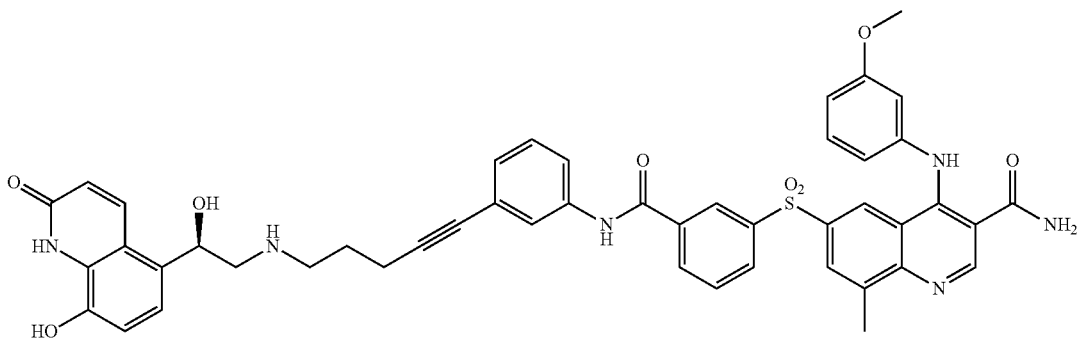 [SMILES: COc1cccc(Nc2c(C(N)=O)cnc3c(C)cc(S(=O)(=O)c4cccc(C(=O)Nc5cccc(C#CCCCNC[C@H](O)c6ccc(O)c7[nH]c(=O)ccc67)c5)c4)cc23)c1]

The title compound was synthesized in a manner analogous to that described for Example 1, using Intermediate 157 as a substrate.

$^1$H NMR (400 MHz, DMSO-d6) δ 10.80 (s, 1H), 10.54 (s, 1H), 10.35 (bs, 2H), 9.09 (s, 1H), 8.36 (s, 1H), 8.32 (s, 1H), 8.24-8.15 (m, 3H), 8.04 (s, 1H), 7.91-7.83 (m, 1H), 7.80-7.71 (m, 4H), 7.37 (t, 1H, J=8.0 Hz), 7.18-7.06 (m, 2H), 6.92 (d, 1H, J=8.0 Hz), 6.63 (m, 2H), 6.55-6.49 (m, 2H), 5.11 (m, 1H), 3.59 (s, 3H), 2.82 (m, 2H), 2.71 (s, 3H), 2.67 (m, 2H), 2.59 (m, 2H), 1.77-1.73 (m, 2H); ES/MS calcd. for $C_{47}H_{43}N_6O_8S^+$ 851.3. Found m/z=851.4 (M+H)$^+$.

Example 10

(R)-6-[[3-[[4-[5-[[2-Hydroxy-2-(8-hydroxy-2-oxo-1,2-dihydroquinolin-5-yl)ethyl]amino]pentyl]phenyl]carbamoyl]phenyl]sulfonyl]-4-[(3-methoxyphenyl)amino]-8-methylquinoline-3-carboxamide 2,2,2-trifluoroacetate

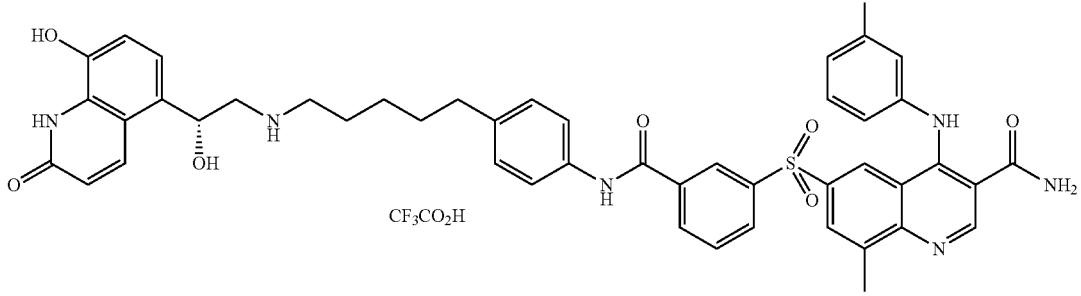

The title compound was prepared in a manner analogous to that described for Example 4 using Intermediate 120 in place of Intermediate 115.

$^1$H NMR (400 MHz, DMSO-d6) δ 11.02-10.90 (m, 1H), 10.53-10.49 (m, 1H), 10.48-10.43 (m, 2H), 9.12-9.03 (m, 1H), 8.60-8.44 (m, 2H), 8.41-8.28 (m, 2H), 8.24-8.19 (m, 1H), 8.17-8.13 (m, 1H), 8.09-8.03 (m, 1H), 7.93-7.85 (m, 1H), 7.83-7.73 (m, 2H), 7.71-7.64 (m, 2H), 7.25-7.18 (m, 2H), 7.17-7.10 (m, 2H), 7.03-6.93 (m, 1H), 6.71-6.61 (m, 2H), 6.60-6.52 (m, 3H), 6.18-6.12 (m, 1H), 5.34-5.25 (m, 1H), 3.60 (s, 3H), 3.13-2.91 (m, 4H), 2.71 (s, 3H), 2.62-2.56 (m, 1H), 1.72-1.55 (m, 4H), 1.38-1.27 (m, 2H); ES/MS calcd. for $C_{47}H_{47}N_6O_8S^+$ 855.31. Found m/z=855.4 (M+H)$^+$.

Example 11

6-[3-[[4-[2-[[2-Hydroxy-2-(8-hydroxy-2-oxo-1,2-dihydroquinolin-5-yl)ethyl]amino]ethyl]piperazine-1-yl]carbonyl]benzenesulfonyl]-4-(3-methoxyphenylamino)-8-methylquinoline-3-carboxyamide

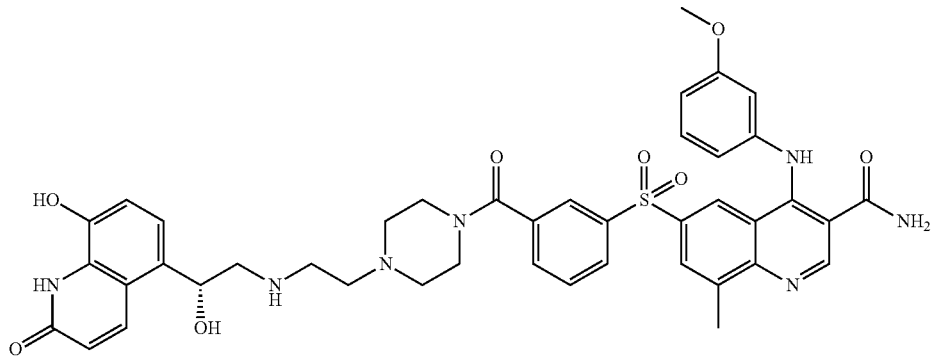 [SMILES: COc1cccc(Nc2c(C(N)=O)cnc3c(C)cc(S(=O)(=O)c4cccc(C(=O)N5CCN(CCNC[C@H](O)c6ccc(O)c7[nH]c(=O)ccc67)CC5)c4)cc23)c1]

The title compound was synthesized in a manner analogous to that described for Example 1, using Intermediate 139 as a substrate.

$^1$H NMR (400 MHz, DMSO-d$_6$) δ 10.80 (s, 1H), 10.50 (s, 1H), 10.45 (s, 1H), 9.08 (s, 1H), 8.38 (s, 1H), 8.30 (s, 1H), 8.17 (d, 1H, J=9.2 Hz), 8.00 (s, 1H), 7.78 (m, 2H), 7.70 (m, 2H), 7.16 (s, 1H), 7.14 (s, 1H), 6.98 (d, 1H, J=7.6 Hz), 6.71 (d, 1H, J=9.6 Hz), 6.67 (s, 1H), 6.60 (m, 1H), 6.53 (d, 1H, J=7.6 Hz), 6.16 (s, 1H), 5.53 (brs, 1H), 3.66 (brs, 7H), 3.15-3.04 (m, 6H), 2.70 (brs, 6H), 2.39 (brs, 2H); ES/MS calcd. for C$_{42}$H$_{44}$N$_7$O$_8$S$^+$ 806.3. Found m/z=806.3 (M+H)$^+$.

Example 12

(R)-6-[[3-[[4-[2-[[2-Hydroxy-2-(8-hydroxy-2-oxo-1,2-dihydroquinolin-5-yl)ethyl]amino]ethyl]phenyl]carbamoyl]phenyl]sulfonyl]-4-[(3-methoxyphenyl)amino]-8-methylquinoline-3-carboxamide

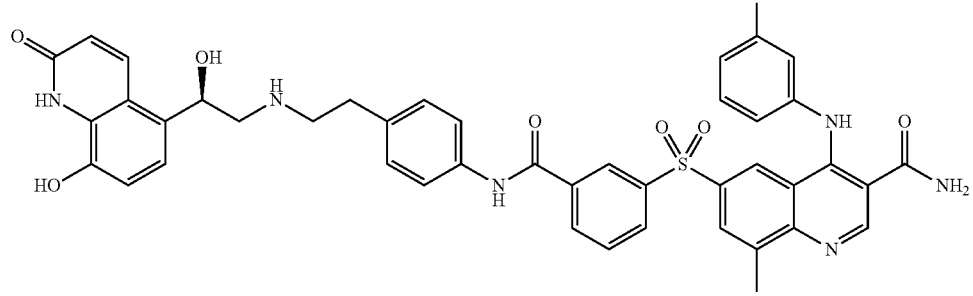

Intermediate 144 (119 mg) was dissolved in a mixture of EtOH (2 mL) and THF (3.5 mL) and hydrogenated in the presence of 10% Pd/C at rt and ambient pressure. After completion, the reaction was filtered and the filtrate purified by reverse-phase preparatory-LC to give the title compound as a yellow solid (65 mg).

$^1$H NMR (400 MHz, DMSO-d$_6$) δ 11.17 (br s, 1H), 10.53 (s, 1H), 10.51 (br s, 1H), 9.04 (s, 1H), 8.73 (br s, 2H), 8.41 (s, 1H), 8.35 (s, 1H), 8.33 (s, 1H), 8.23 (d, J=7.7 Hz, 1H), 8.16 (d, J=10.0 Hz, 1H), 8.10 (s, 1H), 7.91 (d, J=8.0 Hz, 1H), 7.74-7.83 (m, 4H), 7.28 (d, J=8.6 Hz, 2H), 7.10-7.19 (m, 2H), 6.99 (d, J=8.1 Hz, 1H), 6.69-6.73 (m, 2H), 6.57-6.62 (m, 2H), 5.33 (d, J=7.7 Hz, 2H), 3.61 (s, 3H), 2.83-3.50 (m, 7H), 2.71 (s, 3H). ES/MS calcd. for C$_{44}$H$_{41}$N$_6$O$_8$S$^+$ 813.3. Found m/z=813.3 (M+H)$^+$.

Example 13

6-[[3-[[3-[2-[[(R)-2-Hydroxy-2-(8-hydroxy-2-oxo-1,2-dihydroquinolin-5-yl)ethyl]amino]propyl]-N-methylbenzamido]methyl]phenyl]sulfonyl]-4-[(3-methoxyphenyl)amino]-8-methylquinoline-3-carboxamide

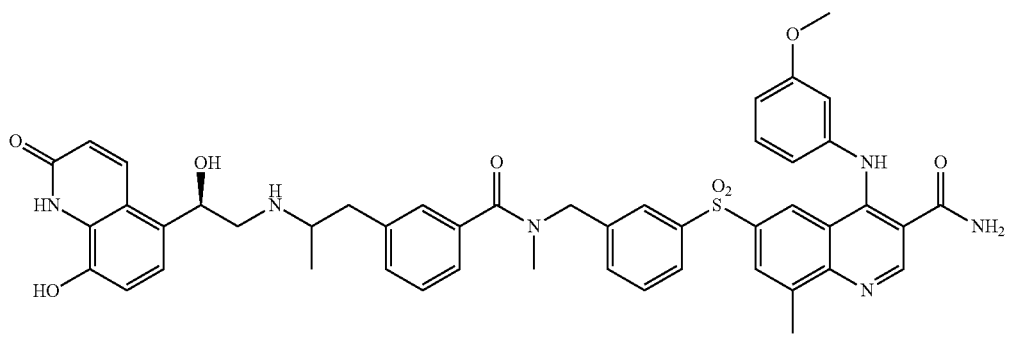 [SMILES: COc1cccc(Nc2c(C(N)=O)cnc3c(C)cc(S(=O)(=O)c4cccc(CN(C)C(=O)c5cccc(CC(C)NC[C@H](O)c6ccc(O)c7[nH]c(=O)ccc67)c5)c4)cc23)c1]

The title compound was synthesized in a manner analogous to that described for Intermediate 148, using Intermediate 6 in place of Intermediate 2 and Intermediate 137 in place of Intermediate 112.

¹H NMR (400 MHz, DMSO-d6) δ 11.08 (brs, 1H), 10.49 (m, 2H), 9.05 (m, 1H), 8.69 (m, 2H), 8.37 (m, 2H), 8.14 (m, 1H), 8.01 (m, 1H), 7.81 (m, 2H), 7.61 (m, 2H), 7.52-7.07 (m, 5H), 6.99 (d, 1H, J=8.2 Hz), 6.85-6.52 (m, 3H), 6.20 (m, 1H), 5.32 (m, 1H), 4.78 (m, 2H), 4.57 (m, 3H), 3.58 (m, 4H), 3.39-2.95 (m, 4H), 2.89 (m, 2H), 2.69 (s, 3H), 1.03 (m, 3H); ES/MS calcd. for $C_{47}H_{47}N_6O_8S^+$ 855.3. Found m/z=855.4 $(M+H)^+$.

Example 14

(R)-6-[[3-[[6-[[2-Hydroxy-2-(8-hydroxy-2-oxo-1,2-dihydroquinolin-5-yl)ethyl]amino]hexyl](methyl)carbamoyl]phenyl]sulfonyl]-4-](3-methoxyphenyl)amino]-8-methylquinoline-3-carboxamide

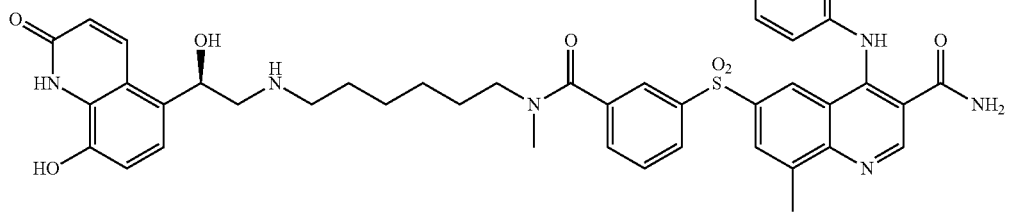

The title compound was synthesized in a manner analogous to that described for Example 4, using Intermediate 114 in place of Intermediate 115.

¹H NMR (400 MHz, DMSO-d₆) δ 11.10-10.96 (m, 1H), 10.48-10.39 (m, 1H), 9.03 (s, 1H), 8.63-8.43 (m, 2H), 8.43-8.28 (m, 2H), 8.18-7.96 (m, 2H), 7.67 (m, 5H), 7.23-7.05 (m, 2H), 7.01-6.90 (m, 1H), 6.78-6.65 (m, 2H), 6.61-6.48 (m, 2H), 6.22-6.03 (m, 1H), 5.32-5.23 (m, 1H), 3.66 (s, 3H), 3.43-3.38 (m, 1H), 3.13-2.99 (m, 3H), 2.97 (m, 2H), 2.81 (s, 3H), 2.67 (s, 3H), 1.71-1.54 (m, 2H), 1.51-1.39 (m, 2H), 1.36-1.22 (m, 2H), 1.13-0.91 (m, 2H); ES/MS calcd. for $C_{43}H_{47}N_6O_8S^+$ 807.3. Found m/z=807 $(M+H)^+$.

Example 15

(R)-6-((3-(4-((6-((2-hydroxy-2-(8-hydroxy-2-oxo-1,2-dihydroquinolin-5-yl)ethyl)amino)hexyl)oxy)piperidine-1-carbonyl)phenyl)sulfonyl)-4-((3-methoxyphenyl)amino)-8-methylquinoline-3-carboxamide

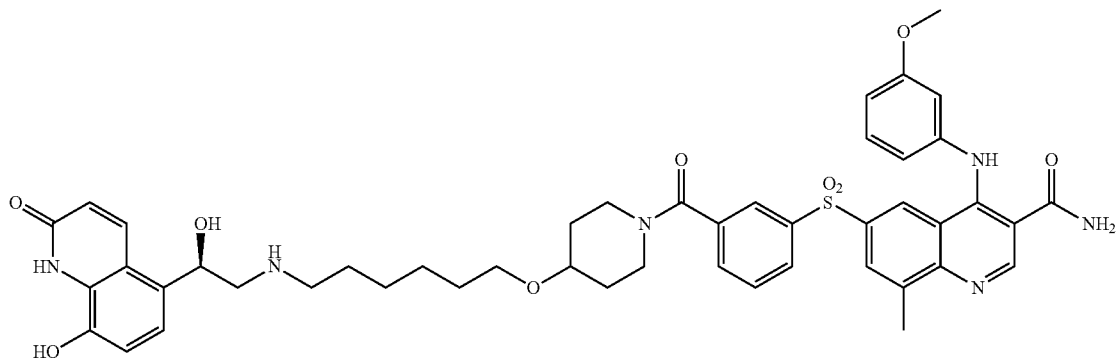 [SMILES: COc1cccc(Nc2c(C(N)=O)cnc3c(C)cc(S(=O)(=O)c4cccc(C(=O)N5CCC(OCCCCCCNC[C@H](O)c6ccc(O)c7[nH]c(=O)ccc67)CC5)c4)cc23)c1]

The title compound was synthesized in a manner analogous to that described for Example 13, using Intermediate 121 in place of Intermediate 137.

$^1$H NMR (400 MHz, dmso-d6) δ 11.56 (brs, 1H), 10.48 (s, 1H), 9.16 (brs, 1H), 8.99 (s, 1H), 8.64 (brs, 1H), 8.48 (d, J=22.5 Hz, 2H), 8.26 (d, J=9.9 Hz, 1H), 8.17 (s, 1H), 7.94-7.77 (m, 1H), 7.75-7.61 (m, 1H), 7.48-7.19 (m, 3H), 7.15 (d, J=8.3 Hz, 1H), 7.00 (d, J=7.9 Hz, 1H), 6.89-6.77 (m, 1H), 6.78-6.64 (m, 1H), 6.55 (d, J=9.5 Hz, 1H), 6.19 (brs, 1H), 5.44 (dd, J=10.2, 2.8 Hz, 1H), 4.67 (d, J=6.7 Hz, 1H), 4.52 (d, J=7.9 Hz, 1H), 4.20-0.69 (m, 29H); ES/MS calcd. for $C_{47}H_{53}N_6O_9S^+$ 877.4. Found m/z=877.4 (M+H)$^+$ Example 16

(R)-6-((3-(4-(6-((2-hydroxy-2-(8-hydroxy-2-oxo-1,2-dihydroquinolin-5-yl)ethyl)amino)hexyl)piperazine-1-carbonyl)phenyl)sulfonyl)-4-((3-methoxyphenyl)amino)-8-methylquinoline-3-carboxamide

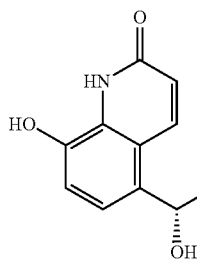
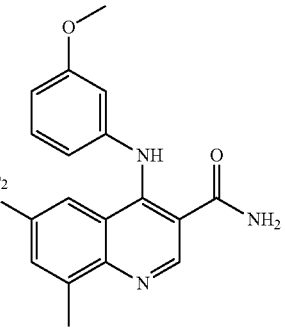

The title compound was synthesized in a manner analogous to that described for Example 13, using Intermediate 122 in place of Intermediate 137.

$^1$H NMR (400 MHz, dmso-d6) δ 12.50 (brs, 1H), 11.58 (brs, 1H), 10.51 (brs, 1H), 9.56 (s, 1H), 8.90 (s, 1H), 8.76 (s, 1H), 8.61 (s, 1H), 8.41-8.29 (m, 1H), 8.06 (s, 1H), 7.97-7.65 (m, 4H), 7.43-7.23 (m, 4H), 7.17 (d, J=8.2 Hz, 1H), 7.04 (d, J=8.2 Hz, 1H), 7.01-6.88 (m, 2H), 6.54 (d, J=9.8 Hz, 1H), 5.52 (d, J=8.0 Hz, 1H), 4.80-1.21 (m, 29H); ES/MS calcd. for $C_{46}H_{52}N_7O_8S^+$ 862.4. Found m/z=862.3 (M+H)$^+$.

Example 17

6-((3-(4-(3-(2-(((R)-2-hydroxy-2-(8-hydroxy-2-oxo-1,2-dihydroquinolin-5-yl)ethyl)amino)propyl)benzoyl)piperazine-1-carbonyl)phenyl)sulfonyl)-4-((3-methoxyphenyl)amino)-8-methylquinoline-3-carboxamide

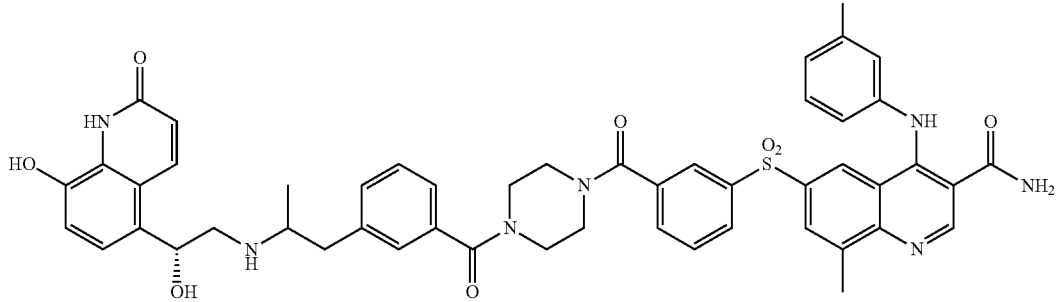

The title compound was synthesized in a manner analogous to that described for Example 13, using Intermediate 97 in place of Intermediate 137.

¹H NMR (400 MHz, dmso-d6) δ 11.02 (s, 1H), 10.49 (d, J=18.1 Hz, 2H), 9.05 (s, 1H), 8.73 (s, 2H), 8.41 (s, 1H), 8.32 (s, 1H), 8.15 (dd, J=9.9, 5.2 Hz, 1H), 8.05 (s, 1H), 7.91-7.59 (m, 4H), 7.37 (d, J=42.3 Hz, 4H), 7.24-7.11 (m, 2H), 6.99 (d, J=8.2 Hz, 1H), 6.83-6.66 (m, 2H), 6.60 (t, J=9.7 Hz, 2H), 6.21 (s, 1H), 5.41-5.25 (m, 1H), 4.13-2.91 (m, 17H), 2.68 (s, 3H), 1.12 (s, 3H); ES/MS calcd. for $C_{50}H_7O_9S^+$ 924.3. Found m/z=924.3 (M+H)⁺.

Example 18

(R)-6-((3-(4-(3-(2-((2-hydroxy-2-(8-hydroxy-2-oxo-1,2-dihydroquinolin-5-yl)ethyl)amino)-2-methylpropyl)benzoyl)piperazine-1-carbonyl)phenyl)sulfonyl)-4-((3-methoxyphenyl)amino)-8-methylquinoline-3-carboxamide

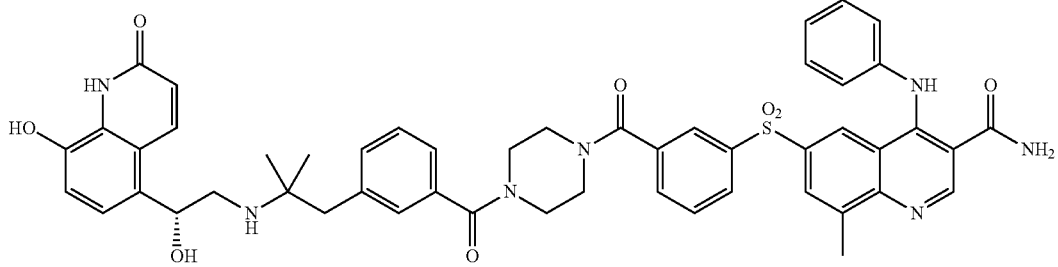

The title compound was synthesized in a manner analogous to that described for Example 12, using Intermediate 146 as a substrate.

¹H NMR (400 MHz, dmso-d6) δ 10.77 (s, 1H), 10.38 (brs, 1H), 9.08 (s, 1H), 8.38 (s, 1H), 8.29 (s, 1H), 8.18 (d, J=10.0 Hz, 1H), 7.99 (s, 1H), 7.86 (s, 1H), 7.75 (d, J=14.7 Hz, 5H), 7.46-7.08 (m, 7H), 6.95 (d, J=8.0 Hz, 1H), 6.71 (d, J=8.1 Hz, 1H), 6.65 (s, 1H), 6.53 (d, J=6.6 Hz, 2H), 5.26-4.92 (m, 1H), 3.87-2.57 (m, 20H), 1.30-0.84 (m, 6H); ES/MS calcd. for $C_{51}H_{52}N_7O_9S^+$ 938.4. Found m/z=938.3 (M+H)⁺.

Example 19

(R)-6-((3-((3-(2-((2-hydroxy-2-(8-hydroxy-2-oxo-1,2-dihydroquinolin-5-yl)ethyl)amino)-2-methylpropyl)-N-methylbenzamido)methyl)phenyl)sulfonyl)-4-((3-methoxyphenyl)amino)-8-methylquinoline-3-carboxamide

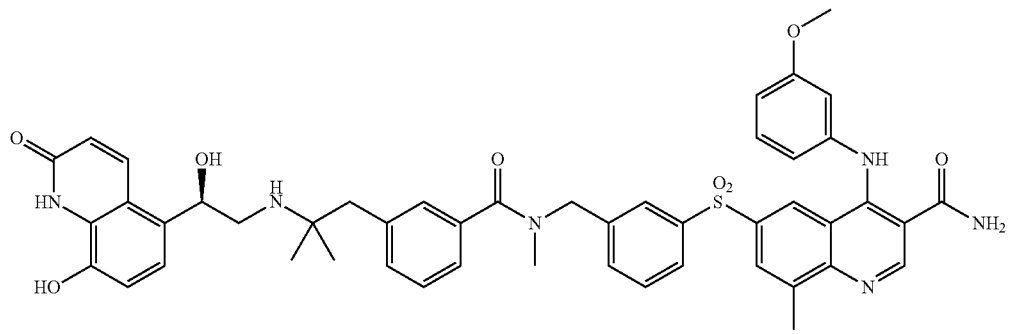 [SMILES: COc1cccc(Nc2c(C(N)=O)cnc3c(C)cc(S(=O)(=O)c4cccc(CN(C)C(=O)c5cccc(CC(C)(C)NC[C@H](O)c6ccc(O)c7[nH]c(=O)ccc67)c5)c4)cc23)c1]

The title compound was synthesized in a manner analogous to that described for Example 18, using Intermediate 147 as a substrate.

¹H NMR (400 MHz, dmso-d6) δ 11.17 (brs, 1H), 10.51 (s, 1H), 9.03 (s, 1H), 8.65 (d, J=46.4 Hz, 2H), 8.38 (d, J=24.5 Hz, 2H), 8.11 (d, J=9.5 Hz, 1H), 8.02 (s, 1H), 7.82 (s, 1H), 7.71-7.06 (m, 8H), 7.00 (d, J=8.1 Hz, 1H), 6.67 (dd, J=46.0, 25.2 Hz, 4H), 6.36-6.07 (m, 1H), 5.38-5.21 (m, 1H), 5.03-2.58 (m, 18H), 1.23 (s, 3H), 1.06 (s, 3H); ES/MS calcd. for $C_{48}H_{49}N_6O_8S^+$ 869.3. Found m/z=869.4 $(M+H)^{4"}$.

Example 20

(R)-6-((3-((4'-(((2-hydroxy-2-(8-hydroxy-2-oxo-1,2-dihydroquinolin-5-yl)ethyl)amino)methyl)-[1,1'-biphenyl]-4-yl)carbamoyl)phenyl)sulfonyl)-4-((3-methoxyphenyl)amino)-8-methylquinoline-3-carboxamide

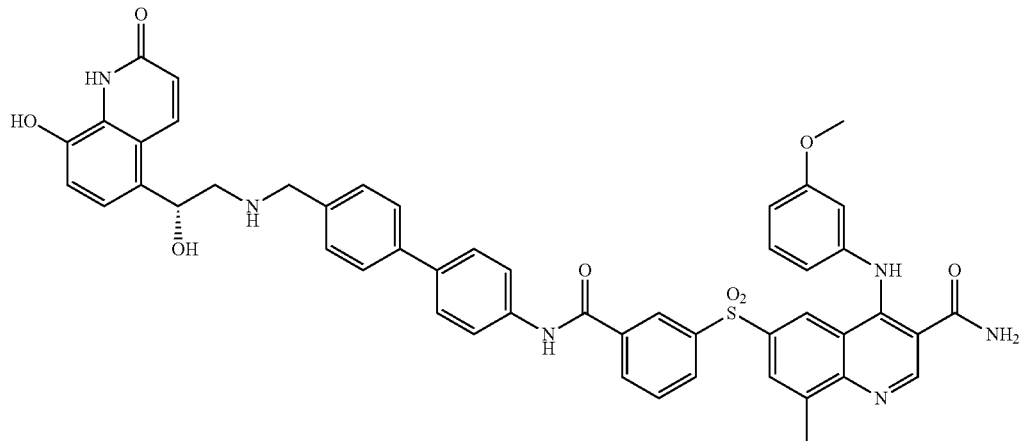 [SMILES: COc1cccc(Nc2c(C(N)=O)cnc3c(C)cc(S(=O)(=O)c4cccc(C(=O)Nc5ccc(-c6ccc(CNC[C@H](O)c7ccc(O)c8[nH]c(=O)ccc78)cc6)cc5)c4)cc23)c1]

The title compound was synthesized in a manner analogous to that described for Example 13, using Intermediate 123 in place of Intermediate 137.

¹H NMR (400 MHz, dmso-d6) δ 11.03 (brs, 1H), 10.65 (s, 1H), 10.51 (s, 1H), 10.46 (s, 1H), 9.06 (s, 3H), 8.40 (s, 1H), 8.34 (s, 2H), 8.25 (d, J=7.6 Hz, 1H), 8.08 (d, J=6.0 Hz, 2H), 7.91 (d, J=7.4 Hz, 2H), 7.86-7.69 (m, 5H), 7.61 (d, J=6.5 Hz, 2H), 7.18-7.09 (m, 2H), 6.97 (d, J=7.4 Hz, 1H), 6.69 (d, J=9.5 Hz, 2H), 6.57 (d, J=9.9 Hz, 2H), 6.25-6.10 (m, 1H), 5.35 (d, J=9.3 Hz, 1H), 4.42-2.34 (m, 12H); ES/MS calcd. for $C_{49}H_{43}N_6O_8S^+$ 875.3. Found m/z=875.1 $(M+H)^+$.

Example 21

(R)-6-((3-((4'-(4-((2-hydroxy-2-(5-hydroxy-3-oxo-3,4-dihydro-2H-benzo[b][1,4]oxazin-8-yl)ethyl)amino)butyl)-(1,1'-biphenyl]-4-yl)carbamoyl)phenyl)sulfonyl)-4-((3-methoxyphenyl)amino)-8-methylquinoline-3-carboxamide

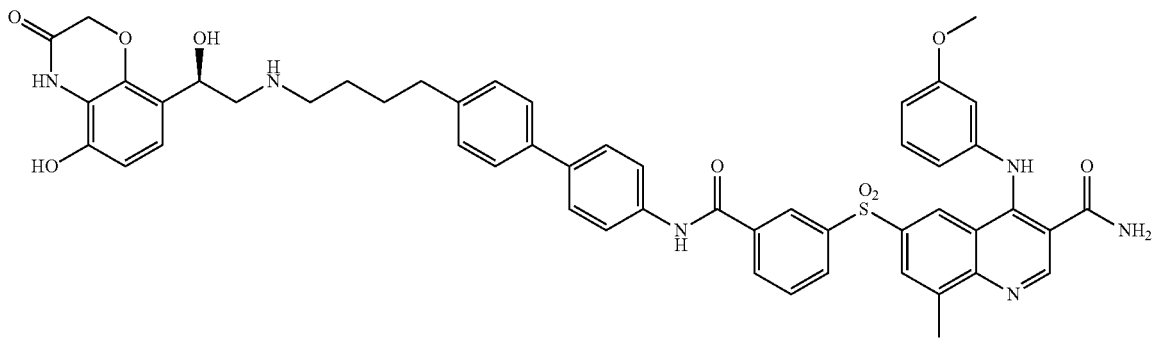 [SMILES: COc1cccc(Nc2c(C(N)=O)cnc3c(C)cc(S(=O)(=O)c4cccc(C(=O)Nc5ccc(-c6ccc(CCCCNC[C@H](O)c7ccc(O)c8c7OCC(=O)N8)cc6)cc5)c4)cc23)c1]

The title compound was synthesized in a manner analogous to that described for Example 1, using Intermediate 151 as a substrate.

$^1$H NMR (400 MHz, dmso) δ11.19 (brs, 1H), 10.73 (s, 1H), 10.18-10.01 (m, 2H), 9.17 (s, 1H), 8.53 (s, 3H), 8.47 (s, 2H), 8.37 (d, J=8.1 Hz, 1H), 8.22 (s, 1H), 8.10-7.83 (m, 5H), 7.81 (d, J=8.6 Hz, 2H), 7.74 (d, J=8.2 Hz, 2H), 7.42 (d, J=8.1 Hz, 2H), 7.27 (t, J=8.0 Hz, 1H), 7.03 (d, J=8.5 Hz, 1H), 6.87-6.78 (m, 2H), 6.77-6.63 (m, 2H), 6.10-5.93 (m, 1H), 5.16 (d, J=9.9 Hz, 1H), 4.77-1.68 (m, 18H); ES/MS calcd. for $C_{51}H_{49}N_6O_9S^+$ 921.3. Found m/z=921.3 (M+H)$^+$.

Example 22

(R)-6-((3-((4'-(4-((2-hydroxy-2-(5-hydroxy-3-oxo-3,4-dihydro-2H-benzo[b][(1,4]oxazin-8-yl)ethyl)amino)butyl)-(1,1'-biphenyl]-3-yl)carbamoyl)phenyl)sulfonyl)-4-((3-methoxyphenyl)amino)-8-methylquinoline-3-carboxamide

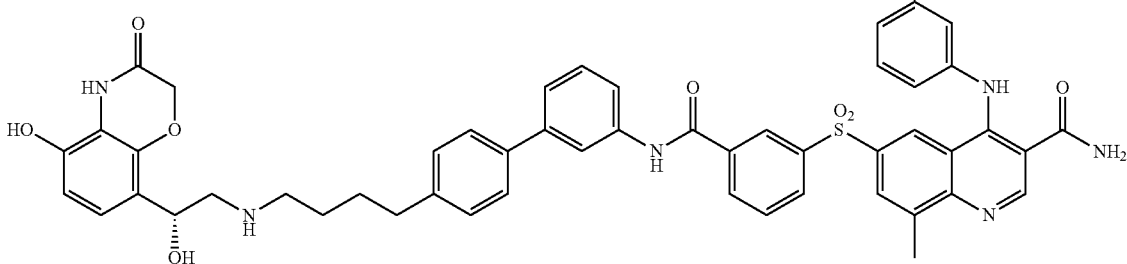

The title compound was synthesized in a manner analogous to that described for Example 1, using Intermediate 152 as a substrate.

$^1$H NMR (400 MHz, dmso-d6) δ11.07 (brs, 1H), 10.61 (s, 1H), 10.04-9.88 (m, 2H), 9.05 (s, 1H), 8.63-8.29 (m, 5H), 8.26 (d, J=7.4 Hz, 1H), 8.11 (d, J=9.5 Hz, 2H), 7.91 (d, J=7.9 Hz, 1H), 7.85-7.70 (m, 3H), 7.59 (d, J=8.0 Hz, 2H), 7.53-7.38 (m, 2H), 7.34 (d, J=8.1 Hz, 2H), 7.15 (t, J=7.9 Hz, 1H), 6.91 (d, J=8.4 Hz, 1H), 6.70 (d, J=8.3 Hz, 2H), 6.57 (t, J=9.4 Hz, 2H), 6.00-5.81 (m, 2H), 5.04 (d, J=9.9 Hz, 1H), 4.61-4.45 (m, 2H), 4.17-1.49 (m, 15H); ES/MS calcd. for $C_{51}H_{49}N_6O_9S^+$ 921.3. Found m/z=921.3 (M+H)$^+$.

Example 23

(R)-6-((3-((6-((2-hydroxy-2-(6-hydroxy-3-oxo-3,4-dihydro-2H-benzo[b][1,4]oxazin-8-yl)ethyl)amino)hexyl)carbamoyl)phenyl)sulfonyl)-4-((3-methoxyphenyl)amino)-8-methylquinoline-3-carboxamide

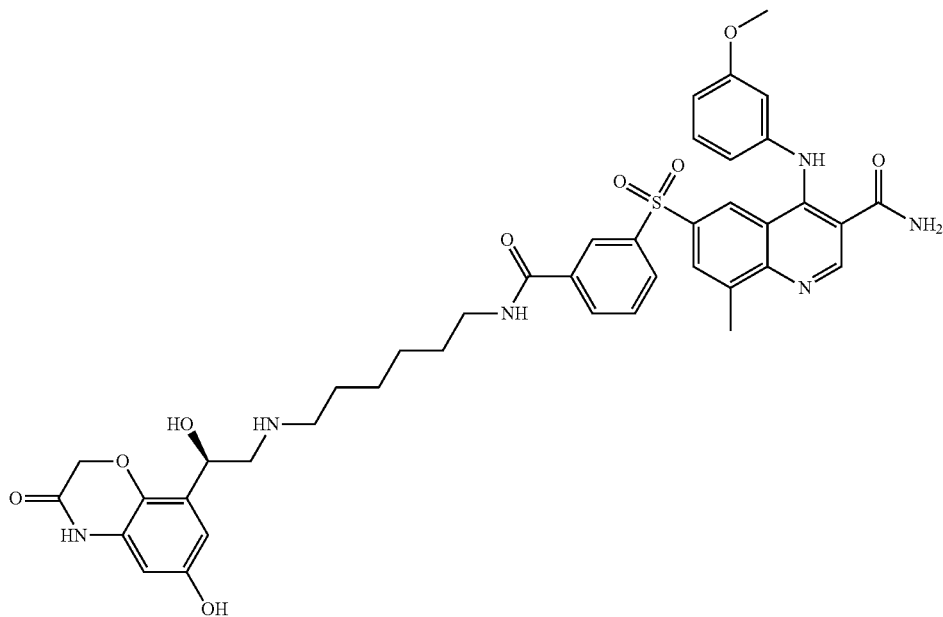 [SMILES: COc1cccc(Nc2c(C(N)=O)cnc3c(C)cc(S(=O)(=O)c4cccc(C(=O)NCCCCCCNC[C@H](O)c5cc(O)cc6c5OCC(=O)N6)c4)cc23)c1]

The title compound was synthesized in a manner analogous to that described for Example 1, using Intermediate 164 as a substrate.

¹H NMR (400 MHz, DMSO-d₆) δ 10.97 (br s, 1H), 10.62 (s, 1H), 9.27 (br s, 1H), 9.06 (s, 1H), 8.75 (t, J=5.7 Hz, 1H), 8.54 (br s, 1H), 8.47 (br s, 1H), 8.37-8.28 (m, 2H), 8.11 (d, J=7.4 Hz, 1H), 8.03 (s, 1H), 7.79 (m, 2H), 7.69 (t, J=7.6 Hz, 1H), 7.22 (s, 1H), 7.16 (t, J=8.2 Hz, 1H), 7.09 (s, 1H), 6.96 (s, 1H), 6.72 (d, J=8.0 Hz, 1H), 6.65 (s, 1H), 6.58 (d, J=8.0 Hz, 1H), 6.51 (d, J=2.8 Hz, 1H), 6.34 (d, J=2.8 Hz, 1H), 6.03 (br s, 1H), 5.06 (dm, J=8.7 Hz, 1H), 4.53-4.45 (ABq, J=18.0 Hz, 2H), 3.64 (s, 3H), 3.29 (ABq, J=6.4 Hz, 2H), 3.09-3.01 (m, 1H), 2.96-2.82 (m, 2H), 2.70 (s, 3H), 1.66-1.50 (m, 4H), 1.38-1.28 (m, 4H). ES/MS calcd. for $C_{41}H_{45}N_6O_9S^+$ 797.3. Found m/z=797.4 (M+H)⁺.

Example 24

(R)-6-((3-((4-(5-((2-hydroxy-2-(6-hydroxy-3-oxo-3,4-dihydro-2H-benzo[b][1,4]oxazin-8-yl)ethyl)amino)pent-1-yn-1-yl)phenyl)carbamoyl)phenyl)sulfonyl)-4-((3-methoxyphenyl)amino)-8-methylquinoline-3-carboxamide

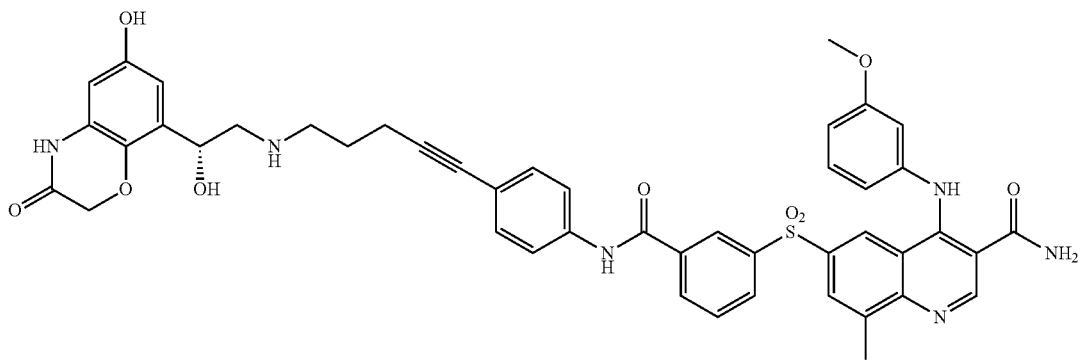 [SMILES: COc1cccc(Nc2c(C(N)=O)cnc3c(C)cc(S(=O)(=O)c4cccc(C(=O)Nc5ccc(C#CCCCNC[C@H](O)c6cc(O)cc7c6OCC(=O)N7)cc5)c4)cc23)c1]

The title compound was synthesized in a manner analogous to that described for Example 1, using Intermediate 165 as a substrate.

¹H NMR (400 MHz, DMSO-d₆) δ 11.08 (br s, 1H), 10.63 (d, J=5.1 Hz, 1H), 9.31 (br s, 1H), 9.05 (s, 1H), 8.71 (br s, 1H), 8.61 (br s, 1H), 8.40-8.31 (m, 2H), 8.21 (d, J=8.2 Hz, 1H), 8.09 (s, 1H), 7.91 (d, J=8.2 Hz, 1H), 7.80-7.75 (m, 2H), 7.43 (d, J=8.6 Hz, 1H), 7.14 (t, J=8.4 Hz, 1H), 6.69-6.68 (m, 2H), 6.58 (d, J=7.9 Hz, 1H), 6.54 (d, J=2.8 Hz, 1H), 6.34 (d, J=2.8 Hz, 1H), 6.08 (br s, 1H), 5.09 (dm, J=10.2 Hz, 1H), 4.55-4.46 (ABq, J=15.2 Hz, 2H), 3.65 (s, 3H), 3.17-3.05 (m, 2H), 3.00-2.89 (m, 1H), 2.71 (s, 3H), 2.58-2.45 (m, 2H), 1.99-1.85 (m, 2H). ES/MS calcd. for $C_{46}H_{43}N_6O_9S^+$ 855.3. Found m/z=855.4 (M+H)⁺.

Example 25

(R)-6-((3-((2-(4-(2-((2-hydroxy-2-(8-hydroxy-2-oxo-1,2-dihydroquinolin-5-yl)ethyl)amino)ethyl)phenoxy)ethyl)(methyl)carbamoyl)phenyl)sulfonyl)-4-((3-methoxyphenyl)amino)-8-methylquinoline-3-carboxamide

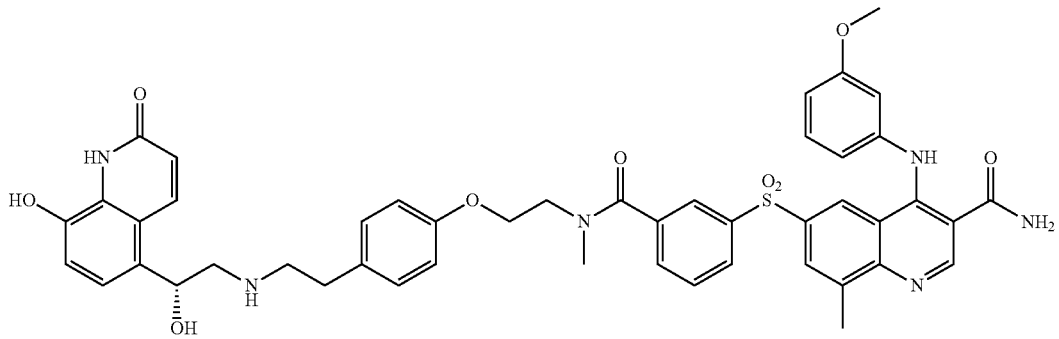 [SMILES: COc1cccc(Nc2c(C(N)=O)cnc3c(C)cc(S(=O)(=O)c4cccc(C(=O)N(C)CCOc5ccc(CCNC[C@H](O)c6ccc(O)c7[nH]c(=O)ccc67)cc5)c4)cc23)c1]

The title compound was synthesized in a manner analogous to that described for Example 1, using Intermediate 145 as a substrate. $^1$H NMR (400 MHz, DMSO-d$_6$): δ 11.00 (br s, 1H), 10.50 (s, 1H), 10.44 (s, 1H), 9.04 (s, 1H), 8.66 (br s, 1H), 8.40 (s, 1H), 8.32 (s, 1H), 8.14 (d, 1H, J=10.0 Hz), 8.03-8.00 (m, 1H), 7.91 (s, 1H), 7.80-7.66 (m, 4H), 7.19-7.10 (m, 4H), 6.99-6.97 (m, 2H), 6.84-6.82 (d, 1H, J=7.2 Hz), 6.74-6.70 (m, 2H), 6.60-6.55 (m, 2H), 6.17 (br s, 1H), 5.31 (br d, 1H, J=9.2 Hz), 4.237 (m, 2H), 4.00 (m, 2H), 3.83 (m, 1H), 3.65 (s, 3H), 3.53 (m, 1H), 3.04-2.88 (m, 4H), 2.69-2.63 (m, 4H), 2.54 (s, 3H); ES/MS calcd for C$_{47}$H$_{47}$N$_6$O$_9$S$^+$ 871.31. Found m/z 871.3 (M+H)$^+$.

Example 26

(R)-6-[[3-[[4-[5-[[2-Hydroxy-2-[4-hydroxy-3-(hydroxymethyl)phenyl]ethyl]amino]pentyl]phenyl]carbamoyl]phenyl]sulfonyl]-4-[(3-methoxyphenyl)amino]-8-methylquinoline-3-carboxamide 2,2,2-trifluoroacetate

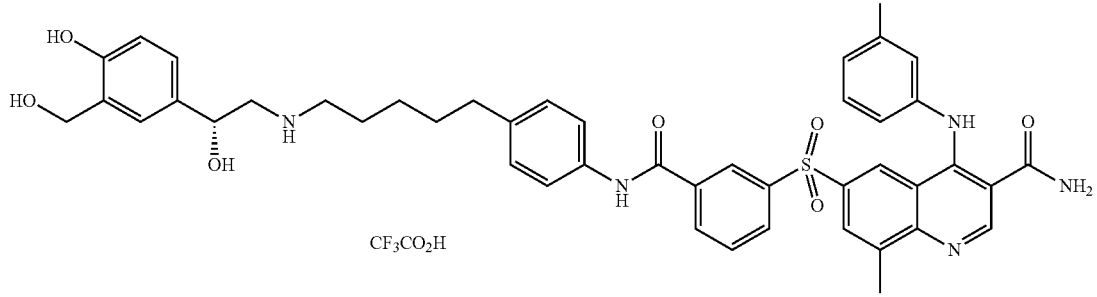

Intermediate 166 (100 mg, 0.1 mmol) was dissolved in THF (4 ml) and HF/Pyridine (30% in H$_2$O (w/w) 0.1 mL) was added. The solution was stirred at rt for 1 h, after which time NH$_3$ (2.0 M in MeOH, 10 mL) was added to neutralize. All solvents were removed in vacuo and the crude product was purified by preparative HPLC 0-80% water (0.1% TFA) to acetonitrile (0.1% TFA) to afford the title compound as a yellow solid (32 mg).

$^1$H NMR (400 MHz, DMSO-d6) δ 11.13-10.97 (m, 1H), 10.46 (s, 1H), 9.49-9.34 (m, 1H), 9.06 (s, 1H), 8.55-8.44 (m, 2H), 8.40 (s, 1H), 8.38-8.33 (m, 1H), 8.32 (s, 1H), 8.21 (m, 1H), 8.08 (s, 1H), 7.90 (dd, J=7.97, 1.09 Hz, 1H), 7.84-7.80 (m, 1H), 7.77 (d, J=7.82 Hz, 1H), 7.68 (d, J=8.48 Hz, 2H), 7.21 (d, J=8.52 Hz, 2H), 7.14 (m, 1H), 7.08-7.03 (m, 1H), 6.76 (d, J=8.20 Hz, 1H), 6.68 (m, 2H), 6.61-6.55 (m, 1H), 6.00 (bs, 1H), 4.83-4.73 (m, 1H), 4.49 (s, 2H), 3.61 (s, 3H), 3.12-3.00 (m, 1H), 2.99-2.87 (m, 4H), 2.71 (s, 3H), 2.58 (m, 2H), 1.69-1.56 (m, 4H), 1.39-1.29 (m, 2H); ES/MS calcd. for C$_{45}$H$_{48}$N$_5$O$_8$S$^+$ 818.3. Found m/z=818.4 (M+H)$^+$.

Example 27

(R)-6-[[3-[[6-[[2-(3-Formamido-4-hydroxyphenyl)-2-hydroxyethyl]amino]hexyl]carbamoyl]phenyl]sulfonyl]-4-((3-methoxyphenyl)amino]-8-methylquinoline-3-carboxamide

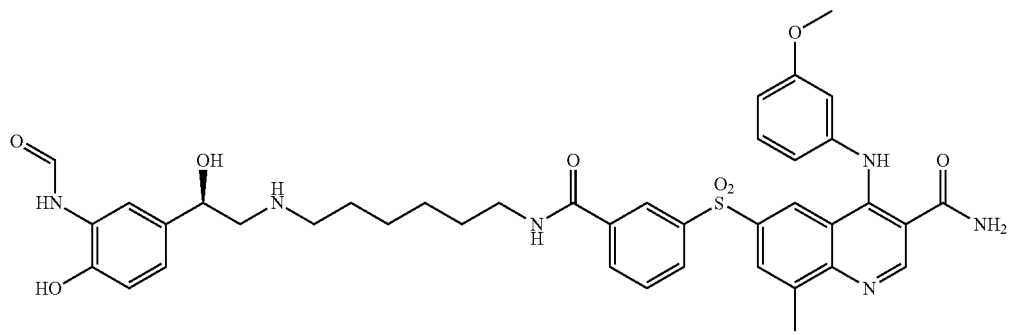 [SMILES: COc1cccc(Nc2c(C(N)=O)cnc3c(C)cc(S(=O)(=O)c4cccc(C(=O)NCCCCCCNC[C@H](O)c5ccc(O)c(NC=O)c5)c4)cc23)c1]

The title compound was synthesized in a manner analogous to that described for Example 1, using Intermediate 167 as a substrate.

¹H NMR (400 MHz, DMSO-d$_6$) δ 11.05-10.97 (s, 1H), 9.99-9.89 (s, 1H), 9.57-9.41 (s, 1H), 9.12 (s, 1H), 8.74-8.63 (m, 1H), 8.58-8.49 (m, 2H), 8.33-8.26 (m, 3H), 8.18-8.14 (m, 1H), 8.11 (m, 5H), 7.91 (s, 1H), 7.72-7.66 (d, 1H, J=9.2 Hz), 7.65-7.55 (m, 1H), 7.12 (m, 1H), 6.96-6.89 (m, 1H), 6.87 (m, 1H), 6.73-6.65 (d, 1H, J=8.3 Hz), 6.58-6.47 6.12-5.89 (s, 1H), (s, 2H), 4.87-4.73 (d, 1H, J=8.8), 3.64 (s, 4H), 3.10-2.83 (m, 4H), 2.72 (s, 3H), 1.75-1.49 (m, 4H), 1.38 (m, 4H); ES/MS calcd. C$_{40}$H$_{45}$N$_6$O$_8$S$^+$ 769.3. Found m/z=769 (M+H)$^+$.

Example 28

(R)-6-((3-((6-((2-(3-formamido-4-hydroxyphenyl)-2-hydroxyethyl)amino)hexyl)(methyl)carbamoyl)phenyl)sulfonyl)-4-((3-methoxyphenyl)amino)-8-methylquinoline-3-carboxamide

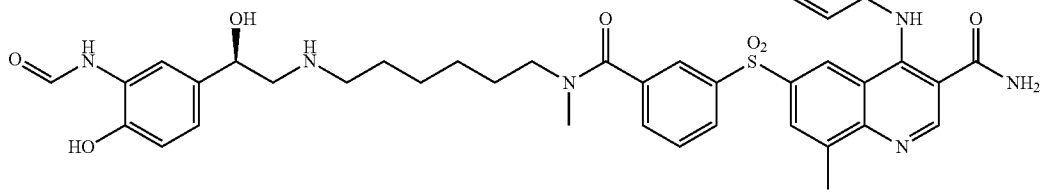

The title compound was synthesized in a manner analogous to that described in Example 1, using Intermediate 168 as a substrate.

¹H NMR (400 MHz, dmso-d6) δ 10.98-10.77 (s, 1H), 10.09-9.99 (s, 1H), 9.63-9.52 (s, 1H), 9.10-8.99 (s, 1H), 8.43-8.21 (m, 5H), 8.19-8.08 (m, 1H), 8.06-7.94 (m, 1H), 7.83-7.60 (m, 5H),), 7.20-7.08 (m, 1H), 6.90-6.78 (m, 2H), 6.77-6.62 (m, 2H), 6.11-5.95 (s, 1H), 4.84-4.63 (m, 1H), 3.66 (s, 3H), 3.02-2.91 (m, 4H), 2.87-2.75 (m, 5H), 2.68 (s, 3H), 1.39-1.17 (m, 4H), 1.73-1.51 (m, 4H)

ES/MS calcd. for O$_{41}$H$_{46}$N$_6$O$_8$S 782.31. Found m/z=783 (M+H)$^+$.

Example 29

(R)-6-((3-((6-((2-hydroxy-2-(5-hydroxy-3-oxo-3,4-dihydro-2H-benzo[b][1,4]oxazin-8-yl)ethyl)amino)hexyl)carbamoyl)phenyl)sulfonyl)-4-((3-methoxyphenyl)amino)-8-methylquinoline-3-carboxamide

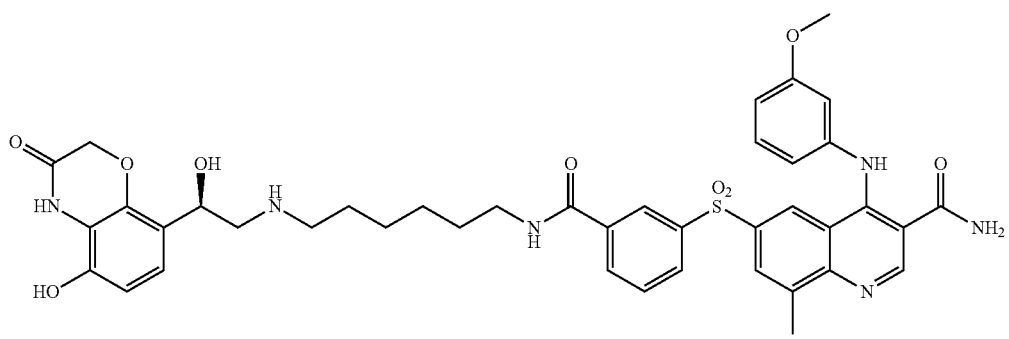 [SMILES: COc1cccc(Nc2c(C(N)=O)cnc3c(C)cc(S(=O)(=O)c4cccc(C(=O)NCCCCCCNC[C@H](O)c5ccc(O)c6c5OCC(=O)N6)c4)cc23)c1]

The title compound was synthesized in a manner analogous to that described in Example 1, using Intermediate 170 as a substrate.

$^1$H NMR (400 MHz, dmso-d6) δ ppm 10.98-10.89 (s, 1H), 10.04-9.92 (s, 1H), 9.12-9.01 (s, 1H), 8.82-8.70 (m, 1H), 8.43-8.22 (m, 2H), 8.17-7.97 (m, 2H), 7.86-7.62 (m, 2H), 7.22-7.09 (m, 1H), 6.96-6.85 (m, 1H), 6.78-6.49 (m, 4H), 6.05-5.84 (m, 1H), 5.10-4.97 (m, 1H), 4.53 (d, 2H, J=), 3.65-3.61 (s, 3H), 3.04-2.83 (m, 5H), 2.70 (s, 5H), 2.50 (s, 2H), 1.69-1.45 (m, 5H), 1.32 (m, 5H); ES/MS calcd. for $O_{41}H_{44}N_6O_9S$ 796.3. Found m/z=797 (M+H)$^+$.

Example 30

(R)-6-((3-(((6-((2-hydroxy-2-(5-hydroxy-3-oxo-3,4-dihydro-2H-benzo[b][1,4]oxazin-8-yl)ethyl)amino)hexyl)(methyl)carbamoyl)phenyl)sulfonyl)-4-((3-methoxyphenyl)amino)-8-methylquinoline-3-carboxamide

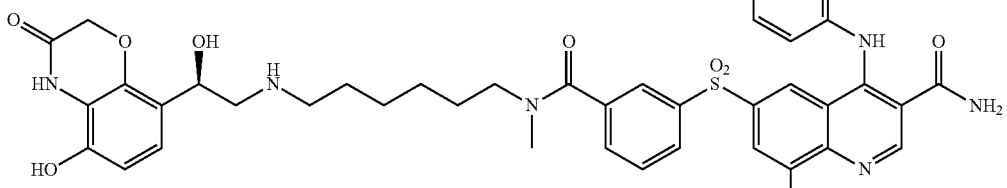

The title compound was synthesized in a manner analogous to that described in Example 1, using Intermediate 169 as a substrate.

$^1$H NMR (400 MHz, dmso-d6) δ 11.05-10.86 (s, 1H), 10.04-9.90 (s, 1H), 9.11-9.01 (s, 1H), 8.45-8.27 (m, 2H), 8.09-7.96 (m, 1H), 7.85-7.62 (m, 4H), 7.21-7.08 (m, 1H), 6.97-6.84 (m, 1H), 6.79-6.65 (m, 2H), 6.63-6.48 (m, 2H), 6.00-5.84 (m, 1H), 5.09-4.97 (m, 1H), 4.59-4.46 (m, 2H), 3.67 (s, 3H), 3.23-2.93 (m, 8H), 2.88-2.76 (m, 4H), 2.70 (s, 4H), 1.69-1.41 (m, 4H), 1.41-1.24 (m, 3H); ES/MS calcd. for $C_{42}H_{46}N_6O_9S$ 810.3. Found m/z=811 (M+H)$^+$.

Example 31

(R)-6-[[3-[[4-[5-[[2-(3-Formamido-4-hydroxyphenyl)-2-hydroxyethyl]amino]pent-1-ynyl]phenyl]carbamoyl]phenyl]sulfonyl]-4-[(3-methoxyphenyl)amino]-8-methylquinoline-3-carboxamide

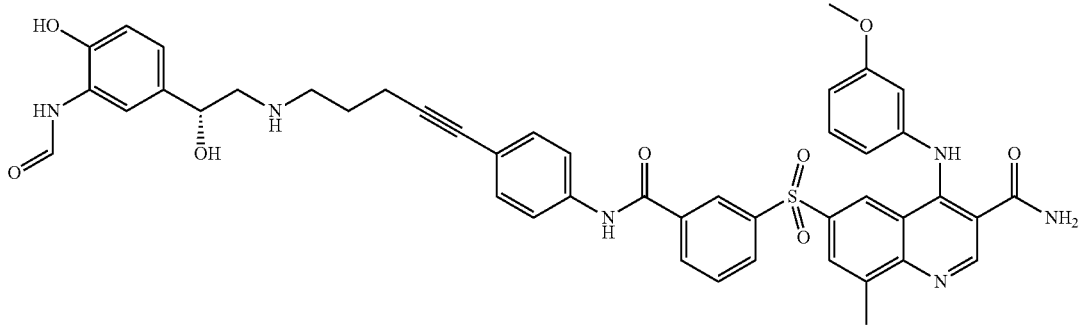 [SMILES: COc1cccc(Nc2c(C(N)=O)cnc3c(C)cc(S(=O)(=O)c4cccc(C(=O)Nc5ccc(C#CCCCNC[C@H](O)c6ccc(O)c(NC=O)c6)cc5)c4)cc23)c1]

The title compound was synthesized in a manner analogous to that described for Example 1, using Intermediate 171 as a substrate.

¹H NMR (400 MHz, DMSO-d₆) δ 10.64 (s, 1H), 10.07 (s, 1H), 9.61 (s, 1H), 9.07 (s, 1H), 8.53 (brs, 2H), 8.29 (m, 4H), 8.18 (d, 1H, J=2.0), 8.06 (s, 1H), 7.88 (m, 1H), 7.77 (d, 4H, J=8.8 Hz), 7.43 (d, 2H, J=8.7 Hz), 7.11 (t, 1H, J=8.4 Hz), 6.94 (dd, 1H, J=2.1, 8.3 Hz), 6.87 (d, 1H, J=8.2 Hz), 6.65 (m, 2H), 6.5 (d, 1H, J=8.4 Hz), 6.07 (brs, 1H), 4.76 (m, 1H), 3.59 (s, 3H), 3.27 (m, 2H), 2.93 (s, 2H), 2.70 (s, 3H), 1.33 (m, 2H), 0.92 (q, 2H, J=7.4 Hz); ES/MS calcd. for C₄₆H₄₃N₆O₈S⁺ 827.3. Found m/z=827.3 (M+H)⁺.

Example 32

(R)-6-((3-((4-(5-((2-hydroxy-2-(5-hydroxy-3-oxo-3,4-dihydro-2H-benzo[b][1,4]oxazin-8-yl)ethyl)amino)pent-1-yn-1-yl)phenyl)carbamoyl)phenyl)sulfonyl)-4-((3-methoxyphenyl)amino)-8-methylquinoline-3-carboxamide

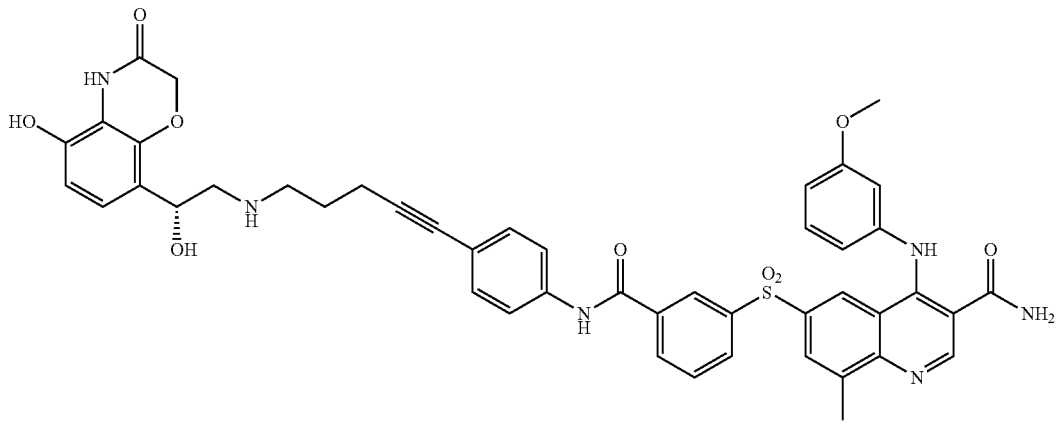 [SMILES: COc1cccc(Nc2c(C(N)=O)cnc3c(C)cc(S(=O)(=O)c4cccc(C(=O)Nc5ccc(C#CCCCNC[C@H](O)c6ccc(O)c7c6OCC(=O)N7)cc5)c4)cc23)c1]

The title compound was synthesized in a manner analogous to that described in Example 5, using Intermediate 172 as a substrate.

¹H NMR (400 MHz, dmso-d6) δ 11.15-10.99 (s, 1H), 10.64 (s, 1H), 9.98 (s, 1H), 9.05 (s, 1H), 8.60-8.51 (m, 2H), 8.31 (m, 4H), 8.13-8.02 (m, 1H), 7.78 (m, 5H), 7.42 (d, J=8.57 Hz, 2H), 7.20-7.06 (m, 1H), 6.91 (s, 1H), 6.74-6.49 (m, 4H), 6.13-5.81 (brs, 1H), 5.13-5.00 (m, 1H), 4.54 (d, J=4.42 Hz, 2H), 3.64-3.58 (s, 3H), 3.19-2.89 (m, 5H), 2.70 (s, 2H), 2.58-2.51 (m, 2H), 2.00-1.80 (m, 2H); ES/MS calcd. for C₄₆H₄₂N₆O₉S 854.3. Found m/z=855 (M+H)⁺.

Example 33

(R)-6-((3-((4-(5-((2-hydroxy-2-(8-hydroxy-2-oxo-1,2-dihydroquinolin-5-yl)ethyl)amino)pent-1-yn-1-yl)phenyl)(methyl)carbamoyl)phenyl)sulfonyl)-4-((3-methoxyphenyl)amino)-8-methylquinoline-3-carboxamide

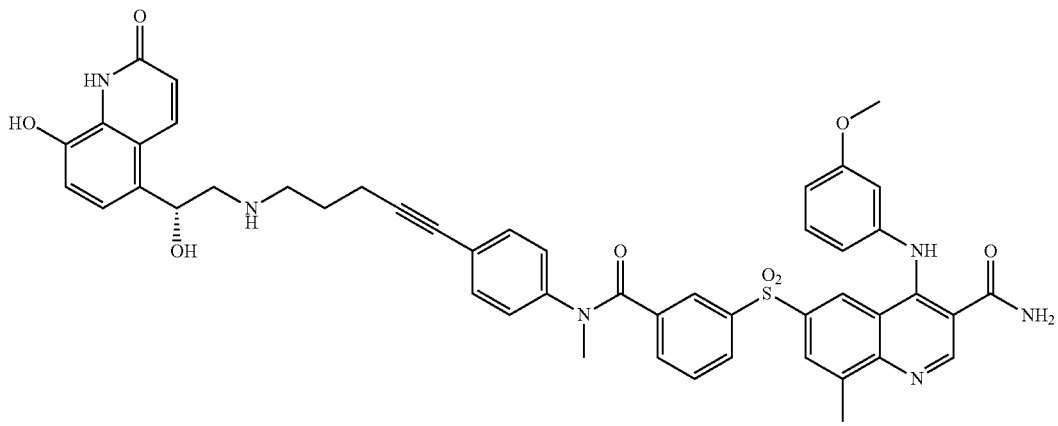 [SMILES: COc1cccc(Nc2c(C(N)=O)cnc3c(C)cc(S(=O)(=O)c4cccc(C(=O)N(C)c5ccc(C#CCCCNC[C@H](O)c6ccc(O)c7[nH]c(=O)ccc67)cc5)c4)cc23)c1]

The title compound was synthesized in a manner analogous to that described in Example 13, using Intermediate 116 in place of Intermediate 137.

¹H NMR (400 MHz, dmso-d6) δ ppm 11.00-10.87 (s, 1H), 10.49 (s, 1H), 9.05 (s, 1H), 8.68-8.50 (brs, 2H), 8.29 (s, 2H), 8.13 (d, J=9.97 Hz, 1H), 7.83 (s, 2H), 7.70-7.41 (m, 4H), 7.19-6.90 (m, 6H), 6.78-6.47 (m, 4H), 6.27-6.03 (m, 1H), 5.33-5.20 (m, 1H), 3.67-3.60 (m, 3H), 3.36-3.33 (s, 3H), 3.04 (m, 5H), 2.71 (s, 3H), 2.47 (m, 2H), 1.96-1.74 (m, 2H); ES/MS calcd. $C_{48}H_{44}N_6O_8S$ 864.3. Found m/z=865 (M+H)⁺.

Example 34

(R)-6-((3-((4-(5-((2-hydroxy-2-(8-hydroxy-2-oxo-1,2-dihydroquinolin-5-yl)ethyl)amino)pent-1-yn-1-yl)-2-methylphenyl)carbamoyl)phenyl)sulfonyl)-4-((3-methoxyphenyl)amino)-8-methylquinoline-3-carboxamide

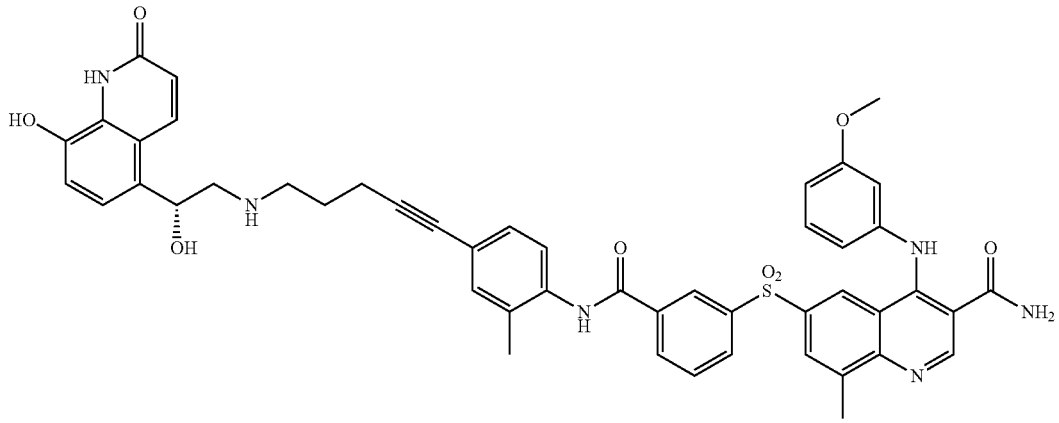 [SMILES: COc1cccc(Nc2c(C(N)=O)cnc3c(C)cc(S(=O)(=O)c4cccc(C(=O)Nc5ccc(C#CCCCNC[C@H](O)c6ccc(O)c7[nH]c(=O)ccc67)cc5C)c4)cc23)c1]

The title compound was synthesized in a manner analogous to that described in Example 5, using Intermediate 154 as a substrate.

¹H NMR (400 MHz, dmso-d6) δ 11.16-10.98 (s, 1H), 10.58-10.41 (s, 1H), 10.19 (s, 1H), 9.06 (s, 1H), 8.67-8.56 (m, 2H), 8.47-8.03 (m, 5H), 7.78 (d, J=7.88 Hz, 3H), 7.45-7.10 (m, 4H), 6.99 (d, J=8.16 Hz, 1H), 6.79-6.53 (m, 3H), 6.31-6.09 (m, 1H), 5.38-5.25 (m, 1H), 3.63-3.62 (m, 3H), 3.26-3.04 (m, 4H), 2.71 (s, 3), 2.61-2.52 (m, 4H), 2.22 (s, 3H), 2.11-1.83 (m, 2H); ES/MS calcd. for $C_{48}H_{44}N_6O_8S$ 864.3. Found m/z=865 (M+H)⁺.

Example 35

(R)-6-((3-((4-(5-((2-hydroxy-2-(5-hydroxy-3-oxo-3,4-dihydro-2H-benzo[b][1,4]oxazin-8-yl)ethyl)amino)pent-1-yn-1-yl)-2-methylphenyl)carbamoyl)phenyl)sulfonyl)-4-((3-methoxyphenyl)amino)-8-methylquinoline-3-carboxamide

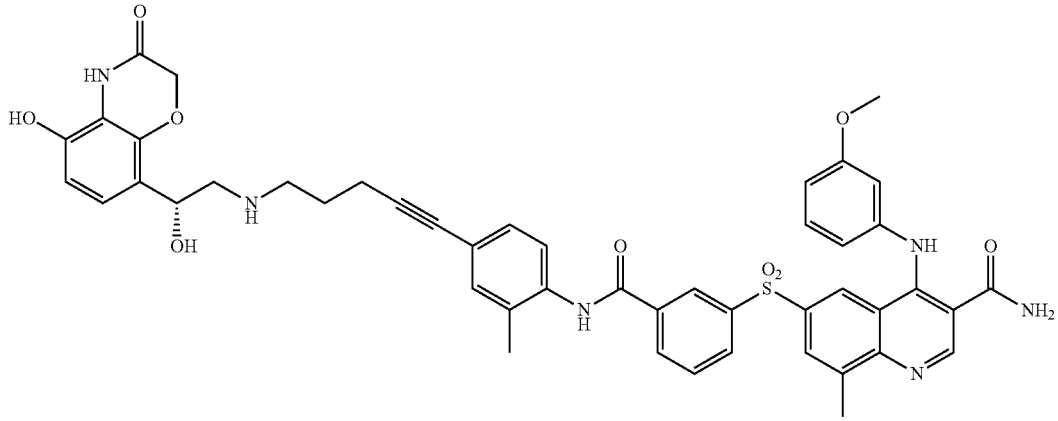 [SMILES: COc1cccc(Nc2c(C(N)=O)cnc3c(C)cc(S(=O)(=O)c4cccc(C(=O)Nc5ccc(C#CCCCNC[C@H](O)c6ccc(O)c7c6OCC(=O)N7)cc5C)c4)cc23)c1]

The title compound was synthesized in a manner analogous to that described in Example 5, using Intermediate 162 as a substrate.

$^1$H NMR (400 MHz, dmso-d6) δ 11.28-11.04 (2, 1H), 10.25-10.13 (2, 1H), 10.04-9.91 (2, 1H), 9.10-8.98 (m, 1H), 8.78-8.50 (m, 2H), 8.46-8.32 (m, 2H), 8.27-8.23 (d, J=7.49, 1H), 8.15-8.03 (m, 1H), 7.94-7.70 (m, 3H), 7.44-7.11 (m, 4H), 6.98-6.85 (m, J=8.30, 1H), 6.80-6.49 (m, 4H), 5.14-4.99 (m, 1H), 4.63-4.45 (m, 2H), 3.63 (s, 3H), 3.19-2.89 (m, 5H), 2.71 (s, 3H), 2.49 (m, 4H), 2.22 (s, 3H), 2.00-1.82 (m, 2H); ES/MS calcd. for $C_{47}H_{44}N_6O_9S$ 868.3. Found m/z=869 (M+H)$^+$.

Example 36

(R)-6-((3-((4-(5-((2-hydroxy-2-(5-hydroxy-3-oxo-3, 4-dihydro-2H-benzo[b][1,4]oxazin-8-yl)ethyl) amino)pent-1-yn-1-yl)-3-methylphenyl)carbamoyl) phenyl)sulfonyl)-4-((3-methoxyphenyl)amino)-8-methylquinoline-3-carboxamide

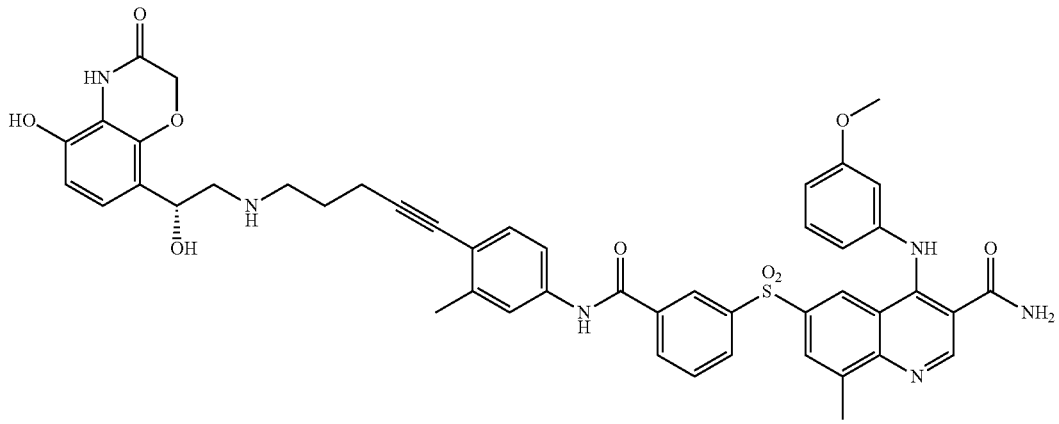 [SMILES: COc1cccc(Nc2c(C(N)=O)cnc3c(C)cc(S(=O)(=O)c4cccc(C(=O)Nc5ccc(C#CCCCNC[C@H](O)c6ccc(O)c7c6OCC(=O)N7)c(C)c5)c4)cc23)c1]

The title compound was synthesized in a manner analogous to that described in Example 5, using Intermediate 163 as a substrate.

$^1$H NMR (400 MHz, dmso-d6) δ 11.15-11.00 (brs, 1H), 10.56 (s, 1H), 9.98 (s, 1H), 9.05 (s, 1H), 8.77-8.51 (m, 2H), 8.43-8.29 (m, 3H), 8.24-8.18 (d, J=7.9 1H), 8.08 (s, 1H), 7.92-7.73 (m, 3H), 7.71-7.68 (s, 1H), 7.65-7.60 (d, J=8.4 1H), 7.37 (d, J=8.42 Hz, 1H), 7.21-7.06 (m, 1H), 6.92 (d, J=8.47 Hz, 1H), 6.72-6.66 (m, 2H), 6.60-6.54 (m, 2H), 5.14-5.00 (m, 1H), 4.54 (d, J=4.05 Hz, 2H), 3.61 (s, 3H), 3.11 (m, 4H), 2.72-2.68 (s, 3H), 2.61-2.48 (m, 2H), 2.40-2.34 (s, 3H), 2.02-1.86 (m, 2H); ES/MS calcd. for $C_{47}H_{44}N_6O_9S$ 868.3 found m/z=869 (M+H)$^+$.

Example 37

(R)-6-((3-((4-(2-(4-((2-hydroxy-2-(8-hydroxy-2-oxo-1,2-dihydroquinolin-5-yl)ethyl)amino)butyl)-1,3-dithiolan-2-yl)phenyl)carbamoyl)phenyl)sulfonyl)-4-((3-methoxyphenyl)amino)-8-methylquinoline-3-carboxamide

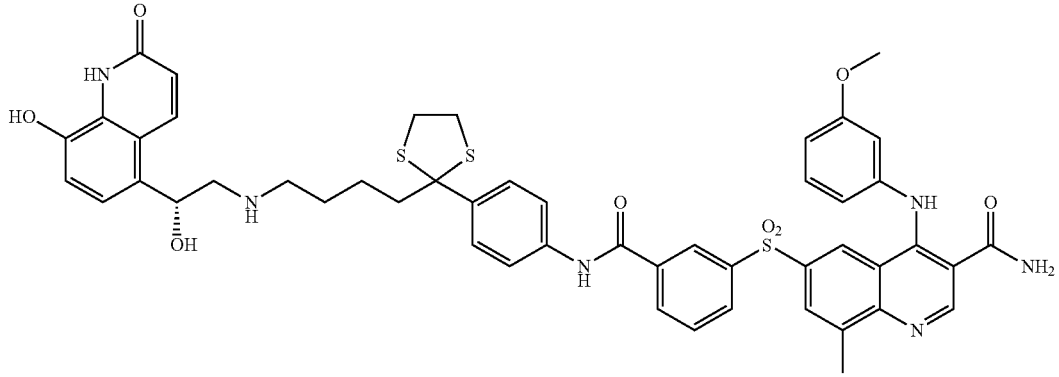 [SMILES: COc1cccc(Nc2c(C(N)=O)cnc3c(C)cc(S(=O)(=O)c4cccc(C(=O)Nc5ccc(C6(CCCCNC[C@H](O)c7ccc(O)c8[nH]c(=O)ccc78)SCCS6)cc5)c4)cc23)c1]

Intermediate 158 (90 mg, 0.08 mmol) was taken up in dichloromethane and treated with trifluoroacetic acid (0.50 mL). After 30 minutes of stirring, the mixture was concentrated to a residue under reduced pressure, taken up in tetrahydrofuran (1 mL) and treated successively with TBAF solution (1.0 M in THF, 1 mL) and glacial acetic acid (0.50 mL). The mixture was left overnight at room temperature and then concentrated under reduced pressure. The residue was purified by reverse-phase high performance liquid chromatography (RP-HPLC, acetonitrile/water/0.1% TFA) to provide, after concentration, the trifluoroacetic acid salt of the title compound as a bright yellow foam (22 mg).

$^1$H NMR (400 MHz, DMSO-d6) δ 11.03 (bs, 1H), 10.57 (s, 1H), 10.48 (m, 2H), 9.06 (s, 1H), 8.50 (bs, 2H), 8.40 (s, 1H), 8.33 (m, 2H), 8.22 (d, 1H, J=8.0 Hz), 8.12 (d, 1H, J=9.6 Hz), 8.08 (s, 1H), 7.89 (d, 1H, J=7.6 Hz), 7.83-7.71 (m, 4H), 7.64 (m, 2H), 7.17-7.11 (m, 2H), 6.97 (d, 1H, J=8.4 Hz), 6.68 (m, 2H), 6.60-6.56 (m, 2H), 5.27 (m, 1H), 3.61 (s, 3H), 3.45-3.39 (m, 2H), 3.34-3.28 (m, 2H), 3.10-2.85 (m, 2H), 2.71 (s, 3H), 2.57-2.43 (m, 2H), 2.40-2.30 (m, 2H), 1.62 (m, 2H), 1.26 (m, 2H); ES/MS calcd. for $C_{49}H_{49}N_6O_8S_3^+$ 945.3. Found m/z=945.5 (M+H)$^+$.

Example 38
(R)-6-((3-((4-(4-((6-((2-hydroxy-2-(8-hydroxy-2-oxo-1,2-dihydroquinolin-5-yl)ethyl)amino)hexyl)oxy)butyl)phenyl)carbamoyl)phenyl)sulfonyl)-4-((3-methoxyphenyl)amino)-8-methylquinoline-3-carboxamide

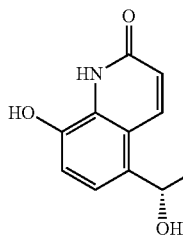
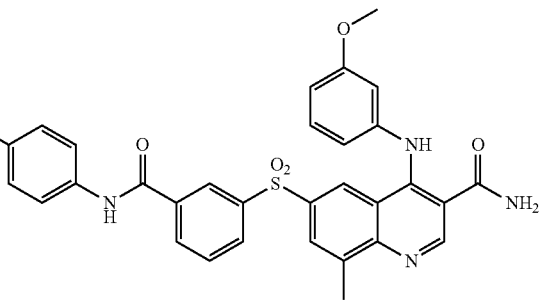

The concentrated reaction mixture containing Intermediate 159 was taken up in dichloromethane (5 mL) and treated with trifluoroacetic acid (1 mL). After stirring overnight at room temperature, the mixture was concentrated under reduced pressure. The residue was taken up in tetrahydrofuran (1 mL) and treated with TBAF solution (1.0 M in THF, 1 mL) and glacial acetic acid (0.30 mL). The mixture was stirred overnight in a 40° C. oil bath, and then concentrated under reduced pressure. The residue was purified by reverse-phase high performance liquid chromatography (RP-HPLC, acetonitrile/water/0.1% TFA) to provide, after concentration, the trifluoroacetic acid salt of the title compound as a yellow powder (16 mg).

$^1$H NMR (400 MHz, DMSO-d6) δ 11.04 (bs, 1H), 10.48 (m, 2H), 9.05 (s, 1H), 8.51 (bs, 2H), 8.41 (s, 1H), 8.33 (m, 2H), 8.21 (d, 1H, J=7.6 Hz), 8.14 (d, 1H, J=9.6 Hz), 8.09 (s, 1H), 7.89 (d, 1H, J=8.0 Hz), 7.83-7.73 (m, 4H), 7.67 (m, 2H), 7.22-7.11 (m, 4H), 6.97 (d, 1H, J=8.0 Hz), 6.69 (m, 2H), 6.58 (m, 2H), 5.29 (m, 1H), 3.61 (s, 3H), 3.39-3.29 (m, 4H), 3.14-2.79 (m, 2H), 2.71 (s, 3H), 2.60-2.43 (m, 4H), 1.68-1.43 (m, 10H), 1.36-1.25 (m, 2H); ES/MS calcd. for $C_{52}H_{57}N_6O_9S^+$ 941.4. Found m/z=941.5 (M+H)$^+$.

Example 39
(R)-6-((3-((4-(2-((6-((2-hydroxy-2-(8-hydroxy-2-oxo-1,2-dihydroquinolin-5-yl)ethyl)amino)hexyl)oxy)ethyl)phenyl)carbamoyl)phenyl)sulfonyl)-4-((3-methoxyphenyl)amino)-8-methylquinoline-3-carboxamide

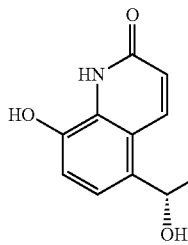
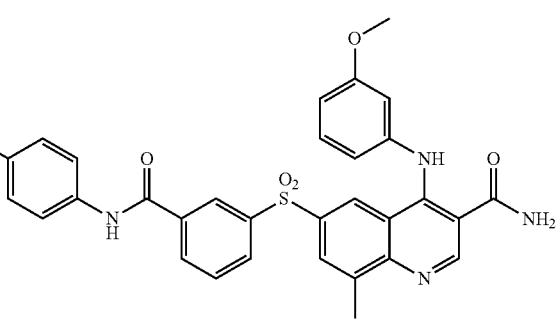

The title compound was synthesized in a manner analogous to that described for Example 38, using Intermediate 160 as a substrate.

$^1$H NMR (400 MHz, dmso-d6) δ 11.04 (s, 1H), 10.48 (m, 2H), 9.06 (s, 1H), 8.53 (s, 2H), 8.40 (s, 1H), 8.33 (m, 2H), 8.21 (d, J=7.8 Hz, 1H), 8.15 (d, J=9.9 Hz, 1H), 8.08 (s, 1H), 7.89 (d, J=7.9 Hz, 1H), 7.80-7.70 (m, 2H), 7.67 (d, J=8.4 Hz, 2H), 7.24 (d, J=8.5 Hz, 2H), 7.14 (m, 2H), 6.98 (d, J=8.1 Hz, 1H), 6.69 (m, 2H), 6.63-6.53 (m, 2H), 5.30 (m, 1H), 3.94 (bs, 1H), 3.61 (s, 3H), 3.56 (t, J=7.0 Hz, 2H), 3.39 (t, J=6.4 Hz, 2H), 3.26-2.83 (m, 5H), 2.79 (t, J=6.9 Hz, 2H), 2.71 (s, 3H), 1.56 (m, 4H), 1.27 (m, 4H).; ES/MS calcd. for $C_{50}H_{53}N_6O_9S^+$ 913.4. Found m/z=913.3 (M+H)$^+$.

Example 40

(R)-6-((3-((4-(4-((6-((2-hydroxy-2-(8-hydroxy-2-oxo-1,2-dihydroquinolin-5-yl)ethyl)amino)hexyl)oxy)butyl)phenyl)(methyl)carbamoyl)phenyl)sulfonyl)-4-((3-methoxyphenyl)amino)-8-methylquinoline-3-carboxamide

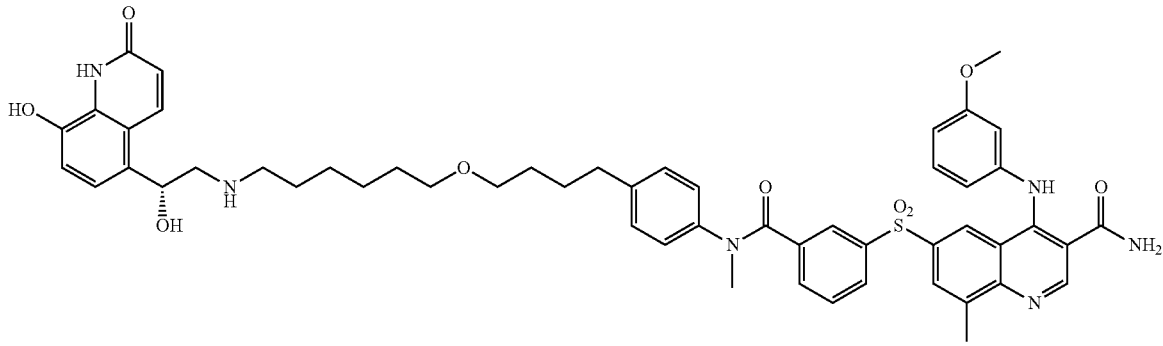 [SMILES: COc1cccc(Nc2c(C(N)=O)cnc3c(C)cc(S(=O)(=O)c4cccc(C(=O)N(C)c5ccc(CCCCOCCCCCCNC[C@H](O)c6ccc(O)c7[nH]c(=O)ccc67)cc5)c4)cc23)c1]

The title compound was synthesized in a manner analogous to that described for Example 1, using Intermediate 161 as a substrate. The crude product was purified by reverse-phase high performance liquid chromatography (RP-HPLC, acetonitrile/water/0.1% TFA) to provide, after concentration, the title compound as a yellow solid (84 mg, 72%).

$^1$H NMR (400 MHz, dmso) δ 11.04 (s, 1H), 10.51 (m, 1H), 9.07 (s, 1H), 8.53 (m, 2H), 8.32 (m, 2H), 8.15 (d, J=9.9 Hz, 1H), 7.93 (s, 1H), 7.80 (s, 1H), 7.68 (s, 1H), 7.62-7.39 (m, 3H), 7.17-7.10 (m, 2H), 7.03 (m, 2H), 6.98 (d, J=8.0 Hz, 1H), 6.86 (m, 2H), 6.75 (m, 1H), 6.64 (s, 1H), 6.55 (m, 2H), 5.30 (m, 1H), 3.61 (s, 3H), 3.35 (s, 3H), 3.29-3.19 (m, 4H), 3.14-2.87 (m, 4H), 2.72 (s, 3H), 2.24 (m, 2H), 1.60 (m, 2H), 1.44 (m, 2H), 1.30 (m, 10H); ES/MS calcd. for $C_{53}H_{59}N_6O_9S^+$ 955.4. Found m/z=955.4 (M+H)$^+$.

Example 41

(R)-6-[[3-[[6-[[2-Hydroxy-2-[4-hydroxy-3-(hydroxymethyl)phenyl]ethyl]amino]hexyl]carbamoyl]phenyl]sulfonyl]-4-[(3-methoxyphenyl)amino]-8-methylquinoline-3-carboxamide

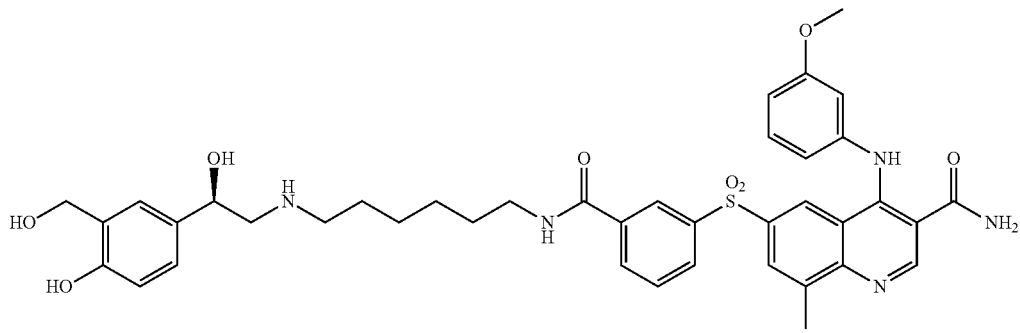 [SMILES: COc1cccc(Nc2c(C(N)=O)cnc3c(C)cc(S(=O)(=O)c4cccc(C(=O)NCCCCCCNC[C@H](O)c5ccc(O)c(CO)c5)c4)cc23)c1]

The title compound was synthesized in a manner analogous to that described for Example 1, using Intermediate 173 as a substrate. $^1$H NMR (400 MHz, DMSO-d$_6$) δ 11.24-11.08 (s, 1H), 9.49-9.32 (s, 1H), 9.03 (s, 1H), 8.84-8.71 (m, 1H), 8.34 (m, 5H), 8.06 (s, 2H), 7.81 (d, 2H, J=8.0 Hz), 7.69 (t, 1H, J=7.8 Hz), 7.33 (s, 1H), 7.18 (s, 1H), 7.03 (d, 1H, J=8.2 Hz), 6.75 (d, 1H, J=8.2 Hz), 6.68 (s, 1H), 6.61 (d, 1H J=7.8 Hz), 5.05 (m, 1H), 4.80 (d, 1H, J=8.4 Hz), 4.45-4.27 (m, 2H), 3.64 (s, 3H), 3.28 (d, 2H, J=6.19 Hz), 2.93 (s, 4H), 2.70 (s, 3H), 1.79-1.47 (m, 4H), 1.33 (s, 4H); ES/MS calcd. for $C_{40}H_{46}N_5O_8S^+$ 756.3. Found m/z=756 (M+H)$^+$.

Example 42

(R)-6-[[3-[[4-[[2-Hydroxy-2-[4-hydroxy-3-(hydroxymethyl)phenyl]ethyl]amino]piperidine-1-yl]carbonyl]phenyl]sulfonyl]-4-[(3-methoxyphenyl)amino]-8-methylquinoline-3-carboxamide

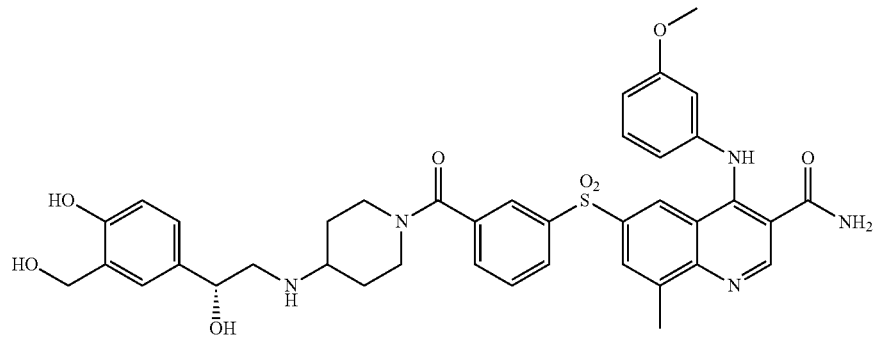 [SMILES: COc1cccc(Nc2c(C(N)=O)cnc3c(C)cc(S(=O)(=O)c4cccc(C(=O)N5CCC(NC[C@H](O)c6ccc(O)c(CO)c6)CC5)c4)cc23)c1]

The title compound was synthesized in a manner analogous to that described for Example 1, using Intermediate 174 as a substrate.

$^1$H NMR (400 MHz, DMSO-d6) δ11.19-11.05 (s, 1H), 9.53-9.34 (s, 1H), 9.05 (s, 1H), 8.89-8.70 (m, 1H), 8.70-8.57 (m, 1H), 8.42 (s, 2H), 8.05 (s, 1H), 7.89-7.62 (m, 5H), 7.36 (m, 1H), 7.19 (m, 3H), 6.77 (d, 2H, J=8.22 Hz), 6.73 (s, 1H), 6.66-6.55 (m, 1H), 4.86-4.79 (m, 1H), 4.50 (s, 2H), 6.19-5.91 (m, 1H), 3.68 (s, 3H), 3.53-3.31 (m, 2H), 3.21-2.93 (m, 3H), 2.71 (s, 3H), 1.71-1.39 (m, 2H), 2.32-1.83 (m, 2H); ES/MS calcd. for $C_{39}H_{42}N_5O_8S^+$ 740.3. Found m/z=740 (M+H)$^+$.

Example 43

(R)-6-[[3-[[6-[[2-Hydroxy-2-[4-hydroxy-3-(methylsulfonamido)phenyl]ethyl]amino]hexyl]carbamoyl]phenyl]sulfonyl]-4-[(3-methoxyphenyl)amino]-8-methylquinoline-3-carboxamide

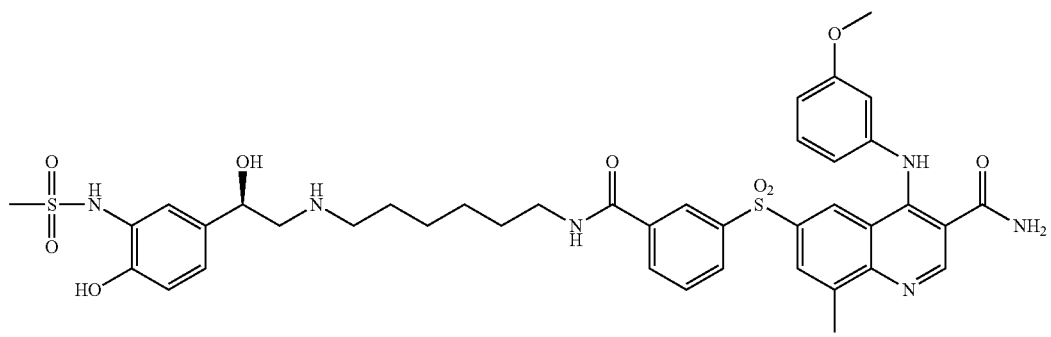 [SMILES: COc1cccc(Nc2c(C(N)=O)cnc3c(C)cc(S(=O)(=O)c4cccc(C(=O)NCCCCCCNC[C@H](O)c5ccc(O)c(NS(C)(=O)=O)c5)c4)cc23)c1]

The title compound was synthesized in a manner analogous to that described for Example 1, using Intermediate 175 as a substrate.

¹H NMR (400 MHz, DMSO-d6) δ11.15-10.93 (s, 1H), 10.13-9.90 (s, 1H), 9.02 (s, 1H), 8.72 (s, 2H), 8.57-8.42 (m, 2H), 8.26 (s, 2H), 8.12-8.05 (d, 1H, J=7.7 Hz), 8.02 (s, 1H), 7.83-7.73 (d, 2H, J=7.1), 7.71-7.63 (t, 1H J=7.8 Hz), 7.21 (s, 1H), 7.18-7.10 (m, 1H), 7.07-6.98 (m, 1H), 6.88 (d, 1H, J=8.3 Hz), 6.75-6.67 (d, 1H, J=8.3 Hz), 6.63 (s, 1H), 6.59-6.53 (d, 1H, J=7.8 Hz), 4.79-4.69 (m, 1H), 3.61 (s, 3H), 3.32-3.19 (m, 2H), 3.19-3.10 (m, 2H), 2.92 (brs, 4H), 2.67 (brs, 2H), 1.53 (m, 4H), 1.30-1.24 (m, 4H), 0.91 (t, 3H, J=7.32 Hz); ES/MS calcd. for $C_{40}H_{47}N_6O_6S_2^+$ 819.3. Found m/z=819 (M+H)⁺

Example 44

(R)-6-[[3-[[6-[[2-Hydroxy-2-(4-hydroxy-3-(hydroxymethyl)phenyl]ethyl]amino)hexyl](methyl)carbamoyl]phenyl]sulfonyl]-4-[(3-methoxyphenyl)amino]-8-methylquinoline-3-carboxamide

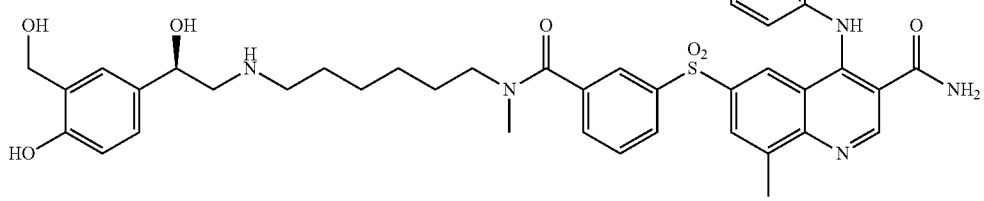

The title compound was synthesized in a manner analogous to that described for Example 1, using Intermediate 176 as a substrate.

¹H NMR (400 MHz, DMSO-d₆) δ 11.06-10.93 (s, 1H), 9.48-9.39 (s, 1H), 9.07 (s, 1H), 8.62-8.27 (m, 4H), 8.16-7.98 (m, 1H), 7.69 (m, 5H), 7.42-7.27 (m, 1H), 7.25-6.98 (m, 2H), 6.81-6.66 (m, 3H), 6.66-6.50 (m, 1H), 6.12-5.90 (m, 1H), 4.82-4.74 (m, 1H), 4.49 (s, 2H), 3.68 (s, 3H), 3.00 (s, 5H), 2.84 (m, 2H), 2.71 (s, 3H), 1.72-1.55 (m, 3H), 1.54-1.42 (m, 2H), 1.42-1.30 (m, 2H), 1.11-0.91 (m, 2H); ES/MS calcd. for $C_{41}H_{48}N_5O_8S^+$ 770.3. Found m/z=770 (M+H)⁺.

Example 45

(R)-6-((11-((2-hydroxy-2-(8-hydroxy-2-oxo-1,2-dihydroquinolin-5-yl)ethyl)amino)undecyl)sulfonyl)-4-((3-methoxyphenyl)amino)-8-methylquinoline-3-carboxamide

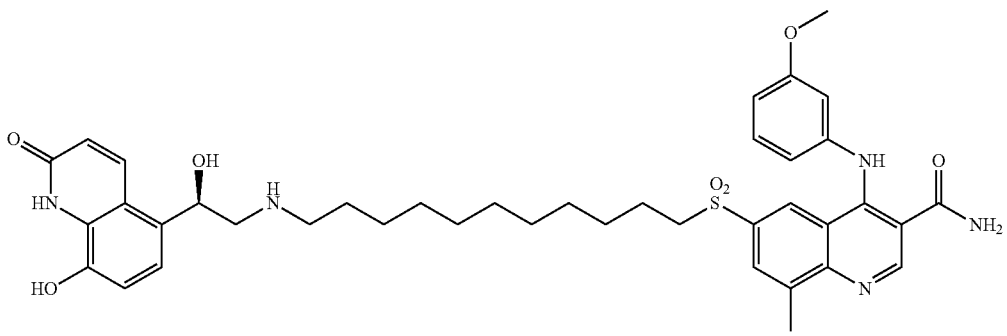 [SMILES: COc1cccc(Nc2c(C(N)=O)cnc3c(C)cc(S(=O)(=O)CCCCCCCCCCCNC[C@H](O)c4ccc(O)c5[nH]c(=O)ccc45)cc23)c1]

The title compound was synthesized in a manner analogous to that described for Example 13, using Intermediate 126 in place of Intermediate 137. $^1$H NMR (400 MHz, DMSO-$d_6$) δ 10.92 (br s, 1H), 10.50 (s, 1H), 10.46 (br s, 1H), 9.07 (s, 1H), 8.51 (br s, 2H), 8.33 (s, 1H), 8.30 (s, 1H), 8.14 (d, J=10.2 Hz, 1H), 7.99 (s, 1H), 7.79 (s, 1H), 7.20-7.13 (m, 2H), 6.98 (d, J=7.9 Hz, 1H), 6.69-6.57 (m, 3H), 6.14 (br s, 1H), 5.29 (dm, J=7.0 Hz, 1H), 3.65 (s, 3H), 3.19-3.15 (m, 2H), 3.11-2.90 (m, 5H), 2.75 (s, 3H), 1.66-1.53 (m, 2H), 1.44-1.34 (m, 2H), 1.30-1.14 (m, 14H). ES/MS calcd. for $C_{40}H_{50}N_6O_7S^+$ 744.3. Found m/z=744.5 (M+H)$^+$.

Example 46

(R)-6-((11-((2-hydroxy-2-(6-hydroxy-3-oxo-3,4-dihydro-2H-benzo[b][1,4]oxazin-8-yl)ethyl)amino)undecyl)sulfonyl)-4-((3-methoxyphenyl)amino)-8-methylquinoline-3-carboxamide

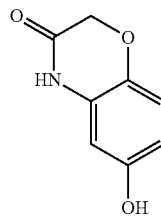

The title compound was synthesized in a manner analogous to that described for Example 5, using Intermediate 177 as a substrate.

$^1$H NMR (400 MHz, DMSO-$d_6$) δ 11.06 (br s, 1H), 10.62 (s, 1H), 9.06 (s, 1H), 8.60 (br s, 1H), 8.49 (br s, 1H), 8.34-8.32 (m, 2H), 8.02 (s, 1H), 7.80 (s, 1H), 7.20 (t, J=9.0 Hz, 1H), 6.71-6.66 (m, 3H), 6.51 (d, J=2.7 Hz, 1H), 6.34 (d, J=2.3 Hz, 1H), 5.06 (dm, J=7.8 Hz, 1H), 4.52-4.44 (ABq, J=15.7 Hz, 2H), 3.69 (s, 3H), 3.20-3.16 (m, 2H), 3.10-3.00 (m, 1H), 2.95-2.84 (m, 2H), 2.75 (s, 3H), 1.66-1.51 (m, 2H), 1.45-1.33 (m, 2H), 1.32-1.13 (m, 14H). ES/MS calcd. for $C_{39}H_{50}N_6O_8S^+$ 748.3. Found m/z=748.5 (M+H)$^+$.

Example 47

(R)-6-((4'-(((2-hydroxy-2-(8-hydroxy-2-oxo-1,2-dihydroquinolin-5-yl)ethyl)amino)methyl)-[1,1'-biphenyl]-3-yl)sulfonyl)-4-((3-methoxyphenyl)amino)-8-methylquinoline-3-carboxamide

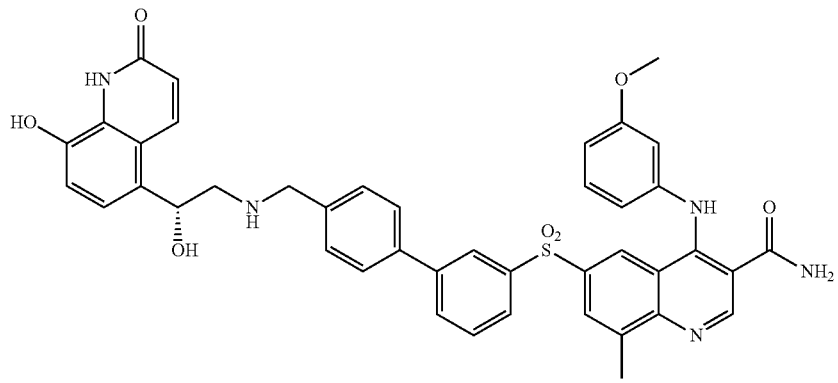 [SMILES: COc1cccc(Nc2c(C(N)=O)cnc3c(C)cc(S(=O)(=O)c4cccc(-c5ccc(CNC[C@H](O)c6ccc(O)c7[nH]c(=O)ccc67)cc5)c4)cc23)c1]

The title compound was synthesized in a manner analogous to that described for Example 13, using NMP in place of DMF, Intermediate 127 in place of Intermediate 137. The crude product was purified by PREP-HPLC to give the title compound. $^1$H NMR (400 MHz, DMSO-$d_6$) δ 11.22 (br s, 1H), 10.49 (br s, 2H), 9.15 (br s, 1H), 9.03 (s, 1H), 8.42 (s, 1H), 8.37 (s, 1H), 8.17 (s, 1H), 8.10 (d, J=9.8 Hz, 1H), 8.05 (s, 1H), 8.04-8.00 (m, 1H), 7.81 (d, J=7.8 Hz, 2H), 7.73-7.68 (m, 3H), 7.12 (d, J=7.8 Hz, 1H), 7.06 (t, J=8.2 Hz, 1H), 6.96 (d, J=8.2 Hz, 1H), 6.70 (s, 1H), 6.64-6.54 (m, 3H), 6.22 (br s, 1H), 5.36 (dm, J=8.3 Hz, 1H), 4.32 (br s, 2H), 3.69 (s, 3H), 3.27-2.98 (m, 2H), 2.71 (s, 3H). ES/MS calcd. for $C_{42}H_{38}N_5O_7S^+$ 756.3. Found m/z=756.4 (M+H)$^+$.

Example 48

(R)-6-((4'-(((2-hydroxy-2-(8-hydroxy-2-oxo-1,2-dihydroquinolin-5-yl)ethyl)amino)methyl)-[1,1'-biphenyl]-4-yl)sulfonyl)-4-((3-methoxyphenyl)amino)-8-methylquinoline-3-carboxamide

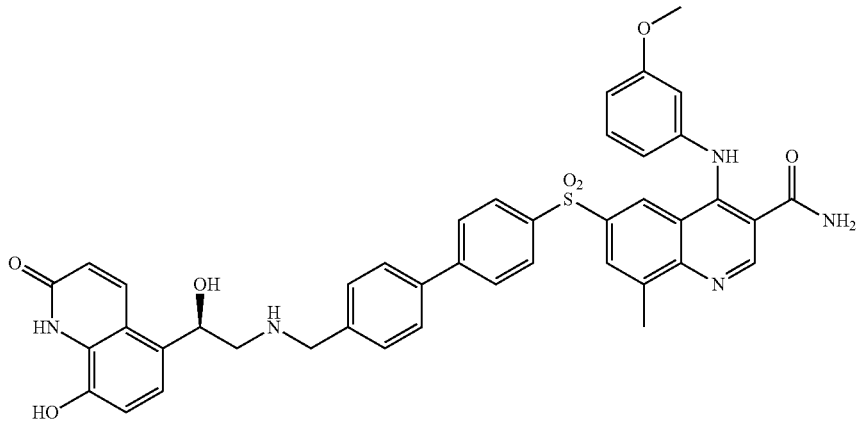 [SMILES: COc1cccc(Nc2c(C(N)=O)cnc3c(C)cc(S(=O)(=O)c4ccc(-c5ccc(CNC[C@H](O)c6ccc(O)c7[nH]c(=O)ccc67)cc5)cc4)cc23)c1]

The title compound was synthesized in a manner analogous to that described for Intermediate 18, using NMP in place of DMF, Intermediate 128 in place of Intermediate 137. The crude product was purified by PREP-HPLC to give the title compound. $^1$H NMR (400 MHz, DMSO-$d_6$) δ 11.17 (br s, 1H), 10.50 (br s, 2H), 9.12 (br s, 2H), 9.06 (s, 1H), 8.41 (s, 1H), 8.37 (s, 1H), 8.13-8.06 (m, 2H), 7.92 (d, J=7.8 Hz, 2H), 7.86-7.79 (m, 3H), 7.66 (d, J=7.8 Hz, 1H), 7.26 (t, J=7.8 Hz, 1H), 7.12 (d, J=7.8 Hz, 1H), 6.97 (d, J=8.2 Hz, 1H), 6.83 (d, J=8.2 Hz, 1H), 6.70-6.63 (m, 2H), 6.56 (d, J=10.2 Hz, 1H), 6.19 (br s, 1H), 5.35 (dm, J=7.8 Hz, 1H), 4.30 (s, 2H), 3.61 (s, 3H), 3.16-2.96 (m, 2H), 2.72 (s, 3H). ES/MS calcd. for $C_{42}H_{38}N_6O_7S^+$ 756.3. Found m/z=756.4 (M+H)$^+$.

Example 49

(R)-6-((4'-(3-((2-hydroxy-2-(5-hydroxy-3-oxo-3,4-dihydro-2H-benzo[b][1,4]oxazin-8-yl)ethyl)amino)propyl)-[1,1'-biphenyl]-4-yl)sulfonyl)-4-((3-methoxyphenyl)amino)-8-methylquinoline-3-carboxamide

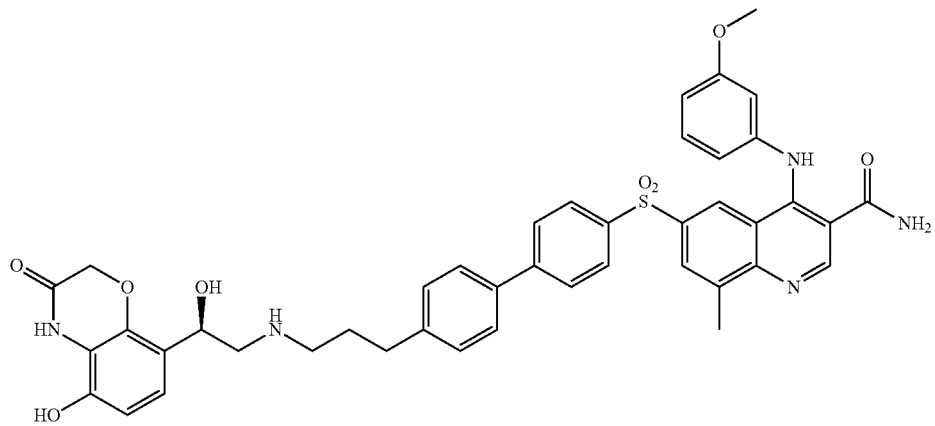 [SMILES: COc1cccc(Nc2c(C(N)=O)cnc3c(C)cc(S(=O)(=O)c4ccc(-c5ccc(CCCNC[C@H](O)c6ccc(O)c7c6OCC(=O)N7)cc5)cc4)cc23)c1]

The title compound was synthesized in a manner analogous to that described for Example 1, using Intermediate 178 as a substrate.

$^1$H NMR (400 MHz, DMSO-$d_6$) δ 11.20 (br s, 1H), 9.97 (s, 2H), 9.04 (s, 1H), 8.63 (br s, 1H), 8.53 (br s, 1H), 8.41 (s, 1H), 8.37 (s, 1H), 8.09 (s, 1H), 7.87 (d, J=8.6 Hz, 1H), 7.83 (br s, 1H), 7.69 (d, J=8.2 Hz, 1H), 7.39-7.34 (m, 2H), 7.27 (t, J=8.0 Hz, 1H), 6.91 (d, J=8.6 Hz, 1H), 6.86-6.81 (m, 1H), 6.71-6.65 (m, 2H), 6.55 (d, J=8.6 Hz, 1H), 5.92 (br s, 1H), 5.04 (dm, J=7.5 Hz, 1H), 4.57-4.48 (ABq, J=14.9 Hz, 2H), 3.62 (s, 3H), 3.12-3.02 (m, 1H), 3.01-2.90 (m, 3H), 2.73-2.66 (m, 2H), 2.71 (s, 3H), 2.03-1.90 (m, 2H). ES/MS calcd. for $C_{43}H_{42}N_6O_8S^+$ 788.3. Found m/z=788.2 (M+H)$^+$.

Example 50

(R)-6-((4'-(3-((2-hydroxy-2-(5-hydroxy-3-oxo-3,4-dihydro-2H-benzo[b][1,4]oxazin-8-yl)ethyl)amino)propyl)-[1,1'-biphenyl]-3-yl)sulfonyl)-4-((3-methoxyphenyl)amino)-8-methylquinoline-3-carboxamide

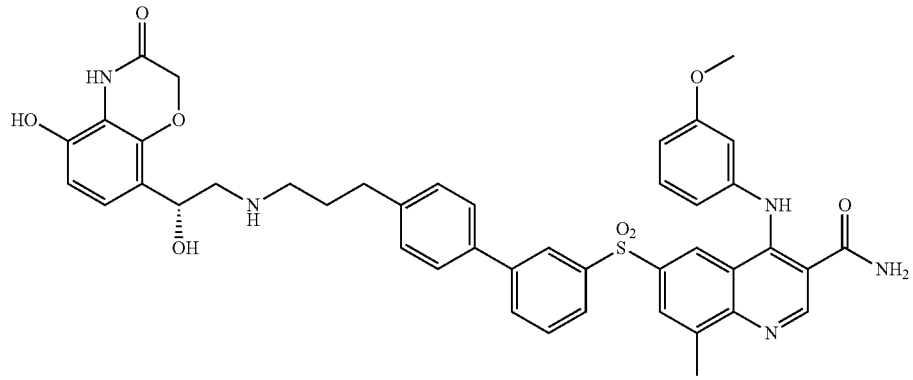 [SMILES: COc1cccc(Nc2c(C(N)=O)cnc3c(C)cc(S(=O)(=O)c4cccc(-c5ccc(CCCNC[C@H](O)c6ccc(O)c7c6OCC(=O)N7)cc5)c4)cc23)c1]

The title compound was synthesized in a manner analogous to that described for Example 1, using Intermediate 179 as a substrate.

$^1$H NMR (400 MHz, DMSO-$d_6$) δ 11.14 (br s, 1H), 9.98 (s, 2H), 9.04 (s, 1H), 8.64 (br s, 1H), 8.56 (br s, 1H), 8.42 (s, 1H), 8.35 (s, 1H), 8.15 (s, 1H), 8.01 (s, 1H), 7.99-7.93 (m, 1H), 7.82 (s, 1H), 7.71-7.63 (m, 3H), 7.39 (d, J=7.4 Hz, 2H), 7.07 (t, J=8.1 Hz, 1H), 6.91 (d, J=8.6 Hz, 1H), 6.70 (s, 1H), 6.65-6.52 (m, 3H), 5.91 (br s, 1H), 5.05 (dm, J=7.9 Hz, 1H), 4.57-4.49 (ABq, J=14.8 Hz, 2H), 3.61 (s, 3H), 3.12-3.03 (m, 1H), 3.03-2.89 (m, 3H), 2.72-2.67 (m, 2H), 2.71 (s, 3H), 2.06-1.91 (m, 2H). ES/MS calcd. for $C_{43}H_{42}N_6O_8S^+$ 788.3. Found m/z=788.2 (M+H)$^+$.

Example 51

(R)-6-((4'-(5-((2-hydroxy-2-(5-hydroxy-3-oxo-3,4-dihydro-2H-benzo[b][1,4]oxazin-8-yl)ethyl)amino)pentyl)-[1,1'-biphenyl]-4-yl)sulfonyl)-4-((3-methoxyphenyl)amino)-8-methylquinoline-3-carboxamide

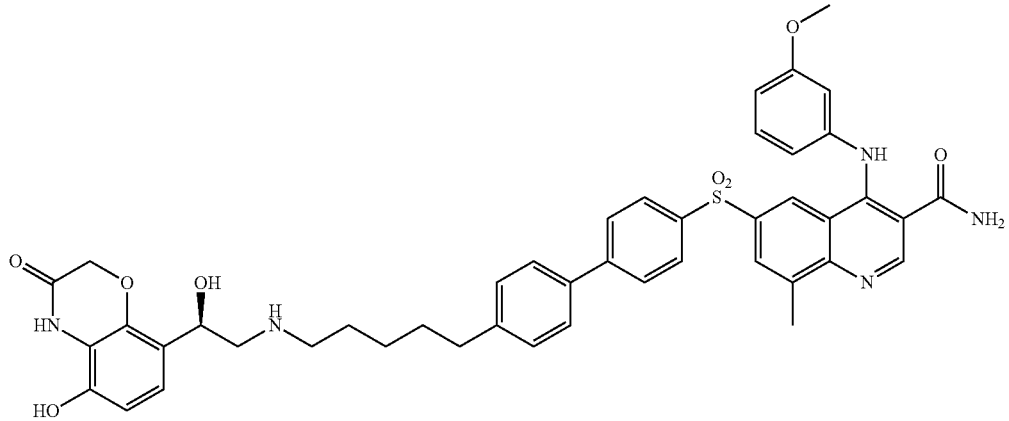 [SMILES: COc1cccc(Nc2c(C(N)=O)cnc3c(C)cc(S(=O)(=O)c4ccc(-c5ccc(CCCCCNC[C@H](O)c6ccc(O)c7c6OCC(=O)N7)cc5)cc4)cc23)c1]

The title compound was synthesized in a manner analogous to that described for Example 1, using Intermediate 180 as a substrate.

¹H NMR (400 MHz, DMSO-d₆) δ 11.12 (br s, 1H), 9.98 (s, 2H), 9.05 (s, 1H), 8.56 (br s, 1H), 8.46 (br s, 1H), 8.40 (s, 1H), 8.36 (s, 1H), 8.07 (s, 1H), 7.85 (d, J=8.2 Hz, 1H), 7.82 (s, 1H), 7.78 (d, J=8.3 Hz, 1H), 7.66 (d, J=7.8 Hz, 1H), 7.27-7.23 (m, 1H), 7.12 (s, 1H), 6.99 (s, 1H), 6.91 (d, J=8.6 Hz, 1H), 6.82 (d, J=8.6 Hz, 1H), 6.70-6.62 (m, 2H), 6.56 (d, J=8.6 Hz, 1H), 5.91 (br s, 1H), 5.04 (dm, J=7.4 Hz, 1H), 4.57-4.49 (ABq, J=14.5 Hz, 2H), 3.61 (s, 3H), 3.08-2.99 (m, 1H), 2.96-2.85 (m, 2H), 2.71 (s, 3H), 2.63 (t, J=7.2 Hz, 2H), 1.72-1.55 (m, 4H), 1.38-1.27 (m, 2H). ES/MS calcd. for $C_{46}H_{46}N_6O_8S^+$ 816.3. Found m/z=816.3 (M+H)⁺.

Example 52

(R)-6-((4'-(5-((2-hydroxy-2-(5-hydroxy-3-oxo-3,4-dihydro-2H-benzo[b][1,4]oxazin-8-yl)ethyl)amino)pentyl)-[1,1'-biphenyl]-3-yl)sulfonyl)-4-((3-methoxyphenyl)amino)-8-methylquinoline-3-carboxamide

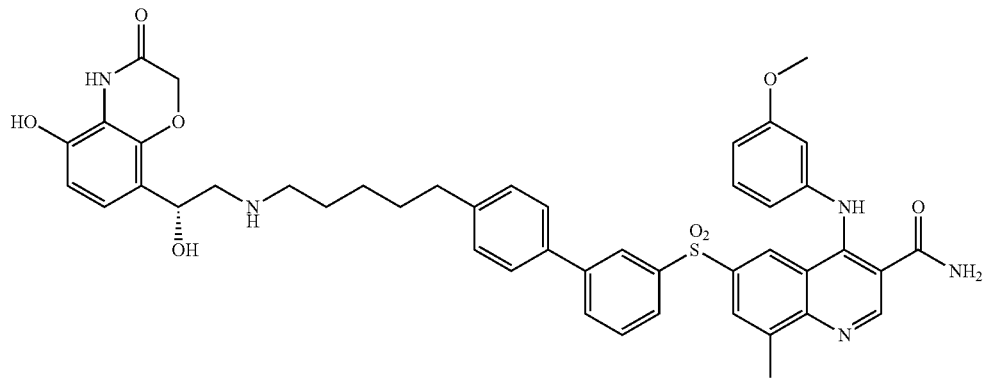 [SMILES: COc1cccc(Nc2c(C(N)=O)cnc3c(C)cc(S(=O)(=O)c4cccc(-c5ccc(CCCCCNC[C@H](O)c6ccc(O)c7c6OCC(=O)N7)cc5)c4)cc23)c1]

The title compound was synthesized in a manner analogous to that described for Example 1, using Intermediate 181 as a substrate.

¹H NMR (400 MHz, DMSO-d₆) δ 11.14 (br s, 1H), 9.98 (s, 2H), 9.04 (s, 1H), 8.64 (br s, 1H), 8.56 (br s, 1H), 8.42 (s, 1H), 8.35 (s, 1H), 8.15 (s, 1H), 8.01 (s, 1H), 7.99-7.93 (m, 1H), 7.82 (s, 1H), 7.65 (d, J=3.2 Hz, 1H), 7.61 (d, J=7.4 Hz, 2H), 7.39 (d, J=7.4 Hz, 2H), 7.07 (t, J=8.1 Hz, 1H), 6.91 (d, J=8.6 Hz, 1H), 6.70 (s, 1H), 6.65-6.52 (m, 3H), 5.91 (br s, 1H), 5.04 (dm, J=7.4 Hz, 1H), 4.57-4.49 (ABq, J=14.5 Hz, 2H), 3.61 (s, 3H), 3.08-2.99 (m, 1H), 2.96-2.85 (m, 2H), 2.71 (s, 3H), 2.63 (t, J=7.2 Hz, 2H), 1.72-1.55 (m, 4H), 1.38-1.27 (m, 2H). ES/MS calcd. for $C_{45}H_{46}N_5O_8S^+$ 816.3. Found m/z=816.3 (M+H)⁺.

Examples 53 to 60

Additional compounds of formula I that may be prepared using the general synthetic route described above include:

(R)-6-(3-((4-(4-(4-(2-hydroxy-2-(8-hydroxy-2-oxo-1,2-dihydroquinolin-5-yl)ethylamino)butyl)phenyl)-N-methylpiperidine-1-carboxamido)methyl)phenylsulfonyl)-4-(3-methoxyphenylamino)-8-methylquinoline-3-carboxamide

53

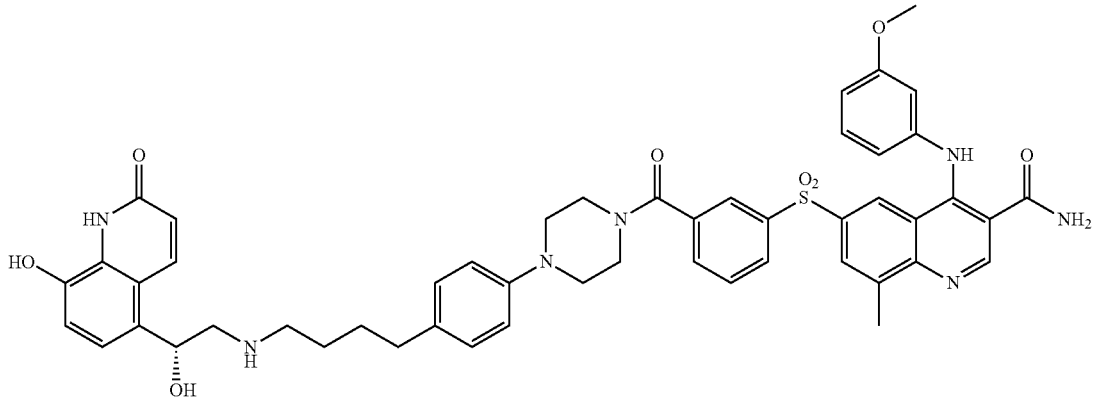

(R)-6-(3-(4-(4-(4-(2-hydroxy-2-(8-hydroxy-2-oxo-1,
2-dihydroquinolin-5-yl)ethylamino)butyl)phenyl)
piperidine-1-carbonyl)phenylsulfonyl)-4-(3-methox-
yphenylamino)-8-methylquinoline-3-carboxamide

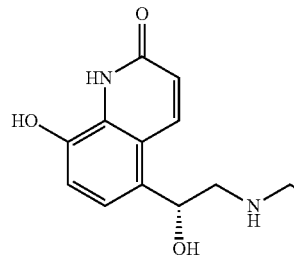
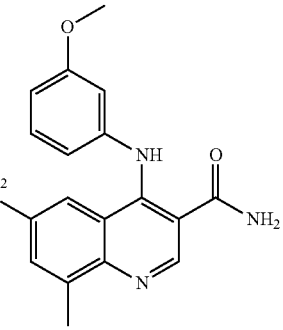

54

(R)-6-(3-(4-(4-(4-(2-hydroxy-2-(8-hydroxy-2-oxo-1,
2-dihydroquinolin-5-yl)ethylamino)butyl)cyclo-
hexyl)piperidine-1-carbonyl)phenylsulfonyl)-4-(3-
methoxyphenylamino)-8-methylquinoline-3-
carboxamide

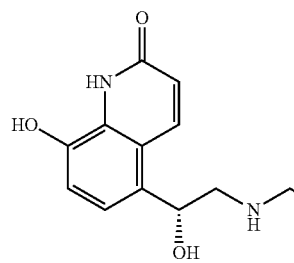
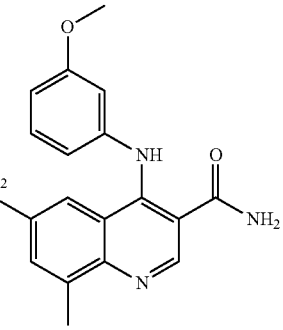

55

(R)-6-(3-((4-(4-(4-(2-hydroxy-2-(8-hydroxy-2-oxo-
1,2-dihydroquinolin-5-yl)ethylamino)butyl)phenyl)-
N-methylpiperazine-1-carboxamido)methyl)phenyl-
sulfonyl)-4-(3-methoxyphenylamino)-8-
methylquinoline-3-carboxamide

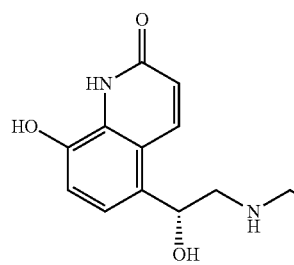
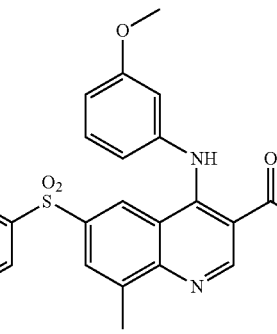

56

(R)-6-(3-((4-(4-(4-(2-hydroxy-2-(8-hydroxy-2-oxo-1,2-dihydroquinolin-5-yl)ethylamino)butyl)phenyl)-N-methylpiperidine-1-carboxamido)methyl)phenyl-sulfonyl)-4-(3-methoxyphenylamino)-8-methylquinoline-3-carboxamide

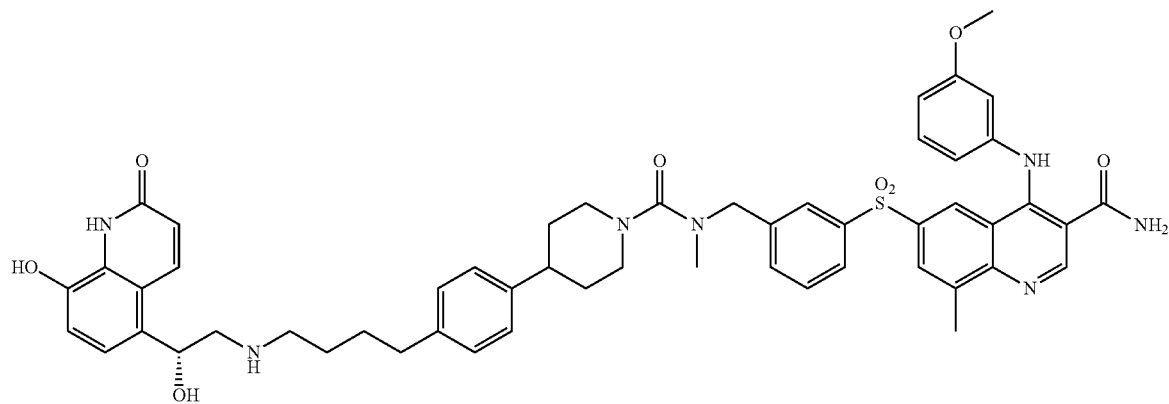

57

(R)-3-(3-carbamoyl-4-(3-methoxyphenylamino)-8-methylquinolin-6-ylsulfonyl)benzyl 4-(4-(4-(2-hydroxy-2-(8-hydroxy-2-oxo-1,2-dihydroquinolin-5-yl)ethylamino)butyl)phenyl)piperazine-1-carboxylate

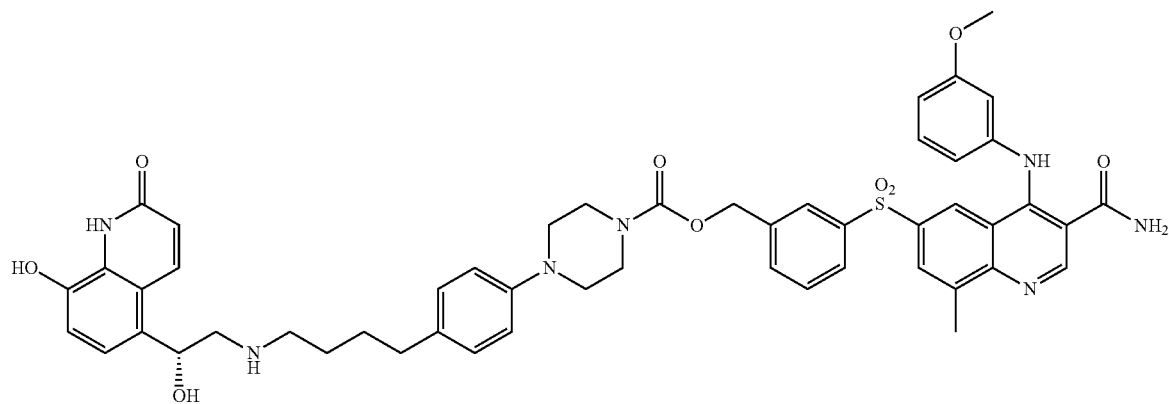

58

(R)-6-(2-hydroxy-2-(8-hydroxy-2-oxo-1,2-dihydroquinolin-5-yl)ethylamino)hexyl 3-(3-carbamoyl-4-(3-methoxyphenylamino)-8-methylquinolin-6-ylsulfonyl)benzylcarbamate

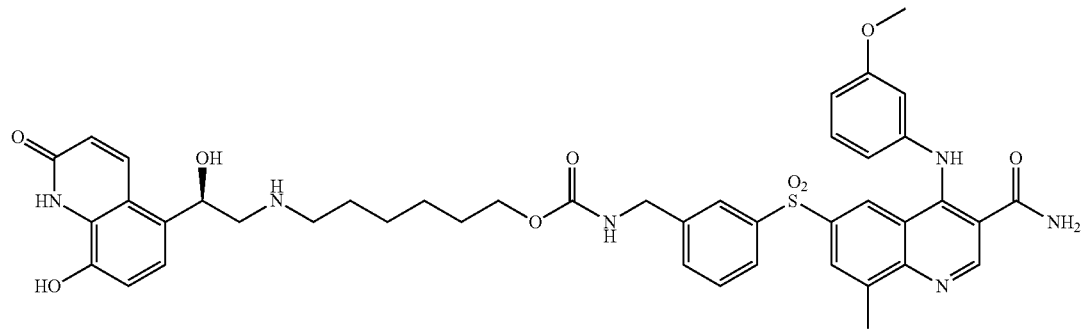

59

(R)-6-(3-(5-(5-(2-hydroxy-2-(8-hydroxy-2-oxo-1,2-dihydroquinolin-5-yl)ethylamino)pentyl)indoline-1-carbonyl)phenylsulfonyl)-4-(3-methoxyphenylamino)-8-methylquinoline-3-carboxamide

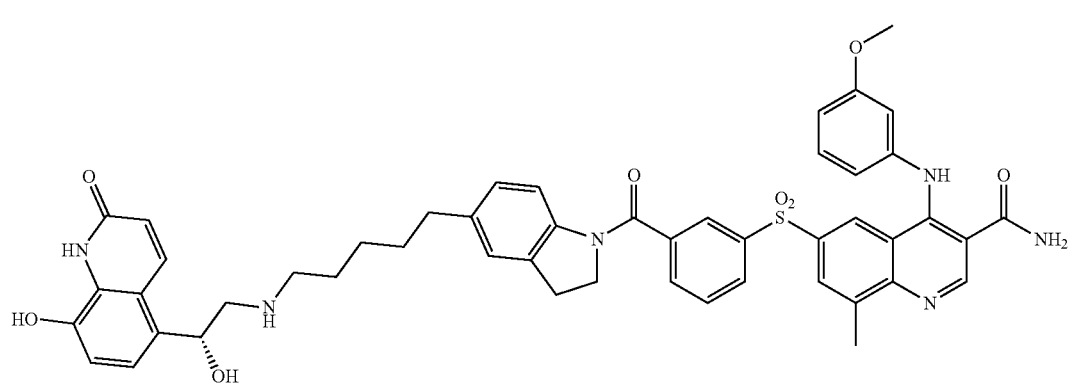

60

Biological Examples
Inhibition of PDE4B4 Enzyme Activity

The inhibitory activity of test compounds were determined using the PDE Glo Assay (Promega, V1361). The PDE-Glo Reaction Buffer was prepared (1 mL 5× buffer+4 mL water) and 150 nM solution of test compound dissolved in the Reaction Buffer, followed by 1:3 serial dilutions into Reaction Buffer. DMSO was used for the initial dilution of test compounds and the final concentration used in the assay did not exceed 0.1% DMSO. Human recombinant PDE4B2 (BPS Bioscience) was added to test compound in Reaction Buffer at a concentration of 0.12 nM per reaction. The enzyme and test compound were pre-incubated together at rt for 10 min. 50 nM of the enzyme substrate cAMP was then added to initiate the enzyme reaction, with the reaction terminated after one hour. Termination Buffer (1 mL 5× termination buffer+3.9 mL water+100 μL of 100 mM IBMX (ICN Chemicals, in DMSO)), was added to each reaction well to terminate the reaction. Detection Buffer (1 mL 5×PDE-Glo Detection buffer+3.96 mL water+40 μL PKA (supplied in kit)) was added to the cAMP-enzyme-test compound mix and this secondary reaction proceeded for 20 minutes at rt. An equal volume of Kinase Glo Reagent was then added to the reaction mixture and after 10 min luminescence was measured using a luminometer (EnVision, 0.1 sec read for luminescence). Luminescence values were directly related to levels of cAMP in the reaction mixture. Data were plotted as relative light units (RLU) versus test compound concentration and the $IC_{50}$ determined using GraphPad Prism 5.0, using a nonlinear curve fit in a single-site binding model.

IC50 determinations for the compounds presented above are seen in the first column of Table 1 (PDE4IC50).

Beta-2 Adrenoceptor Binding Assay

Test compounds were incubated for 120 min with Chinese hamster oocyte (CHO) cells expressing the human recombinant beta-2 adrenoreceptors. Binding of test compounds to the beta-2 adrenoreceptors was determined by measuring the displacement of the radiolabeled ligand [$^3$H](−)CGP-12177 (0.3 nM) from the receptor measured by a scintillation counting. Concentration response curves were generated for test compounds and the $IC_{50}$ (molar concentration of the compound which produced 50% inhibition for the maximal response for that compound) was determined. These assays were performed using a protocol based on the original description of the assay by Joseph et al., (2004) Naun.-Sch. Arch. Pharm.; 369:525-532.

IC50 determinations for the compounds presented above are seen in the second column of Table 1 (Beta 2 IC50).

Functional Agonism of Human Recombinant Beta-2 Adrenoreceptors Expressed in Chinese Hamster Oocytes (CHO)

Test compounds were incubated for 30 min with CHO cells expressing the human recombinant beta-2 adrenoreceptors. Agonism of the receptor was measured by the elevation of intracellular cyclic-AMP over control levels detected using a homogeneous time resolved fluorescence (HTRF) format. Compounds were determined to be "full" or "partial" agonists based on the maximum level of cAMP accumulated compared to the control compound isoproterenol which is a full agonist in this assay system. Concentration response curves were generated for test compounds and the $EC_{50}$ (molar concentration of the agonist which produced 50% of the maximal response for that compound) was determined. These assays were performed using a protocol based on the original description of the assay by Baker, J. G. (2005) Brit. J. Pharmacol.; 144:317-322.

EC50 determinations for the compounds presented above are seen in the third column of Table 1 (Beta 2 EC50).

Inhibition of Lipopolysaccharide (LPS)-Induced Tumour Necrosis Factor Alpha (TNF-α) Release from Human Peripheral Blood Mononuclear Cells (PBMC)

Human whole blood was drawn from donors and cell purification initiated within two hours. Peripheral blood mononuclear cells (PBMC) were purified using a standard Ficoll gradient purification technique and aliquoted at a concentration of 100,000 cells/well in 96 well plates. Beta-2 adrenoreceptor agonists are also anti-inflammatory for some immune cells expressing the receptor and in this assay they can inhibit tumor necrosis factor-alpha (TNF-α) production. Therefore PBMC were pre-incubated for 30 min in the presence of the beta-2 adrenoreceptor antagonist ICI-118551 [3-(isopropylamino)-1-[(7-methyl-4-indanyl)oxy]butan-2-ol] (10 μM) to determine the PDE4 directed activity of test compounds, and in the absence of ICI-118551 for the combined PDE4 and beta-2 receptor directed activity. Test compounds were dissolved in DMSO and diluted in buffer (final DMSO concentration of 0.1% v/v) and were then added to the cell suspensions and pre-incubated for a further 1 h at 37° C. LPS solution was then added (0.4 ng/mL) and the cells incubated for a further 6 h. At the end of the incubation period the cell supernatants were collected and TNF-α was measured using a Procarta Cytokine Assay Kit (Affymetrix, Santa Clara, Calif.) according to the manufacturers' instructions. Data were analyzed using MiraiBio Masterplex QT v4.0 software (MasterPlex Version 1.0.1.18 Copyright 2008, Hitachi Software Engineering Co., Ltd) and used to extrapolate Mean Fluorescence Intensity (MFI) into concentrations of TNF-α and mean values from replicate wells were determined. Inhibition curves were plotted using a nonlinear curve fit employing a single-site binding model to determine the $IC_{50}$ value for each test compound in the presence or absence of ICI-118551 using GraphPad Prism 5 for Windows, version 5.02 (GraphPad Software, San Diego Calif.).

EC50 determinations for the compounds presented above are seen in the fourth column of Table 1 (PBMC TNF EC50).

Inhibition of Lipoploysaccharide (LPS)-Induced Neutrophil Recruitment into the Lungs of Lewis Rats Rats were anesthetized with 4% isoflurane, placed in the supine position at an angle of 30°, the mouth opened and the trachea exposed. A 22-gauge needle with a syringe attached was introduced into the trachea and test compound in suspension (200 μl volume per 400 g) was delivered into the lungs from approximately one centimeter above the carina. The rats were allowed to recover and two hrs later conscious animals were placed into a chamber and exposed to aerosolized LPS (1.0 mg/mL) at a rate of 3.0 L/min for 20 min. Rats were euthanized 4 h post-LPS exposure by an overdose of pentobarbital (90 mg/kg) by intra-peritoneal injection. Broncheoalveolar lavage (BAL) was then performed with a 14 gauge blunt needle into the exposed trachea. Five, 5 ml washes of PBS were collect from the lungs and placed into Falcon tubes then centrifuged at a 1600 g for 10 min at 4° C. The supernatant was discarded, the cells were re-suspended in PBS and total cell counts were determined based on a 10 μl sample of re-suspended cells stained with trypan blue and counts performed using a Countess® cell counter (Invitrogen). Differential cell counts to determine the number of neutrophils in the BAL wash were performed on cytospun cells stained with May-Grunwald and Giemsa solution. Manual eye counting was performed to determine the percentage number of cells in the cytospun sample (determined as macrophages, neutrophils, eosinophils, T-lymphocytes and eosinophils) and these values were used to determine the total number of each cell type per sample. Typically experiments contained a minimum of six rats per experimental group and the mean±SEM number of neutrophils was determined for each group. The level of neutrophil inhibition caused by test compounds dosed directly into the lungs was determined compared to the vehicle-treated and LPS-exposed control rats. Statistical analysis to determine significant differences between groups were performed by one-way analysis of variance (ANOVA) using GraphPad Prism 5 for Windows, version 5.02 (GraphPad Software, San Diego Calif.).

The compounds of Examples 5, 8, 10, 12, 24, 26, 27, and 35 were tested in this assay alltested compounds, except the compound of Example 26, exhibited a neutrophil inhibition of greater than 40% at a dose of 300 μg/kg.

Inhibition of Acetylcholine-Induced Bronchoconstriction in Dunkin-Hartley Guinea Pigs Guinea pigs (Dunkin-Hartley from Charles River Laboratories, male, 500 to 800 g) were anesthetized with 4% isoflurane, placed in the supine position at an angle of 30°, the mouth opened and the trachea exposed. A 22-gauge needle with a syringe attached was introduced into the trachea and test compound in suspension (200 μl volume) was delivered into the lungs from approximately one centimeter above the carina. In vivo bronchoprotective effects of the test compounds against acetylcholine (ACh)-induced bronchoconstriction were tested in conscious guinea pigs using a whole body plethysmograph system (WBP) (Buxco Research Systems) 4 hrs after intra-tracheal dosing of test compounds. The lung function was measured in this system and expressed as an enhanced PAUSE (Penh) which has been widely used in scientific research and preclinical drug screening as a surrogate methodology for measuring lung resistance in conscious animals (Chong et al., *J. Pharmnacol. Toxicol. Methods* 1998; 39:163-168. Pennock et al., *J. Appl. Physiol.* 1979; 46:399-406). Guinea pigs were placed in the WBP system chambers and exposed to aerosol of either 0.9% saline solution or ACh solution (4 mg/mL) for 1 min. Lung function measurements (expressed as Penh and calculated by peak expiratory flow/peak inspiratory flow×pause) was continuously recorded for 20 min immediately after saline or ACh challenge. The results were expressed as area under curves (AUC) of airway response (Penh) over the responding time (20 min). Twenty four hrs before the assessment of test compounds took place, airway responses of guinea pigs were measured to determine their baseline responses prior to compound treatments. Each animal therefore acted as it's own control for the evaluation of bronchoprotection of test compounds and the efficacy of test compounds were calculated as the percentage inhibition of airway response compared to this value. Assessment of the duration of bronchoprotection could also be determined by re-challenging animals up to 24 hrs post test compound dosing. Typically experiments contained a minimum of six guinea pigs per experimental group and the mean±SEM inhibition of PenH was determined for each group. Statistical analysis to determine significant differences between groups were performed by one-way analysis of variance (ANOVA) using GraphPad Prism 5 for Windows, version 5.02 (GraphPad Software, San Diego Calif.).

The compounds of Examples 5 and 12 were tested in this assay and exhibited bronchoprotection at 4 hour of greater than 75% at doses below of 125 μg/kg.

TABLE I

| Example # | PDE4 IC50 | Beta 2 IC50 | Beta 2 EC50 | PBMC TNF EC50 |
|---|---|---|---|---|
| 1 | ++ | ++ | ++ | ++ |
| 2 | ++ | ++ | ++ | ++ |
| 3 | ++ | − | ++ | ++ |
| 4 | ++ | ++ | ++ | ++ |
| 5 | ++ | ++ | ++ | ++ |
| 6 | ++ | ++ | ++ | ++ |
| 7 | ++ | ++ | ++ | ++ |
| 8 | ++ | − | − | ++ |
| 9 | ++ | ++ | ++ | ++ |
| 10 | ++ | ++ | ++ | ++ |
| 11 | ++ | ++ | ++ | ++ |
| 12 | ++ | ++ | ++ | ++ |
| 13 | ++ | ++ | ++ | ++ |
| 14 | ++ | − | − | ++ |
| 15 | ++ | ++ | ++ | ++ |
| 16 | ++ | − | + | ++ |
| 17 | ++ | ++ | ++ | ++ |
| 18 | ++ | ++ | ++ | ++ |
| 19 | ++ | ++ | ++ | ++ |
| 20 | ++ | ++ | ++ | ++ |
| 21 | ** | ++ | ** | ++ |
| 22 | ** | ++ | ++ | ++ |
| 23 | ++ | ++ | ++ | ++ |
| 24 | ** | ++ | + | ++ |
| 25 | ++ | − | ++ | ++ |
| 26 | ++ | − | − | ++ |
| 27 | ++ | ++ | ++ | ++ |
| 28 | ++ | − | ++ | ++ |
| 29 | ++ | ++ | ++ | ++ |
| 30 | ++ | ++ | ++ | ++ |
| 31 | ++ | + | + | ++ |
| 32 | ++ | ++ | ++ | ++ |
| 33 | ++ | ++ | ++ | ++ |
| 34 | ++ | ++ | ++ | ++ |
| 35 | ** | ++ | ++ | ++ |
| 36 | ** | ++ | ** | ++ |
| 37 | ++ | ++ | ++ | ++ |
| 38 | ++ | ++ | ++ | ++ |
| 39 | ++ | ++ | ++ | ++ |

TABLE I-continued

| Example # | PDE4 IC50 | Beta 2 IC50 | Beta 2 EC50 | PBMC TNF EC50 |
|---|---|---|---|---|
| 40 | ** | ++ | ++ | ** |
| 41 | ++ | ++ | ++ | ++ |
| 42 | ++ | + | ** | ++ |
| 43 | ++ | ++ | ++ | ++ |
| 44 | ++ | – | – | ++ |
| 45 | ++ | ++ | ++ | ++ |
| 46 | ++ | ++ | + | ++ |
| 47 | ++ | – | – | ++ |
| 48 | ++ | ++ | ++ | ++ |
| 49 | ** | ++ | ** | ++ |
| 50 | ** | ++ | ** | ++ |
| 51 | ** | ++ | ++ | ++ |
| 52 | ** | ** | ** | ** |

<100 nM = ++
<300 nM = +
>300 nM = –
Not measured = **

Dry Powder Formulation

A dry powder formulation of one or more compounds of the invention for administration by inhalation may be prepared by as follows:

Particles of a compound of the invention (API) are micronized using conventional processes including but not limited to jet milling, to achieve a distribution with a mass median aerodynamic diameter (MMAD) of about 2 and a GSD<about 2.5. The micronized particles are then blended with a conventional dry powder excipient such as lactose. Specific examples of suitable forms of commercially available lactose include Lactohale LH100 which comprises particles >60 micron and Lactohale LH200 which comprises large (>60 microns) lactose particles mixed with lactose "fines" (<10 microns). A typical formulation will include less than 10% API, with the remainder being the dry powder excipient. This bulk formulation can be filled into a multi-dose DPI, e.g. Valois Prohaler, with a fill weight designed to permit emission of the desired dose.

That which is claimed is:

1. A compound of Formula I:

I wherein
X is a substituted phenyl ring selected from:

and

Z is a bond or a moiety selected from:

$R^1$ is $CH_2OH$, $CH_2CH_2OH$, $N(H)C(O)H$, or $N(H)S(O_2)$ $C_1$-$c_3$ alkyl, and $R^2$ is H;

or $R^1$ and $R^2$ together with the phenyl to which they are bound form a bicyclic, fused heterocyclic ring having 9 or 10 ring atoms wherein 1 or 2 ring atoms are selected from N, O and S, wherein said bicyclic fused heterocyclic ring is optionally substituted with one, two or three additional substituents independently selected from alkyl, oxo and OH;

$R^3$ is selected from $C_{4-12}$alkylene, $C_{4-12}$alkenylene, $C_{4-12}$alkynylene, $R^8$—O—$R^8$, $R^8$—N($R^7$)—$R^8$, $C_{3-6}$cycloalkylene, $R^8$—$C_{3-6}$cycloalkylene, $R^8$—$C_{3-6}$cycloalkylene-Het, $C_{3-6}$cycloalkylene-$R^8$, $R^8$—$C_{3-6}$cycloalkylene-$R^8$, $C_{6-10}$arylene, $R^8$—$C_{6-10}$arylene, $C_{6-10}$arylene-$R^8$, $R^8$—$C_{6-10}$arylene-$R^8$, $R^8$—$C_{6-10}$arylene-O—$R^8$, $R^8$—$C_{6-10}$arylene-N($R^7$)—$R^8$, $R^8$—$C_{6-10}$arylene-$C_{6-10}$arylene, Het, $R^8$-Het, Het-$R^8$, $R^8$-Het-$R^8$, $R^8$—O-Het, $R^8$—$C_{6-10}$arylene-O-Het, $R^8$—$C_{6-10}$arylene-C(O)-Het, $R^8$—$C_{6-10}$arylene-N($R^7$)-Het, $R^8$-Het-$C_{6-10}$arylene, $R^8$—$C_{6-10}$arylene-Het, and $R^8$—O—$R^8$—$C_{6-10}$arylene;

wherein said alkylene, alkenylene or alkynylene are each optionally substituted with 1, 2 or 3 substituents selected from halo, oxo, and $OR^7$;

wherein said phenylene groups are each optionally substituted with 1, 2, 3, or 4 substituents selected from halo, alkyl, and $OR^7$;

Het is 5-6 membered saturated or unsaturated monocyclic heterocyclene or an 8-10 membered saturated or unsaturated bicyclic heterocyclene wherein 1 or 2 ring atoms are selected from N, O and S, and wherein said monocyclic or bicyclic heterocyclene is optionally substituted with 1, 2 or 3 substituents selected from halo, alkyl, alkoxy, oxo and OH;

Y is C(O), OC(O), C(O)N($R^7$), C(O)N($R^7$)$CH_2$, OC(O)N$R^7CH_2$, N($R^7$)C(O), or N($R^7$)C(O)N($R^7$);

a is 0, 1, 2, 3, or 4;

$R^4$ is selected from halo, alkyl, and $OR^7$;

$R^5$ is H or alkyl;

b is 1, 2, 3, 4, or 5;

$R^6$ is selected from halo, alkyl, haloalkyl, $OR^7$, O-haloalkyl, $R^8$—$OR^7$, O—$R^8$—$OR^7$, C(O)alkyl, O—$R^8$—C(O)alkyl, CON($R^7$)$_2$, $R^8$—CON($R^7$)$_2$, $R^8$—N($R^7$)$_2$, N($R^7$)C(O)alkyl, N($R^7$)C(O)N($R^7$)$_2$, N($R^7$)$SO_2$alkyl, $R^8$—$SO_2$N($R^7$)$_2$, and CN;

or two $R^6$ on adjacent carbons, together with the phenyl to which they are bound form a bicyclic heterocyclic ring having 9 or 10 ring atoms wherein 1 or 2 ring atoms are selected from N, O and S;

$R^7$ is H or alkyl; and $R^8$ is $C_{1-10}$alkylene, $C_{2-10}$alkenylene, or $C_{2-10}$alkynylene wherein each $R^8$ is optionally substituted with 1, 2 or 3 substituents selected from halo, oxo, and $OR^7$; with the proviso that the total number of carbon atoms in the $C_{1-10}$alkylene, $C_{2-10}$alkenylene, or $C_{2-10}$alkynylene chains of two $R^8$ groups in any definition of $R^3$ is not greater than 12;

$R^9$ is H or $C_1$-$C_3$ alkyl;

or a pharmaceutically acceptable salt thereof.

2. The compound of claim 1 wherein $R^3$ is selected from $C_{4-12}$alkylene, $C_{4-12}$alkenylene, $C_{4-12}$alkynylene, $R^8$—O—

R⁸, R⁸—N(R⁷)—R⁸, C₃₋₆cycloalkylene, R⁸—C₃₋₆cycloalkylene, R⁸—C₃₋₆ cycloalkylene-Het, C₃₋₆cycloalkylene-R⁸, R⁸—C₃₋₆cycloalkylene-R⁸, phenylene, R⁸-phenylene, phenylene-R⁸, R⁸-phenylene-R⁸, R⁸-phenylene-O—R⁸, R⁸-phenylene-N(R⁷)—R⁸, R⁸-phenylene-phenylene, Het, R⁸-Het, Het-R⁸, R⁸-Het-R⁸, R⁸—O-Het, R⁸-phenylene-O-Het, R⁸-phenylene-C(O)-Het, R⁸-phenylene-N(R⁷)-Het, R⁸-Het-phenylene, R⁸-phenylene-Het, and R⁸—O—R⁸-phenylene; or a pharmaceutically acceptable salt thereof.

3. The compound of claim 1 selected from Formula II(a) or Formula II(b):

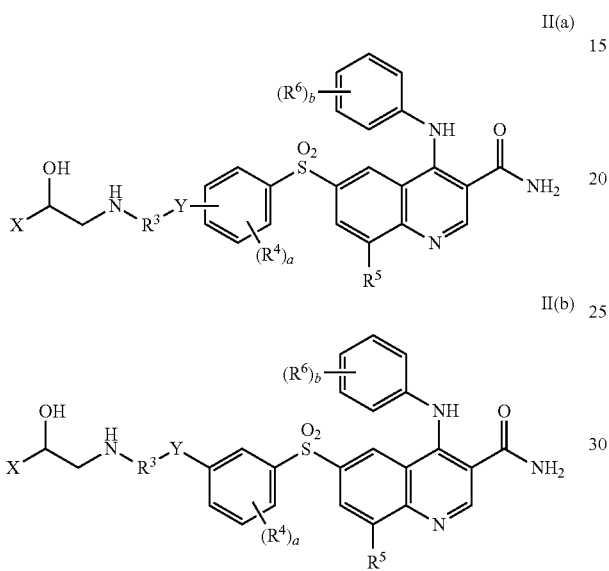

or a pharmaceutically acceptable salt thereof;
wherein:
X is a substituted phenyl ring selected from:

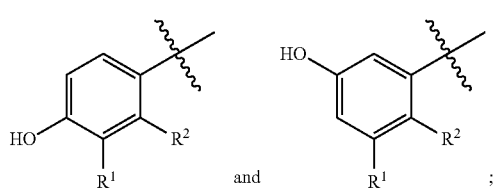

R¹ is CH₂OH, CH₂CH₂OH, N(H)C(O)H, or N(H)S(O)₂CH₃, and R² is H;
or R¹ and R² together with the phenyl to which they are bound form a bicyclic, fused heterocyclic ring selected from;

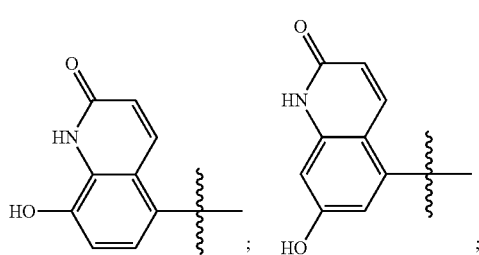

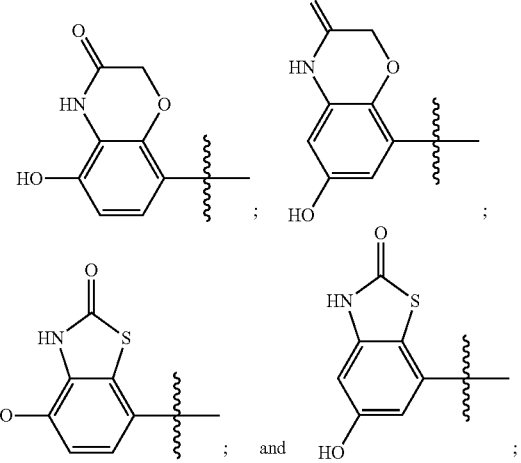

R³ is selected from C₄₋₁₂alkylene, C₄₋₁₂alkenylene, C₄₋₁₂alkynylene, R⁸—O—R⁸, R⁸—C₃₋₆cycloalkylene-Het, R⁸-phenylene, R⁸-phenylene-O—R⁸, R⁸-phenylene-phenylene, Het, R⁸-Het, R⁸—O-Het, R⁸-phenylene-C(O)-Het, R⁸-Het-phenylene, R⁸-phenylene-Het, and R⁸—O—R⁸-phenylene;
  wherein said alkylene, alkenylene or alkynylene are each optionally substituted with 1, 2 or 3 substituents selected from halo, oxo, and OR⁷;
  wherein said phenylene groups are each optionally substituted with 1, 2, 3, or 4 substituents selected from halo, alkyl, and OR⁷;
  Het is 5-6 membered saturated or unsaturated monocyclic heterocyclene or an 8-10 membered saturated or unsaturated bicyclic heterocyclene wherein 1 or 2 ring atoms are selected from N, O and S, and wherein said monocyclic or bicyclic heterocyclene is optionally substituted with 1, 2 or 3 substituents selected from halo, alkyl, alkoxy, oxo and OH;
Y is C(O), OC(O), C(O)N(R⁷), C(O)N(R⁷)CH₂, OC(O)NR⁷CH₂, N(R⁷)C(O), or N(R⁷)C(O)N(R⁷);
a is 0, 1, 2, 3, or 4;
R⁴ is selected from halo, alkyl, and OR⁷;
R⁵ is H or alkyl;
b is 1, 2, 3, 4, or 5;
R⁶ is selected from halo, alkyl, haloalkyl, OR⁷, O-haloalkyl, R⁸—OR⁷, O—R⁸—OR⁷, C(O)alkyl, O—R⁸—C(O)alkyl, CON(R⁷)₂, R⁸—CON(R⁷)₂, R⁸—N(R⁷)₂, N(R⁷)C(O)alkyl, N(R⁷)C(O)N(R⁷)₂, N(R⁷)SO₂alkyl, R⁸—SO₂N(R⁷)₂, and CN;
or two R⁶ on adjacent carbons, together with the phenyl to which they are bound form a bicyclic heterocyclic ring having 9 or 10 ring atoms wherein 1 or 2 ring atoms are selected from N, O and S;
R⁷ is H or alkyl; and
R⁸ is C₁₋₁₀alkylene, C₂₋₁₀alkenylene, or C₂₋₁₀alkynylene wherein each R⁸ is optionally substituted with 1, 2 or 3 substituents selected from halo, oxo, and OR⁷; with the proviso that the total number of carbon atoms in the C₁₋₁₀alkylene, C₂₋₁₀alkenylene, or C₂₋₁₀alkynylene chains of two R⁸ groups in any definition of R³ is not greater than 12.

4. The compound according to claim 1 or a pharmaceutically acceptable salt thereof wherein R¹ is CH₂OH and R² is H.

5. The compound according to claim 1 or a pharmaceutically acceptable salt thereof wherein $R^1$ and $R^2$ together with the phenyl to which they are bound form a bicyclic, fused heterocyclic ring having 9 or 10 ring atoms wherein 1 or 2 ring atoms are selected from N, O and S, and said bicyclic fused heterocyclic ring is optionally substituted with one additional substituent selected from alkyl, oxo and OH.

6. The compound according to claim 1 or a pharmaceutically acceptable salt thereof wherein $R^1$ and $R^2$ together with the phenyl to which they are bound form

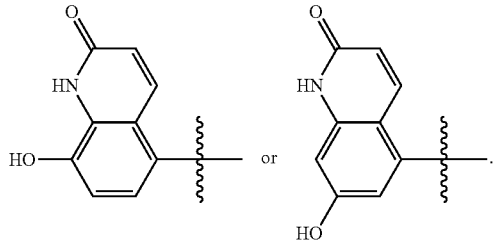 [SMILES: *c1ccc(O)c2[nH]c(=O)ccc12 ; *c1cc(O)cc2[nH]c(=O)ccc12]

7. The compound according to claim 1, or a pharmaceutically acceptable salt thereof, wherein $R^3$ is selected from $C_{4-12}$alkylene, $C_{4-12}$alkenylene, $C_{4-12}$alkynylene, $R^8$—O—$R^8$, and $R^8$—N($R^7$)—$R^8$, wherein said alkylene, alkenylene or alkynylene are each optionally substituted with 1, 2 or 3 substituents selected from halo, oxo, and $OR^7$.

8. The compound according to claim 1, or a pharmaceutically acceptable salt thereof, wherein $R^3$ is selected from $C_{5-8}$alkylene, $C_{5-8}$alkenylene, $C_{5-8}$alkynylene, $R^8$—O—$R^8$, and $R^8$—N($R^7$)—$R^8$, wherein each $R^8$ is $C_{1-4}$alkylene, $C_{2-4}$alkenylene, or $C_{2-4}$alkynylene each alkylene, alkenylene and alkynylene optionally substituted with 1 or 2 substituents selected from halo, oxo, and $OR^7$.

9. The compound according to claim 1, or a pharmaceutically acceptable salt thereof, wherein $R^3$ is unsubstituted $C_{5-8}$alkylene.

10. The compound according to claim 1, or a pharmaceutically acceptable salt thereof, wherein $R^3$ is selected from $R^8$-phenylene, $R^8$-phenylene-$R^8$, Het, $R^8$-Het, $R^8$-Het-$R^8$, $R^8$-phenylene-O-Het, and $R^8$-phenylene-N($R^7$)-Het.

11. The compound according to claim 1, or a pharmaceutically acceptable salt thereof, wherein $R^3$ is selected from $R^8$-phenylene, $R^8$-phenylene-$R^8$, Het, $R^8$-Het, $R^8$-Het-$R^8$, $R^8$-phenylene-O-Het, and $R^8$-phenylene-N($R^7$)-Het.

12. The compound according to claim 1, or a pharmaceutically acceptable salt thereof, wherein $R^3$ is selected from $R^8$-phenylene, Het, and $R^8$-Het.

13. The compound according to claim 1, or a pharmaceutically acceptable salt thereof, wherein Y is C(O) or N($R^7$)C(O).

14. The compound according to claim 1, or a pharmaceutically acceptable salt thereof, wherein a is 0.

15. The compound according to claim 1, or a pharmaceutically acceptable salt thereof, wherein $R^5$ is $CH_3$.

16. The compound according to claim 1, or a pharmaceutically acceptable salt thereof, wherein b is 1.

17. The compound according to claim 1, or a pharmaceutically acceptable salt thereof, wherein $R^6$ is selected from F, Cl, Br, alkyl, haloalkyl, $OR^7$, O-haloalkyl, and CN.

18. The compound according to claim 1, or a pharmaceutically acceptable salt thereof, wherein $R^6$ is $OCH_3$.

19. A compound selected from:
(R)-6-[[3-[[8-[[2-Hydroxy-2-(8-hydroxy-2-oxo-1,2-dihydroquinolin-5-yl)ethyl]amino]octyl]carbamoyl]phenyl]sulfonyl]-4-[(3-methoxyphenyl)amino]-8-methylquinoline-3-carboxamide;
(R)-6-[[3-[[6-[[2-Hydroxy-2-(8-hydroxy-2-oxo-1,2-dihydroquinolin-5-yl)ethyl]amino]hexyl]carbamoyl]phenyl]sulfonyl]-4-[(3-methoxyphenyl)amino]-8-methylquinoline-3-carboxamide;
(R)-6-[[3-[[4-[[2-Hydroxy-2-(8-hydroxy-2-oxo-1,2-dihydroquinolin-5-yl)ethyl]amino]piperidine-1-yl]carbonyl)phenyl]sulfonyl]-4-[(3-methoxyphenyl)amino]-8-methylquinoline-3-carboxamide;
(R)-6-[[3-[5-[[2-Hydroxy-2-(8-hydroxy-2-oxo-1,2-dihydroquinolin-5-yl)ethyl]amino]pent-1-ynyl]phenyl]carbamoyl]phenyl]sulfonyl]-4-[(3-methoxyphenyl)amino]-8-methylquinoline-3-carboxamide;
(R)-6-[[3-[[4-[5-[[2-Hydroxy-2-(8-hydroxy-2-oxo-1,2-dihydroquinolin-5-yl)ethyl]amino]pent-1-ynyl]phenyl]carbamoyl]phenyl]sulfonyl]-4-[(3-methoxyphenyl)amino]-8-methylquinoline-3-carboxamide;
(R)-6-[[3-[[4-[5-[[2-Hydroxy-2-(8-hydroxy-2-oxo-1,2-dihydroquinolin-5-yl)ethyl]amino]pent-1-ynyl]phenyl]carbamoyl]phenyl]sulfonyl]-4-[(3-methoxyphenyl)amino]-8-methylquinoline-3-carboxamide;
(R)-6-((3-((4-(6-((2-hydroxy-2-(8-hydroxy-2-oxo-1,2-dihydroquinolin-5-yl)ethyl)amino)hex-1-yn-1-yl)phenyl)carbamoyl)phenyl)sulfonyl)-4-((3-methoxyphenyl)amino)-8-methylquinoline-3-carboxamide;
(R)-6-((3-((4-(5-((2-hydroxy-2-(8-hydroxy-2-oxo-1,2-dihydroquinolin-5-yl)ethyl)(methyl)amino)pent-1-yn-1-yl)phenyl)carbamoyl)phenyl)sulfonyl)-4-((3-methoxyphenyl)amino)-8-methylquinoline-3-carboxamide;
(R)-6-((3-((3-(5-((2-hydroxy-2-(8-hydroxy-2-oxo-1,2-dihydroquinolin-5-yl)ethyl)amino)pent-1-yn-1-yl)phenyl)carbamoyl)phenyl)sulfonyl)-4-((3-methoxyphenyl)amino)-8-methylquinoline-3-carboxamide;
(R)-6-[[3-[5-[[2-Hydroxy-2-(8-hydroxy-2-oxo-1,2-dihydroquinolin-5-yl)ethyl]amino]pentyl]phenyl]carbamoyl]phenyl]sulfonyl]-4-[(3-methoxyphenyl)amino-8-methylquinoline-3-carboxamide;
(R)-6-[3-[[4-[5-[[2-Hydroxy-2-(8-hydroxy-2-oxo-1,2-dihydroquinolin-5-yl)ethyl]amino]ethyl]piperazine-1-yl]carbonyl]benzenesulfonyl]-4-(3-methoxyphenylamino)-8-methylquinoline-3-carboxyamide;
(R)-6-[[3-[[4-[2-[[2-Hydroxy-2-(8-hydroxy-2-oxo-1,2-dihydroquinolin-5-yl)ethyl]amino]ethyl]phenyl]carbamoyl]phenyl]sulfonyl]-4-[(3-methoxyphenyl)amino]-8-methylquinoline-3-carboxamide;
6-[[3-[[3-[2-[[(R)-2-Hydroxy-2-(8-hydroxy-2-oxo-1,2-dihydroquinolin-5-yl)ethyl]amino]propyl]-N-methylbenzamido]methyl]phenyl]sulfonyl]-4-[(3-methoxyphenyl)amino]-8-methylquinoline-3-carboxamide;
(R)-6-[[3-[[6-[[2-Hydroxy-2-(8-hydroxy-2-oxo-1,2-dihydroquinolin-5-yl)ethyl]amino]hexyl](methyl)carbamoyl]phenyl]sulfonyl]-4-[(3-methoxyphenyl)amino]-8-methylquinoline-3-carboxamide;
(R)-6-((3-(4-((6-((2-hydroxy-2-(8-hydroxy-2-oxo-1,2-dihydroquinolin-5-yl)ethyl)amino)hexyl)oxy)piperidine-1-carbonyl)phenyl)sulfonyl)-4-((3-methoxyphenyl)amino)-8-methylquinoline-3-carboxamide;
(R)-6-((3-(4-(6-((2-hydroxy-2-(8-hydroxy-2-oxo-1,2-dihydroquinolin-5-yl)ethyl)amino)hexyl)piperazine-1-carbonyl)phenyl)sulfonyl)-4-((3-methoxyphenyl)amino)-8-methylquinoline-3-carboxamide;
6-((3-(4-(3-(2-(((R)-2-hydroxy-2-(8-hydroxy-2-oxo-1,2-dihydroquinolin-5-yl)ethyl)amino)propyl)benzoyl)piperazine-1-carbonyl)phenyl)sulfonyl)-4-((3-methoxyphenyl)amino)-8-methylquinoline-3-carboxamide;

(R)-6-((3-(4-(3-(2-((2-hydroxy-2-(8-hydroxy-2-oxo-1,2-dihydroquinolin-5-yl)ethyl)amino)-2-methylpropyl)benzoyl)piperazine-1-carbonyl)phenyl)sulfonyl)-4-((3-methoxyphenyl)amino)-8-methylquinoline-3-carboxamide;

(R)-6-((3-((3-(2-((2-hydroxy-2-(8-hydroxy-2-oxo-1,2-dihydroquinolin-5-yl)ethyl)amino)-2-methylpropyl)-N-methylbenzamido)methyl)phenyl)sulfonyl)-4-((3-methoxyphenyl)amino)-8-methylquinoline-3-carboxamide;

(R)-6-((3-((4'-(((2-hydroxy-2-(8-hydroxy-2-oxo-1,2-dihydroquinolin-5-yl)ethyl)amino)methyl)-[1,1'-biphenyl]-4-yl)carbamoyl)phenyl)sulfonyl)-4-((3-methoxyphenyl)amino)-8-methylquinoline-3-carboxamide;

(R)-6-((3-((4'-(4-((2-hydroxy-2-(5-hydroxy-3-oxo-3,4-dihydro-2H-benzo[b][1,4]oxazin-8-yl)ethyl)amino)butyl)-[1,1'-biphenyl]-4-yl)carbamoyl)phenyl)sulfonyl)-4-((3-methoxyphenyl)amino)-8-methylquinoline-3-carboxamide;

(R)-6-((3-((4'-(4-((2-hydroxy-2-(5-hydroxy-3-oxo-3,4-dihydro-2H-benzo[b][1,4]oxazin-8-yl)ethyl)amino)butyl)-[1,1'-biphenyl]-3-yl)carbamoyl)phenyl)sulfonyl)-4-((3-methoxyphenyl)amino)-8-methylquinoline-3-carboxamide;

(R)-6-((3-((6-((2-hydroxy-2-(6-hydroxy-3-oxo-3,4-dihydro-2H-benzo[b][1,4]oxazin-8-yl)ethyl)amino)hexyl)carbamoyl)phenyl)sulfonyl)-4-((3-methoxyphenyl)amino)-8-methylquinoline-3-carboxamide;

(R)-6-((3-((4-(5-((2-hydroxy-2-(6-hydroxy-3-oxo-3,4-dihydro-2H-benzo[b][1,4]oxazin-8-yl)ethyl)amino)pent-1-yn-1-yl)phenyl)carbamoyl)phenyl)sulfonyl)-4-((3-methoxyphenyl)amino)-8-methylquinoline-3-carboxamide;

(R)-6-((3-((2-(4-(2-((2-hydroxy-2-(8-hydroxy-2-oxo-1,2-dihydroquinolin-5-yl)ethyl)amino)ethyl)phenoxy)ethyl)(methyl)carbamoyl)phenyl)sulfonyl)-4-((3-methoxyphenyl)amino)-8-methylquinoline-3-carboxamide;

(R)-6-[[3-[[4-[5-[[2-Hydroxy-2-[4-hydroxy-3-(hydroxymethyl)phenyl]ethyl]amino]pentyl]phenyl]carbamoyl]phenyl]sulfonyl]-4-[(3-methoxyphenyl)amino]-8-methylquinoline-3-carboxamide;

(R)-6-[[3-[[6-[[2-(3-Formamido-4-hydroxyphenyl)-2-hydroxyethyl]amino]hexyl]carbamoyl]phenyl]sulfonyl]-4-[(3-methoxyphenyl)amino]-8-methylquinoline-3-carboxamide;

(R)-6-((3-((6-((2-(3-formamido-4-hydroxyphenyl)-2-hydroxyethyl)amino)hexyl)(methyl)carbamoyl)phenyl)sulfonyl)-4-((3-methoxyphenyl)amino)-8-methylquinoline-3-carboxamide;

(R)-6-((3-((6-((2-hydroxy-2-(5-hydroxy-3-oxo-3,4-dihydro-2H-benzo[b][1,4]oxazin-8-yl)ethyl)amino)hexyl)carbamoyl)phenyl)sulfonyl)-4-((3-methoxyphenyl)amino)-8-methylquinoline-3-carboxamide;

(R)-6-((3-((6-((2-hydroxy-2-(5-hydroxy-3-oxo-3,4-dihydro-2H-benzo[b][1,4]oxazin-8-yl)ethyl)amino)hexyl)(methyl)carbamoyl)phenyl)sulfonyl)-4-((3-methoxyphenyl)amino)-8-methylquinoline-3-carboxamide;

(R)-6-[[3-[[4-[5-[[2-(3-Formamido-4-hydroxyphenyl)-2-hydroxyethyl]amino]pent-1-ynyl]phenyl]carbamoyl]phenyl]sulfonyl]-4-[(3-methoxyphenyl)amino]-8-methylquinoline-3-carboxamide;

(R)-6-((3-((4-(5-((2-hydroxy-2-(5-hydroxy-3-oxo-3,4-dihydro-2H-benzo[b][1,4]oxazin-8-yl)ethyl)amino)pent-1-yn-1-yl)phenyl)carbamoyl)phenyl)sulfonyl)-4-((3-methoxyphenyl)amino)-8-methylquinoline-3-carboxamide;

(R)-6-((3-((4-(5-((2-hydroxy-2-(8-hydroxy-2-oxo-1,2-dihydroquinolin-5-yl)ethyl)amino)pent-1-yn-1-yl)phenyl)(methyl)carbamoyl)phenyl)sulfonyl)-4-((3-methoxyphenyl)amino)-8-methylquinoline-3-carboxamide;

(R)-6-((3-((4-(5-((2-hydroxy-2-(8-hydroxy-2-oxo-1,2-dihydroquinolin-5-yl)ethyl)amino)pent-1-yn-1-yl)-2-methylphenyl)carbamoyl)phenyl)sulfonyl)-4-((3-methoxyphenyl)amino)-8-methylquinoline-3-carboxamide;

(R)-6-((3-((4-(5-((2-hydroxy-2-(5-hydroxy-3-oxo-3,4-dihydro-2H-benzo[b][1,4]oxazin-8-yl)ethyl)amino)pent-1-yn-1-yl)-2-methylphenyl)carbamoyl)phenyl)sulfonyl)-4-((3-methoxyphenyl)amino)-8-methylquinoline-3-carboxamide;

(R)-6-((3-((4-(5-((2-hydroxy-2-(5-hydroxy-3-oxo-3,4-dihydro-2H-benzo[b][1,4]oxazin-8-yl)ethyl)amino)pent-1-yn-1-yl)-3-methylphenyl)carbamoyl)phenyl)sulfonyl)-4-((3-methoxyphenyl)amino)-8-methylquinoline-3-carboxamide;

(R)-6-((3-((4-(2-(4-((2-hydroxy-2-(8-hydroxy-2-oxo-1,2-dihydroquinolin-5-yl)ethyl)amino)butyl)-1,3-dithiolan-2-yl)phenyl)carbamoyl)phenyl)sulfonyl)-4-((3-methoxyphenyl)amino)-8-methylquinoline-3-carboxamide;

(R)-6-((3-((4-(4-((6-((2-hydroxy-2-(8-hydroxy-2-oxo-1,2-dihydroquinolin-5-yl)ethyl)amino)hexyl)oxy)butyl)phenyl)carbamoyl)phenyl)sulfonyl)-4-((3-methoxyphenyl)amino)-8-methylquinoline-3-carboxamide;

(R)-6-((3-((4-(2-((6-((2-hydroxy-2-(8-hydroxy-2-oxo-1,2-dihydroquinolin-5-yl)ethyl)amino)hexyl)oxy)ethyl)phenyl)carbamoyl)phenyl)sulfonyl)-4-((3-methoxyphenyl)amino)-8-methylquinoline-3-carboxamide;

(R)-6-((3-((4-(4-((6-((2-hydroxy-2-(8-hydroxy-2-oxo-1,2-dihydroquinolin-5-yl)ethyl)amino)hexyl)oxy)butyl)phenyl)(methyl)carbamoyl)phenyl)sulfonyl)-4-((3-methoxyphenyl)amino)-8-methylquinoline-3-carboxamide;

(R)-6-[[3-[[6-[[2-Hydroxy-2-[4-hydroxy-3-(hydroxymethyl)phenyl]ethyl]amino]hexyl]carbamoyl]phenyl]sulfonyl]-4-[(3-methoxyphenyl)amino]-8-methylquinoline-3-carboxamide;

(R)-6-[[3-[[4-[[2-Hydroxy-2-[4-hydroxy-3-(hydroxymethyl)phenyl]ethyl]amino]piperidine-1-yl]carbonyl]phenyl]sulfonyl]-4-((3-methoxyphenyl)amino)-8-methylquinoline-3-carboxamide;

(R)-6-[[3-[[6-[[2-Hydroxy-2-[4-hydroxy-3-(methylsulfonamido)phenyl]ethyl]amino]hexyl]carbamoyl]phenyl]sulfonyl]-4-[(3-methoxyphenyl)amino]-8-methylquinoline-3-carboxamide;

(R)-6-[[3-[[6-[[2-Hydroxy-2-(4-hydroxy-3-(hydroxymethyl)phenyl]ethyl]amino]hexyl]methyl)carbamoyl]phenyl]sulfonyl]-4-((3-methoxyphenyl)amino)-8-methylquinoline-3-carboxamide;

(R)-6-((11-((2-hydroxy-2-(8-hydroxy-2-oxo-1,2-dihydroquinolin-5-yl)ethyl)amino) undecyl)sulfonyl)-4-((3-methoxyphenyl)amino)-8-methylquinoline-3-carboxamide;

(R)-6-((11-((2-hydroxy-2-(6-hydroxy-3-oxo-3,4-dihydro-2H-benzo[b][1,4]oxazin-8-yl)ethyl)amino)undecyl)sulfonyl)-4-((3-methoxyphenyl)amino)-8-methylquinoline-3-carboxamide;

(R)-6-((4'-(((2-hydroxy-2-(8-hydroxy-2-oxo-1,2-dihydroquinolin-5-yl)ethyl)amino)methyl)-[1,1'-biphenyl]-3-yl)sulfonyl)-4-((3-methoxyphenyl)amino)-8-methylquinoline-3-carboxamide;

(R)-6-((4'-(((2-hydroxy-2-(8-hydroxy-2-oxo-1,2-dihydroquinolin-5-yl)ethyl)amino)methyl)-[1,1'-biphenyl]-

4-yl)sulfonyl)-4-((3-methoxyphenyl)amino)-8-methylquinoline-3-carboxamide;

(R)-6-((4'-(3-((2-hydroxy-2-(5-hydroxy-3-oxo-3,4-dihydro-2H-benzo[b][1,4]oxazin-8-yl)ethyl)amino)propyl)-[1,1'-biphenyl]-4-yl)sulfonyl)-4-((3-methoxyphenyl)amino)-8-methylquinoline-3-carboxamide (R)-6-((4'-(3-((2-hydroxy-2-(5-hydroxy-3-oxo-3,4-dihydro-2H-benzo[b][1,4]oxazin-8-yl)ethyl)amino)propyl)-[1,1'-biphenyl]-3-yl)sulfonyl)-4-((3-methoxyphenyl)amino)-8-methylquinoline-3-carboxamide;

(R)-6-((4'-(5-((2-hydroxy-2-(5-hydroxy-3-oxo-3,4-dihydro-2H-benzo[b][1,4]oxazin-8-yl)ethyl)amino)pentyl)-[1,1'-biphenyl]-4-yl)sulfonyl)-4-((3-methoxyphenyl)amino)-8-methylquinoline-3-carboxamide;

(R)-6-((4'-(5-((2-hydroxy-2-(5-hydroxy-3-oxo-3,4-dihydro-2H-benzo[b][1,4]oxazin-8-yl)ethyl)amino)pentyl)-[1,1'-biphenyl]-3-yl)sulfonyl)-4-((3-methoxyphenyl)amino)-8-methylquinoline-3-carboxamide;

(R)-6-(3-((4-(4-(4-(2-hydroxy-2-(8-hydroxy-2-oxo-1,2-dihydroquinolin-5-yl)ethylamino)butyl)phenyl)-N-methylpiperidine-1-carboxamido)methyl)phenylsulfonyl)-4-(3-methoxyphenylamino)-8-methylquinoline-3-carboxamide;

(R)-6-(3-(4-(4-(4-(2-hydroxy-2-(8-hydroxy-2-oxo-1,2-dihydroquinolin-5-yl)ethylamino)butyl)phenyl)piperidine-1-carbonyl)phenylsulfonyl)-4-(3-methoxyphenylamino)-8-methylquinoline-3-carboxamide;

(R)-6-(3-(4-(4-(4-(2-hydroxy-2-(8-hydroxy-2-oxo-1,2-dihydroquinolin-5-yl)ethylamino)butyl)cyclohexyl)piperidine-1-carbonyl)phenylsulfonyl)-4-(3-methoxyphenylamino)-8-methylquinoline-3-carboxamide;

(R)-6-(3-((4-(4-(4-(2-hydroxy-2-(8-hydroxy-2-oxo-1,2-dihydroquinolin-5-yl)ethylamino)butyl)phenyl)-N-methylpiperazine-1-carboxamido)methyl)phenylsulfonyl)-4-(3-methoxyphenylamino)-8-methylquinoline-3-carboxamide;

(R)-6-(3-((4-(4-(4-(2-hydroxy-2-(8-hydroxy-2-oxo-1,2-dihydroquinolin-5-yl)ethylamino)butyl)phenyl)-N-methylpiperidine-1-carboxamido)methyl)phenylsulfonyl)-4-(3-methoxyphenylamino)-8-methylquinoline-3-carboxamide;

(R)-3-(3-carbamoyl-4-(3-methoxyphenylamino)-8-methylquinolin-6-ylsulfonyl)benzyl 4-(4-(4-(2-hydroxy-2-(8-hydroxy-2-oxo-1,2-dihydroquinolin-5-yl)ethylamino)butyl)phenyl)piperazine-1-carboxylate;

(R)-6-(2-hydroxy-2-(8-hydroxy-2-oxo-1,2-dihydroquinolin-5-yl)ethylamino)hexyl 3-(3-carbamoyl-4-(3-methoxyphenylamino)-8-methylquinolin-6-ylsulfonyl)benzylcarbamate; and (R)-6-(3-(5-(5-(2-hydroxy-2-(8-hydroxy-2-oxo-1,2-dihydroquinolin-5-yl)ethylamino)pentyl)indoline-1-carbonyl)phenylsulfonyl)-4-(3-methoxyphenylamino)-8-methylquinoline-3-carboxamide;

or a pharmaceutically acceptable salt thereof.

20. A composition comprising a compound according to claim 1, or a pharmaceutically acceptable salt thereof, and a pharmaceutically acceptable carrier, diluent or excipient.

21. The composition according to claim 18, or a pharmaceutically acceptable salt thereof, wherein said composition is suitable for inhalation.

22. The composition according to claim 18 further comprising a therapeutically active agent selected from anti-inflammatory agents, anticholinergic agents, peroxisome proliferator-activated receptor agonists, epithelial sodium channel blockers, kinase inhibitors, protease inhibitors, anti-infective agents and antihistamines.

23. A method for treating pulmonary inflammation or bronchoconstriction in a human in need thereof, comprising administering to said human an effective amount of a compound of claim 1, or a pharmaceutically acceptable salt thereof.

24. A method for treating a disease associated with reversible or irreversible airway obstruction selected from chronic obstructive pulmonary disease (COPD), asthma, bronchiectasis, acute bronchitis, chronic bronchitis, emphysema, panbronchiolitis, transplant-associated bronchiolitis, sinusitis, and ventilator-associated tracheobronchitis in a human in need thereof, said method comprising administering to said human an effective amount of a compound of claim 1, or a pharmaceutically acceptable salt thereof.

25. A method for treating chronic obstructive pulmonary disease (COPD) in a human in need thereof, said method comprising administering to said human an effective amount of a compound of claim 1, or a pharmaceutically acceptable salt thereof.

26. A method for treating asthma in a human in need thereof, said method comprising administering to said human an effective amount of a compound of claim 1, or a pharmaceutically acceptable salt thereof.

* * * * *